United States Patent
Yoshino et al.

(10) Patent No.: US 10,858,356 B2
(45) Date of Patent: Dec. 8, 2020

(54) PYRAZOLOPYRIDINE DERIVATIVE HAVING GLP-1 RECEPTOR AGONIST EFFECT

(71) Applicant: Chugai Seiyaku Kabushiki Kaisha, Tokyo (JP)

(72) Inventors: Hitoshi Yoshino, Shizuoka (JP); Satoshi Tsuchiya, Shizuoka (JP); Atsushi Matsuo, Shizuoka (JP); Tsutomu Sato, Shizuoka (JP); Masahiro Nishimoto, Shizuoka (JP); Kyoko Oguri, Shizuoka (JP); Hiroko Ogawa, Shizuoka (JP); Yoshikazu Nishimura, Shizuoka (JP); Yoshiyuki Furuta, Kanagawa (JP); Hirotaka Kashiwagi, Shizuoka (JP); Nobuyuki Hori, Shizuoka (JP); Takuma Kamon, Shizuoka (JP); Takuya Shiraishi, Shizuoka (JP); Shoshin Yoshida, Shizuoka (JP); Takahiro Kawai, Shizuoka (JP); Satoshi Tanida, Shizuoka (JP); Masahide Aoki, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/759,872

(22) PCT Filed: Sep. 26, 2017

(86) PCT No.: PCT/JP2017/034620
§ 371 (c)(1),
(2) Date: Mar. 14, 2018

(87) PCT Pub. No.: WO2018/056453
PCT Pub. Date: Mar. 29, 2018

(65) Prior Publication Data
US 2019/0225604 A1  Jul. 25, 2019

(30) Foreign Application Priority Data

Sep. 26, 2016 (JP) .................................. 2016-187605

(51) Int. Cl.
| A61K 31/437 | (2006.01) |
| A61P 3/04 | (2006.01) |
| C07D 471/04 | (2006.01) |
| C07D 519/00 | (2006.01) |
| A61P 3/10 | (2006.01) |
| A61P 1/16 | (2006.01) |
| A61K 31/506 | (2006.01) |
| A61K 31/4725 | (2006.01) |
| A61P 3/06 | (2006.01) |
| A61K 31/444 | (2006.01) |
| A61K 31/496 | (2006.01) |
| A61P 9/10 | (2006.01) |
| A61K 31/5386 | (2006.01) |
| A61K 31/5377 | (2006.01) |
| A61P 25/16 | (2006.01) |
| A61P 25/28 | (2006.01) |
| A61K 31/4709 | (2006.01) |

(52) U.S. Cl.
CPC .......... *C07D 471/04* (2013.01); *A61K 31/437* (2013.01); *A61K 31/444* (2013.01); *A61K 31/4709* (2013.01); *A61K 31/4725* (2013.01); *A61K 31/496* (2013.01); *A61K 31/506* (2013.01); *A61K 31/5377* (2013.01); *A61K 31/5386* (2013.01); *A61P 1/16* (2018.01); *A61P 3/04* (2018.01); *A61P 3/06* (2018.01); *A61P 3/10* (2018.01); *A61P 9/10* (2018.01); *A61P 25/16* (2018.01); *A61P 25/28* (2018.01); *C07D 519/00* (2013.01)

(58) Field of Classification Search
CPC ....... A61K 31/437; A61P 3/04; C07D 471/04; C07D 519/00
See application file for complete search history.

(56) References Cited

FOREIGN PATENT DOCUMENTS

| JP | 2006510582 A | 3/2006 |
| JP | 2010510987 A | 4/2010 |
| JP | 2012522060 A | 9/2012 |
| JP | 2016508506 A | 3/2016 |
| WO | WO-2004017908 A1 | 3/2004 |
| WO | WO-2008066789 A2 | 6/2008 |
| WO | WO-2010114824 A1 | 10/2010 |
| WO | WO-2014122067 A1 | 8/2014 |
| WO | WO-2016038045 A1 | 3/2016 |

*Primary Examiner* — Brenda L Coleman
(74) *Attorney, Agent, or Firm* — Macharri Vorndran-Jones

(57) ABSTRACT

The present invention provides a compound having the basic structure shown by Formula (I) in which the indole ring and the pyrazolopyridine structure is bound through a substituent, a salt thereof or a solvate of either the compound or a salt of the compound, as well as a preventative agent or a therapeutic agent for non-insulin-dependent diabetes mellitus (Type 2 diabetes) or obesity containing such compound, salt or solvate as an active ingredient.

17 Claims, 6 Drawing Sheets

Sample 160a

Sample 160b

Sample 161a

Sample 161b

Sample 162a

Sample 162b

Sample 160a

Sample 162a

Mean value ± standard error

Mean value ± standard error

Mean value ± standard deviation

PYRAZOLOPYRIDINE DERIVATIVE HAVING GLP-1 RECEPTOR AGONIST EFFECT

CROSS REFERENCE TO RELATED APPLICATIONS

This application is a U.S. National Phase of PCT Application No. PCT/JP2017/034620, filed Sep. 26, 2017, which claims priority to Japanese Patent Application No. 2016-187605, filed Sep. 26, 2016, each of which is incorporated herein by reference in its entirety.

TECHNICAL FIELD

The present invention relates to a compound which is a GLP-1 receptor agonist having the same effect as GLP-1, a salt thereof, or a solvate of either the compound or a salt of the compound. The present invention further relates to a preventative agent or a therapeutic agent for non-insulin-dependent diabetes mellitus (Type 2 diabetes) or obesity comprising such a compound, a salt or a solvate as an active ingredient.

BACKGROUND ART

Glucagon-like peptide-1 (GLP-1) is an incretin secreted from L cells in the small intestine when nutrients pass through the digestive tract, and it is known that the GLP-1 demonstrates a wide variety of effects through the GLP-1 receptor, such as promotion of glucose dependent insulin secretion, inhibition of glucagon secretion, delaying of gastric emptying, suppression of feeding. Although GLP-1 analog is already commercialized as a therapeutic agent for diabetes, and seen as one of the most effective therapeutic agent for diabetes due to its potent effect in HbA1c reduction and weight loss, all of them require an invasive subcutaneous administration. As such, development of a GLP-1 receptor agonist that can be non-invasively administered is awaited. Attempts were made, for example, to improve the bioavailability at the time of oral administration of a GLP-1 analog: Semaglutide by using an absorbefacient (sodium N-(8-(2-hydroxybenzoyl)amino)caprylate: SNAC) (Patent Document 1) and to develop a low molecular GLP-1 receptor agonist (Patent Documents 2 and 3), but a further improvement is required in medicinal properties including activity, metabolic stability and bioavailability.

The following two compounds for a chemical library are known as 2-[(2,4,6,7-tetrahydro-5H-pyrazolo[4,3-c]pyridine-5-yl)carbonyl]-1H-indol.

[Chemical Formula 1]

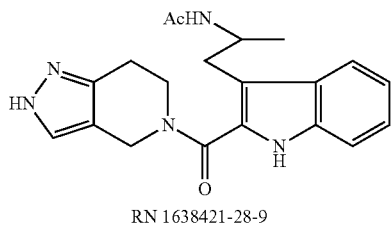

RN 1638421-28-9

-continued

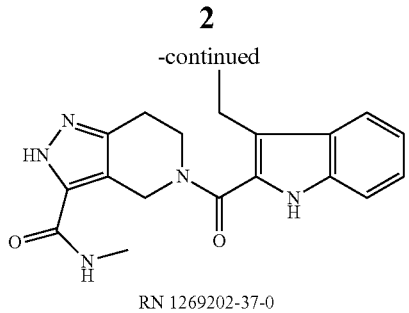

RN 1269202-37-0

Further, Patent Document 4 describes the following pyrazolopyridine derivative as a compound that is useful in the prevention/therapy of sleeping sickness, leishmaniasis or the like caused by eukaryote: such as blastocrithidia (e.g. Trypanosomatidae) parasitizing the patient.

[Chemical Formula 2]

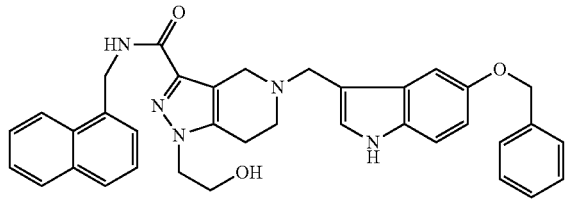

CITATION LIST

Patent Literature

Patent Document 1: WO 2012/080471
Patent Document 2: WO 2009/111700
Patent Document 3: WO 2010/114824
Patent Document 4: WO 2016/038045

SUMMARY OF INVENTION

Technical Problem

The problem to be solved by the present invention is to provide a compound which is a GLP-1 receptor agonist having the same effect as GLP-1 peptide that may be non-invasively administered and has an improved activity, metabolic stability and bioavailability, a salt thereof, or a solvate of either the compound or a salt of the compound, and also to provide a preventative agent or a therapeutic agent for non-insulin-dependent diabetes mellitus (Type 2 diabetes) or obesity comprising such a compound, salt or solvate as an active ingredient.

Solution to Problem

The present inventors studied extensively to solve this problem and found that a compound represented by Formula (I), in which the indole ring and the pyrazolopyridine structure are bound to each other through a substituent, has the same effect as GLP-1 peptide as a GLP-1 receptor agonis, and thus completed the present invention.

In other words, the following invention is provided as one aspect of the present invention.

[1] A compound represented by Formula (I):

[Chemical Formula 3]

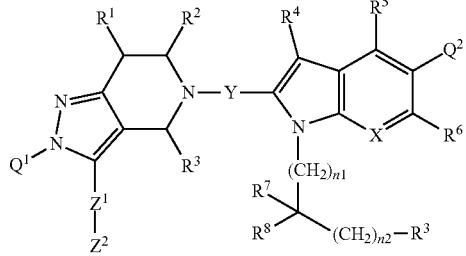

(I)

wherein, X is —N= or —CR$^a$=; R$^a$ is selected from a hydrogen atom, a halogen atom, and C$_{1-6}$ alkyl;

Y is selected from —C(=O)—, —CHR—, and —S(=O)$_2$—; R is a hydrogen atom or C$_{1-6}$ alkyl;

Q$^1$ is C$_{6-10}$ aryl or 5 to 10 membered heteroaryl, wherein C$_{6-10}$ aryl and 5 to 10 membered heteroaryl are optionally substituted with one to five substituents independently selected from a halogen atom, C$_{1-6}$ alkyl (wherein C$_{1-6}$ alkyl is optionally substituted with one or more halogen atoms), and C$_{1-6}$ alkoxy;

Q$^2$ is 3 to 12 membered heterocyclyl or 5 to 10 membered heteroaryl, wherein 3 to 12 membered heterocyclyl and 5 to 10 membered heteroaryl are optionally substituted with one to three substituents independently selected from a halogen atom, C$_{1-6}$ alkyl (wherein C$_{1-6}$ alkyl is optionally substituted with one or more halogen atoms), C$_{1-6}$ alkoxy, and —NR$^{Qa}$R$^{Qb}$, and further, two C$_{1-6}$ alkyl groups together with a carbon atom to which they are attached may form C$_{3-8}$ carbocyclic ring; and R$^{Qa}$ and R$^{Qb}$ are independently selected from a hydrogen atom, C$_{1-6}$ alkyl, and (C$_{1-6}$ alkyl) carbonyl;

R$^1$, R$^2$ and R$^3$ are each independently selected from a hydrogen atom and C$_{1-6}$ alkyl (wherein, C$_{1-6}$ alkyl is optionally substituted with one or more substituents independently selected from a halogen atom, C$_{1-6}$ alkoxy, and hydroxy);

R$^4$, R$^5$ and R$^6$ are independently selected from a hydrogen atom, a halogen atom, and C$_{1-6}$ alkyl;

R$^7$ and R$^8$ are independently a hydrogen atom or C$_{1-6}$ alkyl, wherein C$_{1-6}$ alkyl is optionally substituted with one or more substituents independently selected from a halogen atom and C$_{3-15}$ cycloalkyl, or R$^7$ and R$^8$ together with a carbon atom to which they are attached may form C$_{3-15}$ cycloalkane ring, or C$_{3-15}$ cycloalkane ring formed by R$^7$ and R$^8$ together is optionally substituted with one to three C$_{1-6}$ alkyl, wherein C$_{1-6}$ alkyl is optionally substituted with one or more substituents independently selected from a halogen atom, hydroxy, —NR$^{7a}$R$^{7b}$, C$_{1-6}$ alkoxy, and 3 to 12 membered heterocyclyl, and R$^{7a}$ and R$^{7b}$ are independently selected from a hydrogen atom, C$_{1-6}$ alkyl, and (C$_{1-6}$ alkyl) carbonyl;

n1 is an integer of 0 to 3; n2 is an integer of 0 to 5;

R$^9$ is selected from a group represented by Formula (IIa), (IIb), (IIc), (IId):

[Chemical Formula 4]

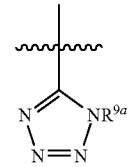 (IIa)

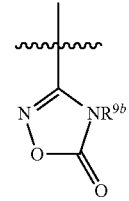 (IIb)

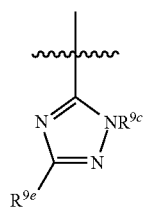 (IIc)

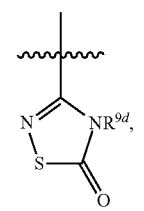 (IId)

—CO$_2$R$^{9f}$, and —C(=O)—NR$^{9g}$R$^{9h}$; and R$^{9a}$, R$^{9b}$, R$^{9c}$, R$^{9d}$, and R$^{9g}$ are each independently selected from a hydrogen atom, C$_{1-6}$ alkyl (wherein C$_{1-6}$ alkyl is optionally substituted with one or more substituents independently selected from a halogen atom and C$_{1-6}$ alkoxy), and (C$_{1-6}$ alkyl)carbonyl, R$^{9e}$ is a hydrogen atom, or C$_{1-6}$ alkyl that is optionally substituted with one or more halogen atoms, R$^{9f}$ is a hydrogen atom or C$_{1-6}$ alkyl, R$^{9h}$ is a hydrogen atom, C$_{1-6}$ alkyl, (C$_{1-6}$ alkyl)carbonyl, cyano, or —S(=O)$_{n3}$—R$^{9i}$; n3 is an integer of 0 to 2, R$^{9i}$ is C$_{1-6}$ alkyl; Z$^1$ is selected from a group represented by Formula (IIIa), (IIIb), (IIIc), (IIId), and (IIIe):

[Chemical Formula 5]

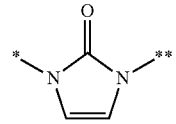 (IIIa)

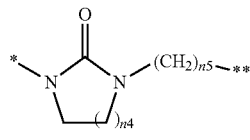 (IIIb)

 (IIIc)

-continued

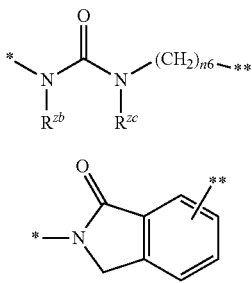

(IIId)

(IIIe)

wherein $R^{za}$ is selected from a hydrogen atom, $C_{1-6}$ alkyl, and ($C_{1-6}$ alkyl)carbonyl, $R^{zb}$ and $R^{zc}$ are independently a hydrogen atom or $C_{1-6}$ alkyl, n4 is an integer of 1 to 3, n5 and n6 are independently an integer of 0 to 10 (* represents a binding position with a pyrazolopyridine structure, ** represents a binding position with $Z^2$);

$Z^2$ is selected from $C_{1-6}$ alkyl, $C_{3-15}$ cycloalkyl, 3 to 12 membered heterocyclyl, $C_{6-10}$ aryl and 5 to 10 membered heteroaryl, wherein $C_{3-15}$ cycloalkyl, 3 to 12 membered heterocyclyl, $C_{6-10}$ aryl, and 5 to 10 membered heteroaryl are optionally substituted with one to five substituents independently selected from Group A:

Group A: a) oxo,
b) a halogen atom,
c) cyano,
d) —$NR^{zd}R^{ze}$; wherein $R^{zd}$ and $R^{ze}$ are independently selected from a hydrogen atom, $C_{1-6}$ alkyl and ($C_{1-6}$ alkyl)carbonyl, wherein $C_{1-6}$ alkyl is optionally substituted with one or more substituents independently selected from hydroxy, a halogen atom and $C_{1-6}$ alkoxy,
e) —C(=O)—$NR^{zf}R^{zg}$; wherein $R^{zf}$ and $R^{zg}$ are independently selected from a hydrogen atom, $C_{1-6}$ alkyl and ($C_{1-6}$ alkyl)carbonyl, wherein $C_{1-6}$ alkyl is optionally substituted with one or more substituents independently selected from hydroxy, a halogen atom and $C_{1-6}$ alkoxy,
f) —S(=)$_{n7}$—$R^{zh}$; wherein n7 is an integer of 0 to 2, $R^{zh}$ is a hydrogen atom or $C_{1-6}$ alkyl,
g) $C_{1-6}$ alkyl; wherein $C_{1-6}$ alkyl is optionally substituted with one or more substituent independently selected from a halogen atom, hydroxy, —$NR^{zi}R^{zj}$, $C_{1-6}$ alkoxy, and 3 to 12 membered heterocyclyl, wherein R and R are independently a hydrogen atom or $C_{1-6}$ alkyl, and wherein 3 to 12 membered heterocyclyl is optionally substituted with one or more substituents independently selected from hydroxy, $C_{1-6}$ alkyl and 3 to 12 membered heterocyclyl,
h) $C_{1-6}$ alkoxy; wherein $C_{1-6}$ alkoxy is optionally substituted with one or more substituent independently selected from hydroxy, a halogen atom, and $C_{1-6}$ alkoxy,
i) 3 to 12 membered heterocyclyl; wherein 3 to 12 membered heterocyclyl is optionally substituted with one or more substituents independently selected from $C_{1-6}$ alkyl and ($C_{1-6}$ alkyl)carbonyl,
j) $C_{6-10}$ aryl; wherein $C_{6-10}$ aryl is optionally substituted with one or more ($C_{1-6}$ alkyl)carbonyl, and
k) 5 to 10 membered heteroaryl; wherein 5 to 10 membered heteroaryl is optionally substituted with one or more substituents independently selected from $C_{1-6}$ alkyl, $C_{1-6}$ alkoxy, —$NR^{zk}R^{zl}$, and 3 to 12 membered heterocyclyl, wherein $R^{zk}$ and $R^{zl}$ are independently selected from a hydrogen atom, $C_{1-6}$ alkyl and ($C_{1-6}$ alkyl)carbonyl, and wherein 3 to 12 membered heterocyclyl is optionally substituted with one or more substituents independently selected from $C_{1-6}$ alkyl and ($C_{1-6}$ alkyl)carbonyl;

a salt thereof, or a solvate of either the compound or a salt of the compound.

[2] The compound according to [1], a salt thereof, or a solvate of either the compound or a salt of the compound, wherein $Q^1$ is phenyl or pyridyl, and phenyl or pyridyl is substituted with one to four substituents independently selected from a halogen atom and $C_{1-6}$ alkyl.

[3] The compound according to either [1] or [2], a salt thereof, or a solvate of either the compound or a salt of the compound, wherein $R^7$ and $R^8$ are both a hydrogen atom; $R^7$ and $R^8$ are both $C_{1-6}$ alkyl; $R^7$ is a hydrogen atom and $R^8$ is $C_{1-6}$ alkyl; or $R^7$ and $R^8$ together with a carbon atom to which they are attached form $C_{3-8}$ cycloalkane ring, wherein $C_{3-8}$ cycloalkane ring that has been formed is optionally substituted with one to two $C_{1-6}$ alkyl, and $C_{1-6}$ alkyl is optionally substituted with one or more substituents independently selected from hydroxy, $C_{1-6}$ alkoxy, and 3 to 12 membered heterocyclyl.

[4] The compound according to anyone of [1] to [3], a salt thereof, or a solvate of either the compound or a salt of the compound, wherein $Z^2$ is selected from $C_{1-6}$ alkyl, $C_{3-15}$ cycloalkyl, 3 to 12 membered heterocyclyl, $C_{6-10}$ aryl, and 5 to 10 membered heteroaryl, wherein $C_{3-15}$ cycloalkyl, 3 to 12 membered heterocyclyl, $C_{6-10}$ aryl, and 5 to 10 membered heteroaryl are optionally substituted with one to four substituents independently selected from Group B:

Group B: a) oxo,
b) a halogen atom,
c) —$NR^{zd1}R^{ze1}$; wherein $R^{zd1}$ and $R^{ze1}$ are independently selected from a hydrogen atom, $C_{1-6}$ alkyl and ($C_{1-6}$ alkyl)carbonyl, and $C_{1-6}$ alkyl is optionally substituted with one or more $C_{1-6}$ alkoxy,
d) —S(=)$_{n7}$—$R^{zh1}$; wherein n7 is an integer of 0 to 2, $R^{zh1}$ is $C_{1-6}$ alkyl, e) $C_{1-6}$ alkyl; wherein $C_{1-6}$ alkyl is optionally substituted with one or more substituents independently selected from a halogen atom, hydroxy, —$NR^{zi}R^{zj}$, $C_{1-6}$ alkoxy, and 3 to 12 membered heterocyclyl, wherein $R^{zi}$ and $R^{zj}$ are independently a hydrogen atom or $C_{1-6}$ alkyl, and wherein 3 to 12 membered heterocyclyl is optionally substituted with one or more substituents independently selected from hydroxy, $C_{1-6}$ alkyl and 3 to 12 membered heterocyclyl,
f) $C_{1-6}$ alkoxy; wherein $C_{1-6}$ alkoxy is optionally substituted with one or more hydroxy,
g) 3 to 12 membered heterocyclyl; wherein 3 to 12 membered heterocyclyl is optionally substituted with one or more ($C_{1-6}$ alkyl)carbonyl,
h) 5 to 10 membered heteroaryl; wherein 5 to 10 membered heteroaryl is optionally substituted with one or more substituents independently selected from $C_{1-6}$ alkyl, —$NR^{zk1}R^{zl1}$, and $R^{zk1}$ and $R^{zl1}$ are independently selected from a hydrogen atom and $C_{1-6}$ alkyl.

[5] The compound according to anyone of [1] to [4], a salt thereof, or a solvate of either the compound or a salt of the compound, wherein Y is —C(=O)—.

[6] The compound according to anyone of [1] to [5], a salt thereof, or a solvate of either the compound or a salt of the compound, wherein $R^1$ is a hydrogen atom.

[7] The compound according to anyone [1] to [6], a salt thereof, or a solvate of either the compound or a salt of the compound, wherein n1 and n2 are both 0.

[8] The compound according to anyone of [1] to [7], a salt thereof, or a solvate of either the compound or a salt of the compound, wherein $R^9$ is represented by Formula (IIb):

[Chemical Formula 6]

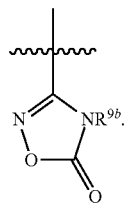

(IIb)

[9] The compound according to any one of [1] to [8], a salt thereof, or a solvate of either the compound or a salt of the compound, wherein X is —N=, —CH=, or —CF=.

[10] The compound according to anyone of [1] to [9], a salt thereof, or a solvate of either the compound or a salt of the compound, wherein Zi is represented by Formula (IIIa):

[Chemical Formula 7]

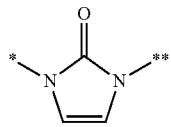

(IIIa)

(* represents a binding position with a pyrazolopyridine structure, ** represents a binding position with $Z^2$).

[11] A pharmaceutical composition comprising the compound according to any one of [1] to [10], a salt thereof, or a solvate of either the compound or a salt of the compound as an active ingredient.

[12] A preventive agent or a therapeutic agent for non-insulin-dependent diabetes mellitus (Type 2 diabetes), hyperglycemia, impaired glucose tolerance, insulin dependent diabetes mellitus (Type 1 diabetes), diabetic complication, obesity, hypertension, hyperlipidemia, arteriosclerosis, coronary heart disease, brain infarction, non-alcoholic steatohepatitis, Parkinson's disease, or dementia, wherein the preventative agent or the therapeutic agent comprises the compound according to any one of [1] to [10], a salt thereof, or a solvate of either the compound or a salt of the compound as an active ingredient. An example of dementia is Alzheimer's disease.

[13] A preventive agent or a therapeutic agent for non-insulin-dependent diabetes mellitus (Type 2 diabetes) or obesity comprising the compound according to any one of [1] to [10], a salt thereof, or a solvate of either the compound or a salt of the compound as an active ingredient.

[14] A method for preventing or treating non-insulin-dependent diabetes mellitus (Type 2 diabetes), hyperglycemia, impaired glucose tolerance, insulin dependent diabetes mellitus (Type 1 diabetes), diabetic complication, obesity, hypertension, hyperlipidemia, arteriosclerosis, coronary heart disease, brain infarction, non-alcoholic steatohepatitis, Parkinson's disease, or dementia, which comprises administering an effective amount of the compound according to any one of [1] to [10], a salt thereof, or a solvate of either the compound or a salt of the compound to a subject. An example of dementia is Alzheimer's disease.

[15] A method for preventing or treating non-insulin-dependent diabetes mellitus (Type 2 diabetes) or obesity, which comprises administering an effective amount of the compound according to any one of [1] to [10], a salt thereof, or a solvate of either the compound or a salt of the compound to a subject.

Advantageous Effects of Invention

The compound, a salt thereof, or a solvate of either the compound or a salt of the compound of the present invention is has an effect similar to GLP-1 peptide as a GLP-1 receptor agonist, and provides a non-peptide agent for preventing or treating non-insulin-dependent diabetes mellitus (Type 2 diabetes) or obesity which is expected to provide a sufficient bioavailability through oral administration.

DESCRIPTION OF EMBODIMENTS

Figure 1:
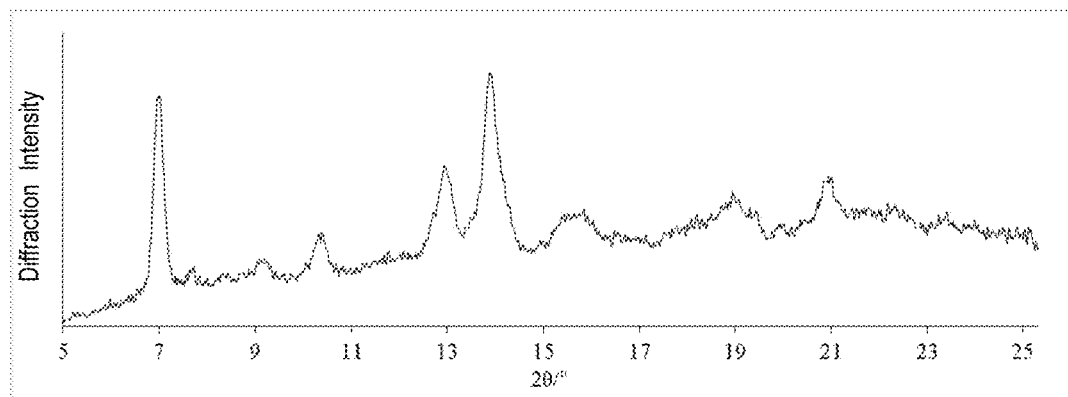
FIG. 1 shows the result of measurement by X-ray powder diffractometry of the crystal of a sodium salt hydrate of Compound 1 obtained in Example 163 (Sample 160a). The vertical axis shows the diffraction intensity and the horizontal axis shows the diffraction angle 2θ (°).
Figure 2:
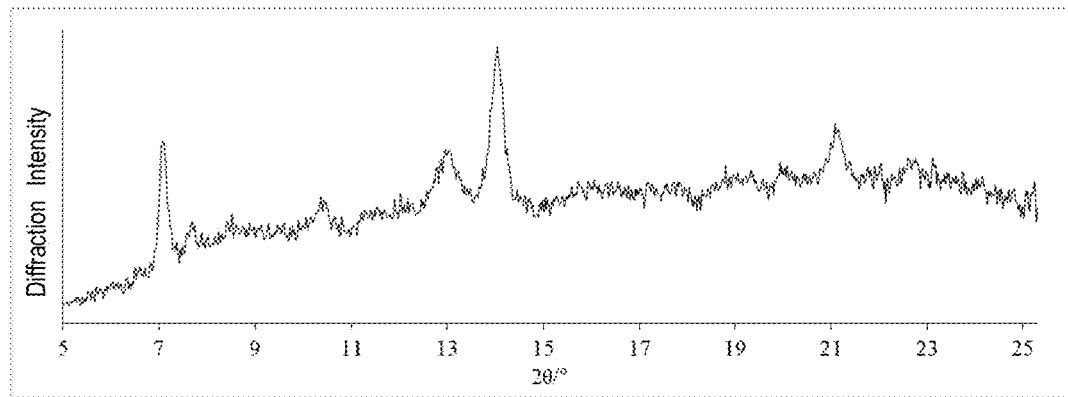
FIG. 2 shows the result of measurement by X-ray powder diffractometry of the crystal of a sodium salt hydrate of Compound 1 obtained in Example 163 (Sample 160b). The vertical axis shows the diffraction intensity and the horizontal axis shows the diffraction angle 2θ (°).
Figure 3:
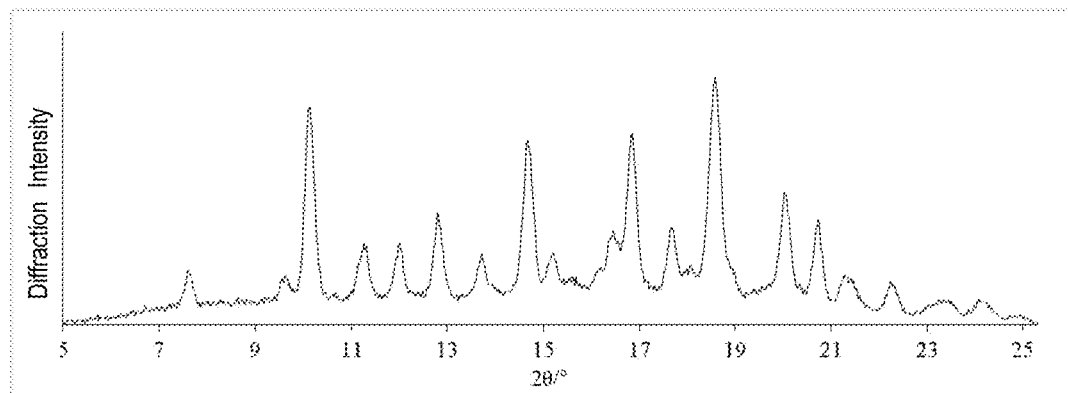
FIG. 3 shows the result of measurement by X-ray powder diffractometry of the crystal of Example Compound 66 obtained in Example 163 (Sample 161a). The vertical axis shows the diffraction intensity and the horizontal axis shows the diffraction angle 2θ (°).
Figure 4:
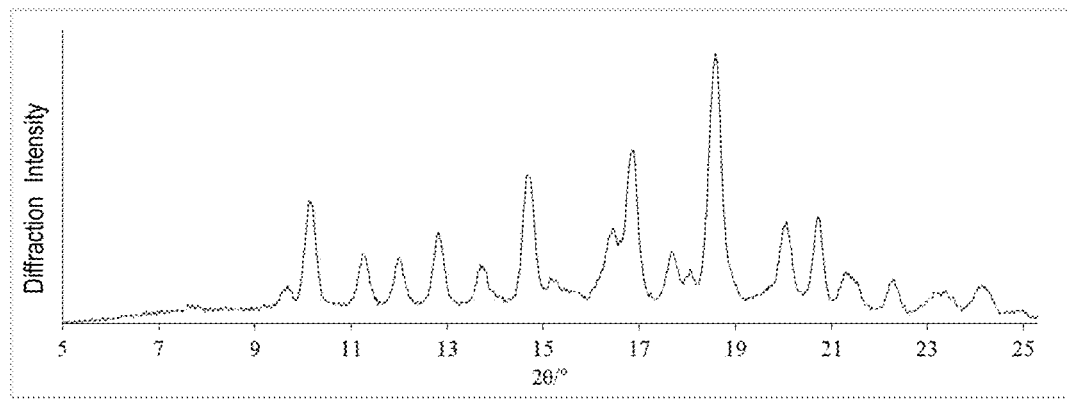
FIG. 4 shows the result of measurement by X-ray powder diffractometry of the crystal of Example Compound 66 obtained in Example 163 (Sample 161b). The vertical axis shows the diffraction intensity and the horizontal axis shows the diffraction angle 2θ (°).
Figure 5:
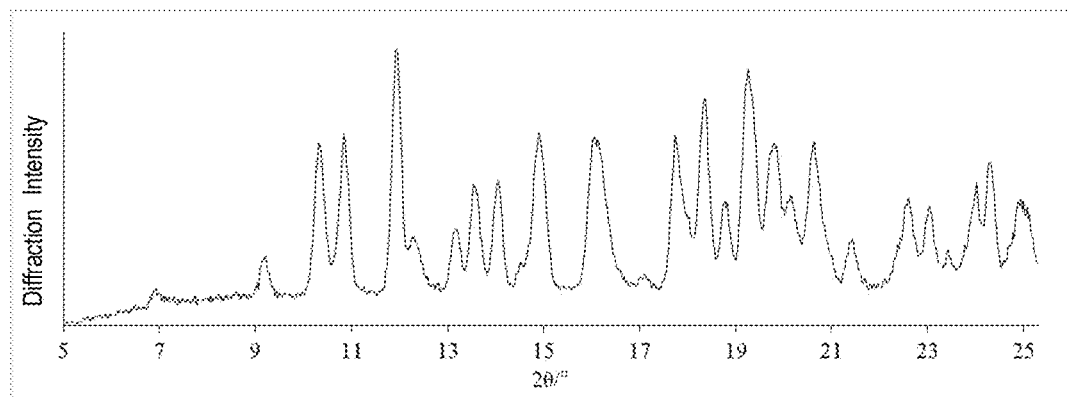
FIG. 5 shows the result of measurement by X-ray powder diffractometry of the crystal of a calcium salt hydrate of Example Compound 67 obtained in Example 163 (Sample 162a). The vertical axis shows the diffraction intensity and the horizontal axis shows the diffraction angle 2θ (°).
Figure 6:
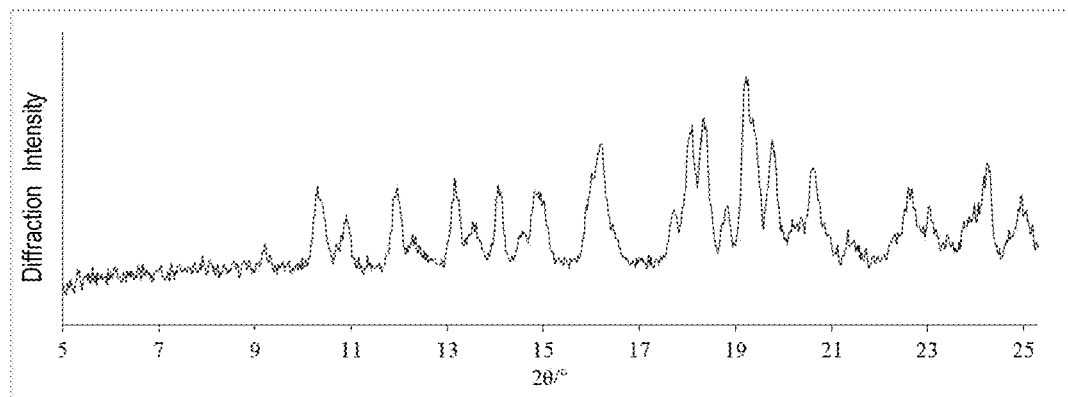
FIG. 6 shows the result of measurement by X-ray powder diffractometry of the crystal of a calcium salt hydrate of Example Compound 67 obtained in Example 163 (Sample 162b). The vertical axis shows the diffraction intensity and the horizontal axis shows the diffraction angle 2θ (°).

The present invention is further described below without being limited thereby.

Definition

The term "a halogen atom" in the present invention means a fluorine atom, a chlorine atom, a bromine atom, an iodine atom and the like. A halogen atoms that is preferred as a substituent of aryl in the present invention (e.g. $R^a$ when X in Formula (I) is —$CR^a$=) is a fluorine atom and a chlorine atom. A halogen atoms that is preferred as a substituent of alkyl in the present invention (e.g. a substituent of $C_{1-6}$ alkyl when the $C_{6-10}$ aryl or the 5 to 10 membered heteroaryl of $Q^1$ is substituted with $C_{1-6}$ alkyl) is a fluorine atom and a chlorine atom. Specific examples of $C_{1-6}$ alkyl having a halogen atom as a substituent include fluoromethyl, difluoromethyl, trifluoromethyl, chloromethyl, pentafluoroethyl, 2-fluoroethyl, 2,2,2-trifluoroethyl, 2-chloroethyl, heptafluoropropyl, 3,3,3-trifluoropropyl, 2,3-dichloropropyl, 1-fluoro-3-bromopropyl, 4-bromobutyl, 3,3,3,4,4-pentafluorobutyl, 4,4-dichlorobutyl, 5-iodopentyl, 5,5-difluoropentyl, 6-chlorohexyl, and 6,6,6-trifluorohexyl.

The term "$C_{1-6}$ alkyl" in the present invention is a straight chain or branched chain alkyl group with 1 to 6 carbons. Examples include methyl, ethyl, n-propyl, i-propyl, n-butyl, i-butyl, sec-butyl, t-butyl, 1-methylpropyl, n-pentyl, isopentyl, 2-methylbutyl, 1,1-dimethylpropyl, 1-ethylpropyl, n-hexyl, 4-methylpentyl, and 2-ethylbutyl.

The term "$C_{1-6}$ alkoxy" in the present invention means a group: $C_{1-6}$ alkyl-O— group, of which $C_{1-6}$ alkyl is already defined. Examples include methoxy, ethoxy, n-propoxy, i-propoxy, n-butoxy, i-butoxy, sec-butoxy, t-butoxy, 1-methylpropoxy, n-pentyloxy, isopentyloxy, 2-methylbutoxy, 1,1-dimethylpropoxy, 1-ethylpropoxy, n-hexyloxy, 4-methylpentyloxy, and 2-ethylbutoxy.

The term "($C_{1-6}$ alkyl)carbonyl" in the present invention means a group: ($C_{1-6}$ alkyl)-C(O)— group, of which $C_{1-6}$ alkyl is already defined. Examples include methylcarbonyl (acetyl), ethylcarbonyl (propionyl), n-propylcarbonyl, i-propylcarbonyl, n-butylcarbonyl, i-butylcarbonyl, sec-butylcarbonyl, t-butylcarbonyl, 1-methylpropylcarbonyl, n-pentylcarbonyl, isopentylcarbonyl, 2-methylbutylcarbonyl, 1,1-dimethylpropylcarbonyl, 1-ethylpropylcarbonyl, n-hexylcarbonyl, 4-methylpentylcarbonyl, and 2-ethylbutylcarbonyl.

The term "$C_{6-10}$ aryl" in the present invention means an aromatic carbocyclic group, and it may contain a non-aromatic portion in addition to the aromatic portion. The ring may be monocyclic, or it may be a bicyclic aryl that is condensed with a benzene ring or a monocyclic aryl ring. Examples include phenyl, 1-naphthyl, 2-naphthyl, azulenyl, isochromanyl, 2,4-dihydro-1H-isoquinolin-3-onyl, and 1,3-dihydrobenzimidazol-2-onyl. A preferable example is phenyl.

The term "heteroaryl" in the present invention means an aromatic 5 to 10 membered cyclic group that comprise, among atoms constituting a ring, one or more hetero atoms selected from a nitrogen atom, an oxygen atom and a sulfur atom, and it may contain a non-aromatic portion in addition to the aromatic portion. The ring may be monocyclic, or it may be a bicyclic heteroaryl that is condensed with a benzene ring or a monocyclic heteroaryl ring. Examples include furyl, thienyl, pyrrolyl, imidazolyl, pyrazolyl, thiazolyl, isothiazolyl, oxazolyl, isooxazolyl, oxadiazolyl, thiadiazolyl, triazolyl, tetrazolyl, pyridyl, pyrimidyl, pyridazinyl, pyrazinyl, triazinyl, benzofuranyl, benzothienyl, benzothiadiazolyl, benzothiazolyl, benzooxazolyl, benzooxadiazolyl, benzoimidazolyl, indolyl, isoindolyl, indazolyl, quinolyl, isoquinolyl, cinnolinyl, quinazolinyl, quinoxalinyl, benzodioxolyl, indolizinyl, imidazopyridyl, benzoisoxazolyl, and benzoisothiazolyl.

The term "heterocyclyl" in the present invention means a non-aromatic cyclic group comprising one or more hetero atoms selected from nitrogen, oxygen and sulfur atoms, and it may be completely saturated or partly unsaturated. The ring may be a monocyclic ring, a bicyclic ring or a spiro ring of 3 to 12 members, preferably 3 to 10 members. Examples include oxetanyl, azetidinyl, 3,7-dioxa-9-azabicyclo[3.3.1]nonanyl, piperazinyl, piperidinyl, morpholinyl, thiomorpholinyl, pyrrolidinyl, tetrahydropyranyl, tetrahydrofuranyl, 2-oxa-6-azaspiro[3.3]heptyl, 2-azaspiro[3.3]heptyl, 2,6-diazaspiro[3.3]heptyl, 2-thia-6-azaspiro[3.3]heptyl, oxazolidinyl, thiazolidinyl, imidazolidinyl, pyrazolidinyl, thianyl, oxanyl, thioxanyl, indolinyl, isoindolinyl, tetrahydroindolinyl, quinuclidinyl, azepinyl, and tropanyl.

The term "$C_{3-15}$ cycloalkyl" of the present invention means a monovalent group derived by removing any single hydrogen atom from a cyclic saturated aliphatic hydrocarbon having 3 to 15 carbons. Also, the term "$C_{3-8}$ cycloalkyl" means a cycloalkyl of three to eight carbons. Examples include cyclopropyl, cyclobutyl, cyclopentyl, cyclohexyl, cycloheptyl, and cyclooctyl. Also, the term "$C_{3-6}$ cycloalkyl" means a cycloalkyl of 3 to 6 carbons. When two groups together form a $C_{3-15}$ cycloalkane ring, the resulting group is bivalent. Examples include cyclopropane-1,1-diyl, cyclobutane-1,1-diyl, cyclopentane-1,1-diyl, cyclohexane-1,1-diyl, cycloheptane-1,1-diyl, and cyclooctane-1,1-diyl.

When the two groups on two carbon atoms are combined to form a $C_{3-8}$ carbocyclic ring, the resulting ring forms a condensed ring. Examples include ring structures such that the two carbon atoms are linked by —$CH_2$—, —$CH_2CH_2$—, —$CH_2CH_2CH_2$—, —$CH_2CH_2CH_2CH_2$—, —$CH_2CH_2CH_2CH_2CH_2$—, and —$CH_2CH_2CH_2CH_2CH_2CH_2$—.

In addition, the cycloalkane ring, the carbocyclic ring, the cyclic hydrocarbon in the cycloalkyl may be a cross-linked ring. Examples of cross-linked rings in the $C_{3-15}$ cycloalkyl include bicyclo[1.1.0]butane, bicyclo[3.2.1]octane, bicyclo[5.2.0]nonane, bicyclo[4,3,2]undecane, tricyclo[2.2.1.0$^{2,6}$]heptane, tricyclo[4.3.1.1$^{2,5}$]undecane, tricyclo[3.3.1.1$^{3,7}$]decane (adamantane), tricyclo[3.3.1.1$^{3,7}$]decane-2-ylidene (2-adamantylidene), pentacyclo[4.2.0.0$^{2,5}$.0$^{3,8}$.0$^{4,7}$]octane (cubane), and examples of $C_{3-15}$ cycloalkyl include bicyclo[1.1.0]butyl, bicyclo[3.2.1]octyl, bicyclo[5.2.0]nonyl, bicyclo[4.3.2]undecyl, tricyclo[2.2.1.0$^{2,6}$]heptyl, tricyclo[4.3.1.1$^{2,5}$]undecyl, adamantyl, 2-adamantylidenyl, and cubanyl.

The present invention provides a compound represented by Formula (I), a salt thereof, or a solvate of either the compound or a salt of the compound.

[Chemical Formula 8]

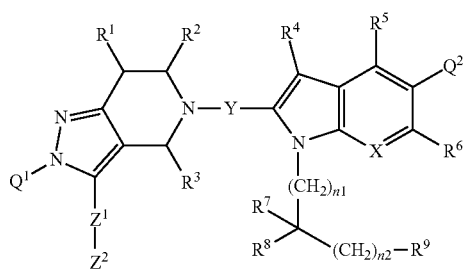

(I)

X is —N= or —CR$^a$=; R$^a$ is selected from a hydrogen atom, a halogen atom, and $C_{1-6}$ alkyl. X is preferably —N=, —CH=, or —CF=, more preferably —CH=.

Y is selected from —C(=O)—, —CHR—, and —S(=O)$_2$—; R is a hydrogen atom or $C_{1-6}$ alkyl.

Q$^1$ is $C_{6-10}$ aryl or 5 to 10 membered heteroaryl, wherein $C_{6-10}$ aryl and 5 to 10 membered heteroaryl are optionally substituted with one to five substituents independently selected from a halogen atom, $C_{1-6}$ alkyl (wherein $C_{1-6}$ alkyl is optionally substituted with one or more halogen atoms), and $C_{1-6}$ alkoxy. Q$^1$ is preferably phenyl or pyridyl, wherein phenyl or pyridyl is substituted with one to four substituents independently selected from a halogen atom and $C_{1-6}$ alkyl. More preferably Q$^1$ is phenyl substituted with two to three substituents independently selected from a halogen atom and $C_{1-6}$ alkyl.

Q$^2$ is 3 to 12 membered heterocyclyl or 5 to 10 membered heteroaryl, wherein 3 to 12 membered heterocyclyl and 5 to 10 membered heteroaryl are optionally substituted with one to three substituents independently selected from a halogen atom, $C_{1-6}$ alkyl (wherein $C_{1-6}$ alkyl is optionally substituted with one or more halogen atoms), $C_{1-6}$ alkoxy, and —NR$^{Qa}$R$^{Qb}$, and two $C_{1-6}$ alkyl groups together with a carbon atom to which they are attached may form $C_{3-8}$ carbocyclic ring; and R$^{Qa}$ and R$^{Qb}$ are independently selected from a hydrogen atom, $C_{1-6}$ alkyl, and ($C_{1-6}$ alkyl)carbonyl. Preferably, Q$^2$ is i) 6 membered heterocyclyl, wherein 6 membered heterocyclyl is optionally substituted with one or more $C_{1-6}$ alkyl, and two $C_{1-6}$ alkyl groups together with a carbon atom to which they are attached may form $C_{3-8}$ carbocyclic ring, or ii) 5 to 6 membered heteroaryl, wherein 5 to 6 membered heteroaryl is optionally substituted with one to three substituents independently selected from a halogen atom, $C_{1-6}$ alkyl, $C_{1-6}$ alkoxy, and —NR$^{Qc}$R$^{Qd}$, and R$^{Qc}$ and R$^{Qd}$ are independently selected from a hydrogen atom and $C_{1-6}$ alkyl. Preferably, Q$^2$ is 5 to 6 membered heterocyclyl or heteroaryl, wherein the 5 to 6 membered heterocyclyl and 5 to 6 membered heteroaryl are optionally substituted with one to three $C_{1-6}$ alkyl.

R$^1$, R$^2$ and R$^3$ are each independently selected from a hydrogen atom and $C_{1-6}$ alkyl (wherein, $C_{1-6}$ alkyl is optionally substituted with one or more substituents independently selected from a halogen atom, $C_{1-6}$ alkoxy, and hydroxy). Preferably, the combination of R$^1$, R$^2$ and R$^3$ is selected from: all hydrogen atoms; R$^1$ is a hydrogen atom, R$^2$ is a hydrogen atom, and R$^3$ is $C_{1-6}$ alkyl; and R$^1$ is a hydrogen atom, R$^2$ is $C_{1-6}$ alkyl, and R$^3$ is $C_{1-6}$ alkyl.

R$^4$, R$^5$ and R$^6$ are independently selected from a hydrogen atom, a halogen atom, and $C_{1-6}$ alkyl. It is preferred that R$^4$, R$^5$ and R$^6$ are independently a hydrogen atom or a fluorine atom. More preferably, the combination of R$^4$, R$^5$, and R$^6$ are: all hydrogen atoms; or R$^4$ is a hydrogen atom, R$^5$ is a hydrogen atom, and R$^6$ is a fluorine atom.

R$^7$ and R$^8$ are independently a hydrogen atom or $C_{1-6}$ alkyl, wherein $C_{1-6}$ alkyl is optionally substituted with one or more substituents independently selected from a halogen atom and $C_{3-15}$ cycloalkyl, or R$^7$ and R$^8$ together with a carbon atom to which they are attached may form $C_{3-15}$ cycloalkane ring, wherein $C_{3-15}$ cycloalkane ring formed by combining R$^7$ and R$^8$ is optionally substituted with one to three $C_{1-6}$ alkyl, wherein $C_{1-6}$ alkyl is optionally substituted with one or more substituents independently selected from a halogen atom, hydroxy, —NR$^{7a}$R$^{7b}$, $C_{1-6}$ alkoxy, and 3 to 12 membered heterocyclyl, and R$^{7a}$ and R$^{7b}$ are independently selected from a hydrogen atom, $C_{1-6}$ alkyl, and ($C_{1-6}$ alkyl)carbonyl. Preferably R$^7$ and R$^8$ together with a carbon atom to which they are attached form $C_{3-8}$ cycloalkane ring, wherein the $C_{3-8}$ cycloalkyl thus formed is optionally substituted with one or more $C_{1-6}$ alkyl, wherein $C_{1-6}$ alkyl is optionally substituted with one or more hydroxy. The $C_{3-8}$ cycloalkyl is preferably $C_{3-6}$ cycloalkyl. A preferable $C_{3-6}$ cycloalkyl is, for example, cyclopentyl.

n1 is an integer of 0 to 3; n2 is an integer of 0 to 5. n1 and n2 are each preferably 0 to 2, more preferably 0 to 1, and even more preferably 0. Also, the combination of n1 and n2 is preferably 0 and 0, 0 and 1, 0 and 2, 1 and 0, 1 and 1, 2 and 0, more preferably 0 and 0, 0 and 1, 1 and 0, 2 and 0, and even more preferably 0 and 0.

R$^9$ is selected from a group represented by Formula (IIa), (IIb), (IIc), (IId):

[Chemical Formula 9]

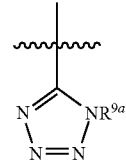

(IIa)

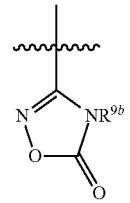

(IIb)

-continued

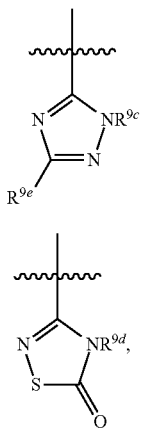

(IIc)

(IId)

—CO$_2$R$^{9f}$, and —C(=O)—NR$^{9g}$R$^{9h}$; and R$^{9a}$, R$^{9b}$, R$^{9c}$, R$^{9d}$, and R$^{9g}$ are each independently selected from a hydrogen atom, C$_{1-6}$ alkyl (wherein C$_{1-6}$ alkyl is optionally substituted with one or more substituents independently selected from a halogen atom and C$_{1-6}$ alkoxy), and (C$_{1-6}$ alkyl)carbonyl, R$^{9e}$ is a hydrogen atom, or C$_{1-6}$ alkyl that is optionally substituted with one or more substituents independently selected from a halogen atom, R$^{9f}$ is a hydrogen atom or C$_{1-6}$ alkyl, R$^{9h}$ is a hydrogen atom, C$_{1-6}$ alkyl, (C$_{1-6}$ alkyl)carbonyl, cyano, or —S(=O)$_{n3}$—R$^{9i}$; n3 is an integer of 0 to 2, and R$^{9i}$ is C$_{1-6}$ alkyl.

Z is selected from a group represented by Formula (IIa), (IIIb), (IIIc), (IId), and (IIIe):

[Chemical Formula 10]

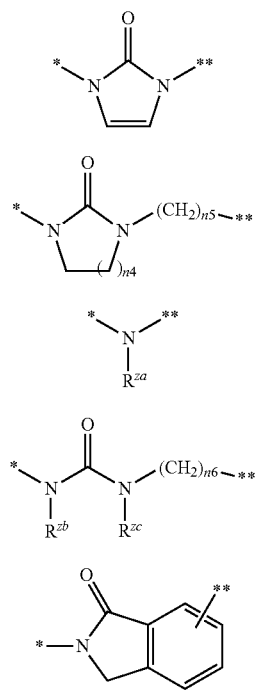

(IIIa)

(IIIb)

(IIIc)

(IIId)

(IIIe)

wherein R$^{za}$ is selected from a hydrogen atom, C$_{1-6}$ alkyl, and (C$_{1-6}$ alkyl)carbonyl, R$^{zb}$ and R$^{zc}$ are independently a hydrogen atom or C$_{1-6}$ alkyl, n4 is an integer of 1 to 3, n5 and n6 are independently an integer of 0 to 10.

* represents a binding position with a pyrazolopyridine structure, ** represents a binding position with Z$^2$.

Z$^2$ is selected from C$_{1-6}$ alkyl, C$_{3-15}$ cycloalkyl, 3 to 12 membered heterocyclyl, C$_{6-10}$ aryl and 5 to 10 membered heteroaryl, wherein C$_{3-15}$ cycloalkyl, 3 to 12 membered heterocyclyl, C$_{6-10}$ aryl, and 5 to 10 membered heteroaryl are optionally substituted with one to five substituents independently selected from Group A.

Group A: a) oxo,
b) a halogen atom,
c) cyano,
d) —NR$^{zd}$R$^{ze}$; wherein R$^{zd}$ and R$^{ze}$ are independently selected from a hydrogen atom, C$_{1-6}$ alkyl and (C$_{1-6}$ alkyl)carbonyl, wherein C$_{1-6}$ alkyl is optionally substituted with one or more substituents independently selected from hydroxy, a halogen atom and C$_{1-6}$ alkoxy,
e) —C(=O)—NR$^{zf}$R$^{zg}$; wherein R$^{zf}$ and R$^{zg}$ are independently selected from a hydrogen atom, C$_{1-6}$ alkyl and (C$_{1-6}$ alkyl)carbonyl, wherein C$_{1-6}$ alkyl is optionally substituted with one or more substituents independently selected from hydroxy, a halogen atom and C$_{1-6}$ alkoxy,
f) —S(=O)$_{n7}$—R$^{zh}$; wherein n7 is an integer of 0 to 2, R$^{zh}$ is a hydrogen atom or C$_{1-6}$ alkyl,
g) C$_{1-6}$ alkyl; wherein C$_{1-6}$ alkyl is optionally substituted with one or more substituents independently selected from a halogen atom, hydroxy, —NR$^{zi}$R$^{zj}$, C$_{1-6}$ alkoxy, and 3 to 12 membered heterocyclyl, wherein R$^{zi}$ and R$^{zj}$ are independently a hydrogen atom or C$_{1-6}$ alkyl, and wherein 3 to 12 membered heterocyclyl is optionally substituted with one or more substituents independently selected from hydroxy, C$_{1-6}$ alkyl and 3 to 12 membered heterocyclyl,
h) C$_{1-6}$ alkoxy; wherein C$_{1-6}$ alkoxy is optionally substituted with one or more substituents independently selected from hydroxy, a halogen atom, and C$_{1-6}$ alkoxy,
i) 3 to 12 membered heterocyclyl; wherein 3 to 12 membered heterocyclyl is optionally substituted with one or more substituents independently selected from C$_{1-6}$ alkyl and (C$_{1-6}$ alkyl)carbonyl,
j) C$_{6-10}$ aryl; wherein C$_{6-10}$ aryl is optionally substituted with one or more (C$_{1-6}$ alkyl)carbonyl, and
k) 5 to 10 membered heteroaryl; wherein 5 to 10 membered heteroaryl is optionally substituted with one or more substituents independently selected from C$_{1-6}$ alkyl, C$_{1-6}$ alkoxy, —NR$^{zk}$R$^{zl}$, and 3 to 12 membered heterocyclyl, wherein R$^{zk}$ and R$^{zl}$ are independently selected from a hydrogen atom, C$_{1-6}$ alkyl and (C$_{1-6}$ alkyl)carbonyl, and wherein 3 to 12 membered heterocyclyl is optionally substituted with one or more substituents independently selected from C$_{1-6}$ alkyl and (C$_{1-6}$ alkyl)carbonyl.

When the C$_{1-6}$ alkyl in R$^{zd}$, R$^{ze}$, R$^{zf}$ and R$^{zg}$ is substituted with hydroxy, C$_{1-6}$ alkyl is preferably C$_{2-6}$ alkyl, and more preferably C$_{2-4}$ alkyl.

When the C$_{1-6}$ alkoxy is substituted with hydroxy, C$_{1-6}$ alkyl is preferably C$_{2-6}$ alkyl, and more preferably C$_{2-4}$ alkyl.

Preferably, Z$^2$ is selected from i) C$_{3-15}$ cycloalkyl that is optionally substituted with one or more —NR$^{zd}$R$^{ze}$ ii) C$_{6-10}$ aryl that is optionally substituted with one to three substituents independently selected from Group C, and iii) 5 to 10 membered heteroaryl that is optionally substituted with one to three substituents independently selected from Group D.

More preferably, Z$^2$ is selected from i) C$_{6-10}$ aryl that is optionally substituted with one to three substituents independently selected from Group C, and ii) 5 to 10 membered heteroaryl that is optionally substituted with one to three substituents independently selected from Group D.

Group C: a) a halogen atom,
b) —NR$^{zd2}$R$^{ze2}$; wherein R$^{zd2}$ and R$^{ze2}$ are independently selected from a hydrogen atom, C$_{1-6}$ alkyl and (C$_{1-6}$ alkyl)carbonyl, wherein C$_{1-6}$ alkyl is optionally substituted with one or more C$_{1-6}$ alkoxy,
c) —S(=O)$_{n7}$—R$^{zh1}$; wherein n7 is an integer of 0 to 2, R$^{zh1}$ is C$_{1-6}$ alkyl,
d) C$_{1-6}$ alkyl;
e) C$_{1-6}$ alkoxy; wherein C$_{1-6}$ alkoxy is optionally substituted with one or more hydroxy,
f) 5 to 10 membered heteroaryl; wherein 5 to 10 membered heteroaryl is optionally substituted with one or more substituents independently selected from —NR$^{zk1}$R$^{zl1}$, wherein R$^{zk1}$ and R$^{zl1}$ are independently selected from a hydrogen atom and C$_{1-6}$ alkyl.

Group D: a) oxo,
b) a halogen atom,
c) C$_{1-6}$ alkyl; wherein C$_{1-6}$ alkyl is optionally substituted with one or more substituents independently selected from a halogen atom, hydroxy, C$_{1-6}$ alkoxy, and 3 to 12 membered heterocyclyl, wherein 3 to 12 membered heterocyclyl is optionally substituted with one or more C$_{1-6}$ alkyl, and
d) 3 to 12 membered heterocyclyl.

The compound represented by Formula (I) of the present invention is preferably such that Z$^1$ is a group represented by Formula (IIIa), Y is —C(=O)—, R$^9$ is a group represented by Formula (IIb), R$^{9b}$ is a hydrogen atom, R$^7$ and R$^8$ together with a carbon atom to which they are attached form C$_{3-15}$ cycloalkane ring that is substituted with one to three C$_{1-6}$ alkyl, and the one to three C$_{1-6}$ alkyl is unsubstituted.

Next, examples of the production method of a compound represented by Formula (I), a salt thereof, or a solvate of either the compound or a salt of the compound are explained by the following schemes.

The compound represented by Formula (I), a salt thereof, or a solvate of either the compound or a salt of the compound are produced by conducting i) General production method A1 or General production method A2, ii) General production method B, and iii) General production method C. This production method is one example of a preferable production method of a compound of Formula (I), in which Zi is a group represented by Formula (IIIa), Y is represented by —C(=O)—, R$^9$ is a group represented by Formula (IIb), and R$^{9b}$ is a hydrogen atom, that is, a compound represented by Formula (Ia).

It is also an example of a preferable production method for a compound in which R$^7$ and R$^8$ together with a carbon atom to which they are attached form a C$_{3-15}$ cycloalkane ring substituted with 1 to 3 C$_{1-6}$ alkyl groups, wherein the alkyl groups are not substituted.

Note that in a case in which a starting material or a target product of a given step undergoes an undesirable chemical transformation under the reaction condition of that step, it is possible to obtain the target product of that step by protecting or deprotecting a functional group. T. W. Greene, P. G. M. Wuts, Protective Groups in Organic Synthesis, Fourth Edition, John Wiley & Sons, Inc., New York (2007) may be referred to in order to select the protecting group and the method of protection and deprotection. Some examples of the protection and deprotection of a functional group are shown in the scheme below.

<General Production Method A1>

Compound f may be synthesized by the General production method A1 illustrated by the following scheme.

[Chemical Formula 11]

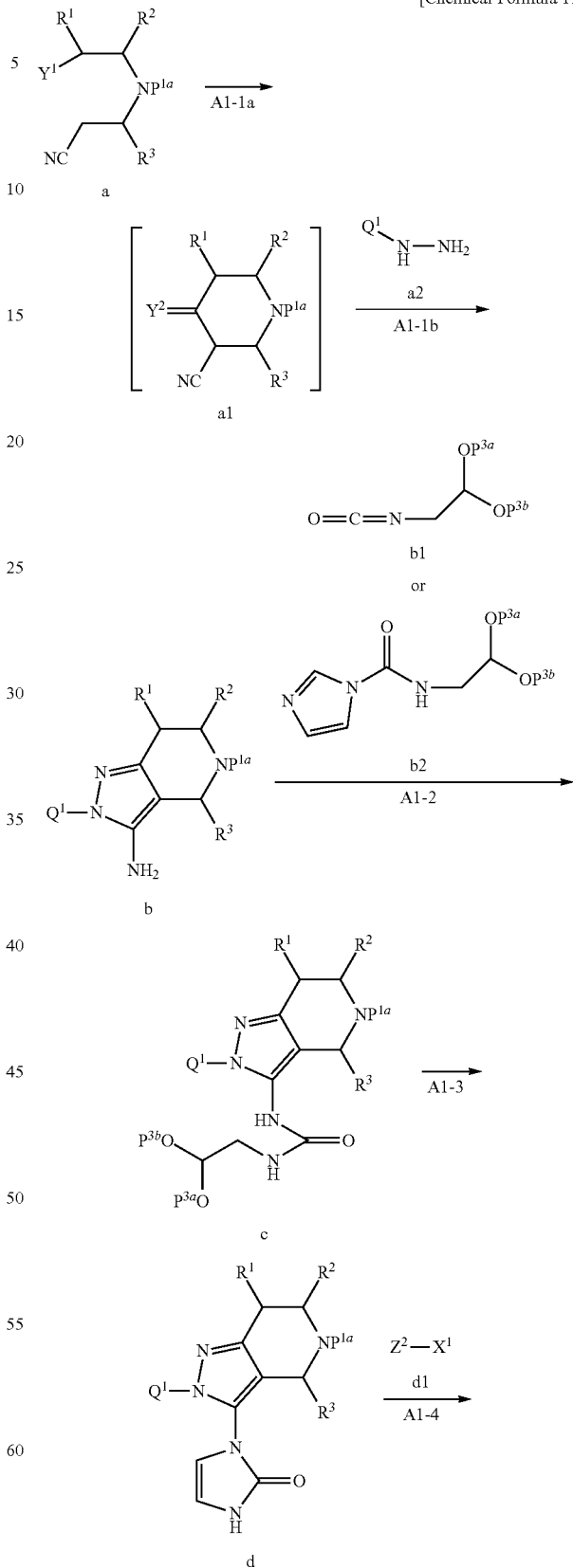

-continued

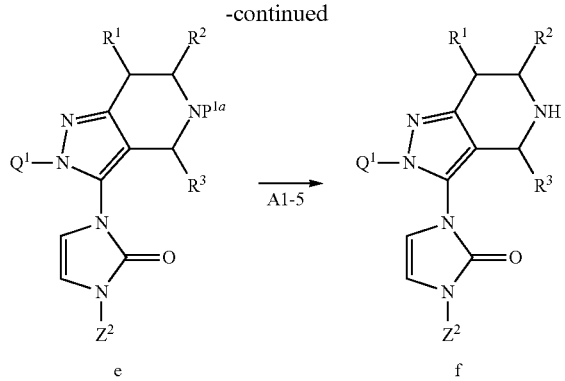

wherein, $P^2$ is a hydrogen atom or $C_{1-6}$ alkyl, $P^{1a}$ is a protective group of amino, $P^{3a}$ and $P^{3b}$ are independently $C_{1-6}$ alkyl, or $P^{3a}$ and $P^{3b}$ together with oxygen atoms to which they are attached and a carbon atom to which the oxygen atoms are attached may form 5 to 7 membered 1,3-dioxacycloalkane ring, $Y^1$ is cyano or —CO—$OP^2$, $Y^2$ is =O or =NH, and $X^1$ is a leaving group.

A protective group of amino includes for example formyl, ($C_{1-6}$ alkyl)carbonyl (acetyl, propionyl, butyryl, isobutyryl, valeryl, isovaleryl, pivaloyl, etc.), carbamoyl, $C_{1-6}$ alkoxycarbonyl (methoxycarbonyl, ethoxycarbonyl, isopropyloxycarbonyl, sec-butoxycarbonyl, t-butoxycarbonyl, etc.), substituted silyl (trimethylsilyl, triethylsilyl, triisopropylsilyl, t-butyldimethylsilyl, t-butyldiphenylsilyl, etc.), aralkyloxycarbonyl (benzyloxycarbonyl, 9-fluorenylmethyloxycarbonyl, etc.) allyl, and aralkyl.

The leaving group includes, for example, a halogen atom, acetyloxy, trifluoroacetyloxy, methanesulfonyloxy, paratoluenesulfonyloxy.

Step A1-1a:
Compound a1 may be obtained by reacting Compound a with a base.
Examples of the base include metal hydrides such as sodium hydride, potassium hydride, lithium hydride; and metal alkoxides such as potassium t-butoxide, sodium t-butoxide, lithium t-butoxide, potassium t-pentoxide, sodium t-pentoxide, and lithium t-pentoxide. A metal alkoxide such as potassium t-butoxide is preferred.
Examples of the solvent include ether-based solvents such as tetrahydrofuran (THF), diethyl ether, and dioxane, and THE is preferred.
The reaction temperature is normally −30° C. to 30° C., preferably −10° C. to 10° C.
The reaction time is normally 15 min. to 5 h., preferably 30 min. to 3 h.
Compound a1 may be isolated, or it may be subjected to step A1-1b without being isolated.
Compound a may be obtained as a commercial product from Aldlab Chemicals, LLC or Tokyo Chemical Industry Co., Ltd. It may also be synthesized by referring to Bioorganic Medicinal Chemistry, 1999, 7, 795-809, or CN 103086955.
Note that Compound a1 may be obtained as an alkali metal salt such as a potassium salt by being brought into contact with a base used in the reaction, and such salt may be subjected to the next step.

Step A1-1b
Compound a1 may be reacted with Compound a2 to obtain Compound b. This reaction may preferably be performed in the presence of an acid.

Examples of the acid include, for example, acids such as hydrochloric acid, acetic acid, methanesulfonic acid, p-toluenesulfonic acid, and salts of a weak base and a strong acid such as pyridine-hydrochloric acid salt.
Examples of the solvent include hydrocarbon-based solvents (hexane, heptane, benzene, toluene, xylene, etc.) and alcohol-based solvents (methanol, ethanol, etc.).
Further, water may exist in the reaction mixture.
The reaction temperature is normally 40° C. to 200° C., preferably 60° C. to 150° C.
The reaction time is normally 6 min. to 30 h., preferably 30 min. to 3 h.
Compound a2 may be commercially obtained as a salt with hydrogen chloride attached to it from Alfa Aesar, etc. By referring to Synlett, 2011, 17, 2555-2558, Compound a2 whose hydrazine portion is protected with t-butoxycarbonyl may be put to use after it is deprotected with an acid such as methanesulfonic acid. Also, by referring to *Journal of Medicinal Chemistry* 2003, 46, 1546-1553, Compound a2 may be synthesized by using compound: $Q^1$-$NH_2$ as the starting compound.

Step A1-2:
Compound b may be reacted with Compound b1 or Compound b2 in the presence of a base to obtain Compound c.
Examples of the base include tertiary amines (triethylamine, N-methylmorpholine, diisopropylethylamine, DBU, DABCO, etc.), nitrogen-containing aromatic compounds (pyridine, dimethylaminopyridine, picoline, (2,6-)lutidine, pyrazine, pyridazine, etc.), metal hydrides such as sodium hydride, potassium hydride, lithium hydride; and metal alkoxides such as potassium t-butoxide, sodium t-butoxide, lithium t-butoxide, potassium t-pentoxide, sodium t-pentoxide, and lithium t-pentoxide. When using Compound b2, a metal alkoxide such as potassium t-butoxide is preferred.
Examples of solvents that may be used include alcohol-based solvents such as methanol, and ethanol; ether-based solvents such as THF, and diethyl ether; ester-based solvents such as ethyl acetate, and methyl acetate; nitrile-based solvents such as acetonitrile, benzonitrile, and benzyl cyanide; amide-based solvents such as N,N-dimethyl acetamide (DMA), N,N-dimethylimidazolidinone (DMI), and DMF. An amide-based solvent such as DMA is preferred.
The reaction temperature is normally −50° C. to 70° C., preferably −30° C. to 50° C.
The reaction time is normally 15 min. to 72 h., preferably 1 h. to 30 h.
Compound b1 may be commercially obtained from Enamine LTD., etc. By referring to WO 2006/048727, Compound b1 may be synthesized by reacting compound: $H_2NCH_2CH(OP^{3a})(Op^{3b})$ and phosgene or triphosgene. Compound b2 may be commercially obtained from UkrOrgSyntez Ltd., etc. By referring to WO 99/50262, Compound b2 may be synthesized by reacting compound: $H_2NCH_2CH(OP^{3a})(Op^{3b})$ and diisocyanate such as CDI.

Step A1-3:
Compound c may be reacted with an acid to obtain Compound d.
Examples of the acid include inorganic acid (hydrochloric acid, hydrobromic acid, hydroiodic acid, sulfuric acid, phosphoric acid, etc.), sulfonic acid (methanesulfonic acid, benzenesulfonic acid, toluenesulfonic acid, etc.), and carboxylic acid (formic acid (FA), acetic acid, oxalic acid, maleic acid, fumaric acid, citric acid, malic acid, succinic acid, malonic acid, gluconic acid, mandelic acid, benzoic acid, salicylic acid, fluoroacetic acid, trifluoroacetic acid (TFA), tartaric acid, propionic acid, glutaric acid, etc.).

Examples of the solvent include ether-based solvents (ether, tetrahydrofuran (THF), dioxane, dimethoxyethane, cyclopentylmethyl ether, etc.), aromatic hydrocarbon-based solvents (benzene, toluene, xylene, quinoline, chlorobenzene, etc.), aliphatic hydrocarbon-based solvents (pentane, hexane, heptane, octane, cyclohexane, etc.), amide-based solvents (N,N-dimethyl formamide, N,N-dimethyl acetamide, N-methylpyrrolidone), alcohol-based solvents (methanol, ethanol, 2,2,2-trifluoroethanol, n-propanol, isopropanol, n-butanol, sec-butanol, pentanol, hexanol, cyclopropanol, cyclobutanol, cyclopentanol, cyclohexanol, ethylene glycol, 1,3-propanediol, 1,4-butanediol, 1,5-pentanediol, etc.), acetate ester-based solvents (methyl acetate, ethyl acetate, isopropyl acetate), acetonitrile, and a mixed solvent thereof. An ether-based solvent such as tetrahydrofuran is preferred.

The reaction temperature is normally 0° C. to 100° C., preferably 10° C. to 80° C.

The reaction time is normally 10 min. to 20 h., preferably 30 min. to 5 h.

Step A1-4:

a) When $Z^2$ is $C_{1-6}$ alkyl, $C_{3-15}$ cycloalkyl and 3 to 12 membered heterocyclyl, Compound d may be reacted with Compound d1 in the presence of a base to obtain Compound e.

Examples of the base include metal hydrides such as sodium hydride, potassium hydride, and lithium hydride; metal alkoxides such as potassium t-butoxide, sodium t-butoxide, lithium t-butoxide, potassium t-pentoxide, sodium t-pentoxide, and lithium t-pentoxide; and metal alkyls such as butyllithium, and ethyllithium.

Examples of the solvent include ether-based solvents (ether, tetrahydrofuran (THF), dioxane, dimethoxyethane, cyclopentylmethyl ether, etc.), aromatic hydrocarbon-based solvents (benzene, toluene, xylene, quinoline, chlorobenzene, etc.), aliphatic hydrocarbon-based solvents (pentane, hexane, heptane, octane, cyclohexane, etc.), and amide-based solvents (N,N-dimethyl formamide, N,N-dimethyl acetamide, N-methylpyrrolidone, etc.). An amide-based solvent such as N,N-dimethyl acetamide is preferred.

The reaction temperature is normally 0° C. to 150° C., preferably 20° C. to 120° C.

The reaction time is normally 15 min. to 24 h., preferably 30 min. to 5 h.

b) When $Z^2$ is $C_{6-10}$ aryl and 5 to 10 membered heteroaryl, Compound d may be reacted with Compound d1 in the presence of a base, a copper catalyst and a ligand, to obtain Compound e.

Examples of the base include a weak basic inorganic salt (sodium carbonate, potassium carbonate, potassium phosphate, cesium carbonate, etc.), and organic base (triethyl amine, pyridine, tetrabutylammonium fluoride, etc.). A weak basic inorganic salt such as potassium carbonate is preferred.

Examples of the copper catalyst include copper iodide (I), copper bromide (I), copper chloride (I), copper acetate (I), copper oxide (II), and copper trifluoromethanesulfonate (I), and copper iodide (I) is preferred.

Examples of the ligand include phenanthroline, quinolin-8-ol, 2,2,6,6-tetramethylheptane-3,5-dione, and diamines such as N,N'-dimethylethane-1,2-diamine, trans-cyclohexane-1,2-diamine, and trans-N,N'-dimethylcyclohexane-1,2-diamine, and trans-N,N'-dimethylcyclohexane-1,2-diamine is preferred.

Examples of the solvent include ether-based solvents (ether, tetrahydrofuran (THF), dioxane, dimethoxyethane, cyclopentylmethyl ether, etc.), aromatic hydrocarbon-based solvents (benzene, toluene, xylene, quinoline, chlorobenzene, etc.), aliphatic hydrocarbon-based solvents (pentane, hexane, heptane, octane, cyclohexane, etc.), amide-based solvents (N,N-dimethyl formamide, N,N-dimethyl acetamide, N-methylpyrrolidone, etc.), alcohol-based solvents (methanol, ethanol, 2,2,2-trifluoroethanol, n-propanol, isopropanol, n-butanol, sec-butanol, pentanol, hexanol, cyclopropanol, cyclobutanol, cyclopentanol, cyclohexanol, ethylene glycol, 1,3-propanediol, 1,4-butanediol, 1,5-pentanediol, etc.), acetate ester-based solvents (methyl acetate, ethyl acetate, isopropyl acetate, etc.), and acetonitrile, and an amide-based solvent such as N-methylpyrrolidone is preferred.

The reaction temperature is normally 30° C. to 200° C., preferably 60° C. to 160° C.

The reaction time is normally 1 h. to 15 h., preferably 3 h. to 9 h.

Step A1-5:

Compound e may be deprotected to obtain Compound f.

When the protective group $P^{1a}$ is $C_{1-6}$ alkoxycarbonyl such as t-butoxycarbonyl, it is preferable to use an acid for deprotection.

Examples of the acid include inorganic acid (hydrogen chloride, hydrobromic acid, hydroiodic acid, sulfuric acid, phosphoric acid, etc.), sulfonic acid (methanesulfonic acid, benzenesulfonic acid, toluene sulfonic acid, etc.), and carboxylic acid (formic acid, acetic acid, oxalic acid, maleic acid, fumaric acid, citric acid, malic acid, succinic acid, malonic acid, gluconic acid, mandelic acid, benzoic acid, salicylic acid, fluoroacetic acid, trifluoroacetic acid, tartaric acid, propionic acid, glutaric acid, etc.).

Examples of the solvent include ether-based solvents (tetrahydrofuran, methyltetrahydrofuran, diethyl ether, t-butylmethyl ether, diisopropyl ether, cyclopentylmethyl ether, 1,2-dimethoxyethane, etc.), hydrocarbon-based solvents (hexane, heptane, benzene, toluene, etc.), amide-based solvents (N,N-dimethyl formamide, N,N-dimethyl acetamide, N-methylpyrrolidone, etc.), and halogen-based solvents (dichloromethane, chloroform, carbon tetrachloride, etc.), and an amide-based solvent such as N-methylpyrrolidone is preferred.

The reaction temperature is normally 0° C. to 200° C., preferably 10° C. to 120° C.

The reaction time is normally 30 min. to 10 h., preferably 1 h. to 6 h.

Note that Compound f may be obtained as a salt with the acid used in the reaction, and such salt may be subjected to the next step.

<General Production Method A2>

When $Z^2$ is a bulky group such as $C_{3-15}$ cycloalkyl that is substituted with $—NR^{zd}R^{ze}$ it is possible to synthesize Compound p corresponding to Compound f by General production method A2 as illustrated by the following scheme.

[Chemical Formula 12]

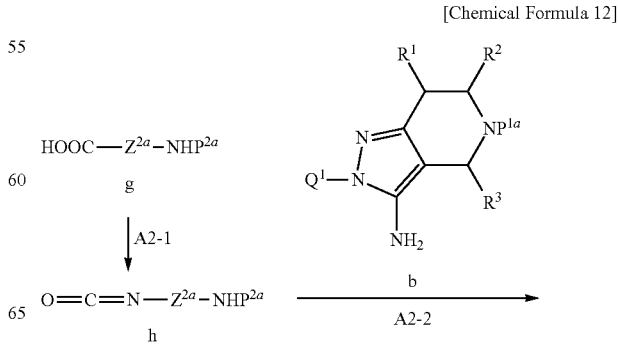

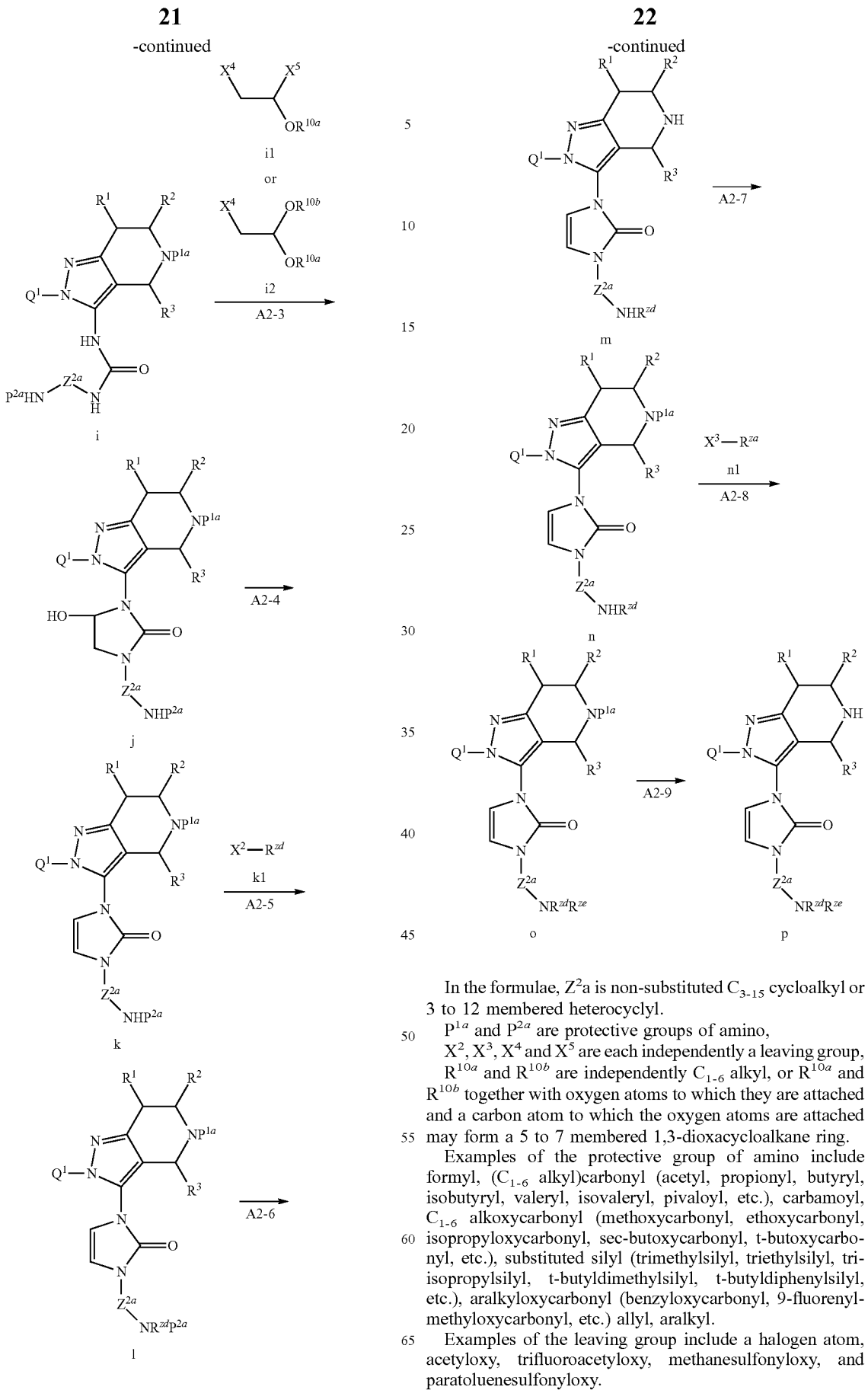

In the formulae, $Z^{2a}$ is non-substituted $C_{3-15}$ cycloalkyl or 3 to 12 membered heterocyclyl.

$P^{1a}$ and $P^{2a}$ are protective groups of amino, $X^2$, $X^3$, $X^4$ and $X^5$ are each independently a leaving group, $R^{10a}$ and $R^{10b}$ are independently $C_{1-6}$ alkyl, or $R^{10a}$ and $R^{10b}$ together with oxygen atoms to which they are attached and a carbon atom to which the oxygen atoms are attached may form a 5 to 7 membered 1,3-dioxacycloalkane ring.

Examples of the protective group of amino include formyl, ($C_{1-6}$ alkyl)carbonyl (acetyl, propionyl, butyryl, isobutyryl, valeryl, isovaleryl, pivaloyl, etc.), carbamoyl, $C_{1-6}$ alkoxycarbonyl (methoxycarbonyl, ethoxycarbonyl, isopropyloxycarbonyl, sec-butoxycarbonyl, t-butoxycarbonyl, etc.), substituted silyl (trimethylsilyl, triethylsilyl, triisopropylsilyl, t-butyldimethylsilyl, t-butyldiphenylsilyl, etc.), aralkyloxycarbonyl (benzyloxycarbonyl, 9-fluorenylmethyloxycarbonyl, etc.) allyl, aralkyl.

Examples of the leaving group include a halogen atom, acetyloxy, trifluoroacetyloxy, methanesulfonyloxy, and paratoluenesulfonyloxy.

Step A2-1:

Compound g may be reacted with an azide in the presence of a base, to obtain Compound h.

Examples of the base include tertiary amines (triethylamine, N-methylmorpholine, diisopropylethylamine, DBU, DABCO, etc.).

Examples of the azide include metal azides such as sodium azide, trimethylsilyl azide, and diphenylphosphoryl azide, and diphenylphosphoryl azide is preferred.

Examples of the solvent include ether-based solvents (tetrahydrofuran, methyltetrahydrofuran, diethyl ether, t-butylmethyl ether, diisopropyl ether, cyclopentylmethyl ether, 1,2-dimethoxyethane, etc.), hydrocarbon-based solvents (hexane, heptane, benzene, toluene, etc.), and amide-based solvents (N,N-dimethyl formamide, N,N-dimethyl acetamide, N-methylpyrrolidone), and a hydrocarbon-based solvent such as toluene is preferred.

The reaction temperature is normally 0° C. to 150° C., preferably 10° C. to 100° C.

The reaction time is normally 1 h. to 10 h., preferably 2 h. to 6 h.

Compound g is described in, for example, *Journal of the American Chemical Society*, 2016, 138, 1698-1708 and WO 2009/152133. It may also be commercially obtained from Enamine Ltd.

Step A2-2:

Compound b obtained in Step A1-1b may be reacted with Compound h in the presence of a base, to obtain Compound i.

Examples of the base include tertiary amines (triethylamine, N-methylmorpholine, diisopropylethylamine, DBU, DABCO, etc.), and nitrogen-containing aromatic compounds (pyridine, dimethylaminopyridine, picoline, (2,6-)lutidine, pyrazine, pyridazine, etc.).

Examples of the solvent include ether-based solvents such as tetrahydrofuran (THF), diethyl ether, dioxane; and hydrocarbon-based solvents such as hexane, heptane, benzene, toluene, etc. A base such as pyridine may also be used as the solvent.

The reaction temperature is normally 0° C. to 60° C., preferably 5° C. to 45° C.

The reaction time is normally 30 min. to 50 h., preferably 2 h. to 10 h.

Step A2-3:

Compound i may be reacted with Compound i1 or Compound i2 in the presence of a base to obtain Compound j.

The base includes a weak basic inorganic salt (sodium carbonate, potassium carbonate, cesium carbonate, etc.), and metal hydrides (sodium hydride, potassium hydride, etc.), and a weak basic inorganic salt such as cesium carbonate is preferred.

Examples of Compound i1 include 1,2-dichloro-1-methoxyethane, 1,2-dichloro-1-ethoxyethane, ans 1,2-dichloro-1-i-propoxyethane, and 1,2-dichloro-1-t-butoxyethane, and 1,2-dichloro-1-ethoxyethane is preferred. Compound i1 may be commercially obtained from Tokyo Chemical Industry Co., Ltd. or FCH Group.

Examples of Compound i2 include 2-chloro-1,1-dimethoxyethane, 2-chloro-1,1-diethoxyethane, 2-bromo-1,1-dimethoxyethane, and 2-bromo-1,1-ethoxyethane. Compound i2 may be commercially obtained from Tokyo Chemical Industry Co., Ltd.

Examples of the solvent include alcohol-based solvents such as methanol, ethanol; ether-based solvents such as THF, diethyl ether; ester-based solvents such as ethyl acetate, methyl acetate; nitrile-based solvents such as acetonitrile, benzonitrile, benzyl cyanide; and amide-based solvents such as N,N-dimethyl acetamide (DMA), N,N-dimethyl imidazolidinone (DMI), DMF. An amide-based solvent such as DMA is preferred.

The reaction temperature is normally 0° C. to 60° C., preferably 20° C. to 45° C.

The reaction time is normally 1 h. to 72 h., preferably 12 min. to 35 h.

Step A2-4:

Compound j may be reacted with acid to obtain Compound k.

Examples of the acid include an inorganic acid (hydrochloric acid, hydrobromic acid, hydroiodic acid, sulfuric acid, phosphoric acid, etc.), a sulfonic acid (methanesulfonic acid, benzenesulfonic acid, toluenesulfonic acid, etc.), and a carboxylic acid (formic acid, acetic acid, oxalic acid, maleic acid, fumaric acid, citric acid, malic acid, succinic acid, malonic acid, gluconic acid, mandelic acid, benzoic acid, salicylic acid, fluoroacetic acid, trifluoroacetic acid, tartaric acid, propionic acid, glutaric acid, etc.), and a sulfonic acid such as methanesulfonic acid is preferred.

Examples of the solvent include ether-based solvents such as tetrahydrofuran (THF), diethyl ether, and dioxane, and THE is preferred.

The reaction temperature is normally 0° C. to 100° C., preferably 20° C. to 80° C.

The reaction time is normally 15 min. to 6 h., preferably 30 min. to 3 h.

Step A2-5:

Compound k may be reacted with Compound k1 in the presence of a base, to obtain Compound 1.

Examples of Compound k1 include $C_{1-6}$ alkyl halides such as methyl iodide, and $(C_{1-6}$ alkyl)carbonyl halides such as acetyl chloride. When $R^{zd}$ is $(C_{1-6}$ alkyl)carbonyl, it is preferred to use an acid anhydride that is represented as $((C_{1-6}$ alkyl)carbonyl)$_2$O, for example, an acetic anhydride in place of Compound k1.

Examples of the base include metal hydrides such as sodium hydride, potassium hydride, and lithium hydride; and metal alkoxides such as potassium t-butoxide, sodium t-butoxide, lithium t-butoxide, potassium t-pentoxide, sodium t-pentoxide, and lithium t-pentoxide. A metal alkoxide such as potassium pentoxide is preferred.

Examples of the solvent includes ether-based solvents such as tetrahydrofuran (THF), diethyl ether, dioxane; and hydrocarbon-based solvents such as hexane, heptane, benzene, toluene. THF is preferred.

The reaction temperature is normally −50° C. to 50° C., preferably −40° C. to 40° C.

The reaction time is normally 1 min. to 2 h., preferably 3 min. to 30 min.

Step A2-6:

Compound 1 may be deprotected to obtain Compound m.

An appropriate reagent or reaction condition may be selected according to the type of the protective group in deprotection. When the protective group is t-butoxycarbonyl, a reaction with an acid is preferred.

Examples of the acid include inorganic acid (hydrochloric acid, hydrobromic acid, hydroiodic acid, sulfuric acid, phosphoric acid, etc.), sulfonic acid (methanesulfonic acid, benzenesulfonic acid, toluenesulfonic acid, etc.), and carboxylic acid (formic acid, acetic acid, oxalic acid, maleic acid, fumaric acid, citric acid, malic acid, succinic acid, malonic acid, gluconic acid, mandelic acid, benzoic acid, salicylic acid, fluoroacetic acid, trifluoroacetic acid, tartaric acid, propionic acid, glutaric acid, etc.), and carboxylic acid such as trifluoroacetic acid is preferred.

Examples of the solvent include ether-based solvents such as diethyl ether, THF, dimethoxyethane, etc.; halogen-based solvents such as dichloromethane ($CH_2CO_2$), chloroform, carbon tetrachloride; N,N-dimethylformamide; and acetonitrile. A halogen-based solvent such as $CH_2Cl_2$ is preferred.

The reaction temperature is normally 0° C. to 60° C., preferably 10° C. to 40° C.

The reaction time is normally 30 min. to 10 h., preferably 1 h. to 5 h.

Note that Compound m may be obtained as a salt with the acid used in the reaction, and such salt may be subjected to Step A2-7.

Step A2-7:

An amino in Compound m may be protected to obtain Compound n.

An appropriate reagent or reaction condition may be selected according to the type of protective group in protection. When the protective group is $C_{1-6}$ alkoxycarbonyl, a reaction with a base is preferred.

Examples of the compound used for protection include methoxycarbonyl chloride, ethoxycarbonyl chloride, 2,2,2-trichloroethoxycarbonyl chloride, benzoyl chloride (Z—Cl), 9-fluorenylmethyloxycarbonyl chloride (Fmoc-Cl), and di-t-butyl dicarbonate, and di-t-butyl dicarbonate is preferred.

Examples of the base include tertiary amines (triethylamine, N-methylmorpholine, diisopropylethylamine, DBU, DABCO, etc.), and nitrogen-containing aromatic compounds (pyridine, dimethylaminopyridine, picoline, (2,6-) lutidine, pyrazine, pyridazine, etc.), and a tertiary amine such as triethyl amine is preferred.

Examples of the solvent includes ether-based solvents such as diethyl ether, THF, dimethoxyethane, etc.; halogen-based solvents such as dichloromethane ($CH_2Cl_2$), chloroform, carbon tetrachloride; N,N-dimethylformamide; and acetonitrile. A halogen-based solvent such as $CH_2Cl_2$ is preferred.

The reaction temperature is normally 0° C. to 60° C., preferably 15° C. to 40° C.

The reaction time is normally 30 min. to 20 h., preferably 1 h. to 5 h.

Step A2-8:

Compound n may be reacted with Compound n1 in the presence of a base to obtain Compound o.

Examples of Compound n1 include $C_{1-6}$ alkyl halides such as methyl iodide, and ($C_{1-6}$ alkyl)carbonyl halide such as acetyl chloride. When $R^{ze}$ is $C_{1-6}$ alkyl, it is preferred that $C_{1-6}$ alkyl is either not substituted or substituted with $C_{1-6}$ alkoxy.

This step is performed similarly to Step A2-5, and the base, and solvent used in the reaction, and reaction temperature, reaction time are similar to Step A2-5.

Step A2-9:

Compound o may be deprotected to obtain Compound p.

An appropriate reagent or reaction condition may be selected according to the type of protective group in deprotection. When the protective group $P^{1a}$ is $C_{1-6}$ alkoxycarbonyl such as t-butoxycarbonyl, deprotection using an acid is preferred.

This step is performed similarly to Step A1-5, and the acid, and solvent used in the reaction, and reaction temperature, reaction time are similar to Step A1-5.

<General Production Method B>

It is possible to synthesize Compound bf by General production method B as illustrated by the following scheme.

[Chemical Formula 13]

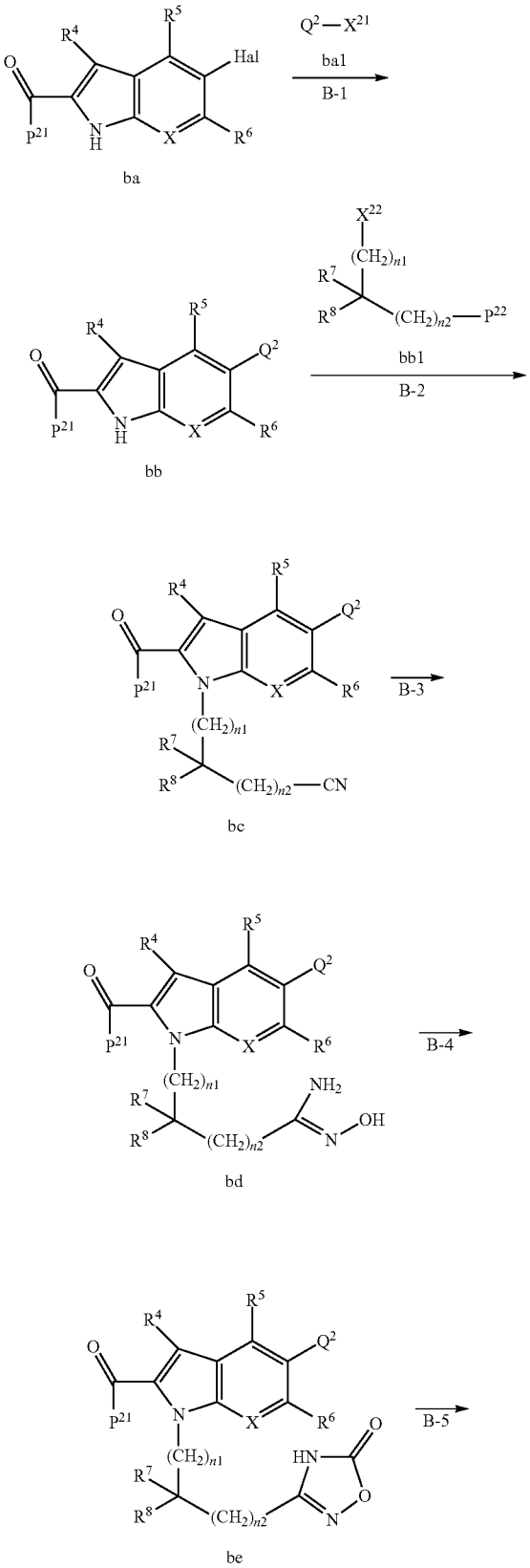

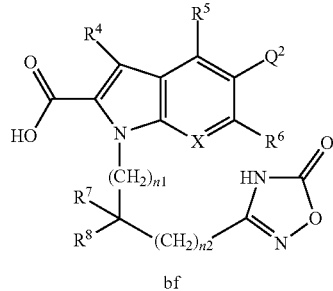

bf

In the formulae, $P^{21}$ is hydroxy, $C_{1-6}$ alkoxy, or $-NR^{21a}R^{21b}$, and $R^{21a}$ and $R^{21b}$ are independently a hydrogen atom, $C_{1-6}$ alkyl or $C_{6-10}$ aryl, $X^{21}$ is a hydrogen atom, a halogen atom, or $-Zn-X^{21a}$;

$X^{21a}$ is a bromine atom or an iodine atom, and $X^{22}$ is a leaving group.

The leaving group includes, for example, a halogen atom, acetyloxy, trifluoroacetyloxy, methanesulfonyloxy, paratoluenesulfonyloxy.

Step B-1:

Compound ba may be reacted with Compound ba1 in the presence of a paradium catalyst to obtain Compound bb.

The complex formed in the reaction mixture by separately adding a palladium compound and a ligand may be used as the palladium catalyst. The complex that has been prepared separately may be used. Examples of the ligand include 4,5-bis(diphenylphosphino)-9,9-dimethyxanthene, trimethylenebis(diphenylphosphine), 2-(di-t-butylphosphino)biphenyl, 2-dicyclohexylphosphino-2',4',6'-triisopropylbiphenyl, 2-(di-t-butylphosphino)-2',4',6'-triisopropyl-3,6-dimethoxy-1,1'-biphenyl, and 2-di-t-butylphosphino-2',4',6'-triisopropylbiphenyl. Examples of palladium compounds that may be combined with a ligand include, for example, di-µ-chlorobis[(η-allyl)palladium(II)], tetrakis(triphenylphosphine)palladium(0).

Examples of the palladium catalyst that may be used with the present step include tris(dibenzylideneacetone)dipalladium(0), 5,10,15,20-tetraphenyl-21H,23H-porphine Cobalt (II), palladium(II) acetate, bis(di-t-butyl(4-dimethylaminophenyl)phosphine)dichloropalladium(II), [1,1'-bis(diphenylphosphino)ferrocene]palladium(II)dichloride dichloromethane adduct, dichlorobis(triphenylphosphine)palladium(II), palladium hydroxide, tetrakis(triphenylphosphine)palladium(0), and di-µ-chlorobis[(η-allyl)palladium (II)]. It is preferred to use a complex formed from a palladium compound of di-µ-chlorobis[(η-allyl)palladium (II)] and a ligand of 2-(di-t-butylphosphino)-2',4',6'-triisopropyl-1,1'-biphenyl as a catalyst in Step 11.

Note that the step may be performed in the presence of abase.

Examples of the base includes a weak basic inorganic salt (sodium carbonate, potassium carbonate, cesium carbonate, sodium acetate, potassium acetate, calcium acetate, etc.), metal hydrides (sodium hydride, potassium hydride, etc.), and metal alkoxides (potassium t-butoxide, sodium t-butoxide, lithium t-butoxide, potassium t-pentoxide, sodium t-pentoxide, lithium t-pentoxide, etc.).

Examples of the reaction solvent include ether-based solvents such as tetrahydrofuran (THF), diethyl ether, dioxane, etc.; amide-based solvents such as N,N-dimethyl acetamide (DMA), N,N-dimethylimidazolidinone (DMI), DMF. The solvent may be a mixture with water.

The reaction temperature is normally 10° C. to 200° C., preferably 40° C. to 130° C.

The reaction time is normally 1 min. to 20 h., preferably 10 min. to 10 h.

Compound ba may be obtained commercially from Aurora Fine Chemicals. It may also be synthesized by referring to *Synthetic Communications*, 39(14), 2506-2515, 2009. It may also be obtained by esterifying or amidating Compound ba in which $-COP^{21}$ is $-COOH$.

Compound ba1 whose $X^{21}$ is $-Zn-X^{21}$ may be obtained commercially from Focus Synthesis LLC. It may be synthesized by referring to WO 2014/201206.

Step B-2:

Compound bb may be reacted with Compound bb1 in the presence of a base to obtain Compound bc.

Examples of the base include metal hydrides such as sodium hydride, potassium hydride, etc., and alkali metal hydroxides such as lithium hydroxide, sodium hydroxide, potassium hydroxide, and cesium hydroxide, and potassium hydroxide is preferred.

Examples of the reaction solvent include amide-based solvents such as N,N-dimethyl acetamide (DMA), N,N-dimethylimidazolidinone (DMI), and DMF, and DMI is preferred. The solvent may be a mixture with water.

The reaction temperature is normally −10° C. to 100° C., preferably 0° C. to 45° C.

The reaction time is normally 30 min. to 10 h., preferably 1 h. to 5 h.

Compound bb may be obtained commercially from Aquila Pharmatech LLC. It may be synthesized by referring to WO 2013/010904, *Organic Letters*, 7(18), 3965-3968, 2005, or U.S. Pat. No. 5,998,438.

Step B-3:

Compound bc may be reacted with hydroxyamine ($H_2NOH$) to obtain Compound bd.

Examples of the reaction solvent include aprotic polar solvents such as dimethylsulfoxide (DMSO), dimethylformamide, dimethylacetamide, and 1-methyl-2-pyrrolidinone, and alcohol-based solvents such as methanol and ethanol, and DMSO is preferred. The solvent may be a mixture with water.

The reaction temperature is normally −10° C. to 100° C., preferably 20° C. to 45° C.

The reaction time is normally 2 h. to 72 h., preferably 3 h. to 36 h.

Compound bd may be subjected to Step B-4 without being isolated or purified.

Step B-4:

Compound bd may be reacted with triphosgene, chlorocarbonic acid ester (methyl chlorocarbonate, ethyl chlorocarbonate, isopropyl chlorocarbonate, etc.), carbonyl diimidazole, etc., preferably carbonyl diimidazole in the presence of a base, to obtain Compound be.

Examples of the base include tertiary amines (triethyl amine, N-methylmorpholine, diisopropylethylamine, 1,8-diazabicycloundec-7-ene (DBU), DABCO, etc.), and metal hydroxides (sodium hydroxide, potassium hydroxide), and a tertiary amine such as DBU is preferred.

Examples of the solvent include aprotic polar solvents such as dimethylsulfoxide (DMSO), dimethylformamide, dimethylacetamide, and 1-methyl-2-pyrrolidinone, alcohol-based solvents such as methanol and ethanol, and ether-based solvents such as tetrahydrofuran (THF), diethyl ether, and dioxane, and DMSO is preferred.

The reaction temperature is normally −10° C. to 100° C., preferably 20° C. to 45° C.

The reaction time is normally 10 min. to 10 h., preferably 15 min. to 2 h.

Step B-5:

Compound be that is protected with $P^{21}$ may be deprotected using a base to obtain Compound bf.

Examples of the base include alkali metal hydroxides such as lithium hydroxide, sodium hydroxide, potassium hydroxide, and cesium hydroxide; and metal alkoxides such as potassium t-butoxide, sodium t-butoxide, lithium t-butoxide, potassium t-pentoxide, sodium t-pentoxide, and lithium t-pentoxide.

Examples of the solvent include alcohol-based solvents such as methanol, ethanol, methoxy ethanol, t-butylalcohol; ether-based solvents such as THF, diethyl ether; and amide-based solvents such as N,N-dimethyl acetamide (DMA), N,N-dimethylimidazolidinone (DM), and DMF. The solvent may also be a mixture with water.

The reaction temperature is normally −20° C. to 120° C., preferably 20° C. to 100° C.

The reaction time is normally 20 min. to 10 h., preferably 30 min. to 5 h.

Note that the order of Steps B-1, B-2, B-3, B-4 and B-5 may be changed. For example, Compound ba may be sequentially subjected to Step B-2, and Step B-1 to obtain Compound bc. Compound ba may be sequentially subjected to Step B-2, Step B-3, Step B-4, Step B-5, and Step B-1 to obtain Compound bf Compound ba may be sequentially subjected to Step B-2, Step B-3, Step B-4, Step B-1 and Step B-5 to obtain Compound bf.

Step B-Aa and Step B-Ab:

Further when $X^{21}$ is a halogen atom, Compound ba may be subjected to the following Step B-Aa and Step B-Ab to obtain Compound bb, and Compound bb may also be subjected to Step B-2.

[Chemical Formula 14]

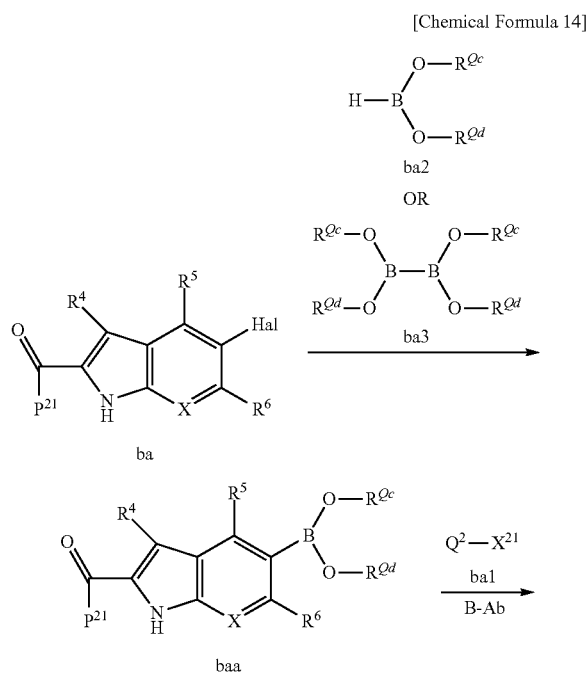

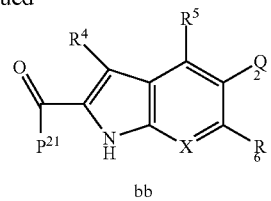

In the formulae, $R^{Qc}$ and $R^{Qd}$ are independently a hydrogen atom or $C_{1-6}$ alkyl, or $R^{Qc}$ and $R^{Qd}$ together with oxygen atoms to which they are attached and a carbon atom to which the oxygen atomes are attached may form 1,3,2-dioxaborolanyl or 1,3,2-dioxaborinanyl.

Step B-Aa:

Compound ba may be reacted with Compound ba2 or Compound Ba3 in the presence of a palladium catalyst to obtain an organic boron Compound baa. This step may be performed in the presence of a base.

This step is performed similarly to Step B-1, and the palladium catalyst, the base, the solvent used in the reaction, or the reaction temperature, reaction time are similar to Step B-1.

Examples of Compound ba2 include pinacol borane, 4,6,6-trimethyl-1,3,2-dioxaborinane. Compound ba3 includes, for example, diboronic acid, pinacol diborane(4, 4,4',4',5,5,5',5'-octamethyl-2,2'-bi(1,3,2-dioxaborolane)), bis(neopentyl glycolato)diboron, and bis(hexylene glycolato)diboron. These compounds may be obtained as a commercial product from Tokyo Chemical Industry Co., Ltd. By referring to Journal of the American Chemical Society, 131(45), 16346-16347, 2009 or Organic Synthesis, 77, 176-185, 2000, they may also be synthesized using i) pinacol and ii) diborane, $BH_3$.THF complex or $BH_3$.dimethyl sulfide complex.

The organic boron compound baa may be subjected to Step B-Ab without being isolated.

Step B-Ab:

An organic boron compound baa may be reacted with Compound ba1 in the presence of base to obtain Compound bb.

Examples of the base include a weak basic inorganic salt (sodium carbonate, potassium carbonate, cesium carbonate, sodium acid carbonate, potassium acid carbonate, etc.), and sodium carbonate is preferred.

The solvent used in the reaction or the reaction temperature, reaction time is the same as Step B-1.

Note that a transformation of Compound ba1 to an organic boron compound similar to the transformation of Compound ba to Compound baa, followed by a reaction thereof with Compound ba also provides Compound bb.

Step B-B:

Further, when Compound bb1 is represented by $X^{21}$—$(CH_2)_{n1}$—$CH_2$—CN, Compound bca corresponding to Compound be obtained in Step B-2 may be subjected to Step B-B, that is, reacted with Compound bc1 in the presence of a base to give Compound bcb corresponding to Compound bc, in which $R^7$ and $R^8$ together with a carbon atom to which they are attached form $C_{3-15}$ cycloalkane ring, and $C_{3-15}$ cycloalkane ring formed by combining $R^7$ and $R^8$ may be substituted with one to three $C_{1-6}$ alkyls, and the resulting compound may be subjected to Step B-3.

31

[Chemical Formula 15]

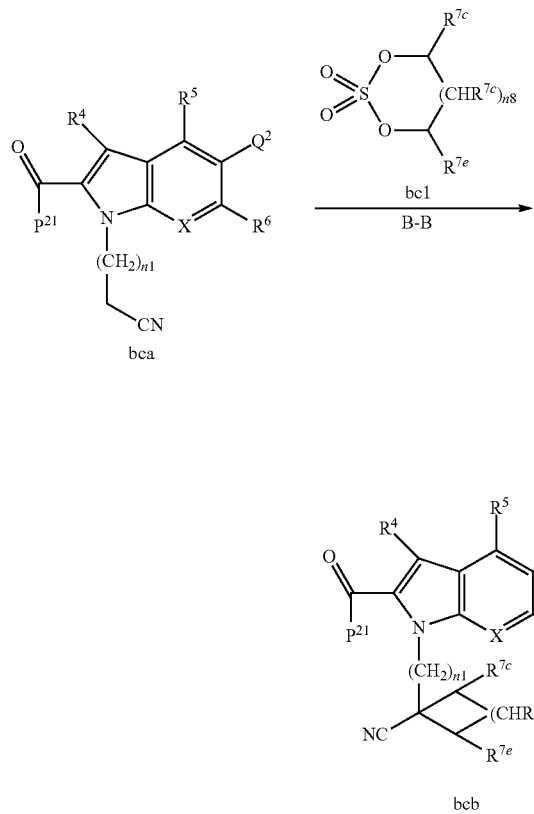

bca bcb

In the formulae, $R^{7c}$, $R^{7e}$ and $R^{7d}$ existing in a number of n8 are each independently a hydrogen atom or $C_{1-6}$ alkyl, and n8 is an integer of 0 to 3.

The base includes, for example, metal hydrides such as sodium hydride, potassium hydride, lithium bis(trimethylsilyl)amide (LiHMDS), and sodium bis(trimethylsilyl)amide (NaHMDS), potassium bis(trimethylsilyl)amide (KHMDS), lithium diisopropylamide (LDA), and lithium 2,2,6,6-tetramethylpyrrolidide, and KHMDS is preferred.

The solvent includes, for example, ether-based solvents such as THF, diethyl ether and dioxane, amide-based solvents such as N,N-dimethyl acetamide (DMA), N,N-dimethylimidazolidinone (DMI), DMF, N,N'-dimethylpropyleneurea (DMPU), and an amide-based solvent such as DMPU is preferred.

The reaction temperature is, for example, −20° C. to 40° C., preferably −10° C. to 10° C.

The reaction time is, for example, 30 min. to 8 h., preferably 1 h. to 4 h.

Compound bc1 may be obtained as a commercial product from CGeneTech. Inc. It may also be synthesized by referring to *Organic Letters*, 12(17), 3938-3941, 2010.

32

<General Production Method C>
Step C-1:

[Chemical Formula 16]

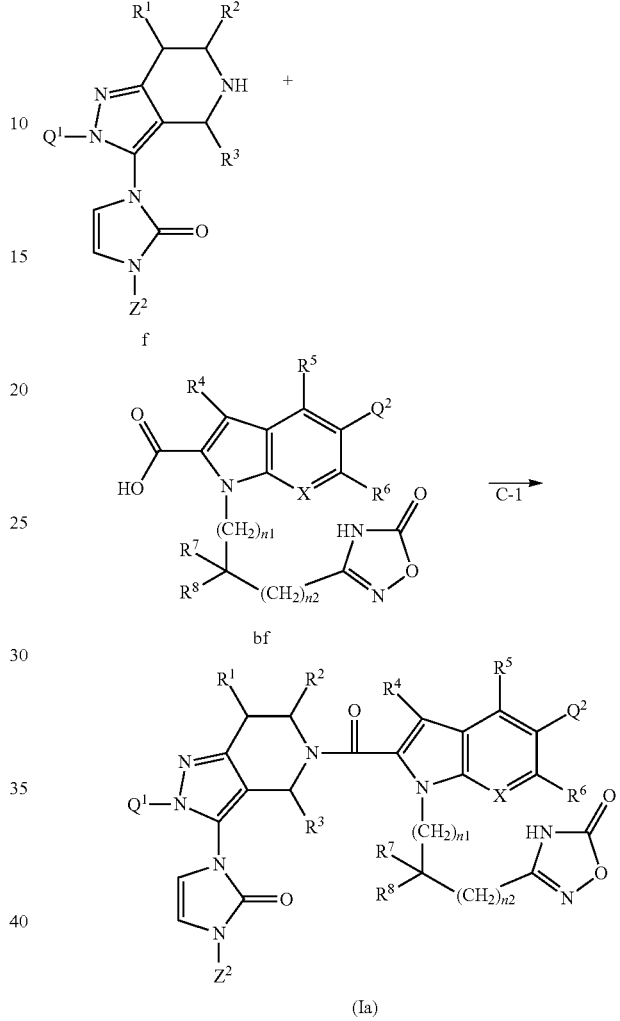

Compound f (or Compound p) and Compound bf may be condensed using a condensation agent in the presence of a base, and Compound (Ia) may be obtained.

Examples of the condensation agent include BOP-based condensation agents such as benzotriazol-1-yloxy-tris(dimethylamino)phosphonium hexafluorophosphate (BOP), benzotriazol-1-yloxy-tris(pyrrolizino)phosphonium hexafluorophosphate (PyBOP(Registered Trademark)), PyAOP, BroP, PyCloP, PyBroP(Registered Trademark), DEPBT; 4-(4,6-dimethoxy-1,3,5-triazin-2-yl)-4-methylmorpholinium chloride n-hydrate (DMT-MM), 2-(1H-benzotriazol-1-yl)-1,1,3,3-tetramethyluronium tetrafluoroborate (TBTU), [dimethylamino(triazolo[4,5-b]pyridin-3-yloxy)methylidene]-dimethylazanium hexafluorophosphate (HATU), and ethyl (hydroxyimino)cyanoacetate (Oxyma). HATU is preferred.

Examples of the base include tertiary amines (triethyl amine, N-methylmorpholine, diisopropyl ethyl amine, DBU, DABCO, etc.), and nitrogen-containing aromatic compounds (pyridine, dimethylaminopyridine, picoline, (2,6-) lutidine, pyrazine, pyridazine, etc.), and a tertiary amine such as diisopropyl ethyl amine is preferred.

Examples of the solvent include ether-based solvents such as THF, diethyl ether and dioxane, aprotic polar solvents such as dimethylsulfoxide (DMSO), dimethylformamide (DMF), dimethylacetamide, and 1-methyl-2-pyrrolidinone, and an aprotic polar solvent such as DMF is preferred.

The reaction temperature is, for example, 0° C. to 80° C., preferably 20° C. to 60° C.

The reaction time is, for example, 1 min. to 10 h., preferably 30 min. to 5 h.

Note that Compound (Ia) may be obtained by changing the order of the steps, for example, by sequentially subjecting Compound d to Step A1-5, Step C-1, Step A1-4, sequentially subjecting Compound ba to Step B-2, Step B-3, Step B-4, Step B-5, Step C-1, and Step B-1.

Further, the compound represented by Formula (I) may be brought in contact with or reacted with an acid or base that may be used in the production of pharmaceutical preparations to obtain the salt thereof. The salt may be any pharmaceutically acceptable salt, and examples of such salts include inorganic acid salts (hydrochloric acid salt, hydrobromic acid salt, hydroiodic acid salt, sulfuric acid salt, phosphoric acid salt, etc.), sulfonic acid salts (methanesulfonic acid salt, ethanesulfonic acid salt, benzenesulfonic acid salt, toluene sulfonic acid salt, etc.), carboxylic acid salts (formic acid salt, acetic acid salt, oxalic acid salt, maleic acid salt, fumaric acid salt, citric acid salt, malic acid salt, succinic acid salt, malonic acid salt, gluconic acid salt, mandelic acid salt, benzoic acid salt, salicylic acid salt, fluoroacetic acid salt, trifluoroacetic acid salt, tartaric acid salt, propionic acid salt, glutaric acid salt, adipic acid salt, nicotinic acid salt, etc.), alkali metal salts (lithium salt, sodium salt, potassium salt, cesium salt, rubidium salt, etc.), alkali earth metal salts (magnesium salt, calcium salt, etc.), ammonium salts (ammonium salt, alkylammonium salt, dialkylammonium salt, trialkylammonium salt, tetraalkylammonium salt, etc.), and basic amino acid salts (lysine salt, arginine salt, etc.), and alkali metal salts and alkali earth metal salts are preferred, and sodium salts and calcium salts are even more preferred. For example, the free form of a compound represented by Formula (I) may be suspended or dissolved in alcohol, such as methanol, and ethanol, or acetonitrile, acetone, dimethylsulfoxide, etc. and a basic aqueous solution containing sodium ion from sodium hydroxide, etc., a methanol solution containing sodium methoxide, or an ethanol solution containing sodium ethoxide is added thereto, to obtain a sodium salt of a compound represented by Formula (I). The reaction temperature is, for example, 0° C. to 80° C., preferably 20° C. to 60° C.

The compound represented by Formula (1) or a salt thereof may be a solvate, or a non-solvate. The solvent contained in a solvate may be either water or an organic solvent. Alcohols (e.g. methanol, ethanol, n-propanol), dimethylformamide, acetonitrile, acetone, dimethylsulfoxide may be used as the organic solvent. The compound represented by Formula (I) and a salt thereof may be preferably used in the form of a hydrate, and it is also preferably used in the form of a non-solvate. The proportion of the solvent molecule (preferably a water molecule) against a single molecule compound represented by Formula (I) or a salt thereof is, for example, 0.1 to 10, and 0.5 to 6 is more preferred. Further, the proportion may fluctuate by humidity, the production method, and the production season.

The solvate of a compound represented by Formula (I) or a salt thereof may be obtained by a common method, such as precipitating the compound represented by Formula (1) or a salt thereof from a solvent. Further, the hydrate may be obtained by precipitating a compound represented by Formula (I) or a salt thereof from a water-containing organic solvent.

The solvate of a compound represented by Formula (I) or a salt thereof may be transformed to a compound represented by Formula (I) or a salt thereof by a common method such as heating under reduced pressure.

A compound used as a pharmaceutical agent is preferably the compound represented by Formula (I) per se (free form), a hydrate of the free form, a salt of the free form, and a hydrate of salt, more preferably, a free form, a hydrate of the free form, a sodium salt of the free form, a hydrate of a sodium salt, a calcium salt of the free form, and a hydrate of the calcium salt.

The compound represented by Formula (I) or a salt thereof, or a solvate of either the compound or a salt of the compound, of the present invention may be used in a form of a crystal, or in an amorphous state.

The present invention includes all stereoisomers of the compound represented by Formula (I) (e.g. enantiomer, diastereomer (including cis- and trans-geometric isomer)), the racemic form of the isomers, and other mixtures. For example, the compound of the present invention may have one or more asymmetric center, and the present invention includes a racemic mixture, a diastereomer mixture, and enantiomers of such compound.

The present invention includes an embodiment in which an atom constituting the compound molecule of the present invention represented by Formula (I) is an isotope, and includes an embodiment in which at least one atom is substituted with an atom having the same atomic number (proton number) and a different mass number (sum of protons and neutrons). Examples of isotopes included in the compound of the present invention include hydrogen atom, carbon atom, nitrogen atom, oxygen atom, phosphorous atom, sulfur atom, fluorine atom, chlorine atom, which respectively include $^2H$, $^3H$, $^{13}C$, $^{14}C$, $^{15}N$, $^{17}O$, $^{18}O$, $^{31}P$, $^{32}P$, $^{35}S$, $^{18}F$, $^{36}Cl$. In particular, radioisotopes which emit radiation as they decay, such as $^3H$ or $^{14}C$, are useful in pharmaceutical preparations or in vivo topographic tests of compounds. The stable isotope neither decays nor changes in their amount, nor have radioactivity, so they can be used safely. When the atom constituting the compound molecule of the present invention is an isotope, it may be transformed according to the common method by replacing the reagent used in synthesis with a reagent containing the corresponding isotope.

The compound of the present invention, a salt thereof, or a solvent of these has a GLP1 receptor agonist effect and a blood glucose level reduction effect, and it may be used for the prevention or therapy of non-insulin-dependent diabetes mellitus (Type 2 diabetes), hyperglycemia, impaired glucose tolerance, insulin-dependent diabetes mellitus (Type 1 diabetes), diabetic complication, obesity, hypertension, hyperlipidemia, arteriosclerosis, myocardial infarction, coronary heart disease, brain infarction, non-alcoholic steatohepatitis, Parkinson's disease, or dementia, by administering it to patients in the form of a pharmaceutical composition in pharmacologically effective amount by an appropriate administration method.

"Diabetes" in the present invention is a state or a disease in which the metabolism for generating and using glucose becomes deficient due to a failure in maintaining an appropriate blood glucose level in the body, and encompasses insulin-dependent diabetes mellitus (Type 1 diabetes) and non-insulin-dependent diabetes mellitus (Type 2 diabetes).

"Hyperglycemia" refers to a state in which the plasma glucose level while fasting or after administration of glucose is higher than the normal value (e.g. 80 to 110 mg/dL in human while fasting), and it is a typical symptom of diabetes.

"Impaired glucose tolerance" includes insulin-resistant impaired glucose tolerance and insulin hyposecretion.

"Diabetic complication" is a complication caused by diabetes or hyperglycemia, and it may be acute complex or chronic complex. The term "acute complex" includes ketoacidosis, and infectious disease (e.g. skin infection, soft tissue infection, biliary system infection, respiratory system infection, urinary tract infection), and the "chronic complex" includes, for example, microangiopathy (e.g. nephropathy, retinopathy), neuropathy (e.g. sensory nerve disorder, motor nerve disorder, autonomic nerve disorder), and gangrene. Major diabetes complexes include diabetic retinopathy, diabetic nephropathy, and diabetic neuropathy. "Coronary heart disease" includes myocardial infarction and angina pectoris.

"Dementia" includes, for example, Alzheimer's disease, vascular dementia, and diabetic dementia.

The administration method may be systemic administration including oral administration, rectal administration, intravenous administration, intramuscular administration, subcutaneous administration, intravaginal administration, intraperitoneal administration, intravesical administration, and aspiration, as well as local administration by ointment, gels, and cream.

When using the compound of the present invention, a salt thereof, or a solvate of either the compound or a salt of the compound in the form of a pharmaceutical composition, it is normally formulated into a certain pharmaceutical formulation (dosage form). Examples of such pharmaceutical formulations include a tablet, a capsule, granules, powders, subtle granules, pills, aqueous or non-aqueous solution or suspension. Further, the compound of the present invention, a salt thereof, or a solvate of either the compound or a salt of the compound may also be used in the form of various controlled release preparations. Examples of such controlled release preparations include, for example, those to be imbedded in the body, those applied to the oral mucosa or nasal mucosa. The solution or suspension may be filled in containers suited for dividing into respective administration amounts to be stored.

The various pharmaceutical formulations may be produced by a well known method by mixing the compound of the present invention, a salt thereof, or a solvate of either the compound or a salt of the compound and a pharmaceutically acceptable additive. Examples of such additives include, for example, an excipient, a lubricant (a coating agent), a binding agent, a disintegrator, a stabilizer, correctives, a base, a dispersant, a diluent, a surfactant, or an emulsifier.

Examples of an excipient include starch (starch, potato starch, corn starch, etc.), lactose, crystalline cellulose, and dicalcium phosphate.

Examples of a lubricant (coating agent) include ethyl cellulose, hydroxypropyl cellulose, hydroxypropylmethyl cellulose, shellac, talc, carnauba wax, and paraffin.

Examples of a binding agent include polyvinyl pyrrolidone, macrogol, and compounds that are the same as the above excipient.

Examples of a disintegrator include chemically modified starch and cellulose, such as croscarmellose sodium, sodium carboxymethyl starch, cross-linked polyvinyl pyrrolidone, and compounds that are the same as the above excipient.

Examples of a stabilizer include para-oxybenzoates such as methyl paraben, and propyl paraben; benzalkonium chloride; phenols such as phenol, and cresol; thimerosal; dehydroacetic acid; and sorbic acid.

Examples of a correctives include sweetener, acidulant, and flavor, that are normally used.

Examples of a base include fats such as lard; vegetable oil such as olive oil and sesame oil; higher alcohols such as stearyl alcohol, and cetanol; animal oil; lanolin acid; Vaseline; paraffin; bentonite; glycerin; and glycol oil.

Examples of a dispersant include cellulose derivative (Arabic rubber, tragacanth, methyl cellulose, etc.), stearic acid polyesters, sorbitan sesquioleate, aluminum monostearate, sodium alginate, polysorbate, and sorbitan fatty acid ester.

Examples of the solvent or diluent in a liquid formulation include phenol, chlorocresol, purified water, distilled water, etc.

Examples of a surfactant or emulsifier include polysorbate 80, polyoxyl 40 stearate, lauromacrogol.

The content of the compound of the present invention, a salt thereof, or a solvate of either the compound or a salt of the compound in the pharmaceutical formulation differs by the dosage form, but it is generally 0.01 to 100 wt %.

The pharmaceutical formulation may contain one type or two or more types of the compound of the present invention, a salt thereof, or a solvate of either the compound or a salt of the compound.

When using the compound of the present invention, a salt thereof, or a solvate of either the compound or a salt of the compound as a preventative agent or a therapeutic agent for non-insulin-dependent diabetes mellitus (Type 2 diabetes) or obesity, the amount to be administered may be appropriately determined according to the severity of the symptom, the age, the body weight, the relative health state, whether other drugs are combined, and the method of administration. For example, when the subject of administration is a homeotherm, particularly a human, the dosage per day is 0.01 to 10000 mg, preferably 0.1 to 1000 mg, in oral administration, and 0.001 to 3000 mg, preferably 0.01 to 300 mg in a non-oral administration. Note that the above dosage may be administered once per a day to a few weeks, or it may be divided into two or more times per day.

The effective amount of the compound of the present invention, a salt thereof, or a solvate of either the compound or a salt of the compound means a therapeutic effective amount or a preventative effective amount, and it may be appropriately determined according to the severity of the symptom, the age, the body weight, the relative health state, whether other drugs are combined, and the method of administration EXAMPLES The content of the present invention is explained in more detail by the following Examples and Reference Examples. All starting materials and reagents were obtained from commercial suppliers or synthesized by commonly known methods. A room temperature (rt) is a temperature of 5 to 35° C. The silica gels that were used were SHOKO Scientific Purif-Pack(Registered Trademark) SI 60 m (Shoko Scientific Co., Ltd.), Biotage (Registered Trademark) SNAP Ultra Silica Cartridge (Biotage), or SNAP KP-Sil Cartridge (Biotage), reversed-phase silica gel was Wakosil (Registered Trademark) 25C18 (Wako Pure Chemical Industries, Ltd.), or Biotage (Registered Trademark) SNAP Ultra C18 Cartridge (Biotage). The HPLC purification of the compound was performed using AutoPurification HPLC/MS System (Waters) or Preprative HPLC system with injection/fractionation function (gilson). The $^1$H-NMR spectrum was measured using or not using $Me_4Si$ as an inner reference material, and using ECP-400 (JEOL), Agilent 400-MR (Agilent Technologies Japan, Ltd), AVANCE3 300 MHz (Bruker) or AVANCE3 600 MHz Cryo-TCI (Bruker) (s=singlet, brs=broad singlet, d=doublet, t=triplet, q=quartet, dd=double doublet, ddd=double double doublet, m=multiplet). The chemical shift of the NMR data uses $Me_4Si$ or deuterized solvent as a reference, and is presented using ppm (parts per million, δ), and the coupling constant (J) was shown using Hz (Hertz). LC/MS was carried out by measuring the retention time and performing mass spectrometry using the device and the analysis condition of Table 1. Microwave was irradiated using Initiator™ (Biotage). The mass spectrometry in LC/MS was performed using the following mass spectrometers: SQD (Waters), SQD2 (Waters), 2020 (Shimadzu), or 2010EV (Shimadzu).

TABLE

Device and Analysis Condition used for LC/MS

| LC/MS Analysis Condition No. | Device | Column | Mobile phase, gradient and flow rate |
|---|---|---|---|
| SMD-FA05-1 | nexera/2020 | Speed Core C18 2.1 mmI.D. × 50 mm, 2.7 μm | 0.1% FA $H_2O$/0.1% FA MeCN = 95/5→0/100 (1.5 min.)→0/100 (0.5 min.), 1 mL/min. |
| SMD-FA05-2 | nexera/2020 | Metoric Core C18 2.1 mmI.D. × 50 mm, 2.7 μm | 0.1% FA $H_2O$/0.1% FA MeCN = 95/5→0/100 (1.5 min.)→0/100 (0.5 min.), 1 mL/min. |
| SMD-FA05-3 | nexera/2020 | Ascentis Express C18 2.1 mmI.D. × 50 mm, 2.7 μm | 0.1% FA $H_2O$/0.1% FA MeCN = 95/5→0/100 (1.5 min.)→0/100 (0.7 min.), 1 mL/min. |
| SMD-FA05-long | nexera/2020 | Speed Core C18 2.1 mmI.D. × 50 mm, 2.7m | 0.1% FA $H_2O$/0.1% FA MeCN = 05/95→0/100 (4.5 min.)→0/100 (0.5 min.), 1 mL/min. |
| SMD-FA10-1 | UFLCXR/2020 | Phenomenex kinetex C18 3.0 mmI.D. × 50 mm, 2.6 μm | 0.1% FA $H_2O$/0.1% FA MeCN = 90/10→0/100 (1.2 min.)→0/100 (0.5 min.), 1.5 mL/min. |
| SMD-FA10-2 | UFLCXR/2020 | Kinetex XB-C18 3.0 mmI.D. × 50 mm 2.6 μm | 0.1% FA $H_2O$/0.1% FA MeCN = 90/10→0/100 (1.2 min.)→0/100 (0.5 min.), 1.5 mL/min. |
| SMD-FA10-3 | UFLCXR/2020 | Kinetex XB-C18 3.0 mmI.D. × 50 mm, 2.6 μm | 0.1% FA $H_2O$/0.1% FA MeCN = 90/10→0/100 (1.1 min.)→0/100 (0.7 min.), 1.5 mL/min. |
| SMD-FA10-4 | UFLCXR/2020 | Acquity BEH C18 2.1 mmI.D. × 50 mm, 1.7 μm | 0.1% FA $H_2O$/0.1% FA MeCN =90/10→0/100 (1.1 min.)→0/100 (0.5 min.), 0.7 mL/min. |
| SMD-FA10-5 | Nexera/2020 | Accucore 2.1 mmI.D. × 50 mm, 2.7 μm | 0.1% FA $H_2O$/0.1% FA MeCN = 90/10→0/100 (1.1 min.)→0/100 (0.5 min.), 1.0 mL/min. |
| SMD-FA1060-1 | UFLCXR/2020 | Kinetex XB-C18 3.0 mmI.D. × 50 mm, 2.6 μm | 0.1% FA $H_2O$/0.1% FA MeCN = 90/10→40/60 (4.0 min.)→5/95 (0.5 min.), 1.5 mL/min. |
| SMD-FA10-long | UFLCXR/2020 | Phenomenex kinetex C18 3.0 mmI.D. × 50 mm, 2.6 μm | 0.1% FA $H_2O$/0.1% FA MeCN = 90/10→0/100 (4.5 min.)→0/100 (1.3 min.), 1.1 mL/min. |
| SMD-TFA05-1 | nexera/2020 | Ascentis Express C18 2.1 mmI.D. × 50 mm, 2.7 μm | 0.05% TFA $H_2O$/0.05% TFA MeCN = 95/5→0/100 (1.5 min.)→0/100 (0.5 min.), 1 mL/min. |
| SMD-TFA05-2 | nexera/2020 | Metoric Core C18 2.1 mmI.D. × 50 mm, 2.7 μm | 0.05% TFA $H_2O$/0.05% TFA MeCN = 95/5→0/100(1.5 min.)→0/100(0.5 min.), 1 mL/min. |
| SMD-TFA05-3 | nexera/2020 | Kinetex 1.7 u C18 2.1 mmI.D. × 50 mm, 1.7 μm | 0.05% TFA $H_2O$/0.05% TFA MeCN = 95/5→0/100 (1.5 min.)→0/100 (0.5 min.), 1 mL/min. |
| SMD-TFA05-4 | nexera/2020 | Ascentis Express C18 2.1 mmI.D. × 50 mm, 2.7 μm | 0.05% TFA $H_2O$/0.05% TFA MeCN = 95/5→0/100 (1.1 min.)→0/100 (0.5 min.), 1 mL/min. |
| SMD-TFA05-5 | UFLCXR/2020 | Shim-pack XR-ODS 3.0 mmI.D. × 50 mm, 2.2 μm | 0.05% TFA $H_2O$/0.05% TFA MeCN = 95/5→0/100(1.2 min.)→0/100 (1.0 min.), 1 mL/min. |
| SMD-TFA05-6 | UFLCXR/2020 | Shim-pack XR-ODS 3.0 mmI.D. × 50 mm, 2.2 μm | 0.05% TFA $H_2O$/0.05% TFA MeCN = 95/5→0/100 (2.2 min.)→0/100 (1.0 min.), 1 mL/min. |
| SMD-FA05-RP | nexera/2020 | Ascentis Express RP-Amide 2.1 mmI.D. × 50 mm, 2.7 μm | 0.1% FA $H_2O$/0.1% FA MeCN = 95/5→0/100 (1.5 min.)→0/100 (0.5 min.), 1 mL/min. |
| SMD-FA50-RP | nexera/2020 | Ascentis Express RP-Amide 2.1 mmI.D. × 50 mm, 2.7 μm | 0.1% FA $H_2O$/0.1% FA MeCN = 50/50→0/100 (1.0 min.)→0/100 (1.0 min.), 1 mL/min. |
| SMD-TFA05-RP | nexera/2020 | Ascentis Express RP-Amide 2.1 mmI.D. × 50 mm, 2.7 μm | 0.05% TFA $H_2O$/0.05% TFA MeCN = 95/5→0/100 (1.5 min.)→0/100 (0.5 min.), 1 mL/min. |
| SMD-TFA50-RP | nexera/2020 | Ascentis Express RP-Amide 2.1 mmI.D. × 50 mm, 2.7 μm | 0.05% TFA $H_2O$/0.05% TFA TFAM eCN = 50/50→0/100(1 min.)→ 0/100 (1 min.), 1 mL/min. |
| SQD-FA05-1 | Aquity UPLC-I-Class/SQD | Ascentis Express C18 2.1 mmI.D. × 50 mm, 2.7 μm | 0.1% FA $H_2O$/0.1% FA MeCN = 95/5→0/100 (1.0 min.)→0/100 (0.4 min.), 0.9 mL/min. |
| SQD-FA05-2 | Aquity UPLC-I-Class/SQD | Ascentis Express RP-Amide 2.1 mmI.D. × 50 mm, 2.7 μm | 0.1% FA $H_2O$/0.1% FA MeCN = 95/5→0/100 (1.0 min.)→0/100 (0.4 min.), 1 mL/min. |
| SQD-FA05-3 | Aquity UPLC/SQD | Ascentis Express C18 2.1 mmI.D. × 50 mm, 2.7 μm | 0.1% FA $H_2O$/0.1% FA MeCN = 95/5→0/100 (1.0 min.)→0/100 (0.4 min.), 1 mL/min. |
| SQD-FA05-4 | Aquity UPLC/SQD2 | Ascentis Express C18 2.1 mmI.D. × 50 mm, 2.7 μm | 0.1% FA $H_2O$/0.1% FA MeCN = 95/5→0/100 (1.0 min.)→0/100 (0.4 min.), 1 mL/min. |
| SQD-FA50-1 | Aquity UPLC-I-Class/SQD | Ascentis Express RP-Amide 2.1 mmI.D. × 50 mm, 2.7 μm | 0.1% FA $H_2O$/0.1% FA MeCN = 50/50→0/100 (0.7 min.)→0/100 (0.7 min.), 1 mL/min. |
| SQD-AA05-1 | Aquity UPLC-I-Class/SQD | Ascentis Express C18 2.1 mmI.D. × 50 mm, 5 μm | 10 mMAcO$NH_4$$H_2O$/ MeOH = 95/5→ 0/100(1 min.)→ 100(0.4 min.), 1 mL/min. |
| SQD-AA05-2 | Aquity UPLC/SQD | Ascentis Express C18 2.1 mmI.D. × 50 mm, 2.7 μm | 10 mMAcO$NH_4$ $H_2O$/MeOH = 95/5-0/100(1 min.)→ 100(0.4 min.), 1 mL/min. |

TABLE-continued

Device and Analysis Condition used for LC/MS

| LC/MS Analysis Condition No. | Device | Column | Mobile phase, gradient and flow rate |
|---|---|---|---|
| SQD-AA50-1 | Aquity UPLC/SQD | Ascentis Express C18 2.1 mmI.D. × 50 mm, 2.7 μm | 10 mMAcONH$_4$ H$_2$O/MeOH = 50/50→0/100 (0.7 min.)→100 (0.7 min.), 1 mL/min. |
| SQD-FA05-long | Aquity UPLC-I-Class/SQD | Ascentis Express C18 2.1 mmI.D. × 50 mm, 2.7 μm | 0.1% FA H$_2$O/0.1% FA MeCN = 95/5→0/100 (4.5 min.)→0/100 (0.5 min.), 1 mL/min. |
| SQD-FA0550-long | Aquity UPLC-I-Class/SQD | Ascentis Express C18 2.1 mmI.D. × 50 mm, 2.7 μm | 0.1% FA H$_2$O/0.1% FA MeCN 95/5→5/50 (4.5 min.)→0/100 (0.01 min.)→0/100 (0.49 min.), 1 mL/min. |
| SQD-AA50-long | Aquity UPLC-I-Class/SQD | Ascentis Express C18 2.1 mmI.D. × 50 mm, 5 μm | 10 mMAcONH$_4$ H$_2$O/MeOH = 50/50→0/100 (4.5 min.)→100 (0.5 min.), 1 mL/min. |
| SQD-AA0550-long | Aquity UPLC-I-Class/SQD | Ascentis Express C18 2.1 mmI.D. × 50 mm, 5 μm | 10 mMAcONH$_4$ H$_2$O/MeOH 95/5→50/50 (4.5 min.)→0/100 (0.01 min.)→0/100 (0.49 min.), 1 mL/min. |

<Example 1> Synthesis of 3-[(1S,2S)-1-[2-[2-(3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one (Compound 1)

[Chemical Formula 13]

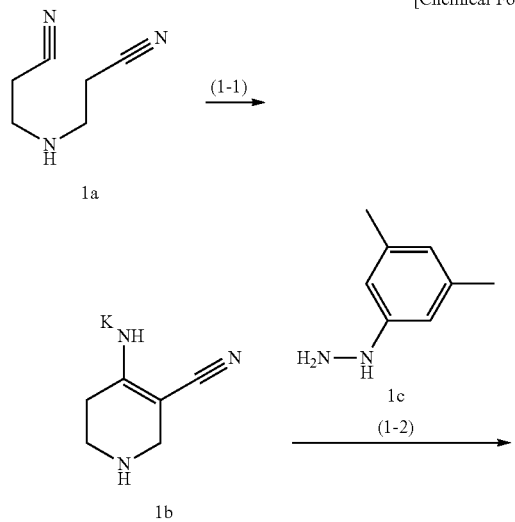

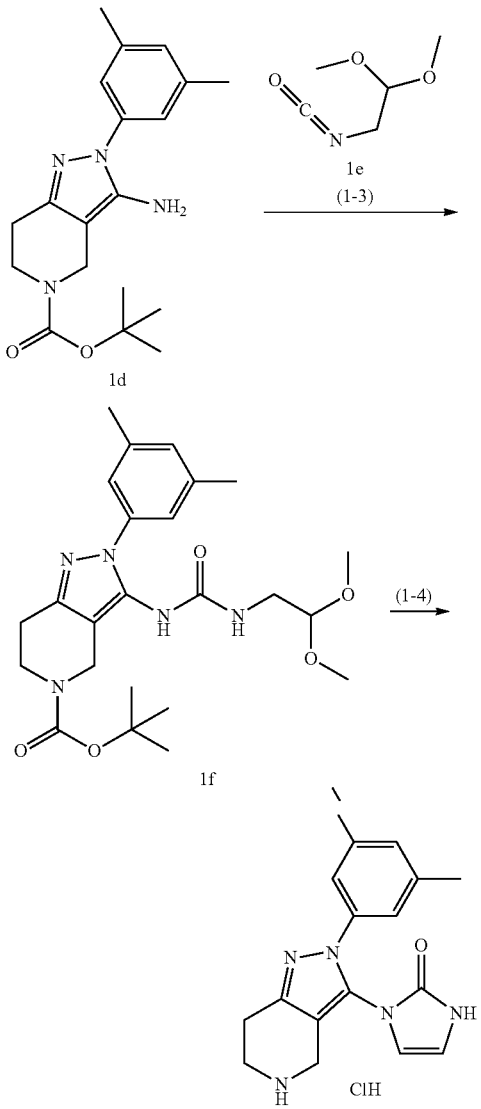

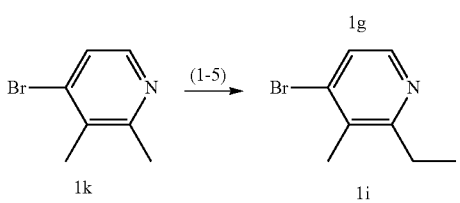

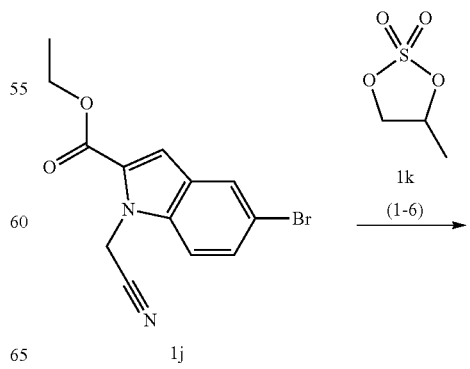

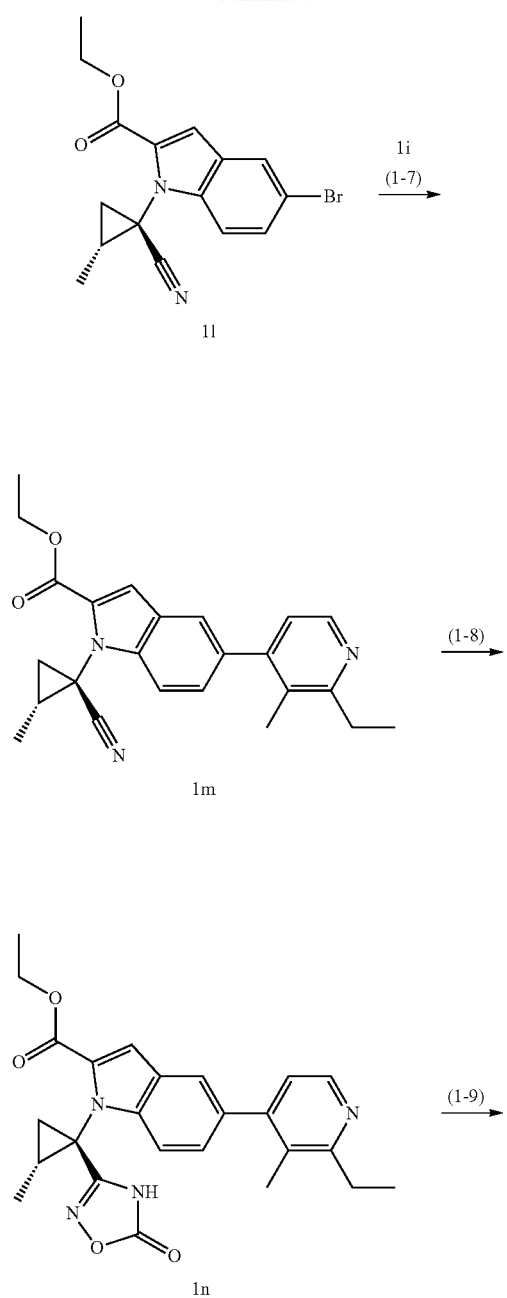

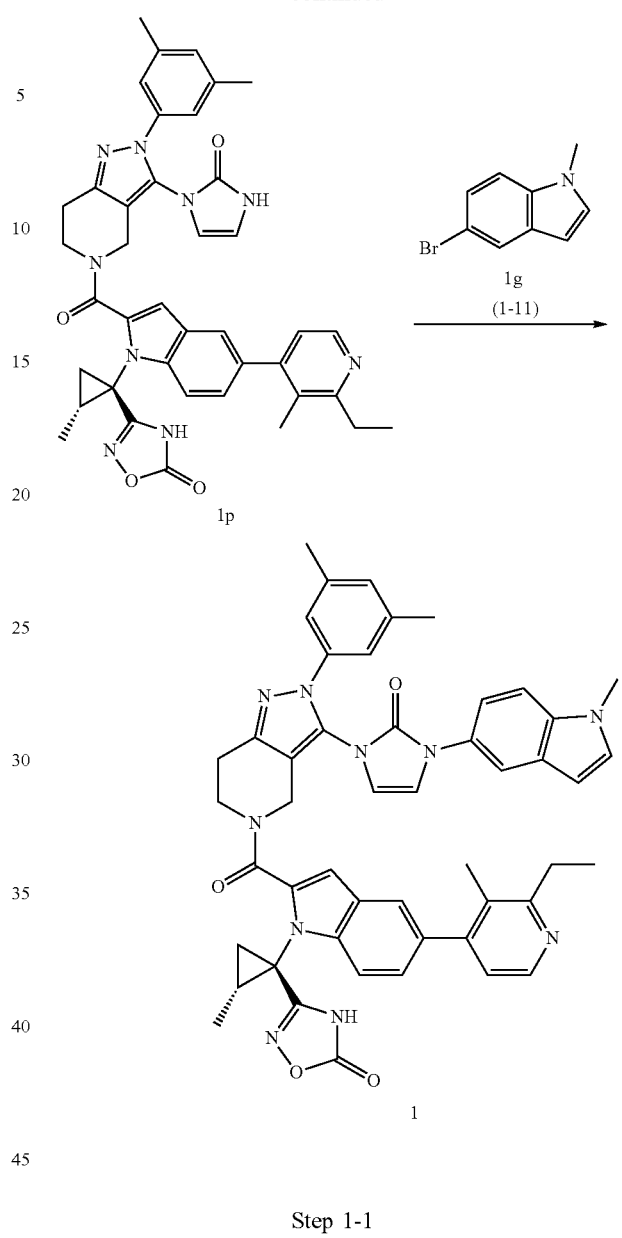

Step 1-1

Potassium [(5-Cyano-1,2,3,6-tetrahydropyridin-4-yl)amide] (Compound 1b)

To a tetrahydrofuran (THF) (179 mL) solution of 3-(2-cyanoethylamino)propanenitrile (Compound 1a, 22.0 g, 179 mmol) was added a THF solution (179 mL) of 1M potassium tert-butoxide and the mixture was stirred at room temperature for 1 h. The reaction mixture was filtered by washing with THF (50 mL), and then the filtrate was dried under reduced pressure to obtain the titled Compound 1b (23.8 g, yield 83%) as a light brown solid.

LC/MS Mass Spectrometry: m/z 124 ([M+H]$^+$).

LC/MS Retention Time: 0.14 min. (Analysis Condition: SMD-FA05-1).

$^1$H-NMR (400 MHz, MeOH-d$_4$) δ:3.33 (2H, t, J=1.3 Hz), 2.90 (2H, t, J=5.9 Hz), 2.21 (2H, tt, J=5.9, 1.3 Hz).

Step 1-2 tert-Butyl 3-amino-2-(3,5-dimethylphenyl)-6,7-dihydro-4H-pyrazolo[4,3-c]pyridine-5-carboxylate (Compound 1d)

To an ethanol (57.9 mL) solution of 3,5-dimethylphenylhydrazine hydrochloride (Compound 1c, 5.00 g, 29.0 mmol) and Compound 1b obtained in Step 1-1 (4.67 g, 29.0 mmol) was added 2N hydrochloric acid (23.2 mL, 46.3 mmol), and the mixture was stirred at 50° C. for 1 h. After the reaction mixture was cooled to 0° C., 5M sodium hydroxide aqueous solution (9.27 mL, 46.3 mmol) and di-tert-butyl dicarbonate (6.64 g, 30.4 mmol) were added and the mixture was stirred at 0° C. for 1 h. Water was added to the reaction mixture and extraction was performed using ethyl acetate, then the organic layer was washed with brine and dried with anhydrous magnesium sulfate. After filtration, the filtrate was concentrated under reduced pressure, and the residue was purified by a silica gel column chromatography (ethyl acetate/hexane=0:1 to 1:1) to obtain the titled Compound 1d (7.82 g, yield 79%) as a pale yellow solid.
LC/MS Mass Spectrometry: m/z 343 ([M+H]$^+$).
LC/MS retention time: 0.99 min. (Analysis condition: SMD-FA05-3).

Step 1-3 tert-Butyl 3-(2,2-dimethoxyethylcarbamoylamino)-2-(3,5-dimethylphenyl)-6,7-dihydro-4H-pyrazolo[4,3-c]pyridine-5-carboxylate (Compound 1f)

To a pyridine (7.39 mL) solution of Compound 1d (2.53 g, 7.39 mmol) obtained in Step 1-2 was added 2-isocyanato-1,1-dimethoxyethane (Compound 1e, 1.94 g, 14.8 mmol), and the mixture was stirred at room temperature. After 3 hours and 15 minutes, diethylamine (1.08 g, 14.8 mmol) was added and the mixture was stirred at room temperature for 5 min., then water (50.6 mL) was added, and the resulting mixture was stirred at room temperature for 20 min. The reaction mixture that had become a suspension was filtered, and the obtained solid was washed with water (12.7 mL) then dried under reduced pressure to obtain the titled Compound 1f (3.20 g, yield 91%) as a pale yellow solid.
LC/MS mass spectrometry: m/z 474 ([M+H]$^+$).
LC/MS retention time: 0.78 min. (Analysis Condition: SQD-FA05-1).

<Step 1-4>

3-[2-(3,5-Dimethylphenyl)-4,5,6,7-tetrahydropyrazolo[4,3-c]pyridin-3-yl]-1H-imidazol-2-one (Compound 1g)

To Compound 1f (158 mg, 0.334 mmol) obtained in Step 1-3 was added formic acid (3.84 mL, 100 mmol), and the mixture was stirred at room temperature for 21 h. The reaction mixture was concentrated under reduced pressure, and toluene was added and the solvent was removed by evaporation under reduced pressure. Dichloromethane (1 mL) was added to the residue to dissolve the residue, and then hydrogen chloride (4M dioxane solution, 0.835 mL, 3.34 mol) was added at room temperature. The reaction mixture was concentrated under reduced pressure. Toluene was added and the solvent was removed by evaporation under reduced pressure to obtain a crude product (176 mg) of the titled Compound 1g.
LC/MS mass spectrometry: m/z 310 ([M+H]$^+$).
LC/MS retention time: 0.39 min. (Analysis Condition: SQD-FA05-3).

Step 1-5

4-Bromo-2-ethyl-3-methylpyridine (Compound 1i)

A THF (75.0 mL) solution of 4-bromo-2,3-dimethylpyridine (Compound 1h, 7.05 g, 37.9 mmol) was cooled to −78° C., and then 1.11 M lithium diisopropylamide n-hexane-THF solution (35.8 mL, 39.8 mmol) was added slowly. The reaction mixture was stirred at −78° C. for 5 min., and then iodomethane (2.84 mL, 45.5 mmol) was added. The reaction mixture was stirred at −78° C. for 5 min., and warmed slowly to room temperature. Then, the reaction mixture was stirred for 30 min. and the solvent was removed by evaporation under reduced pressure. The residue was purified by silica gel column chromatography (dichloromethane/ethyl acetate), and the titled Compound 1i (6.98 g, yield 92%) was obtained as an orange oil-like material.
LC/MS mass spectrometry: m/z 200 ([M+H]$^+$).
LC/MS retention time: 0.38 min. (Analysis Condition: SQD-FA05-3).

Step 1-6

Ethyl 5-bromo-1-[(1S,2S)-1-cyano-2-methylcyclopropyl]indole-2-carboxylate (Compound 1l)

The N,N'-dimethylpropyleneurea (117 mL) solution of ethyl 5-bromo-1-(cyanomethyl)indole-2-carboxylate (Compound 1j, 3.60 g, 11.7 mmol) and (4R)-4-methyl-1,3,2-dioxathiolane 2,2-dioxide (Compound 1k, 4.86 g, 35.2 mmol) was deaerated under reduced pressure, then nitrogen was introduced in the vessel and the mixture was cooled to 0° C. Under nitrogen atmosphere, a THF solution (46.9 mL, 46.9 mmol) of 1.0 M potassium bis(trimethylsilyl)amide was added dropwise slowly. The reaction mixture was stirred at 0° C. for 2.5 h., then formic acid (5.30 mL, 141 mmol) was added and extraction was performed using a mixture of hexane/ethyl acetate (1:3). The organic layer was washed three times with water, twice with a saturated aqueous solution of sodium hydrogen carbonate, and once with brine, and then dried with sodium sulfate. After filtration, the filtrate was concentrated under reduced pressure and the residue was purified by silica gel column chromatography (ethyl acetate/hexane=1:19 to 1:4) to obtain the titled Compound 1l (1.70 g, yield 42%) as a white solid.
LC/MS mass spectrometry: m/z 347 ([M+H]$^+$).
LC/MS retention time: 0.69 min. (Analysis Condition: SQD-AA50-1).

Step 1-7

Ethyl 1-[(1S,2S)-1-cyano-2-methylcyclopropyl]-5-(2-ethyl-3-methylpyridin-4-yl)indole-2-carboxylate (Compound 1m)

The dioxane (44 mL) suspension of Compound 1l (2.70 g, 7.78 mmol) obtained in Step 1-6,4,4,4',4',5,5,5',5'-octamethyl-2,2'-bi(1,3,2-dioxaborolane) (2.17 g, 8.55 mmol) and potassium acetate (1.15 g, 11.7 mmol) were deaerated under reduced pressure, and then nitrogen was introduced in the vessel. Under nitrogen atmosphere, 1,1'-bis (diphenylphosphino)ferrocene-palladium (II) dichloride-dichloromethane complex (1.29 g, 1.56 mmol) was added, and the mixture was stirred at 100° C. for 3 h. After the solution was cooled to room temperature, 4-bromo-2-ethyl-3-methylpyridine (Compound 1i, 2.33 g, 11.7 mmol), sodium carbonate (2.47 g, 23.3 mmol), and water (7.4 mL) were added to the solution, and then the solution was subjected to deaeration under reduced pressure. Nitrogen was introduced in the vessel, and the solution was stirred at 100° C. for 2 h. The solution was cooled to room temperature, and then water (5.4 mL), and N-acetyl cysteine (0.635 g, 3.89 mmol) were added. The mixture was stirred for 0.5 h. The reaction mixture was subjected to extraction with ethyl acetate, and the organic layer was washed once with brine, and then drided using sodium sulfate. After filtration, the filtrate was concentrated under reduced pressure and the residue was purified by silica gel column chromatography (ethyl acetate/hexane=1:19 to 2:3) to obtain the titled Compound 1m (2.92 g, yield 97%) as a pale yellow gum-like product.

LC/MS mass spectrometry: m/z 388 ([M+H]$^+$).

LC/MS retention time: 1.06 min. (Analysis Condition: SQD-AA05-2).

Step 1-8

Ethyl 5-(2-ethyl-3-methylpyridin-4-yl)-1-[(1S,2S)-2-methyl-1-(5-oxo-4H-1,2,4-oxadiazol-3-yl)cyclopropyl]indole-2-carboxylate (Compound 1n)

To a dimethylsulfoxide (DMSO) (2.9 mL) solution of Compound 1m (0.225 g, 0.581 mmol) obtained in Step 1-7 was added 50% hydroxyamine aqueous solution (0.356 mL, 5.81 mmol), and the mixture was stirred at room temperature for 17 h. Ethyl acetate (50 mL) was added, the mixture was washed with water (10 mL) and brine (10 mL), and then dried with magnesium sulfate. After the mixture was filtered, the filtrate was concentrated under reduced pressure, and the obtained residue was dissolved in DMSO (1.9 mL). Then, carbonyl diimidazole (188 mg, 1.16 mmol) and 1,8-diazabicycloundec-7-ene (0.219 mL, 1.45 mmol) were added and the resulting mixture was stirred at room temperature for 0.5 h. Formic acid was added to the mixture, which was then purified by reversed-phase chromatography (acetonitrile/water, 0.1% formic acid) to obtain the titled Compound 1n (169 mg, yield 65%) as a white powder.

LC/MS mass spectrometry: m/z 447 ([M+H]$^+$).

LC/MS retention time: 0.80 min. (Analysis Condition: SMD-FA05-3).

Step 1-9

5-(2-Ethyl-3-methylpyridin-4-yl)-1-[(1S,2S)-2-methyl-1-(5-oxo-4H-1,2,4-oxadiazol-3-yl)cyclopropyl]indole-2-carboxylic acid (Compound 1o)

To a DMSO (40 mL) solution of Compound 1n (3.61 g, 8.08 mmol) obtained in Step 1-8 was added 2M sodium hydroxide aqueous solution (10.1 mL, 20.2 mmol), and the mixture was stirred at room temperature for 1.5 h. Formic acid was added to the mixture, which was then purified by reversed-phase chromatography (acetonitrile/water, 0.1% formic acid) to obtain the titled Compound 1o (3.38 g, yield 100%) as a white powder.

LC/MS mass spectrometry: m/z 419 ([M+H]$^+$).

LC/MS retention time: 0.83 min. (Analysis Condition: SQD-AA05-2).

Step 1-10

3-[(1S,2S)-1-[2-[2-(3,5-dimethylphenyl)-3-(2-oxo-1H-imidazol-3-yl)-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one (Compound 1p)

To a N,N'-dimethylformamide (DMF) (24.1 mL) solution of Compound 1g (1.25 g, 3.61 mmol) obtained in Step 1-4, Compound 1o (1.59 g, 3.80 mmol) obtained in Step 1-9, and [dimethylamino(triazolo[4,5-b]pyridin-3-yloxy)methylidene]-dimethylazanium hexafluorophosphate (1.51 g, 3.98 mmol) was added diisopropylethylamine (3.15 mL, 18.1 mmol), and the mixture was stirred at room temperature for 30 min. The reaction mixture was directly purified by reversed-phase column chromatography (acetonitrile/water, 0.1% formic acid) and the titled Compound 1p (2.44 g, yield 95%) was obtained as a light brown foam.

LC/MS mass spectrometry: m/z 710 ([M+H]$^+$).

LC/MS retention time: 0.85 min. (Analysis Condition: SMD-FA05-3).

Step 1-11

3-[(1S,2S)-1-[2-[2-(3,5-Dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one (Compound 1)

To a N-methylpyrrolidone (0.188 mL) suspension of Compound 1p (20 mg, 0.028 mmol) obtained in Step 1-10, 5-bromo-1-methylindazole (Compound 1q, 11.9 mg, 0.056 mmol), (1S,2S)-1-N,2-N-dimethylcyclohexane-1,2-diamine (1.6 mg, 0.011 mmol) and potassium carbonate (11.7 mg, 0.085 mmol) was added copper (I) iodide (1.1 mg, 0.0056 mmol) at room temperature, and the mixture was stirred under nitrogen atmosphere at 130° C. for 3 h. The reaction mixture was purified by reversed-phase silica gel chromatography (acetonitrile/water, 0.1% formic acid), and the titled Compound 1 (17.2 mg, yield 73%) was obtained as a light brown foam.

LC/MS mass spectrometry: m/z 840 ([M+H]$^+$).

LC/MS retention time: 1.12 min. (Analysis Condition: SMD-TFA05-3).

Examples 2 to 50

An operation similar to Step 1-11 of Example 1 was performed using a combination of the 2-oxoimidazole compound shown in Table 2-2 and the halogen compound shown in Table 2-3 below, as well as an appropriate reagent, and Example Compounds 2 to 50 shown in Table 2-1 were obtained by the following reaction.

[Chemical Formula 18]
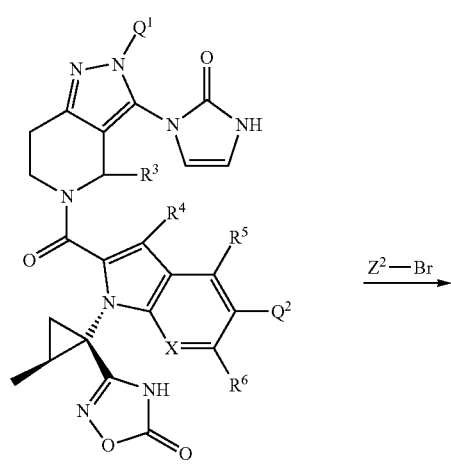
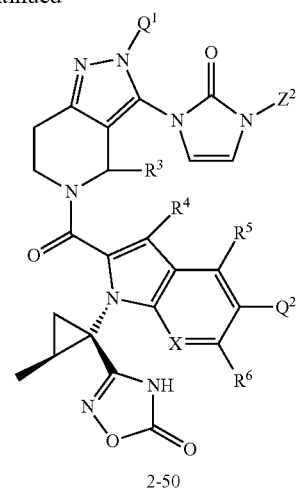
2-50
TABLE 2
The Obtained Example Compounds 2 to 50
| Example No. | Structure | Compound | Analysis Condition | LC/MS retention time (min.) | LC/MS mass spectrometry (m/z) |
|---|---|---|---|---|---|
| 2 | 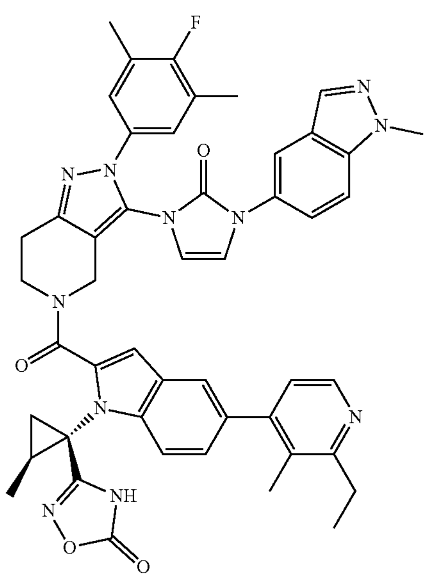 | 3-[(1S,2S)-1-[5-(2-ethyl-3-methylpyridin-4-yl)-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.15 | 858 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 3 | 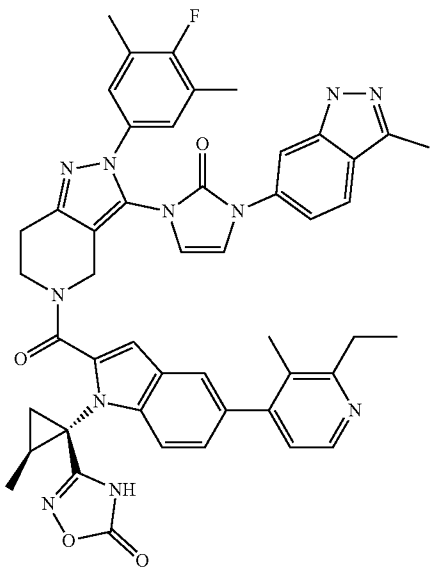 | 3-[(1S,2S)-1-[5-(2-ethyl-3-methylpyridin-4-yl)-2-[2-(4-fluoro-3,5-dimethylphenyl)-3-[3-(3-methyl-1,2-benzothiazol-6-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.22 | 875 ([M + H]+) |
| 4 | 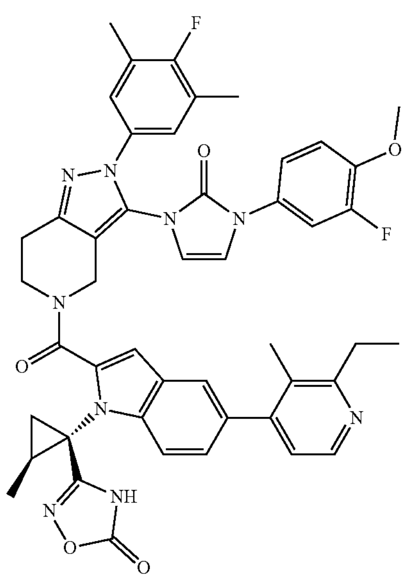 | 3-[(1S,2S)-1-[5-(2-ethyl-3-methylpyridin-4-yl)-2-[2-(4-fluoro-3,5-dimethylphenyl)-3-[3-(3-fluoro-4-methoxyphenyl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.21 | 852 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 5 | 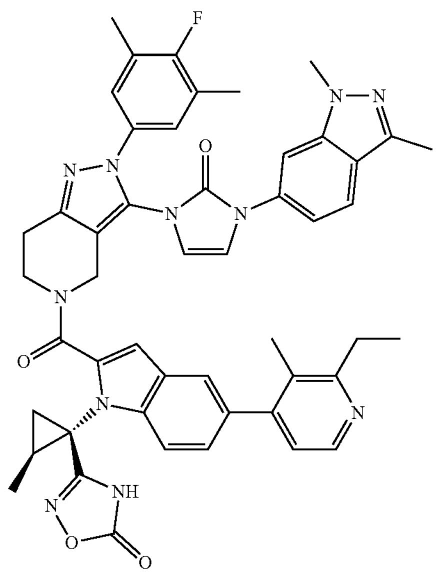 | 3-[(1S,2S)-1-[2-[3-[3-(1,3-dimethylindazol-6-yl)-2-oxoimidazol-1-yl]-2-(4-fluoro-3,5-dimethylphenyl)-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.18 | 872 ([M + H]+) |
| 6 | 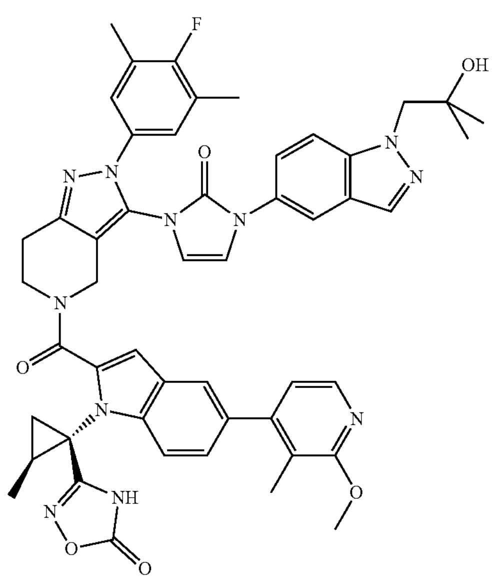 [SMILES: COc1nccc(-c2ccc3c(c2)cc(C(=O)N2CCc4nn(-c5cc(C)c(F)c(C)c5)c(-n5ccn(-c6ccc7c(cnn7CC(C)(C)O)c6)c5=O)c4C2)n3[C@@]2(c3noc(=O)[nH]3)C[C@@H]2C)c1C] | 3-[(1S,2S)-1-[2-[2-(4-fluoro-3,5-dimethylphenyl)-3-[1-(2-hydroxy-2-methylpropyl)indazol-5-yl]-2-oxoimidazol-1-yl]-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one | SMD-TFA05-2 | 1.40 | 919 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 7 | 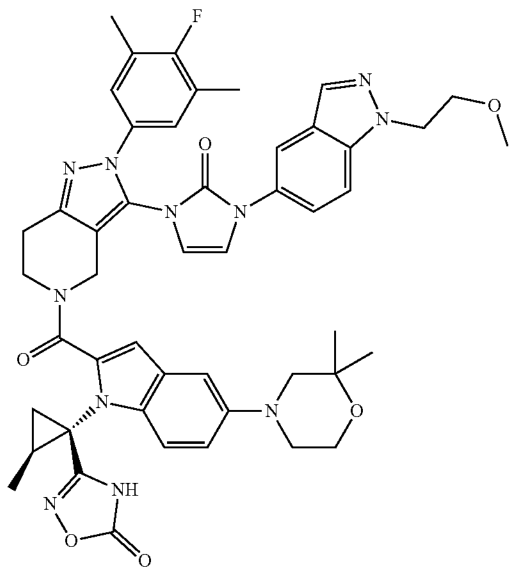 | 3-[(1S,2S)-1-[5-(2,2-dimethylmorpholin-4-yl)-2-[2-(4-fluoro-3,5-dimethylphenyl)-3-[3-[1-(2-methoxyethyl)indazol-5-yl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.32 | 896 ([M + H]$^+$) |
| 8 | 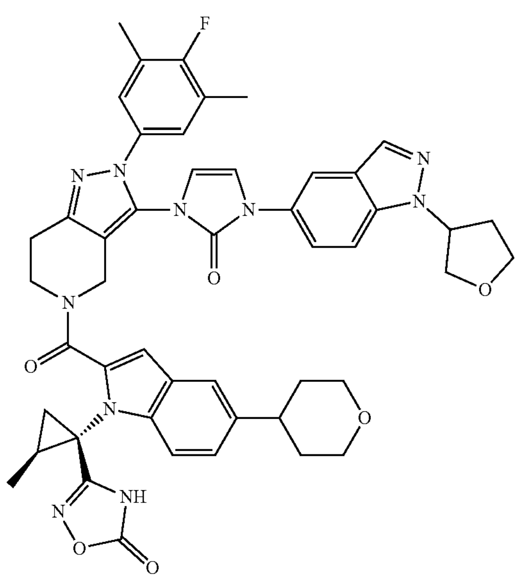 [SMILES: Cc1cc(-n2nc3c(c2-n2ccn(-c4ccc5c(cnn5C5CCOC5)c4)c2=O)CN(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-[2-oxo-3-[1-[(3R)-oxolan-3-yl]indazol-5-yl]imidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-2 | 1.38 | 879 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 9 | 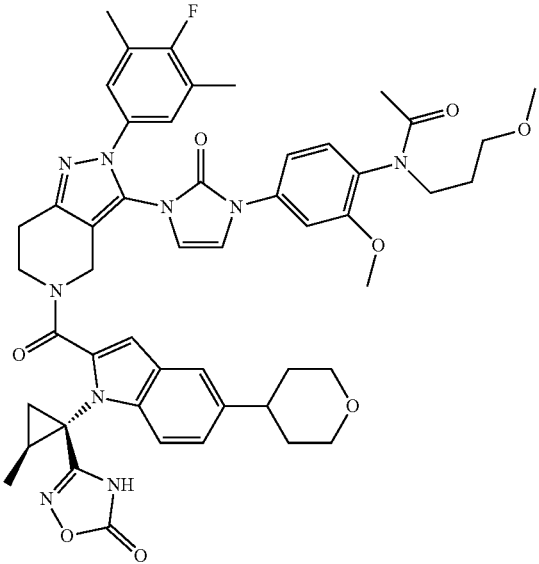 | N-[4-[3-[2-(4-fluoro-3,5-dimethylphenyl)-5-[1-[(1S,2S)-2-methyl-1-(5-oxo-4H-1,2,4-oxadiazol-3-yl)cyclopropyl]-5-(oxan-4-yl)indole-2-carbonyl]-6,7-dihydro-4H-pyrazolo[4,3-c]pyridin-3-yl]-2-oxoimidazol-1-yl]-2-methoxyphenyl]-N-(3-methoxypropyl)acetamide | SMD-TFA05-2 | 1.33 | 929 ([M + H]+) |
| 10 | 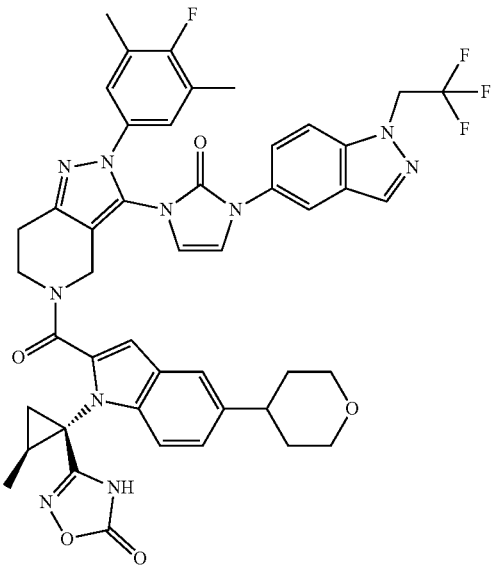 [SMILES: Cc1cc(-n2nc3c(c2-n2ccn(-c4ccc5c(cnn5CC(F)(F)F)c4)c2=O)CN(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-[2-oxo-3-[1-(2,2,2-trifluoroethyl)indazol-5-yl]imidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-2 | 1.47 | 891 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 11 | 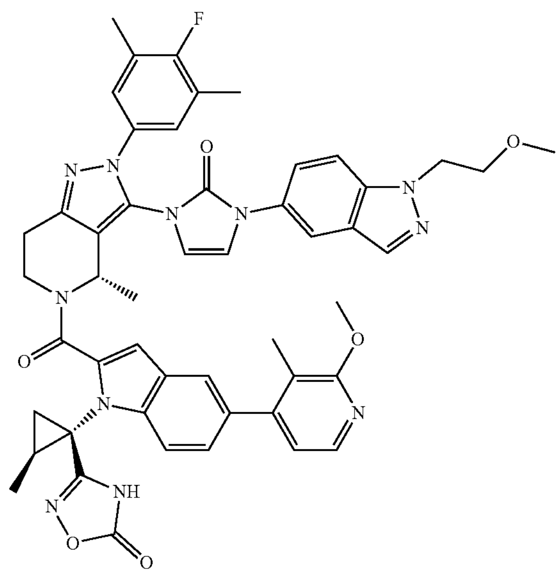 | 3-[(1S,2S)-1-[2-[(4S)-2-(4-fluoro-3,5-dimethylphenyl)-3-[3-[1-(2-methoxyethyl)indazol-5-yl]-2-oxoimidazol-1-yl]-4-methyl-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one | SMD-TFA05-2 | 1.49 | 919 ([M + H]$^+$) |
| 12 | 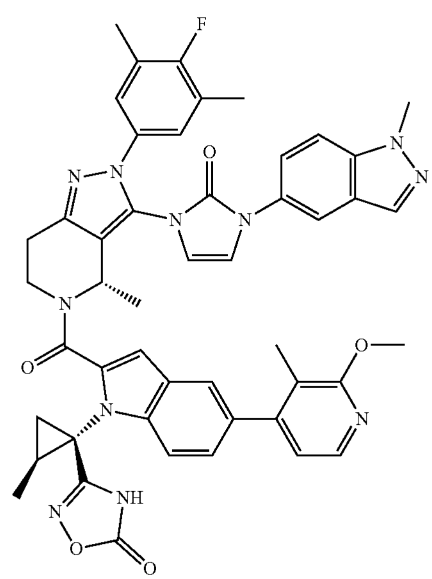 [SMILES: COc1nccc(-c2ccc3c(c2)cc(C(=O)N2CCc4nn(-c5cc(C)c(F)c(C)c5)c(-n5ccn(-c6ccc7c(cnn7C)c6)c5=O)c4[C@@H]2C)n3[C@@]2(c3noc(=O)[nH]3)C[C@@H]2C)c1C] | 3-[(1S,2S)-1-[2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one | SMD-TFA05-1 | 1.45 | 874 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 13 | 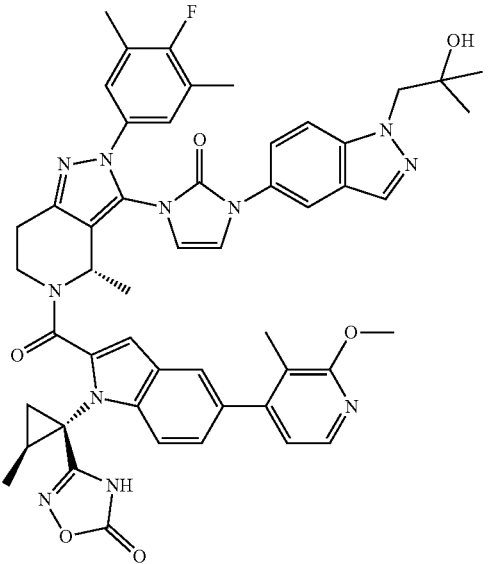 [SMILES: COc1nccc(-c2ccc3c(c2)cc(C(=O)N2CCc4nn(-c5cc(C)c(F)c(C)c5)c(-n5ccn(-c6ccc7c(cnn7CC(C)(C)O)c6)c5=O)c4[C@@H]2C)n3[C@@]2(c3noc(=O)[nH]3)C[C@@H]2C)c1C] | 3-[(1S,2S)-1-[2-[(4S)-2-(4-fluoro-3,5-dimethylphenyl)-3-[3-[1-(2-hydroxy-2-methylpropyl)indazol-5-yl]-2-oxoimidazol-1-yl]-4-methyl-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one | SMD-TFA05-1 | 1.42 | 932 ([M + H]$^+$) |
| 14 | 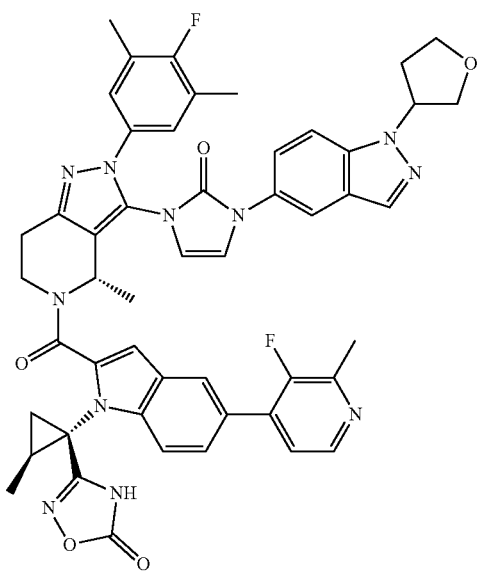 [SMILES: Cc1cc(-n2nc3c(c2-n2ccn(-c4ccc5c(cnn5C5CCOC5)c4)c2=O)[C@H](C)N(C(=O)c2cc4cc(-c5ccnc(C)c5F)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-4-methyl-3-[2-oxo-3-[1-[(3S)-oxolan-3-yl]indazol-5-yl]imidazol-1-yl]-6,7-dihydro-4H-pyrazolo[4,3-c]pyridine-5-carbonyl]-5-(3-fluoro-2-methylpyridin-4-yl)indol-1-yl]-2-methylcyclopropyl]-4H-1,2,4-oxadiazol-5-one | SMD-TFA05-1 | 1.15 | 918 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 15 | 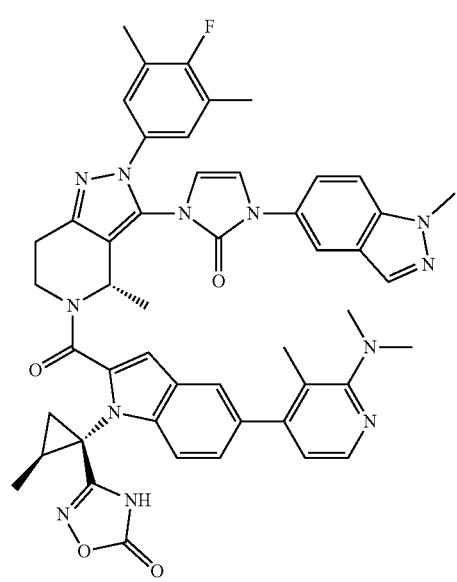 | 3-[(1S,2S)-1-[5-[2-(dimethylamino)-3-methylpyridin-4-yl]-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SQD-FA05-1 | 0.75 | 887 ([M + H]+) |
| 16 | 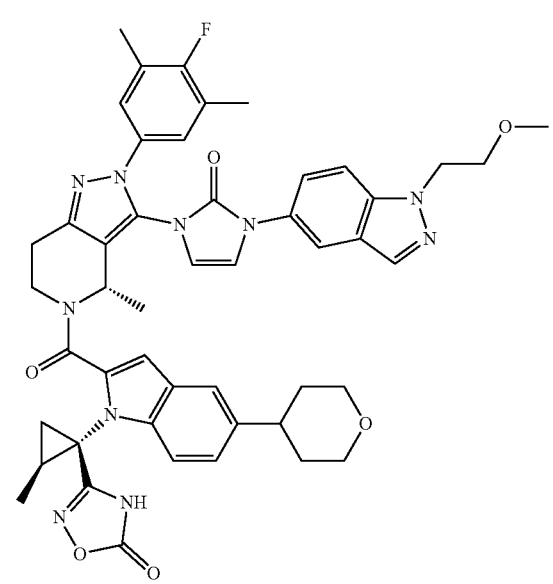 | 3-[(1S,2S)-1-[2-[(4S)-2-(4-fluoro-3,5-dimethylphenyl)-3-[3-[1-(2-methoxyethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-2 | 1.45 | 882 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 17 | 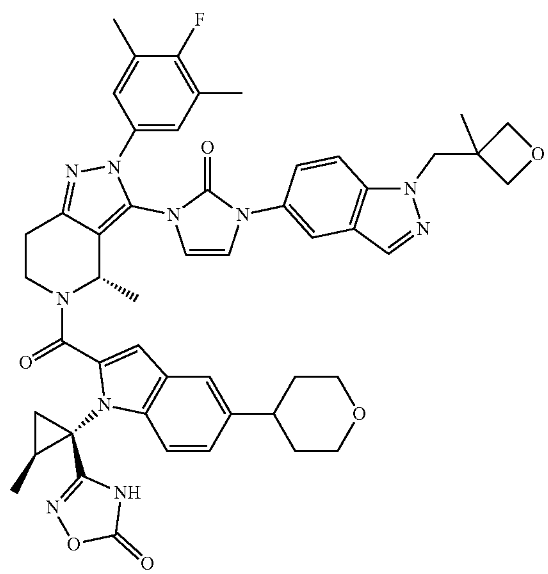 [SMILES: Cc1cc(-n2nc3c(c2-n2ccn(-c4ccc5c(cnn5CC5(C)COC5)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-4-methyl-3-[3-[1-[(3-methyloxetan-3-yl)methyl]indazol-5-yl]-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-2 | 1.45 | 908 ([M + H]$^+$) |
| 18 | 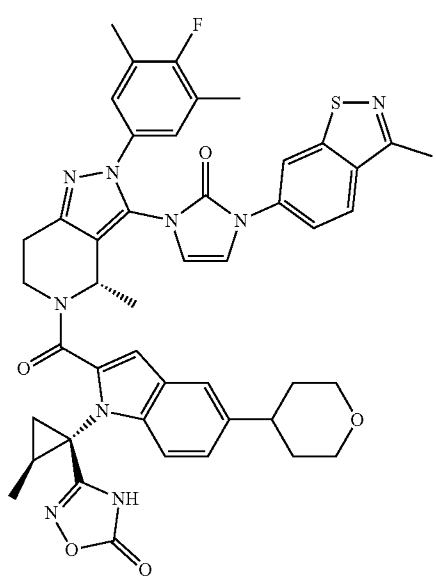 | 3-[(1S,2S)-1-[2-[(4S)-2-(4-fluoro-3,5-dimethylphenyl)-4-methyl-3-[3-(3-methyl-1,2-benzothiazol-6-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.50 | 854 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 19 | 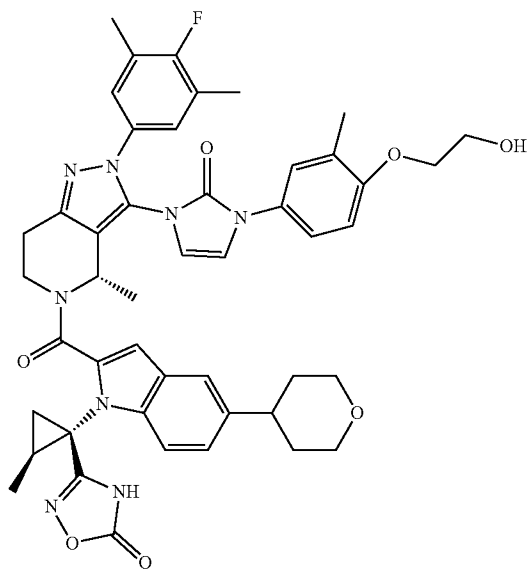 [SMILES: Cc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)ccc1OCCO] | 3-[(1S,2S)-1-[2-[(4S)-2-(4-fluoro-3,5-dimethylphenyl)-3-[3-[4-(2-hydroxyethoxy)-3-methylphenyl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.36 | 857 ([M + H]$^+$) |
| 20 | 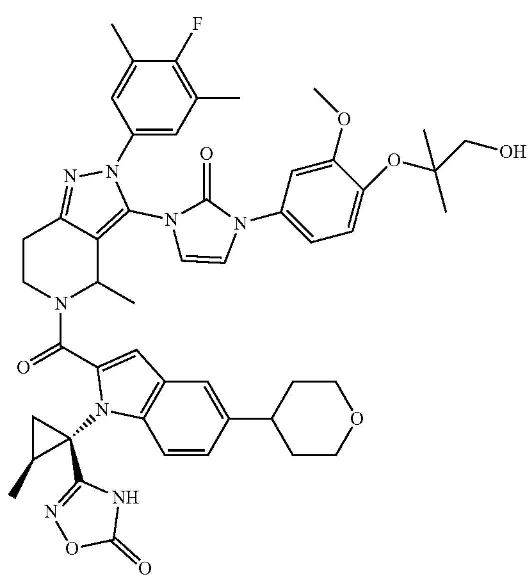 [SMILES: COc1cc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)C4C)c2=O)ccc1OC(C)(C)CO] | 3-[(1S,2S)-1-[2-[(4S)-2-(4-fluoro-3,5-dimethylphenyl)-3-[3-[4-(1-hydroxy-2-methylpropan-2-yl)oxy-3-methoxyphenyl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.40 | 901 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 21 | 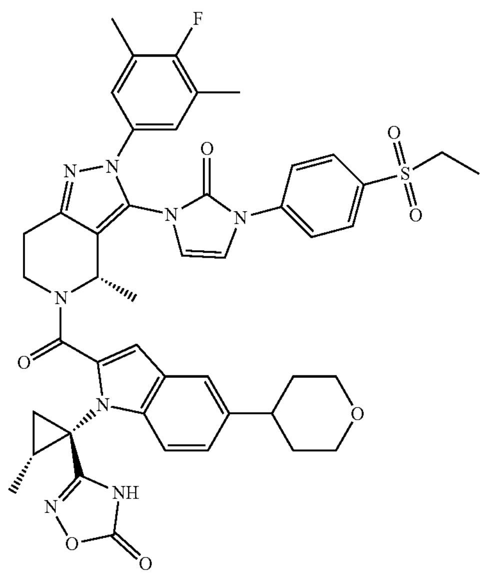 [SMILES: CCS(=O)(=O)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@H]3C)[C@H]4C)c2=O)cc1] | 3-[(1S,2S)-1-[2-[(4S)-3-[3-(4-ethylsulfonylphenyl)-2-oxoimidazol-1-yl]-2-(4-fluoro-3,5-dimethylphenyl)-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.37 | 875 ([M + H]$^+$) |
| 22 | 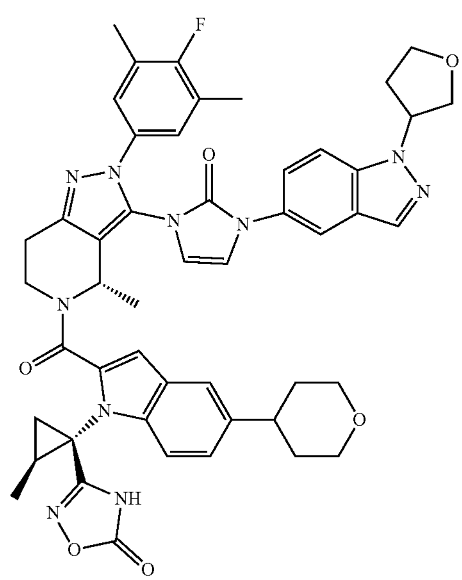 [SMILES: Cc1cc(-n2nc3c(c2-n2ccn(-c4ccc5c(cnn5C5CCOC5)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-4-methyl-3-[2-oxo-3-[1-[(3S)-oxolan-3-yl]indazol-5-yl]imidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.40 | 893 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 23 | 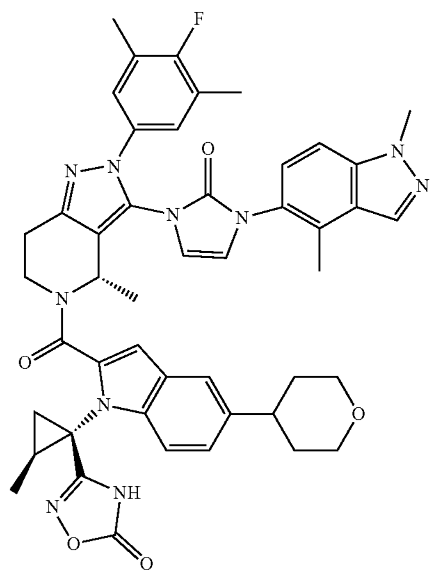 | 3-[(1S,2S)-1-[2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.41 | 855 ([M + H]$^+$) |
| 24 | 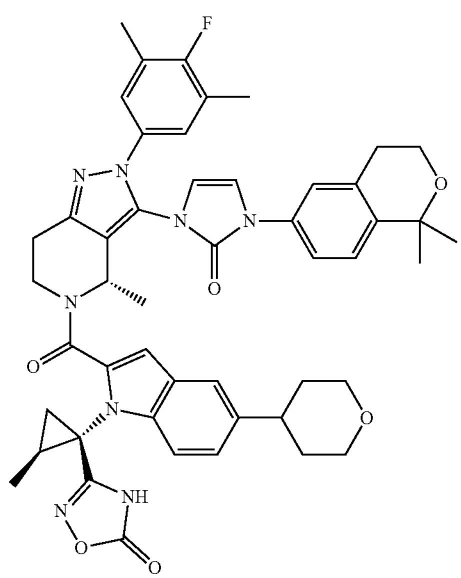 | 3-[(1S,2S)-1-[2-[(4S)-3-[3-(1,1-dimethyl-3,4-dihydroisochromen-6-yl)-2-oxoimidazol-1-yl]-2-(4-fluoro-3,5-dimethylphenyl)-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.52 | 867 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 25 | 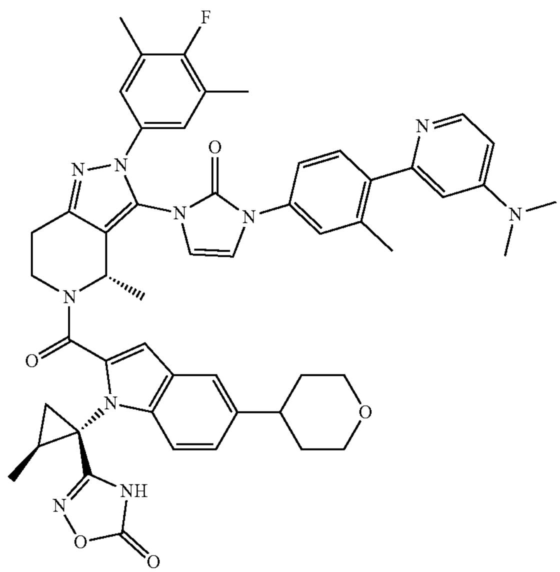 | 3-[(1S,2S)-1-[2-[(4S)-3-[3-[4-[6-(dimethylamino)pyrimidin-4-yl]-3-methylphenyl]-2-oxoimidazol-1-yl]-2-(4-fluoro-3,5-dimethylphenyl)-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.12 | 918 ([M + H]$^+$) |
| 26 | 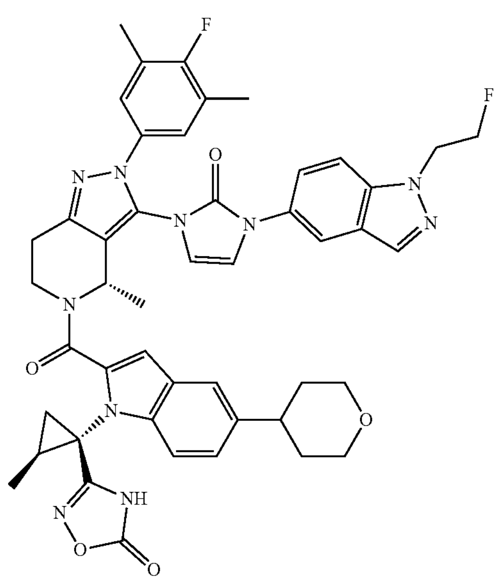 [SMILES: Cc1cc(-n2nc3c(c2-n2ccn(-c4ccc5c(cnn5CCF)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-3-[3-[1-(2-fluoroethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.39 | 869 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 27 | 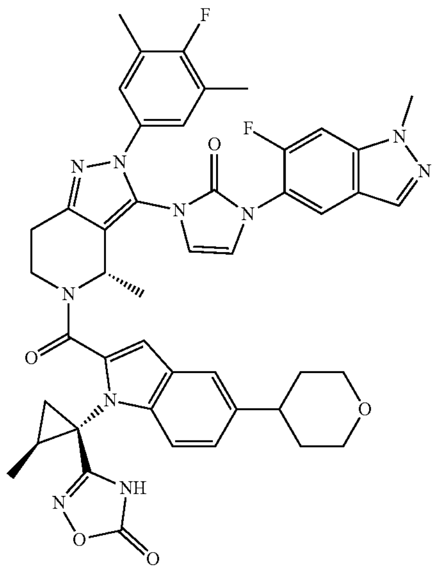 [SMILES: Cc1cc(-n2nc3c(c2-n2ccn(-c4cc5cnn(C)c5cc4F)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-3-[3-(6-fluoro-1-methylindazol-5-yl)-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.39 | 855 ([M + H]$^+$) |
| 28 | 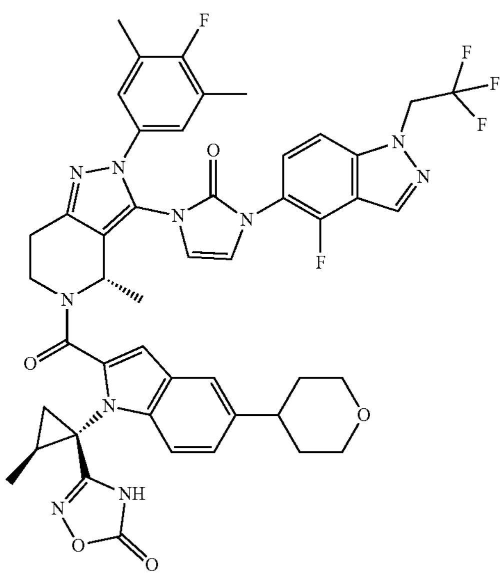 [SMILES: Cc1cc(-n2nc3c(c2-n2ccn(-c4ccc5c(cnn5CC(F)(F)F)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-3-[3-[4-fluoro-1-(2,2,2-trifluoroethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.44 | 923 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 29 | 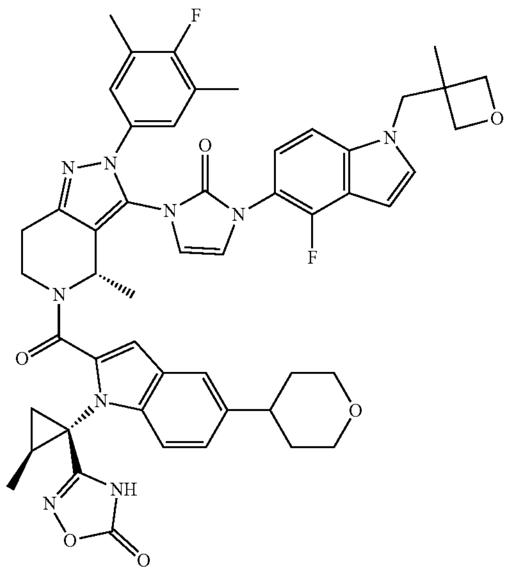 [SMILES: Cc1cc(-n2nc3c(c2-n2ccn(-c4ccc5c(ccn5CC5(C)COC5)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-3-[3-[4-fluoro-1-[(3-methyloxetan-3-yl)methyl]indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.40 | 925 ([M + H]+) |
| 30 | 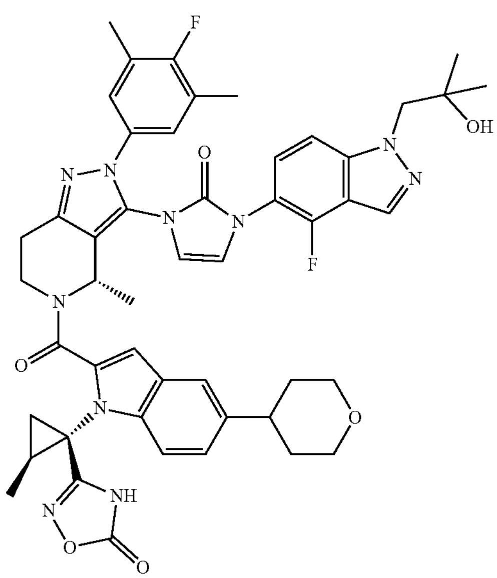 [SMILES: Cc1cc(-n2nc3c(c2-n2ccn(-c4ccc5c(cnn5CC(C)(C)O)c4F)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-3-[3-[4-fluoro-1-(2-hydroxy-2-methylpropyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.36 | 913 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 31 | 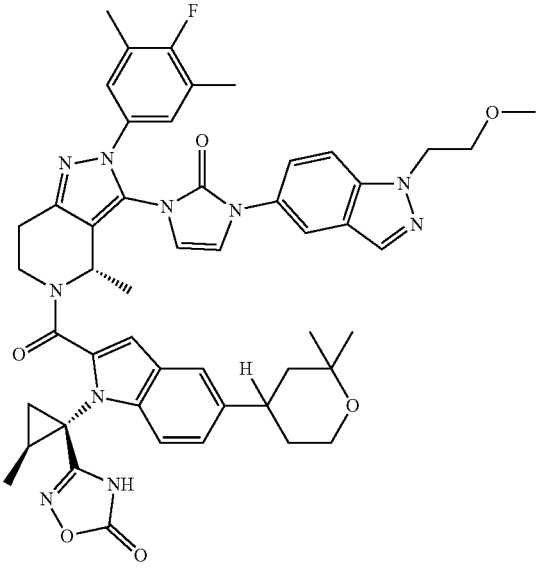 | 3-[(1S,2S)-1-[5-[(4S)-2,2-dimethyloxan-4-yl]-2-[(4S)-2-(4-fluoro-3,5-dimethylphenyl)-3-[3-[1-(2-methoxyethyl)indazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-2 | 1.48 | 909 ([M + H]+) |
| 32 | 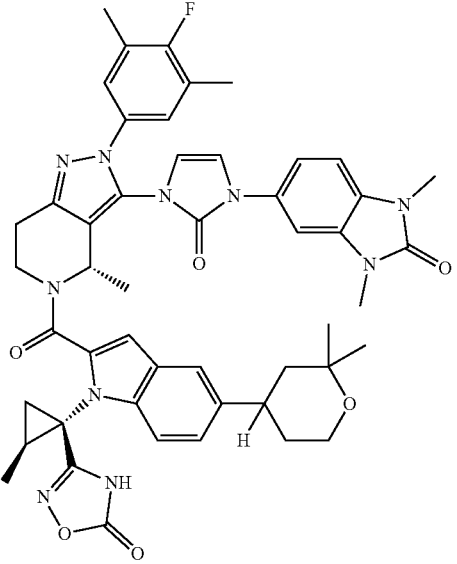 [SMILES: Cc1cc(-n2nc3c(c2-n2ccn(-c4ccc5c(c4)n(C)c(=O)n5C)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 3-[(1S,2S)-1-[5-[(4S)-2,2-dimethyloxan-4-yl]-2-[(4S)-3-[3-(1,3-dimethyl-2-oxobenzoimidazol-5-yl)-2-oxoimidazol-1-yl]-2-(4-fluoro-3,5-dimethylphenyl)-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.39 | 895 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 33 | 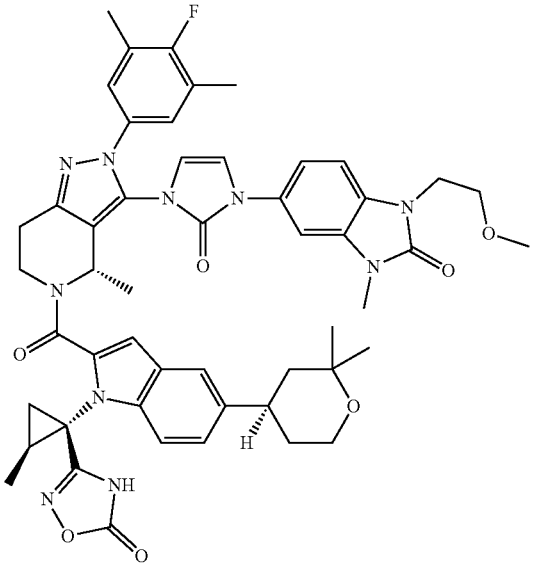 | 3-[(1S,2S)-1-[5-[(4S)-2,2-dimethyloxan-4-yl]-2-[(4S)-2-(4-fluoro-3,5-dimethylphenyl)-3-[3-[1-(2-methoxyethyl)-3-methyl-2-oxobenzoimidazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.41 | 939 ([M + H]$^+$) |
| 34 | 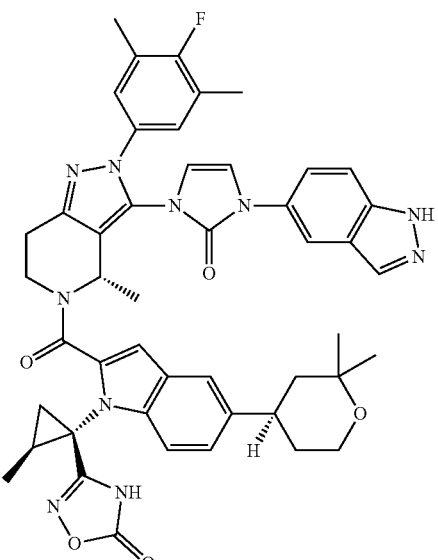 | 3-[(1S,2S)-1-[5-[(4S)-2,2-dimethyloxan-4-yl]-2-[(4S)-2-(4-fluoro-3,5-dimethylphenyl)-3-[3-(1H-indazol-5-yl)-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.37 | 851 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 35 | 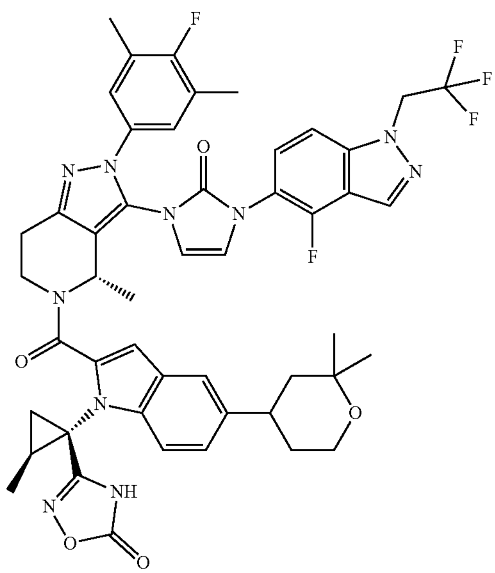 [SMILES: Cc1cc(-n2nc3c(c2-n2ccn(-c4ccc5c(cnn5CC(F)(F)F)c4F)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 3-[(1S,2S)-1-[5-[(4S)-2,2-dimethyloxan-4-yl]-2-[(4S)-2-(4-fluoro-3,5-dimethylphenyl)-3-[3-[4-fluoro-1-(2,2,2-trifluoroethyl)indazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.51 | 951 ([M + H]+) |
| 36 | 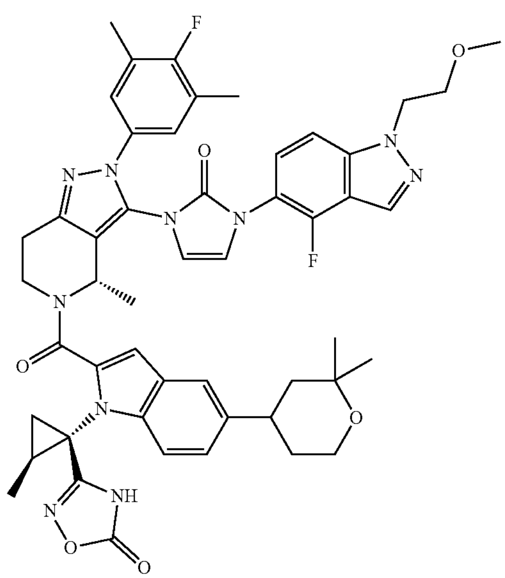 | 3-[(1S,2S)-1-[5-[(4S)-2,2-dimethyloxan-4-yl]-2-[(4S)-2-(4-fluoro-3,5-dimethylphenyl)-3-[3-[4-fluoro-1-(2-methoxyethyl)indazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.46 | 927 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 37 | 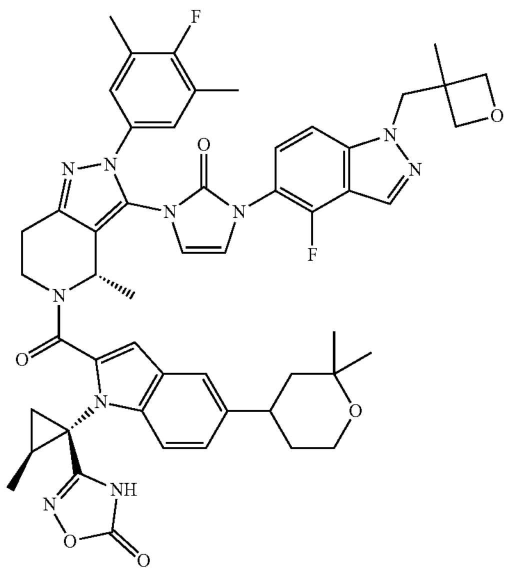 [SMILES: Cc1cc(-n2nc3c(c2-n2ccn(-c4ccc5c(cnn5CC5(C)COC5)c4F)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 3-[(1S,2S)-1-[5-[(4S)-2,2-dimethyloxan-4-yl]-2-[(4S)-2-(4-fluoro-3,5-dimethylphenyl)-3-[3-[4-fluoro-1-[(3-methyloxetan-3-yl)methyl]indazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.46 | 953 ([M + H]$^+$) |
| 38 | 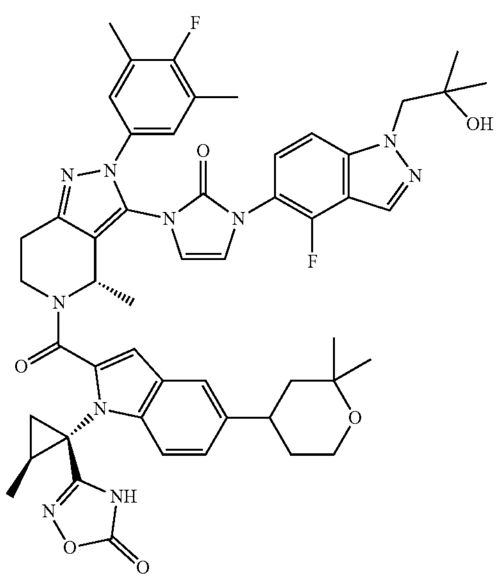 [SMILES: Cc1cc(-n2nc3c(c2-n2ccn(-c4ccc5c(cnn5CC(C)(C)O)c4F)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 3-[(1S,2S)-1-[5-[(4S)-2,2-dimethyloxan-4-yl]-2-[(4S)-2-(4-fluoro-3,5-dimethylphenyl)-3-[3-[4-fluoro-1-(2-hydroxy-2-methylpropyl)indazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.42 | 941 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 39 | 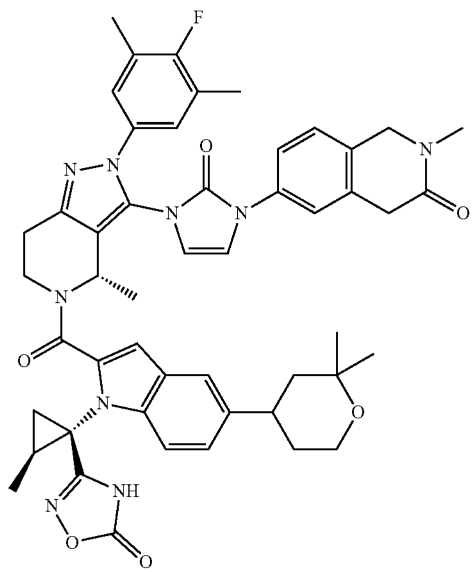 [SMILES: Cc1cc(-n2nc3c(c2-n2ccn(-c4ccc5c(c4)CC(=O)N(C)C5)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 3-[(1S,2S)-1-[5-[(4S)-2,2-dimethyloxan-4-yl]-2-[(4S)-2-(4-fluoro-3,5-dimethylphenyl)-4-methyl-3-[3-(2-methyl-3-oxo-1,4-dihydroisoquinolin-6-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.33 | 894 ([M + H]$^+$) |
| 40 | 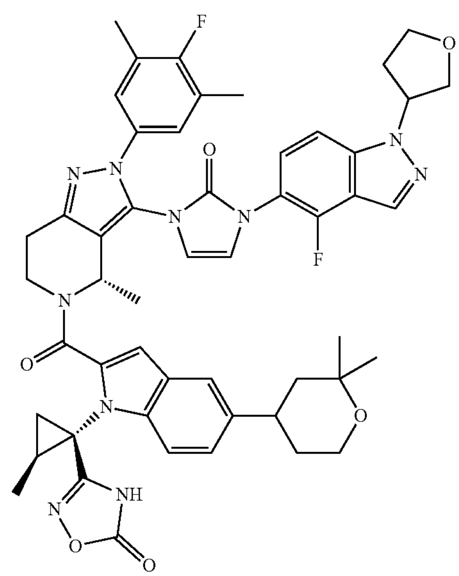 [SMILES: Cc1cc(-n2nc3c(c2-n2ccn(-c4ccc5c(cnn5C5CCOC5)c4F)c2=O)[C@H](C)N(C(=O)c2cc4cc(C5CCOC(C)(C)C5)ccc4n2[C@@]2(c4noc(=O)[nH]4)C[C@@H]2C)CC3)cc(C)c1F] | 3-[(1S,2S)-1-[5-[(4S)-2,2-dimethyloxan-4-yl]-2-[(4S)-2-(4-fluoro-3,5-dimethylphenyl)-3-[3-[4-fluoro-1-[(3S)-oxolan-3-yl]indazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.46 | 939 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 41 | 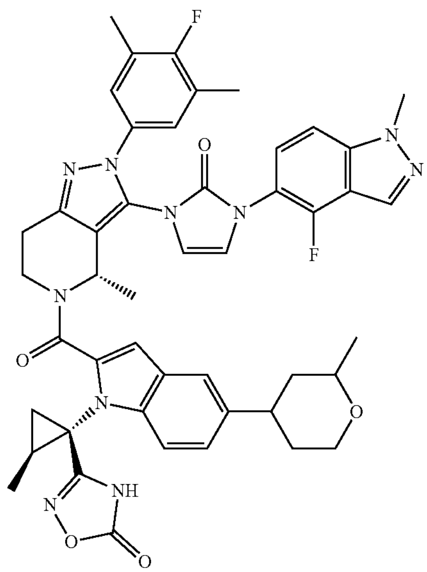 [SMILES: Cc1cc(-n2nc3c(c2-n2ccn(-c4ccc5c(cnn5C)c4F)c2=O)[C@H](C)N(C(=O)c2cc4cc(C5CCOC(C)C5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl]-5-[(2S,4S)-2-methyloxan-4-yl]indol-1-yl]-2-methylcyclopropyl]-4H-1,2,4-oxadiazol-5-one | SMD-TFA05-1 | 1.44 | 869 ([M + H]$^+$) |
| 42 | 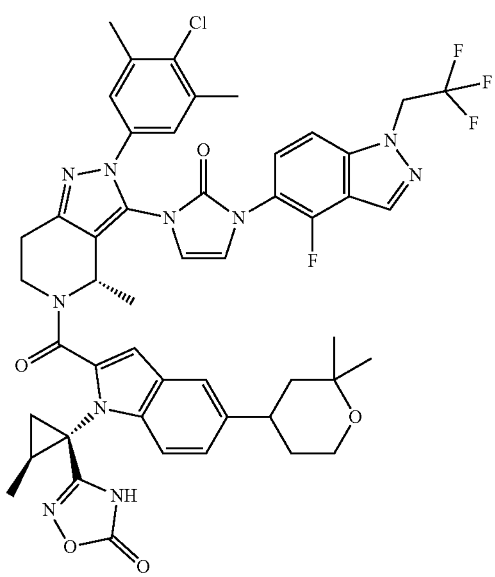 | 3-[(1S,2S)-1-[2-[(4S)-2-(4-chloro-3,5-dimethylphenyl)-3-[3-[4-fluoro-1-(2,2,2-trifluoroethyl)indazol-5-yl]-2-oxoimidazol-1-yl]-4-methyl-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-TFA05-1 | 1.56 | 967 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 43 | 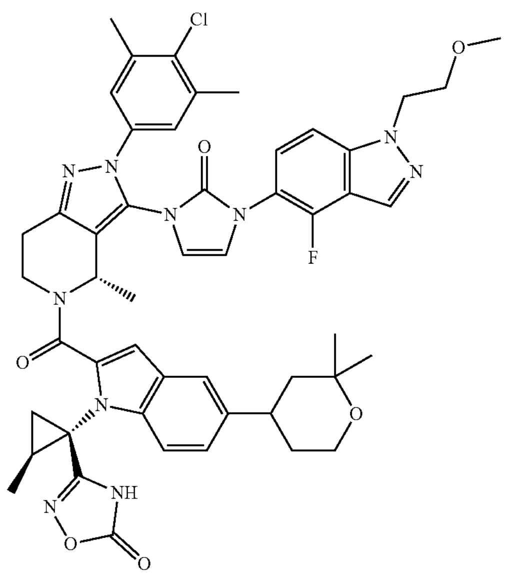 | 3-[(1S,2S)-1-[2-[(4S)-2-(4-chloro-3,5-dimethylphenyl)-3-[3-[4-fluoro-1-(2-methoxyethyl)indazol-5-yl]-2-oxoimidazol-1-yl]-4-methyl-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-TFA05-1 | 1.53 | 943 ([M + H]+) |
| 44 | 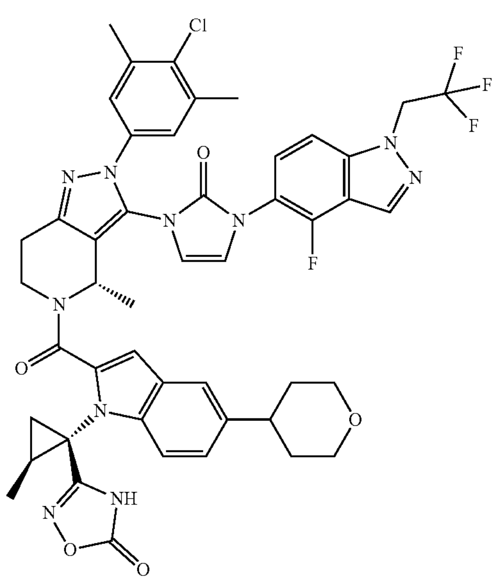 [SMILES: Cc1cc(-n2nc3c(c2-n2ccn(-c4ccc5c(cnn5CC(F)(F)F)c4F)c2=O)[C@H](C)N(C(=O)c2cc4cc(C5CCOCC5)ccc4n2[C@@]2(c4noc(=O)[nH]4)C[C@@H]2C)CC3)cc(C)c1Cl] | 3-[(1S,2S)-1-[2-[(4S)-2-(4-chloro-3,5-dimethylphenyl)-3-[3-[4-fluoro-1-(2,2,2-trifluoroethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.50 | 939 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 45 | 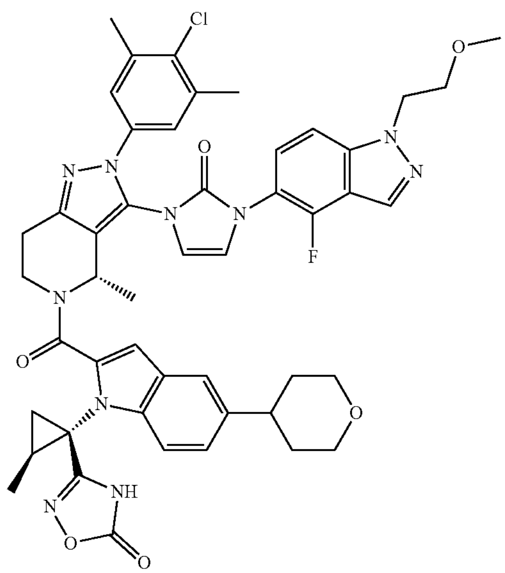 | 3-[(1S,2S)-1-[2-[(4S)-2-(4-chloro-3,5-dimethylphenyl)-3-[3-[4-fluoro-1-(2-methoxyethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.46 | 915 ([M + H]+) |
| 46 | 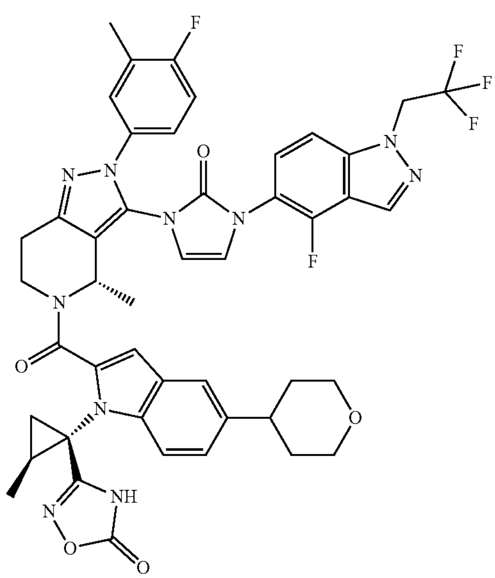 [SMILES: Cc1cc(-n2nc3c(c2-n2ccn(-c4ccc5c(cnn5CC(F)(F)F)c4F)c2=O)[C@H](C)N(C(=O)c2cc4cc(C5CCOCC5)ccc4n2[C@@]2(c4noc(=O)[nH]4)C[C@@H]2C)CC3)ccc1F] | 3-[(1S,2S)-1-[2-[(4S)-2-(4-fluoro-3-methylphenyl)-3-[3-[4-fluoro-1-(2,2,2-trifluoroethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.39 | 909 ([M + H]+) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 47 | 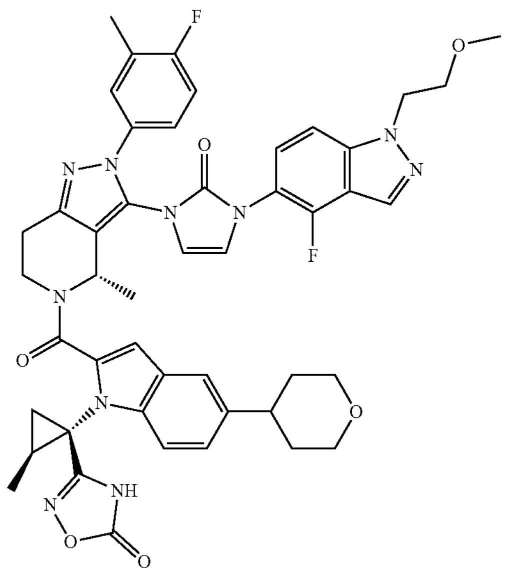 | 3-[(1S,2S)-1-[2-[(4S)-3-[3-[4-fluoro-1-(2-methoxyethyl)indazol-5-yl]-2-oxoimidazol-1-yl]-2-(4-fluoro-3-methylphenyl)-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.34 | 885 ([M + H]$^+$) |
| 48 | 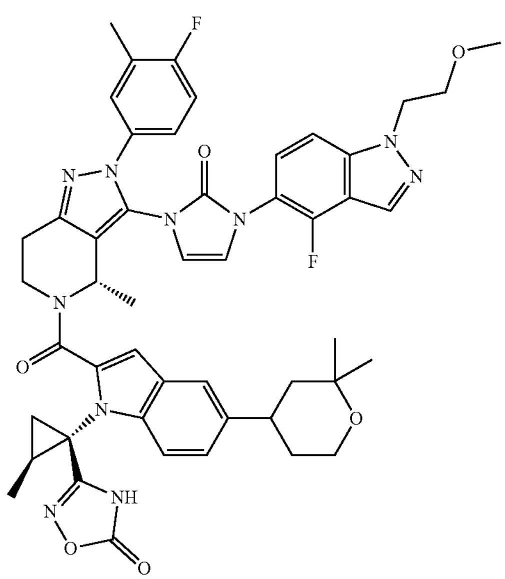 | 3-[(1S,2S)-1-[5-[(4S)-2,2-dimethyloxan-4-yl]-2-[(4S)-3-[3-[4-fluoro-1-(2-methoxyethyl)indazol-5-yl]-2-oxoimidazol-1-yl]-2-(4-fluoro-3-methylphenyl)-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.41 | 913 ([M + H]$^+$) |

TABLE 2-continued

The Obtained Example Compounds 2 to 50

| Example No. | Structure | Compound | Analysis Condition | LC/MS retention time (min.) | LC/MS mass spectrometry (m/z) |
|---|---|---|---|---|---|
| 49 | 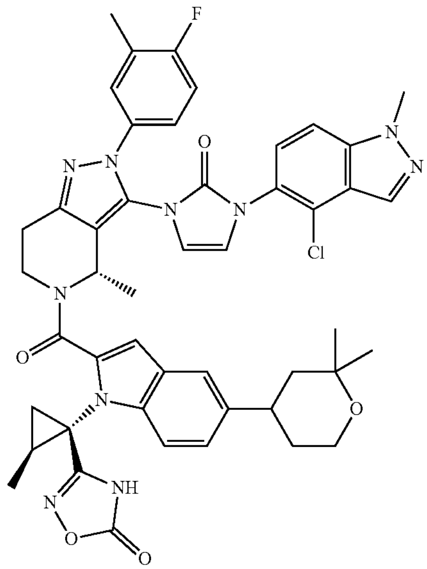 [SMILES: Cc1cc(-n2nc3c(c2-n2ccn(-c4ccc5c(cnn5C)c4Cl)c2=O)[C@H](C)N(C(=O)c2cc4cc(C5CCOC(C)(C)C5)ccc4n2[C@@]2(c4noc(=O)[nH]4)C[C@@H]2C)CC3)ccc1F] | 3-[(1S,2S)-1-[2-[(4S)-3-[3-(4-chloro-1-methylindazol-5-yl)-2-oxoimidazol-1-yl]-2-(4-fluoro-3-methylphenyl)-4-methyl-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-TFA05-1 | 1.42 | 885 ([M + H]$^+$) |
| 50 | 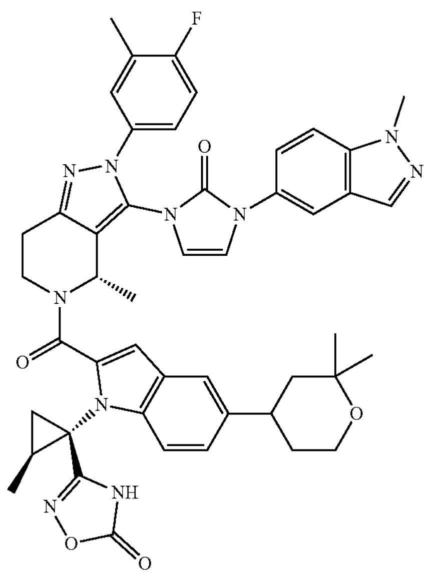 [SMILES: Cc1cc(-n2nc3c(c2-n2ccn(-c4ccc5c(cnn5C)c4)c2=O)[C@H](C)N(C(=O)c2cc4cc(C5CCOC(C)(C)C5)ccc4n2[C@@]2(c4noc(=O)[nH]4)C[C@@H]2C)CC3)ccc1F] | 3-[(1S,2S)-1-[5-[(4S)-2,2-dimethyloxan-4-yl]-2-[(4S)-2-(4-fluoro-3-methylphenyl)-4-methyl-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.37 | 851 ([M + H]$^+$) |

The compounds in Table 2-1 have rotational isomers, and by way of example, the $^1$H-NMR of Example 2 compound is shown below.

Rotational Isomer A $^1$H-NMR (600 MHz, CDCl$_3$) δ: 11.29 (1H, s), 8.40 (1H, d, J=5.2 Hz), 7.93 (1H, s), 7.74 (1H, d, J=1.5 Hz), 7.70 (1H, d, J=8.6 Hz), 7.56 (1H, s), 7.45 (1H, dd, J=9.0, 1.5 Hz), 7.38 (1H, d, J=9.0 Hz), 7.28 (1H, m), 7.14 (1H, d, J=5.2 Hz), 7.04 (2H, d, JH$_F$=5.9 Hz), 6.82 (1H, s), 6.59 (1H, d, J=3.0 Hz), 6.08 (1H, d, J=3.0 Hz), 4.96 (1H, d, J=16.0 Hz), 4.92 (1H, d, J=16.0 Hz), 4.69 (1H, ddd, J=13.1, 4.4, 4.4 Hz), 4.06 (3H, s), 3.75 (1H, ddd, J=13.1, 9.5, 5.0 Hz), 3.07 (2H, m), 2.97 (2H, q, J=7.6 Hz), 2.26 (3H, s), 2.25 (6H, s), 1.88 (1H, s), 1.51 (2H, m), 1.37 (3H, t, J=7.6 Hz), 1.17 (3H, d, J=5.6 Hz).

Rotational Isomer B $^1$H-NMR (600 MHz, CDCl$_3$) δ: 11.29 (1H, s), 8.44 (1H, d, J=5.2 Hz), 8.04 (1H, s), 7.90 (1H, d, J=1.4 Hz), 7.73 (1H, d, J=8.8 Hz), 7.63 (1H, dd, J=9.0, 1.4 Hz), 7.60 (1H, s), 7.51 (1H, d, J=9.0 Hz), 7.30 (1H, m), 7.20 (1H, d, J=5.2 Hz), 7.11 (2H, d, J$_{HF}$=6.0 Hz), 6.81 (1H, s), 6.71 (1H, d, J=3.0 Hz), 6.22 (1H, d, J=3.0 Hz), 5.24 (1H, d, J=16.3 Hz), 4.64 (1H, d, J=16.3 Hz), 4.45 (1H, ddd, J=13.5, 4.6, 4.0 Hz), 4.12 (3H, s), 3.87 (1H, ddd, J=13.5, 10.2, 3.8 Hz), 3.17 (1H, ddd, J=15.5, 10.2, 4.6 Hz), 3.02 (1H, m), 3.00 (2H, q, J=7.6 Hz), 2.30 (3H, s), 2.28 (6H, s), 1.96 (1H, dd, J=6.0 Hz), 1.64 (1H, m), 1.58 (1H, dd, J=9.4, 6.0 Hz), 1.39 (3H, t, J=7.6 Hz), 1.19 (3H, d, J 6.1 Hz).

TABLE 2-2

| Example No. | 2-Oxoimidazole compound | Compound | Analysis Condition | LC/MS retention time (min.) | LC/MS mass spectrometry (m/z) |
|---|---|---|---|---|---|
| 2-5 (Compound 2g) | | 3-[(1S,2S)-1-[5-(2-ethyl-3-methylpyridin-4-yl)-2-[2-(4-fluoro-3,5-dimethylphenyl)-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one | SMD-FA05-3 | 0.86 | 728 ([M + H]⁺) |
| 6 (Compound 6i) | | 3-[(1S,2S)-1-[2-[2-(4-fluoro-3,5-dimethylphenyl)-3-(2-oxo-1H-imidazol-3-yl)-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one | SMD-FA05-2 | 1.33 | 730 ([M + H]⁺) |

TABLE 2-2-continued

| | 2-Oxoimidazole compound that was used | | | | |
|---|---|---|---|---|---|
| Example No. | 2-Oxoimidazole compound | Compound | Analysis Condition | LC/MS retention time (min.) | LC/MS mass spectrometry (m/z) |
| 7 (Compound 7c) | 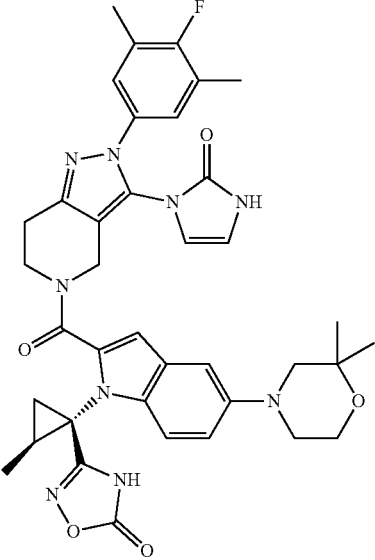 | 3-[(1S,2S)-1-[5-(2,2-dimethylmorpholin-4-yl)-2-[2-(4-fluoro-3,5-dimethylphenyl)-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one | SMD-FA05-3 | 1.22 | 722 ([M + H]⁺) |
| 8-10 (Compound 8c) | 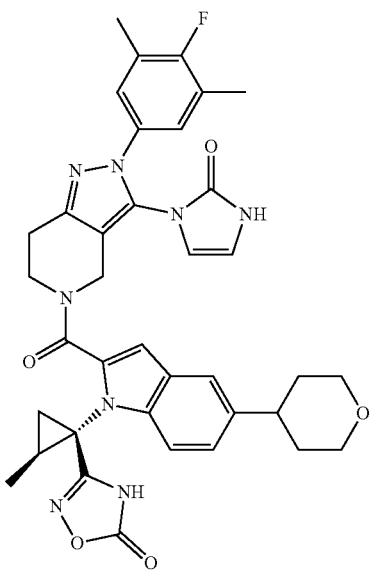 [SMILES: Cc1cc(-n2nc3c(c2-n2cc[nH]c2=O)CN(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-FA05-1 | 1.19 | 693 ([M + H]⁺) |

TABLE 2-2-continued

| | 2-Oxoimidazole compound that was used | | | | |
|---|---|---|---|---|---|
| Example No. | 2-Oxoimidazole compound | Compound | Analysis Condition | LC/MS retention time (min.) | LC/MS mass spectrometry (m/z) |
| 11-13 (Compound 11m) | | 3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one | SMD-FA05-1 | 1.33 | 744 ([M + H]+) |
| 14 (Compound 14d) | | 3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(3-fluoro-2-methylpyridin-4-yl)indol-1-yl]-2-methylcyclopropyl]-4H-1,2,4-oxadiazol-5-one | SMD-FA05-1 | 1.15 | 732 ([M + H]+) |

TABLE 2-2-continued

| Example No. | 2-Oxoimidazole compound | Compound | Analysis Condition | LC/MS retention time (min.) | LC/MS mass spectrometry (m/z) |
|---|---|---|---|---|---|
| 15 (Compound 15d) | | 3-[(1S,2S)-1-[5-[2-(dimethylamino)-3-methylpyridin-4-yl]-2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one | SQD-FA05-1 | 0.67 | 757 ([M + H]⁺) |
| 16-30 (Compound 16a) | | 3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-FA05-1 | 1.21 | 707 ([M + H]⁺) |

TABLE 2-2-continued

| Example No. | 2-Oxoimidazole compound | Compound | Analysis Condition | LC/MS retention time (min.) | LC/MS mass spectrometry (m/z) |
|---|---|---|---|---|---|
| 31-40 (Compound 311) | | 3-[(1S,2S)-1-[5-[(4S)-2,2-dimethyloxan-4-yl]-2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one | SMD-FA05-1 | 1.29 | 735 ([M + H]$^+$) |
| 41 (Compound 41f) | | 3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-[(2S,4S)-2-methyloxan-4-yl]indol-1-yl]-2-methylcyclopropyl]-4H-1,2,4-oxadiazol-5-one | SQD-FA05-1 | 0.96 | 722 ([M + H]$^+$) |

TABLE 2-2-continued

| | 2-Oxoimidazole compound that was used | | | | |
|---|---|---|---|---|---|
| Example No. | 2-Oxoimidazole compound | Compound | Analysis Condition | LC/MS retention time (min.) | LC/MS mass spectrometry (m/z) |
| 42-43 (Compound 42g) | | 3-[(1S,2S)-1-[2-[(4S)-2-(4-chloro-3,5-dimethylphenyl)-4-methyl-3-(2-oxo-1H-imidazol-3-yl)-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-FA05-1 | 1.34 | 751 ([M + H]+) |
| 44-45 (Compound 44a) | | 3-[(1S,2S)-1-[2-[(4S)-2-(4-chloro-3,5-dimethylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-FA05-1 | 1.27 | 723 ([M + H]+) |

TABLE 2-2-continued

| | 2-Oxoimidazole compound that was used | | | | |
|---|---|---|---|---|---|
| Example No. | 2-Oxoimidazole compound | Compound | Analysis Condition | LC/MS retention time (min.) | LC/MS mass spectrometry (m/z) |
| 46-47 (Compound 46f) | | 3-[(1S,2S)-1-[2-[(4S)-2-(4-fluoro-3-methylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-FA05-1 | 1.16 | 693 ([M + H]$^+$) |
| 48-50 (Compound 48a) | | 3-[(1S,2S)-1-[5-[(4S)-2,2-dimethyloxan-4-yl]-2-[(4S)-2-(4-fluoro-3-methylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one | SMD-FA05-1 | 1.24 | 721 ([M + H]$^+$) |

TABLE 2-3

| Halogen compound that was used | |
|---|---|
| Example No. | Halogen compound |
| 2, 12, 15, 50 | 5-bromo-1-methyl-1H-indazole |
| 3, 18 | 6-bromo-3-methyl-1,2-benzisothiazole |

TABLE 2-3-continued
Halogen compound that was used
| Example No. | Halogen compound |
|---|---|
| 4 | 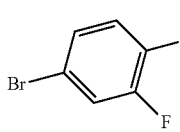 |
| 5 | 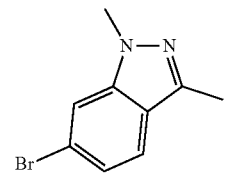 |
| 6, 13 | 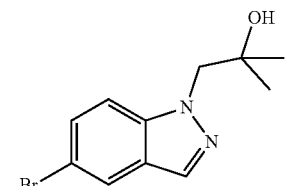 |
| 7, 11, 16, 31 | 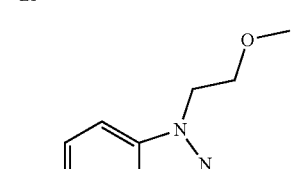 |
| 8 | 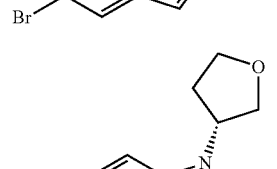 |
| 9 | 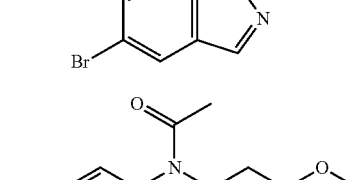 |
| 10 | 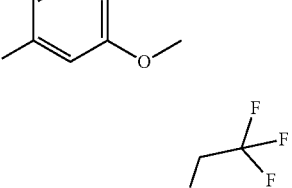 |
| 14, 22 | 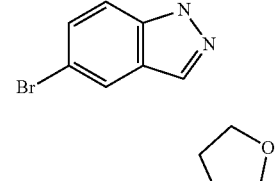 |
TABLE 2-3-continued
Halogen compound that was used
| Example No. | Halogen compound |
|---|---|
| 17 | 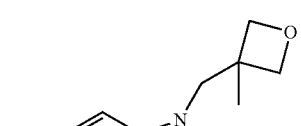 |
| 19 | 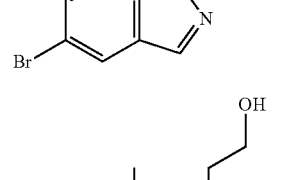 |
| 20 | 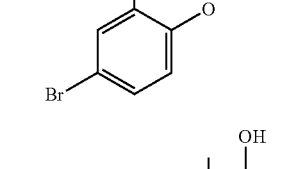 |
| 21 | 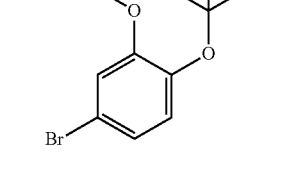 |
| 23, 41, 50 | 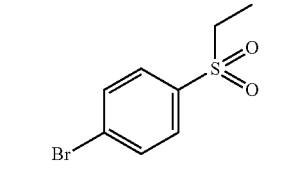 |
| 24 | 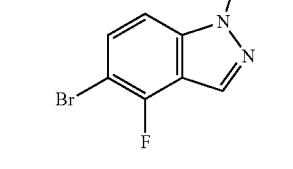 |
| 25 | 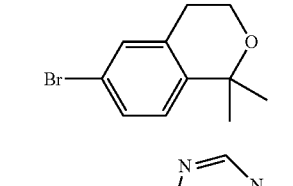 |
| 26 | 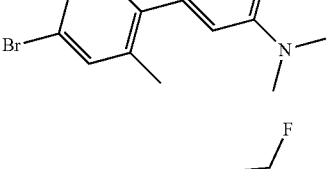 |

TABLE 2-3-continued

| Example No. | Halogen compound |
|---|---|
| 27 | 5-bromo-6-fluoro-1-methyl-1H-indazole |
| 28, 35, 42, 44, 46 | 5-bromo-4-fluoro-1-(2,2,2-trifluoroethyl)-1H-indazole |
| 29, 37 | 5-bromo-4-fluoro-1-[(3-methyloxetan-3-yl)methyl]-1H-indazole |
| 30, 38 | 1-(5-bromo-4-fluoro-1H-indazol-1-yl)-2-methylpropan-2-ol |
| 32 | 5-bromo-1,3-dimethyl-1,3-dihydro-2H-benzimidazol-2-one |
| 33 | 5-bromo-3-(2-methoxyethyl)-1-methyl-1,3-dihydro-2H-benzimidazol-2-one |
| 34 | 5-bromo-1H-indazole |
| 36, 43, 45, 47, 48 | 5-bromo-4-fluoro-1-(2-methoxyethyl)-1H-indazole |
| 39 | 6-bromo-2-methyl-1,2,3,4-tetrahydroisoquinolin-3-one |
| 40 | 5-bromo-4-fluoro-1-[(3R)-tetrahydrofuran-3-yl]-1H-indazole |
| 49 | 5-bromo-4-chloro-1-methyl-1H-indazole |

The 2-oxoimidazole compound (3-[(1S,2S)-1-[5-(2-ethyl-3-methylpyridin-4-yl)-2-[2-(4-fluoro-3,5-dimethyl-phenyl)-3-(2-oxo-1H-imidazol-3-yl)-6,7-dihydro-4H-pyra-zolo[4,3-c]pyridine-5-carbonyl]indol-1-yl]-2-methylcyclopropyl]-4H-1,2,4-oxadiazol-5-one, Compound 2g) used in the synthesis of Example Compounds 2 to 5 was synthesized by the following process.

[Chemical Formula 19]

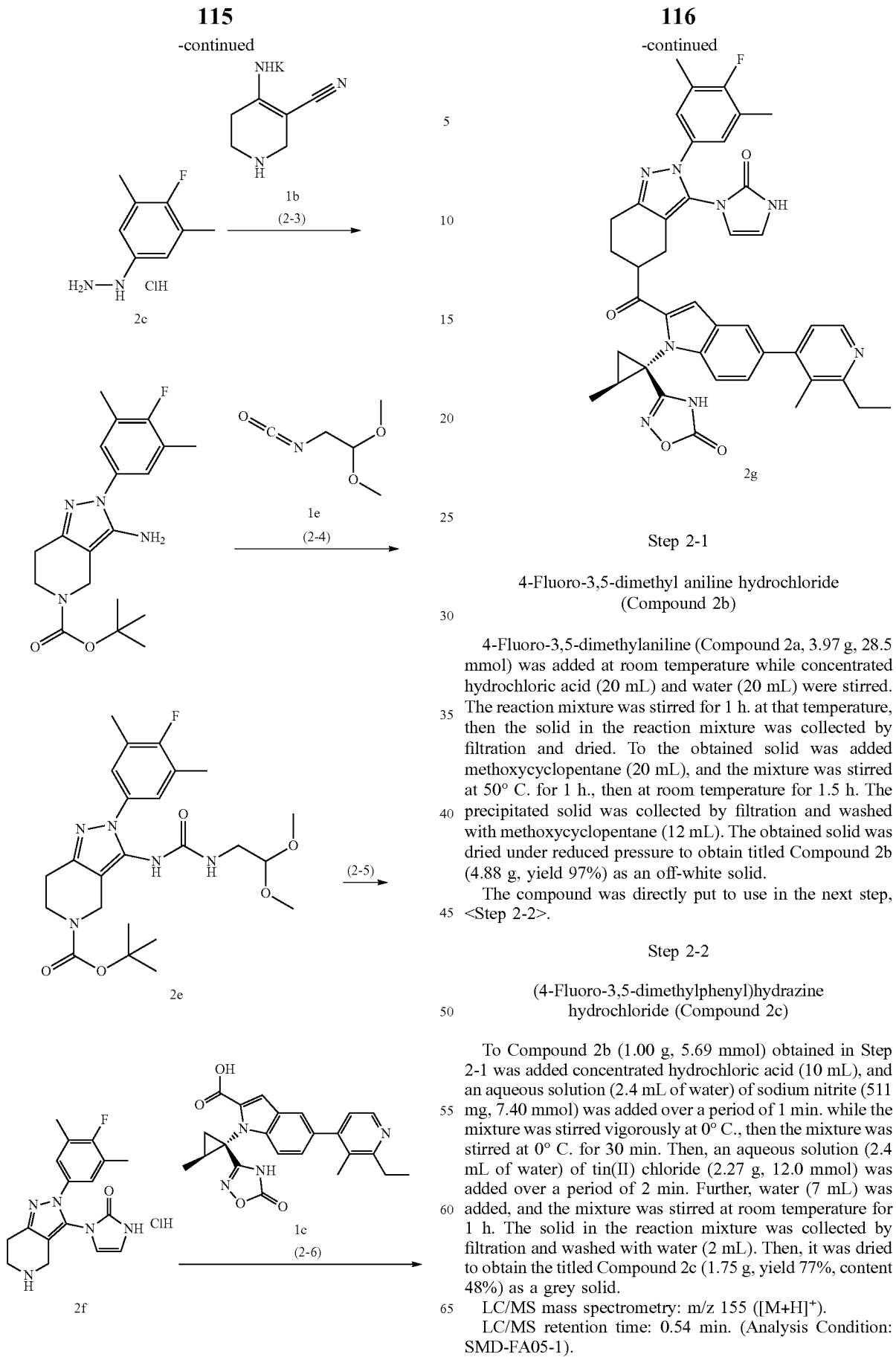

Step 2-1

4-Fluoro-3,5-dimethyl aniline hydrochloride (Compound 2b)

4-Fluoro-3,5-dimethylaniline (Compound 2a, 3.97 g, 28.5 mmol) was added at room temperature while concentrated hydrochloric acid (20 mL) and water (20 mL) were stirred. The reaction mixture was stirred for 1 h. at that temperature, then the solid in the reaction mixture was collected by filtration and dried. To the obtained solid was added methoxycyclopentane (20 mL), and the mixture was stirred at 50° C. for 1 h., then at room temperature for 1.5 h. The precipitated solid was collected by filtration and washed with methoxycyclopentane (12 mL). The obtained solid was dried under reduced pressure to obtain titled Compound 2b (4.88 g, yield 97%) as an off-white solid.

The compound was directly put to use in the next step, <Step 2-2>.

Step 2-2

(4-Fluoro-3,5-dimethylphenyl)hydrazine hydrochloride (Compound 2c)

To Compound 2b (1.00 g, 5.69 mmol) obtained in Step 2-1 was added concentrated hydrochloric acid (10 mL), and an aqueous solution (2.4 mL of water) of sodium nitrite (511 mg, 7.40 mmol) was added over a period of 1 min. while the mixture was stirred vigorously at 0° C., then the mixture was stirred at 0° C. for 30 min. Then, an aqueous solution (2.4 mL of water) of tin(II) chloride (2.27 g, 12.0 mmol) was added over a period of 2 min. Further, water (7 mL) was added, and the mixture was stirred at room temperature for 1 h. The solid in the reaction mixture was collected by filtration and washed with water (2 mL). Then, it was dried to obtain the titled Compound 2c (1.75 g, yield 77%, content 48%) as a grey solid.

LC/MS mass spectrometry: m/z 155 ([M+H]$^+$).

LC/MS retention time: 0.54 min. (Analysis Condition: SMD-FA05-1).

Step 2-3 tert-Butyl 3-amino-2-(4-fluoro-3,5-dimethylphenyl)-6,7-dihydro-4H-pyrazolo[4,3-c]pyridine-5-carboxylate (Compound 2d)

The titled compound was obtained from Compound 1b obtained in Step 1-1 and Compound 2c obtained in Step 2-2 by performing an operation similar to Step 1-2 of Example 1 using an appropriate reagent.

LC/MS mass spectrometry: m/z 361 ([M+H]$^+$).

LC/MS retention time: 1.04 min. (Analysis Condition: SMD-FA05-3).

Step 2-4 tert-Butyl 3-(2,2-dimethoxyethylcarbamoylamino)-2-(4-fluoro-3,5-dimethylphenyl)-6,7-dihydro-4H-pyrazolo[4,3-c]pyridine-5-carboxylate (Compound 2e)

The titled compound was synthesized from Compound 2d obtained in Step 2-3 by performing an operation similar to Step 1-3 of Example 1 using an appropriate reagent.

LC/MS mass spectrometry: m/z 492 ([M+H]$^+$).

LC/MS retention time: 1.07 min. (Analysis Condition: SMD-FA05-3).

Step 2-5

3-[2-(4-Fluoro-3,5-dimethylphenyl)-4,5,6,7-tetrahydropyrazolo[4,3-c]pyridin-3-yl]-1H-imidazol-2-one hydrochloride (Compound 2f)

The titled compound was synthesized from Compound 2e obtained in Step 2-4 by performing an operation similar to Step 1-4 of Example 1 using an appropriate reagent.

LC/MS mass spectrometry: m/z 328 ([M+H]$^+$).

LC/MS retention time: 0.61 min. (Analysis Condition: SMD-FA05-3).

Step 2-6

3-[(1S,2S)-1-[5-(2-Ethyl-3-methylpyridin-4-yl)-2-[2-(4-fluoro-3,5-dimethylphenyl)-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one (Compound 2g)

The titled compound was synthesized from Compound 2f obtained in Step 2-5 and Compound 1o obtained in Step 1-9 by performing an operation similar to Step 1-10 of Example 1 using an appropriate reagent.

The 2-oxoimidazole compound (3-[(1S,2S)-1-[2-[2-(4-fluoro-3,5-dimethylphenyl)-3-(2-oxo-1H-imidazol-3-yl)-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one, Compound 6i) used in the synthesis of Example Compound 6 was synthesized by the following process.

[Chemical Formula 20]

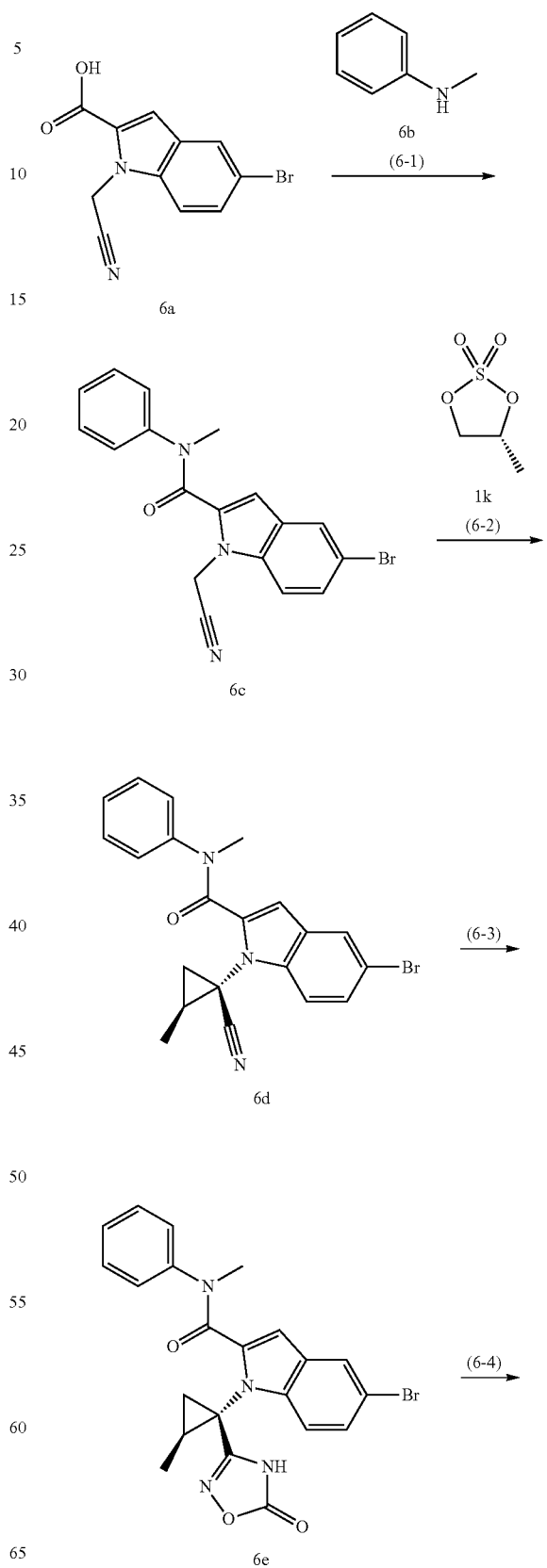

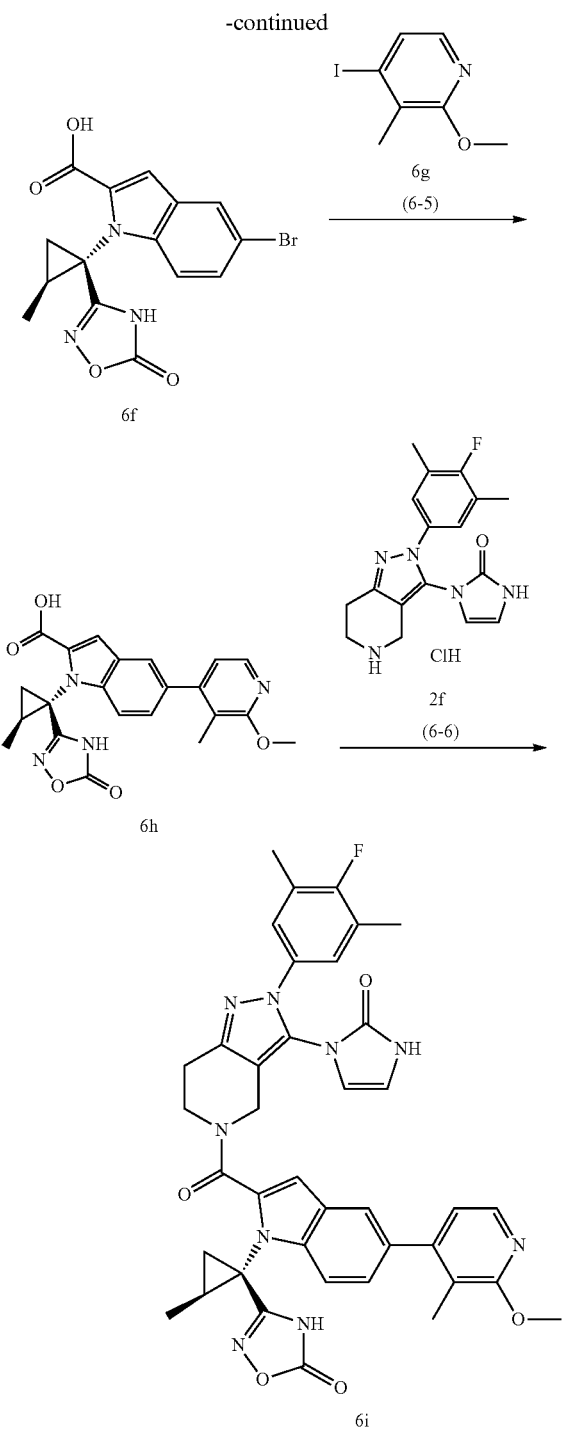

LC/MS mass spectrometry: m/z 368 ([M+H]$^+$).
LC/MS retention time: 1.25 min. (Analysis Condition: SMD-FA05-3).

Step 6-2

5-Bromo-1-[(1S,2S)-1-cyano-2-methylcyclopropyl]-N-methyl-N-phenylindole-2-carboxamide (Compound 6d)

The titled compound was synthesized from Compound 6c obtained in Step 6-1 by performing an operation similar to Step 1-6 of Example 1 using an appropriate reagent.
LC/MS retention time: 1.37 min. (Analysis Condition: SMD-FA05-1).
$^1$H-NMR (400 MHz, DMSO-d$_6$) δ: 7.69 (1H, s), 7.65-7.25 (7H, m), 6.02 (1H, brs), 3.44 (3H, s), 3.31 (3H, d, J=9.5 Hz), 2.04-1.74 (3H, m).

Step 6-3

5-Bromo-N-methyl-1-[(1S,2S)-2-methyl-1-(5-oxo-4H-1,2,4-oxadiazol-3-yl)cyclopropyl]-N-phenylindole-2-carboxamide (Compound 6e)

The titled compound was synthesized from Compound 6d obtained in Step 6-2 by performing an operation similar to Step 1-8 of Example 1 using an appropriate reagent.
LC/MS mass spectrometry: m/z 467 ([M+H]$^+$).
LC/MS retention time: 1.33 min. (Analysis Condition: SMD-FA05-01).

Step 6-4

5-Bromo-1-[(1S,2S)-2-methyl-1-(5-oxo-4H-1,2,4-oxadiazol-3-yl)cyclopropyl]indole-2-carboxylic acid (Compound 6f)

A mixture of Compound 6e (9.70 g, 20.8 mmol) obtained in Step 6-3, potassium hydroxide (11.7 g, 208 mmol), and methoxyethanol (41.5 mL) was stirred at 100° C. for 4 h. 6N Hydrochloric acid (51.9 mL) was added under ice cold condition, and the suspension was stirred at room temperature for 30 min. The solid was collected by filtration and washed with water (29.1 mL), then dried under reduced pressure to obtain the titled Compound 6f (7.42 g, yield 95%) as a light brown solid.
LC/MS mass spectrometry: m/z 376 ([M–H]$^-$).
LC/MS retention time: 1.10 min. (Analysis Condition: SMD-FA05-2).

Step 6-5

5-(2-Methoxy-3-methylpyridin-4-yl)-1-[(1S,2S)-2-methyl-1-(5-oxo-4H-1,2,4-oxadiazol-3-yl)cyclopropyl]indole-2-carboxylic acid (Compound 6h)

The DMSO (34.7 mL) suspension of Compound 6f (3.00 g, 7.93 mmol) obtained in Step 6-4, palladium(II) acetate (0.178 g, 0.793 mmol), dicyclohexyl (2',4',6'-triisopropyl-[1,1'-biphenyl]-2-yl)phosphane (0.756 g, 1.587 mmol), 4,4,4',4',5,5,5',5'-octamethyl-2,2'-bi(1,3,2-dioxaborolane) (3.02 g, 11.9 mmol), potassium phosphate (10.1 g, 47.6 mmol) was deaerated at room temperature under reduced pressure, then, nitrogen was introduced in the vessel. Under nitrogen atmosphere, the suspension was stirred at 100° C. for 0.5 h., then cooled to room temperature. 4-Iodo-2-methoxy-3-methylpyridine (Compound 6g, 1.98 g, 7.93 mmol), water Step 6-1

5-Bromo-1-(cyanomethyl)-N-methyl-N-phenylindole-2-carboxamide (Compound 6c)

The titled compound was synthesized from 5-bromo-1-(cyanomethyl)indole-2-carboxylic acid (Compound 6a) and N-methylaniline (Compound 6b) by performing an operation similar to Step 1-10 of Example 1 using an appropriate reagent.

(4.96 mL) were added to the solution, and the solution was subjected to deaeration under reduced pressure. Nitrogen was introduced in the vessel, and the solution was stirred at 100° C. for 0.5 h. After cooling to room temperature, water (12.4 mL) and formic acid (6 mL) were added to the solution. After filtration, the filtrate was directly purified by reversed-phase chromatography (acetonitrile/water, 0.1% formic acid) to obtain the titled Compound 6h (1.83 g, yield 55%).

LC/MS mass spectrometry: m/z 421 ([M+H]$^+$).

LC/MS retention time: 1.10 min. (Analysis Condition: SMD-FA05-1).

Step 6-6

3-[(1S,2S)-1-[2-[2-(4-Fluoro-3,5-dimethylphenyl)-3-(2-oxo-1H-imidazol-3-yl)-6,7-dihydro-4H-pyrazolo[4,3-c]pyridine-5-carbonyl]-5-(2-methoxy-3-methyl-pyridin-4-yl)indol-1-yl]-2-methylcyclopropyl]-4H-1,2,4-oxadiazol-5-one (Compound 6i)

The titled compound was synthesized from Compound 2f obtained in Step 2-5 and Compound 6h obtained in Step 6-5 by performing an operation similar to Step 1-10 of Example 1 using an appropriate reagent.

The halogen compound (1-(5-bromoindazol-1-yl)-2-methylpropan-2-ol, Compound 6l) used in the synthesis of Example Compound 6 was synthesized by the following process.

Step 6-7

1-(5-Bromoindazol-1-yl)-2-methylpropan-2-ol (Compound 6k)

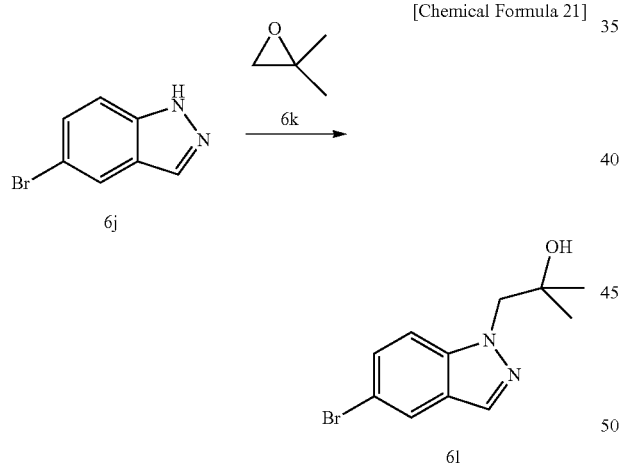

5-Bromoindazole (Compound 6j, 150 mg, 0.761 mmol) and 2,2-dimethyloxirane (Compound 6k, 274 mg, 3.81 mmol) were dissolved in 1-methylpyrrolidin-2-one (NMP) (1.52 mL), to which potassium carbonate (526 mg, 3.81 mmol) was added. The solution was stirred under microwave at 180° C. for 30 min. Water was added to the reaction mixture, and extraction was performed using ethyl acetate. The organic layer was washed with water, and the solvent was removed by evaporation under reduced pressure. The resulting product was purified by silica gel column chromatography (ethyl acetate/hexane=1:1) to obtain the titled Compound 6l (115 mg, yield 56%).

LC/MS mass spectrometry: m/z 269 ([M+H]$^+$).

LC/MS retention time: 1.00 min. (Analysis Condition: SMD-FA05-2).

The 2-oxoimidazole reagent (3-[(1S,2S)-1-[5-(2,2-dimethylmorpholin-4-yl)-2-[2-(4-fluoro-3,5-dimethylphenyl)-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one, Compound 7c) used in the synthesis of Example Compound 7 was synthesized by the following process.

[Chemical Formula 22]

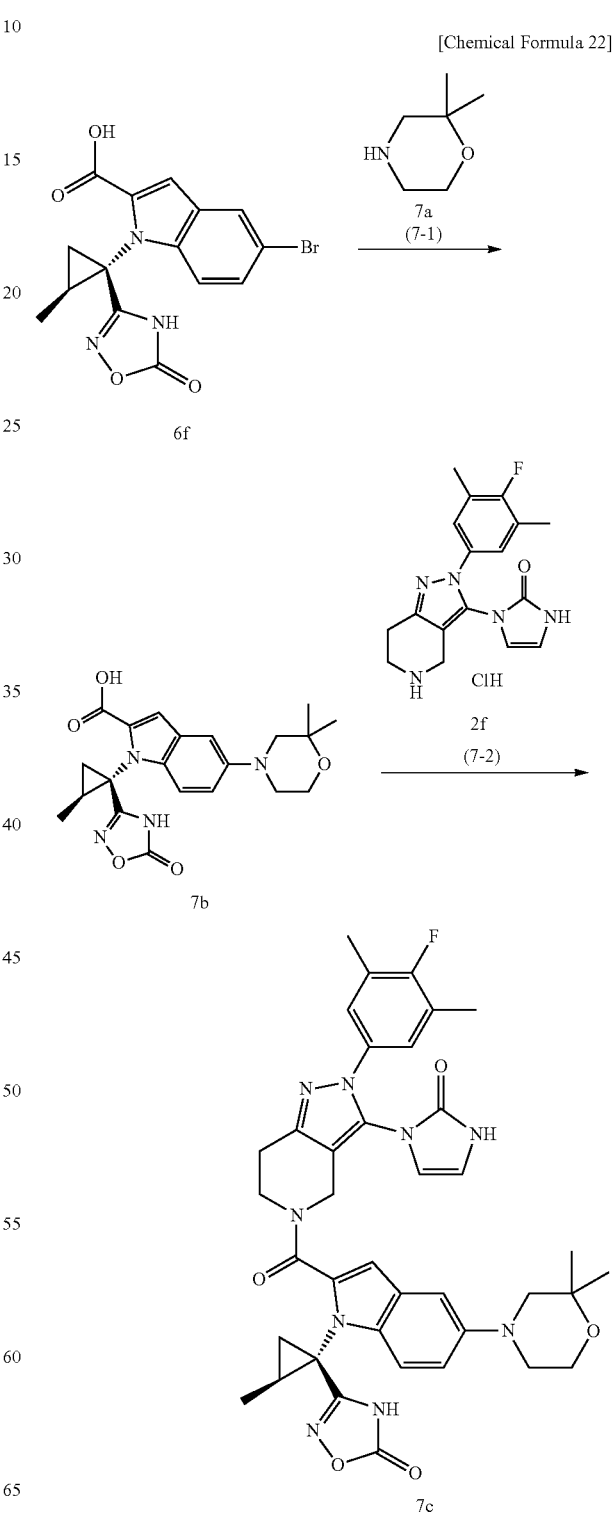

Step 7-1

5-(2,2-Dimethylmorpholin-4-yl)-1-[(1S,2S)-2-methyl-1-(5-oxo-4H-1,2,4-oxadiazol-3-yl)cyclopropyl]indole-2-carboxylic acid (Compound 7b)

The NMP (44 mL) suspension of 2,2-dimethylmorpholine (Compound 7a, 1.98 g, 17.2 mmol), tris (dibenzylideneacetone)dipalladium(0) (0.121 g, 0.132 mmol), 2-dicyclohexylphosphino-2',6'-di-i-propoxy-1,1'-biphenyl (0.123 g, 0.264 mmol), sodium tert-butoxide (5.08 g, 529 mmol) was deaerated at room temperature under reduced pressure, then, nitrogen was introduced in the vessel. Under nitrogen atmosphere, Compound 6f (5.0 g, 13.2 mmol) obtained in Step 6-4 was added to the suspension, and the mixture was stirred at 100° C. for 0.5 h. then cooled to room temperature. Formic acid was added to the mixture, and the resulting product was directly purified by reversed-phase chromatography (acetonitrile/water, 0.1% formic acid) to obtain the titled Compound 7b (5.26 g, yield 96%).

LC/MS mass spectrometry: m/z 413 ([M+H]$^+$).
LC/MS retention time: 1.00 min. (Analysis Condition: SMD-FA05-1).

Step 7-2

3-[(1S,2S)-1-[5-(2,2-Dimethylmorpholin-4-yl)-2-[2-(4-fluoro-3,5-dimethylphenyl)-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one (Compound 7c)

The titled compound was synthesized from Compound 7b obtained in Step 7-1 by performing an operation similar to Step 1-10 of Example 1 using an appropriate reagent.

The 2-oxoimidazole reagent (3-[(1S,2S)-1-[2-[2-(4-fluoro-3,5-dimethylphenyl)-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one, Compound 8c) used in the synthesis of Example Compounds 8 to 10 was synthesized by the following process.

[Chemical Formula 23]

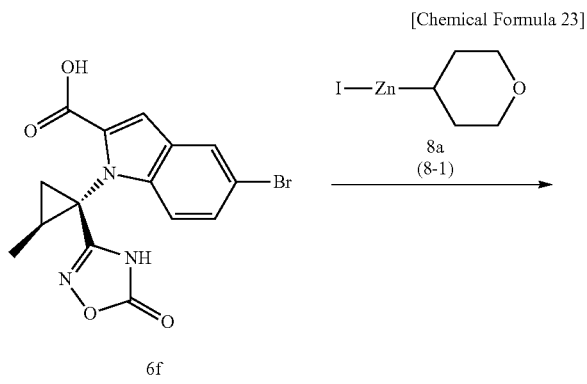

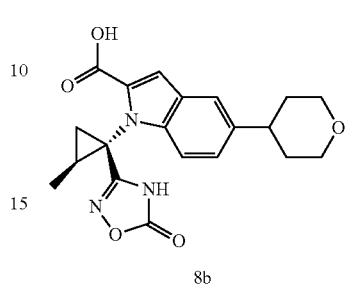

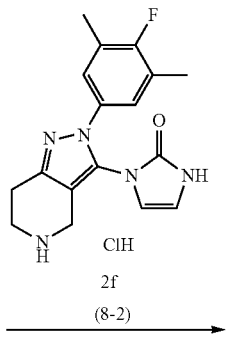

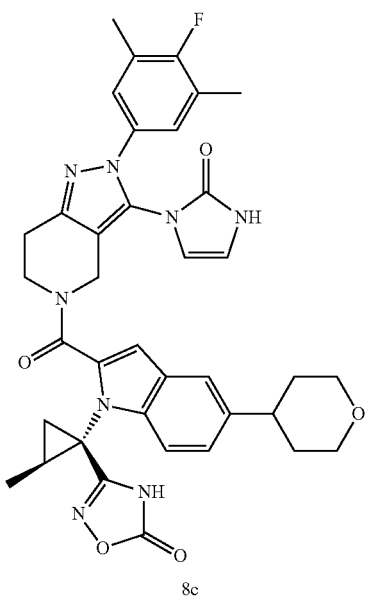

Step 8-1

1-[(1S,2S)-2-Methyl-1-(5-oxo-4H-1,2,4-oxadiazol-3-yl)cyclopropyl]-5-(oxan-4-yl)indole-2-carboxylic acid (Compound 8b)

The N,N-dimethylacetamide (DMA) (2.64 mL) suspension of Compound 6f (0.30 g, 0.793 mmol) obtained in Step 6-4, palladium(II) acetate (35.6 mg, 0.159 mmol), 2-dicyclohexylphosphino-2',6'-diisopropoxybiphenyl (0.148 g, 0.317 mmol) was deaerated under reduced pressure, then, nitrogen was introduced in the vessel and the suspension was stirred at room temperature for 15 min. Under nitrogen atmosphere, a DMA solution (7.9 mL, 7.93 mmol) of 1M (tetrahydro-2H-pyran-4-yl)zinc (II) iodide (Compound 8a) was added, and the mixture was stirred at 80° C. for 15 min., and then the mixture was cooled to room temperature. Formic acid was added to the mixture, and the resulting product was directly purified by reversed-phase chromatography (methanol/water) to obtain the titled Compound 8b (0.19 g, yield 61%).

LC/MS mass spectrometry: m/z 382 ([M−H]$^-$).
LC/MS retention time: 1.00 min. (Analysis Condition: SMD-FA05-2).

Step 8-2

3-[(1S,2S)-1-[2-[2-(4-Fluoro-3,5-dimethylphenyl)-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one (Compound 8c)

The titled compound was synthesized from Compound 8b obtained in Step 8-1 by performing an operation similar to Step 1-10 of Example 1 using an appropriate reagent.

The halogen compound (5-bromo-1-[(3R)-oxolan-3-yl]indazole, Compound 8f) used in the synthesis of Example Compound 8 was synthesized by the following process.

[Chemical Formula 24]

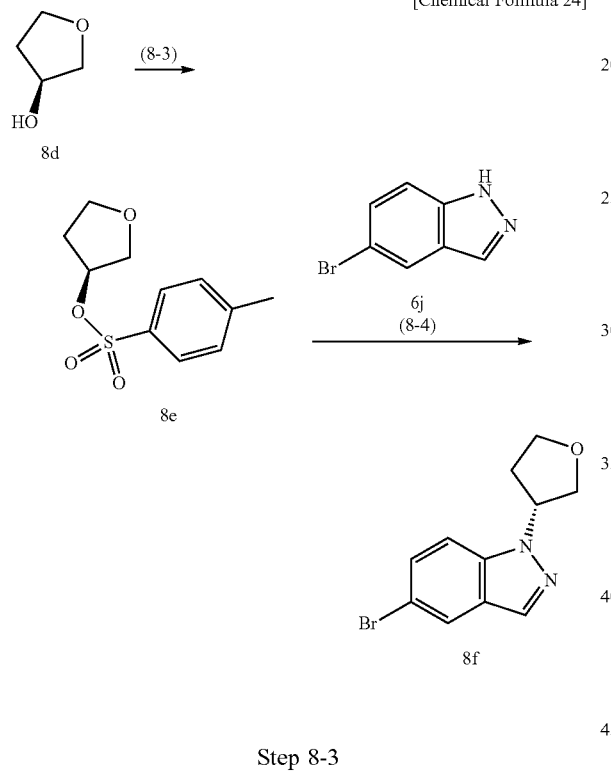

Step 8-3

4-Methylbenzenesulfonic acid [(3S)-oxolan-3-yl] (Compound 8e)

To a dichloromethane solution (3.78 mL) of (3S)-oxolan-3-ol (Compound 8d, 500 mg, 5.68 mmol) was added pyridine (1.28 mL, 15.9 mmol) and 4-methylbenzenesulfonyl chloride (1.51 g, 7.95 mmol) at 0° C. The solution was stirred at room temperature, then 15 h. later, water and 1N hydrochloric acid were added to separate out the organic layer. The organic layer was washed sequentially with saturated sodium hydrogen carbonate solution, and brine. The solvent was removed by evaporation under reduced pressure to obtain the titled Compound 8e (1.36 g, yield 99%).

LC/MS retention time: 0.96 min. (Analysis Condition: SMD-FA05-1).

$^1$H-NMR (400 MHz, CDCl$_3$) δ: 7.79 (2H, d, J=8 Hz), 7.35 (2H, d, J=8 Hz), 5.12 (1H, m), 3.93-3.76 (4H, m), 2.46 (3H, s), 2.13-2.05 (2H, m).

Step 8-4

5-Bromo-1-[(3R)-oxolan-3-yl]indazole (Compound 8f)

To a DMF (3.8 mL) solution of 5-bromo-1H-indazole (Compound 6j, 300 mg, 1.52 mmol) was added cesium carbonate (992 mg, 3.05 mmol) and Compound 8e (369 mg, 1.52 mmol) obtained in Step 8-3, and the mixture was stirred at 100° C. for 2 h. After cooling to room temperature, water was added to the reaction solution and extraction was performed using ethyl acetate. The organic layer was washed with water, and the solvent was removed by evaporation under reduced pressure. The resulting product was purified by silica gel column chromatography (ethyl acetate/hexane=1:1) to obtain the titled Compound 8f (198 mg, yield 49%) as a colorless oil-like product.

LC/MS mass spectrometry: m/z 267 ([M+H]$^+$).

LC/MS retention time: 1.07 min. (Analysis Condition: SMD-FA05-1).

The halogen compound (N-(4-bromo-2-methoxyphenyl)-N-(3-methoxypropyl) acetamide, Compound 9c) used in the synthesis of Example Compound 9 was synthesized by the following process.

Step 9-1

[Chemical Formula 25]

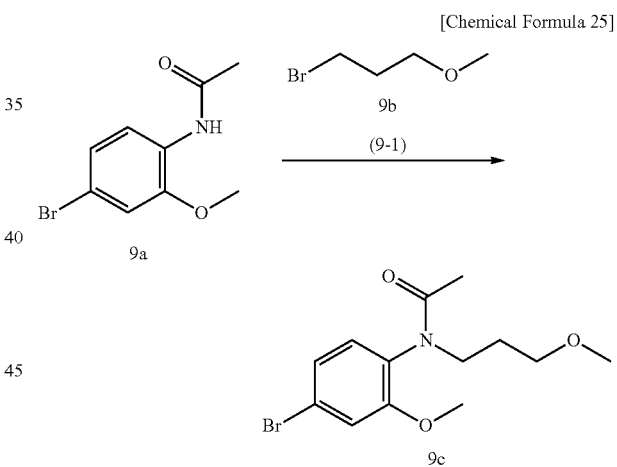

To a DMF (0.8 mL) solution of N-(4-bromo-2-methoxyphenyl)acetamide (Compound 9a, 80 mg, 0.33 mmol) was sequentially added sodium hydride (50 wt % oil dispersion) (18.9 mg, 0.39 mmol) and 1-bromo-3-methoxypropane (75 mg, 0.49 mmol), and the resulting mixture was stirred at room temperature for 12 h. Formic acid was added to the reaction solution, and the resulting product was purified by reversed-phase silica gel chromatography (acetonitrile/water, 0.1% formic acid) to obtain the titled Compound 9c (103 mg, yield 99%) as a colorless gum-like product.

LC/MS mass spectrometry: m/z 316 ([M+H]$^+$).

LC/MS retention time: 1.02 min. (Analysis Condition: SMD-FA05-1).

The halogen compound (5-bromo-1-(2,2,2-trifluoroethyl)indazole, Compound 10b) used in the synthesis of Example Compound 1o was synthesized by the following process.

Step 10-1

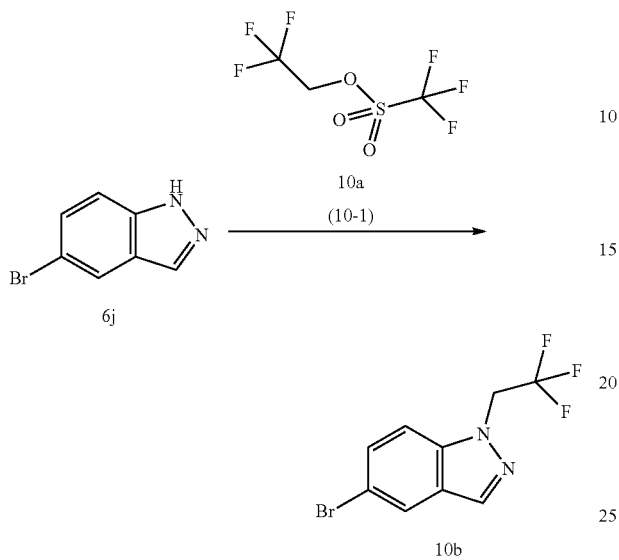

The titled compound was synthesized from 2,2,2-trifluoroethyl trifluoromethanesulfonate (Compound 10a) and 5-bromo-1H-indazole (Compound 6j) by performing an operation similar to Step 8-4 of Example 8 using an appropriate reagent.

LC/MS mass spectrometry: m/z 279 ([M+H]$^+$).

LC/MS retention time: 1.17 min. (Analysis Condition: SMD-FA05-1).

The 2-oxoimidazole reagent (3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one, Compound 11m) used in the synthesis of Example Compounds 11 to 13 was synthesized by the following process.

[Chemical Formula 27]

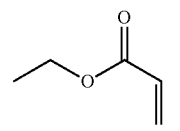

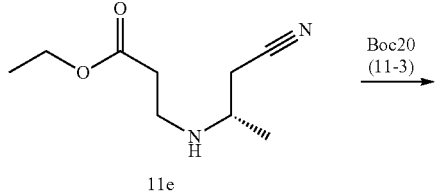

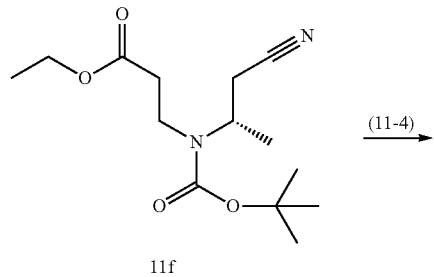

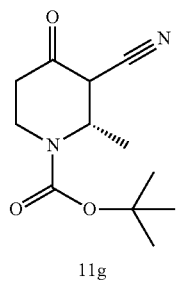

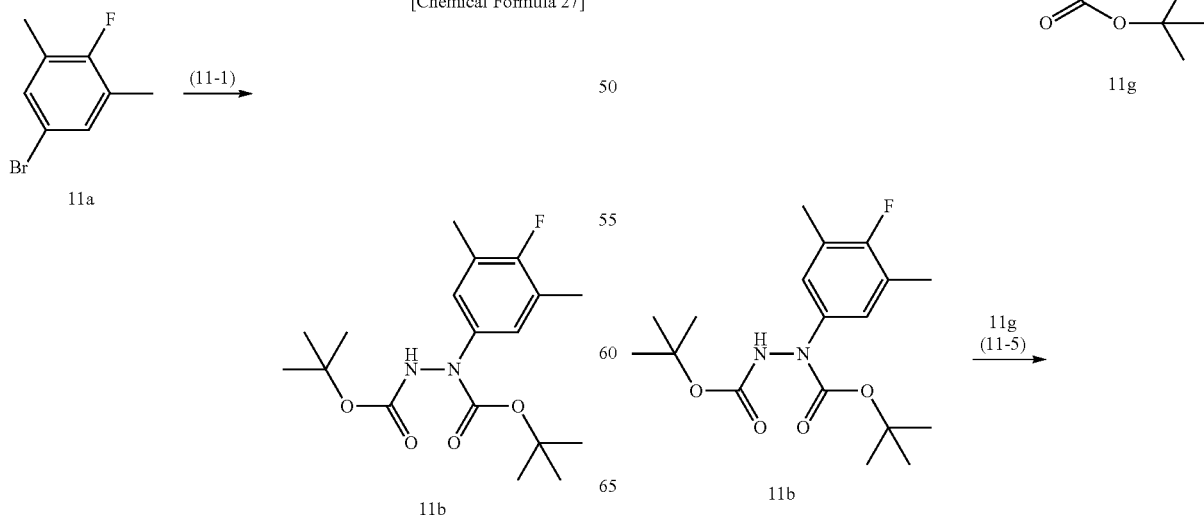

-continued

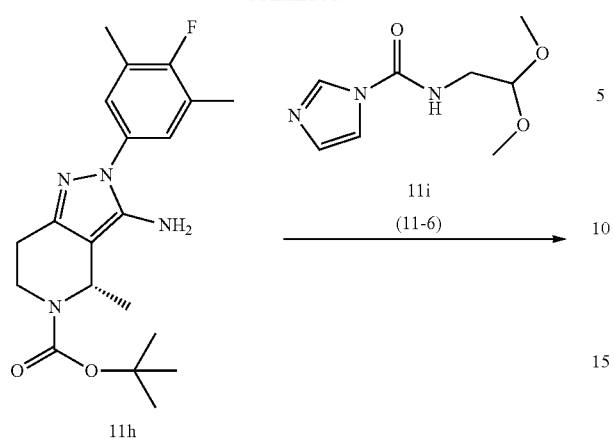

11h 11i
(11-6)

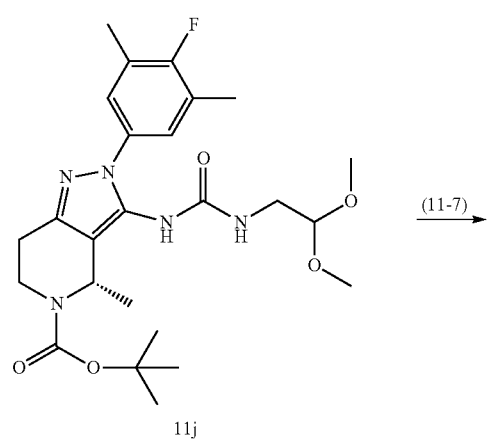

11j (11-7)

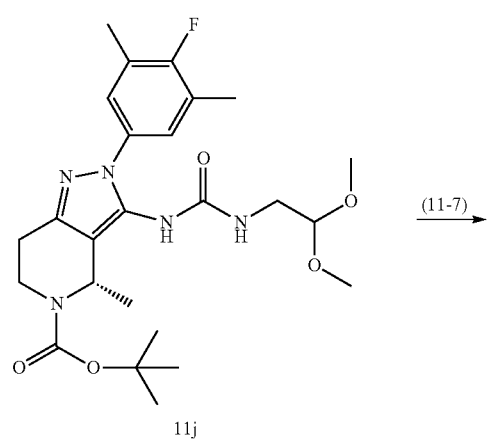

11k (11-8)

11k 8b
(11-9)

-continued

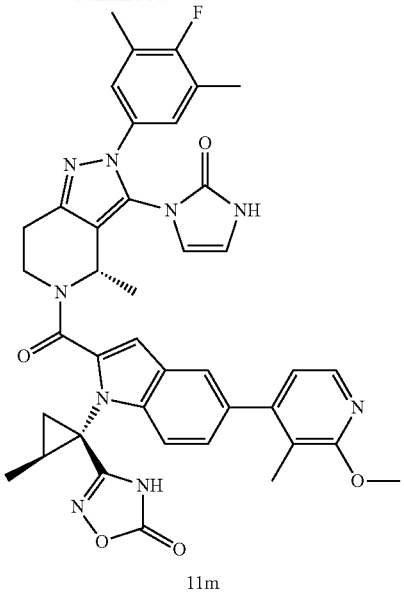

11m

<Step 11-1> tert-Butyl N-(4-fluoro-3,5-dimethylphenyl)-N-[(2-methylpropan-2-yl)oxycarbonylamino]carbamate (Compound 11b)

5-Bromo-2-fluoro-1,3-dimethylbenzene (Compound 11a, 4.66 g, 22.6 mmol) was dissolved in THF (47.6 mL) and cooled under an external temperature of −70° C. 1.55M n-Butyl lithium (13.1 mL, 20.4 mmol) was added dropwise at a temperature of −70° C. or lower and stirred for 1 h. A toluene solution (25.0 g, 21.7 mmol) of 20 wt % di-tert-butyl azodicarboxylate was added dropwise at an internal temperature of −40° C. or lower, and the mixture was stirred for 30 min. Then, the mixture was warmed to room temperature over a period of 1 h., and heptane (23.8 mL) and 20% ammonium chloride solution (47.6 mL) were added to perform extraction. The organic layer was concentrated and heptane (7.14 mL) was added to the concentrated organic layer, and the mixture was heated to an external temperature of 70° C. to promote dissolution. Then, the solution was cooled over a period of 1 h. to induce the precipitation of crystals. The crystals were collected by filtration and washed with heptane (2.38 mL). The crystals were dried to obtain a crude product (3.53 g, yield 44%) of the titled Compound 11b.

$^1$H-NMR (400 MHz, DMSO-D$_6$) δ: 9.64-9.51 (0.8H, m), 9.24-9.07 (0.2H, m), 7.09-6.91 (2H, m), 2.29-2.09 (6H, m), 1.53-1.32 (18H, m).

LC/MS retention time: 1.40 min. (Analysis Condition: SMD-FA05-3).

Steps 11-2, 3, and 4 tert-Butyl (2S)-3-cyano-2-methyl-4-oxopiperidine-1-carboxylate (Compound 11g)

(3S)-3-Aminobutanenitrile hydrochloride (Compound 11c, 10.0 g, 82.9 mmol) was dissolved in ethanol (50.0 mL), and triethyl amine (13.9 mL, 99.5 mmol) and, to the mixture, ethyl acrylate (10.8 mL, 99.5 mmol) were added at room temperature. The solution was stirred at an external temperature of 70° C. for 3 h., then cooled to room temperature to obtain a mixture containing ethyl 3-[[(2S)-1-cyanopropan-2-yl]amino]propanoate (Compound 11e).

To the reaction solution was added di-tert-butyl dicarbonate (21.7 mL, 99.5 mmol) at room temperature. The solution was stirred at room temperature for 14 h., then N-methylpiperazine (2.76 mL, 24.9 mmol) was added and the mixture was stirred for 4 h. Then, 1N hydrochloric acid (50 mL) was added and extraction was performed using toluene (50 mL). The organic layer was washed with 15% sodium chloride aqueous solution (50.0 mL). The organic layer was concentrated under reduced pressure to obtain a mixture containing ethyl 3-[[(2S)-1-cyanopropan-2-yl]-[(2-methylpropan-2-yl)oxycarbonyl]amino]propanoate (Compound 11f).

To the mixture was added THF (50.0 mL), then potassium tert-butoxide (10.2 g, 91.2 mmol) was added at an internal temperature of 30° C. or lower. Then, the mixture was stirred at room temperature for 1 h. At an internal temperature of 15° C., 2N hydrochloric acid (82.9 mL, 99.5 mmol) was added and extraction was performed using ethyl acetate. The organic layer was concentrated after it was washed twice with 15% sodium chloride aqueous solution (50.0 mL) to obtain the titled Compound 11g (15.8 g, yield 80%).

LC/MS mass spectrometry: m/z 237 ([M–H]$^-$).
LC/MS retention time: 0.92 min. (Analysis Condition: SMD-FA05-1).

Step 11-5 tert-Butyl (4S)-3-amino-2-(4-fluoro-3,5-dimethylphenyl)-4-methyl-6,7-dihydro-4H-pyrazolo[4,3-c]pyridine-5-carboxylate (Compound 11h)

Compound 11b (2.13 g, 6.01 mmol) obtained in Step 11-1 was dissolved in NMP (6.39 mL), to which methanesulfonic acid (1.30 g, 13.2 mmol) was added and the mixture was stirred at an external temperature of 80° C. for 7 h. After the reaction solution was cooled to room temperature, toluene (12.8 mL), potassium carbonate (0.914 g), and water (12.8 g) were added to it, and the reaction solution was stirred at room temperature for 10 min. After removing the water layer, a toluene (6.3 mL) solution of Compound 11g (1.43 g, 6.01 mmol) obtained in Step 11-4, pyridine hydrochloride (71.0 mg, 0.60 mmol) and toluene (4.2 mL) were added and the reaction solution was stirred at an external temperature of 90° C. for 1 h. The reaction solution was cooled, then washed with 1M sodium hydroxide aqueous solution (12.6 mL). The organic layer was concentrated under reduced pressure to synthesize the titled Compound 11h (1.68 g, yield 75%).

LC/MS mass spectrometry: m/z 375 ([M+H]$^+$).
LC/MS retention time: 1.08 min. (Analysis Condition: SMD-FA05-1).

Step 11-6 tert-Butyl (4S)-3-(2,2-dimethoxyethylcarbamoylamino)-2-(4-fluoro-3,5-dimethylphenyl)-4-methyl-6,7-dihydro-4H-pyrazolo[4,3-c]pyridine-5-carboxylate (Compound 11j)

To a DMA (0.53 mL) solution of Compound 11h (106 mg, 0.283 mmol) obtained in Step 11-5 was added N-(2,2-dimethoxyethyl)imidazole-1-carboxamide (Compound 11i, 62.0 mg, 0.311 mol), then potassium tert-butoxide (95.0 mg, 0.849 mol) was added under a nitrogen atmosphere, and the mixture was stirred at an external temperature of 25° C. for 4 h. Water was added to the reaction solution and extraction was performed using ethyl acetate. The organic layer was washed with water, and the solvent was removed by evaporation under reduced pressure. The resulting product was purified by silica gel column chromatography (ethyl acetate/hexane=3:2) to obtain the titled Compound 11j (105 mg, yield 73%).

LC/MS mass spectrometry: m/z 506 ([M+H]$^+$).
LC/MS retention time: 1.09 min. (Analysis Condition: SMD-FA05-1).

Step 11-7 tert-Butyl (4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carboxylate (Compound 11k)

Compound 11j (4.45 g, 8.79 mmol) obtained in Step 11-6 was suspended by adding THF (44.5 mL), then methylsulfonic acid (0.676 g, 7.03 mmol) was added, and the resulting mixture was stirred at an external temperature of 60° C. for 2 h. After cooling to room temperature, a solution of tripotassium phosphate (1.87 g, 8.79 mmol) in water (17.8 mL) was added, di-tert-butyl dicarbonate (0.768 g, 3.52 mmol) was added, and the resulting mixture was stirred at room temperature for 1 h. Water was added to the reaction solution and extraction was performed using ethyl acetate. The organic layer was washed with a saturated sodium chloride aqueous solution, then dried using magnesium sulfate. After filtration, the organic layer was concentrated under reduced pressure, and purified by silica gel column chromatography (ethyl acetate/hexane=3:7) to obtain the titled Compound 11k (3.43 g, yield 88%).

LC/MS mass spectrometry: m/z 442 ([M+H]$^+$).
LC/MS retention time: 1.09 min. (Analysis Condition: SMD-FA05-1).

Step 11-8

3-[(4S)-2-(4-Fluoro-3,5-dimethylphenyl)-4-methyl-4,5,6,7-tetrahydropyrazolo[4,3-c]pyridin-3-yl]-1H-imidazol-2-one hydrochloride (Compound 11l)

To a dichloromethane (8.38 ml) solution of Compound 11k (1.85 g, 4.19 mmol) obtained in Step 11-7 was added a 4M hydrogen chloride dioxane solution (10.5 mL, 41.9 mmol). The mixture was stirred at room temperature for 1 h., and the reaction mixture was concentrated under reduced pressure to obtain a crude product (1.63 g) containing the titled Compound 11l as a brown solid.

LC/MS mass spectrometry: m/z 342 ([M+H]$^+$).
LC/MS retention time: 0.63 min. (Analysis Condition: SMD-FA05-1).

Step 11-9

3-[(1S,2S)-1-[2-[(4S)-2-(4-Fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one (Compound 11m)

The titled compound was synthesized from Compound 11l obtained in Step 11-8 and Compound 6h obtained in Step 6-5 by performing an operation similar to Step 1-10 of Example 1 using an appropriate reagent.

The 2-oxoimidazole reagent (3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(3-fluoro-2-methylpyridin-4-yl)indol-1-yl]-2-methylcyclopropyl]-4H-1,2,4-oxadiazol-5-one, Compound 14d) used in the synthesis of Example Compound 14 was synthesized by the following process.

[Chemical Formula 13]

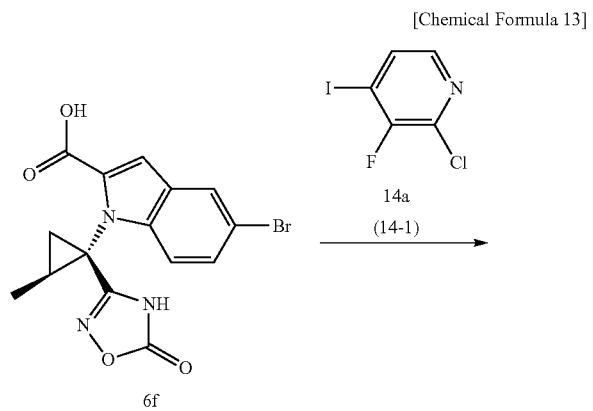

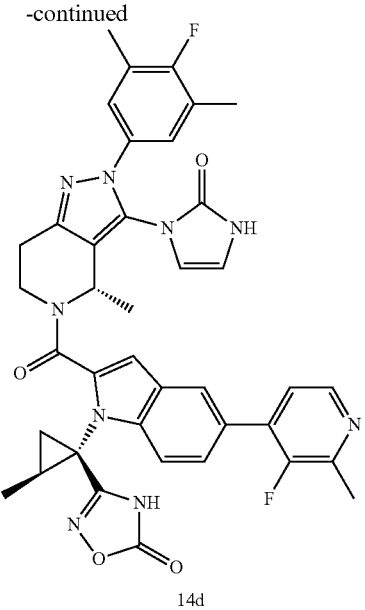

14d

Step 14-1

5-(2-Chloro-3-fluoropyridin-4-yl)-1-[(1S,2S)-2-methyl-1-(5-oxo-4H-1,2,4-oxadiazol-3-yl)cyclopropyl]indole-2-carboxylic acid (Compound 14b)

The titled compound was synthesized from Compound 6f obtained in Step 6-4 and 2-chloro-3-fluoro-4-iodopyridine (Compound 14a) by performing an operation similar to Step 6-5 of Example 6 using an appropriate reagent.

LC/MS mass spectrometry: m/z 429 ([M+H]$^+$).

LC/MS retention time: 1.14 min. (Analysis Condition: SMD-TFA05-3).

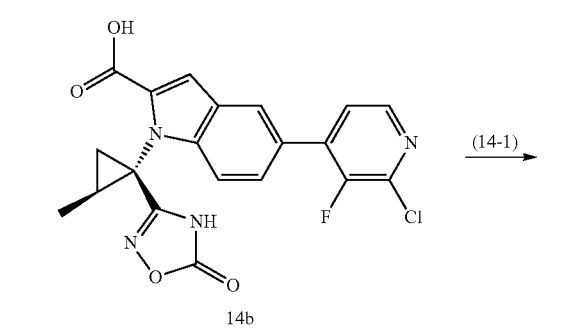

Step 14-2

5-(3-Fluoro-2-methylpyridin-4-yl)-1-[(1S,2S)-2-methyl-1-(5-oxo-4H-1,2,4-oxadiazol-3-yl)cyclopropyl]indole-2-carboxylic acid (Compound 14c)

To a mixed suspension of DMSO/water at 7:1 (13.2 mL) containing Compound 14b (810 mg, 1.32 mmol) obtained in Step 14-1,1,1'-bis (diphenylphosphino)ferrocene-palladium (II) dichloride (48 mg, 0.066 mmol), potassium carbonate (2.74 g, 19.8 mmol), methylboronic acid (792 mg, 13.2 mmol) was deaerated under reduced pressure at room temperature, then nitrogen was introduced in the vessel. Under a nitrogen atmosphere, the mixture was stirred at 100° C. for 0.5 h, then cooled to room temperature. Formic acid was added to the mixture, which was directly purified by reversed-phase chromatography (acetonitrile/water, 0.1% formic acid) to obtain the titled Compound 14c (124 mg, yield 23%) as a pale yellow solid.

LC/MS mass spectrometry: m/z 409 ([M+H]$^+$).

LC/MS retention time: 0.85 min. (Analysis Condition: SMD-FA05-3).

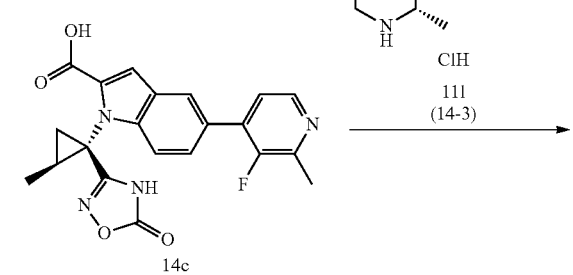

Step 14-3

3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(3-fluoro-2-methylpyridin-4-yl)indol-1-yl]-2-methylcyclopropyl]-4H-1,2,4-oxadiazol-5-one (Compound 14d)

The titled compound was synthesized from Compound 111 obtained in Step 11-8 and Compound 14c obtained in Step 14-2 by performing an operation similar to Step 1-10 of Example 1 using an appropriate reagent.

The 2-oxoimidazole reagent (3-[(1S,2S)-1-[5-[2-(dimethylamino)-3-methylpyridin-4-yl]-2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one, Compound 15d) used in the synthesis of Example Compound 15 was synthesized by the following process.

[Chemical Formula 29]

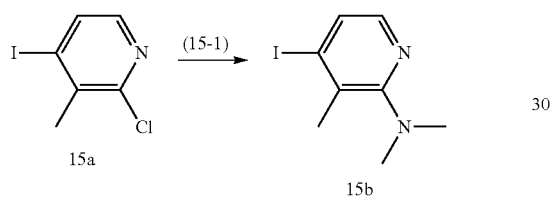

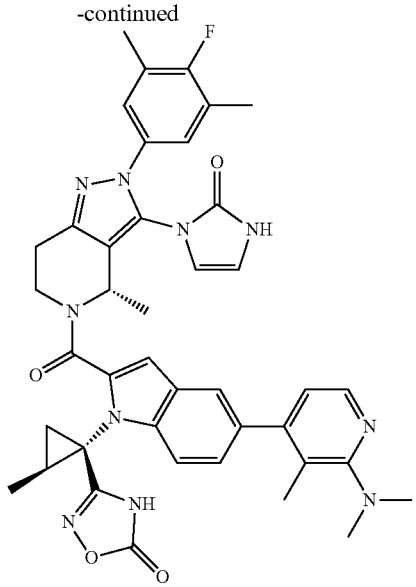

15d

Step 15-1

4-Iodo-N,N,3-trimethylpyridine-2-amine (Compound 15b)

A DMF (7.9 mL) solution of 2-chloro-4-iodo-3-methylpyridine (Compound 15a, 500 mg, 1.97 mmol), N-ethyl-N-propan-2-ylpropane-2-amine (0.515 mL, 2.96 mmol), and a THF solution (2.96 mL, 5.92 mmol) of 2M dimethylamine was stirred at 130° C. for 17 h., then the solution was cooled to room temperature and formic acid (0.4 mL) was added. The solution was purified by reversed-phase chromatography (acetonitrile/water, 0.1% formic acid) to obtain the titled Compound 15b (258 mg, yield 50%) as a light brown solution.

LC/MS mass spectrometry: m/z 263 ([M+H]$^+$).
LC/MS retention time: 0.52 min. (Analysis Condition: SQD-FA05-1).

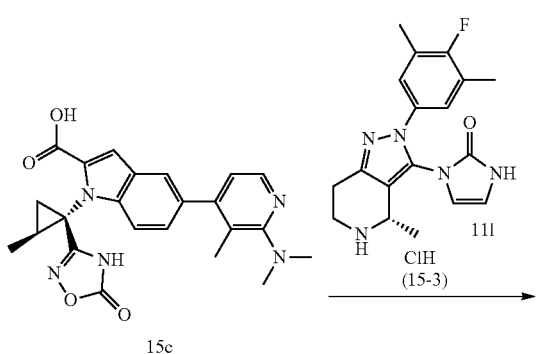

Step 15-2

5-[2-(Dimethylamino)-3-methylpyridin-4-yl]-1-[(1S,2S)-2-methyl-1-(5-oxo-4H-1,2,4-oxadiazol-3-yl)cyclopropyl]indole-2-carboxylic acid (Compound 15c)

The titled compound was obtained from Compound 6f obtained in Step 6-4 and Compound 15b obtained in Step 15-1 by performing an operation similar to Step 6-5 of Example 6 using an appropriate reagent.

LC/MS mass spectrometry: m/z 432 ([M−H]$^−$).
LC/MS retention time: 0.51 min. (Analysis Condition: SQD-FA05-1).

Step 15-3

3-[(1S,2S)-1-[5-[2-(Dimethylamino)-3-methylpyridin-4-yl]-2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one (Compound 15d)

The titled compound was synthesized from Compound 15c obtained in Step 15-2 and Compound 111 obtained in Step 11-8 by performing an operation similar to Step 1-10 of Example 1 using an appropriate reagent.

The 2-oxoimidazole reagent (3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one, Compound 16a) used in the synthesis of Example Compounds 16 to 30 was synthesized by the following process.

[Chemical Formula 30]

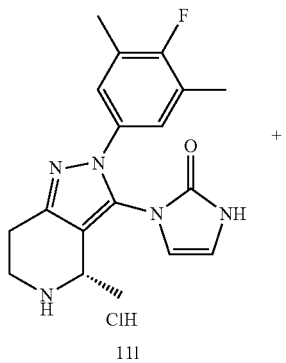

111

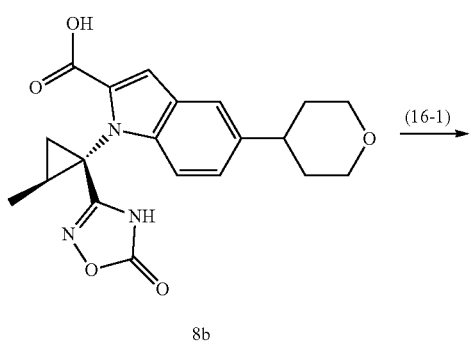

8b

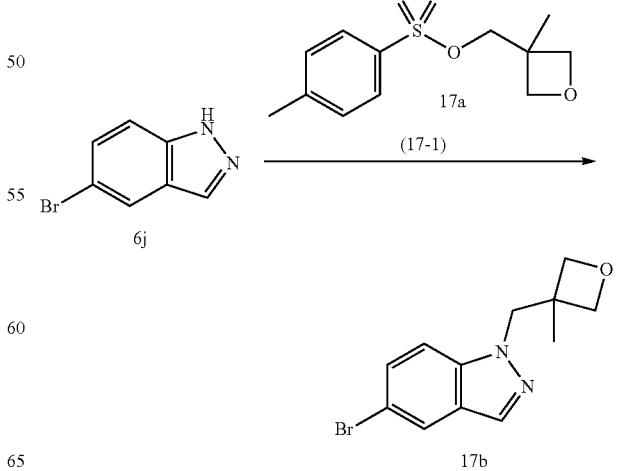

16a

Step 16-1

3-[(1S,2S)-1-[2-[(4S)-2-(4-Fluoro-3,5-dimethylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one (Compound 16a)

The titled compound was obtained from Compound 111 obtained in Step 11-8 and Compound 8b obtained in Step 8-1 by performing an operation similar to Step 1-10 of Example 1 using an appropriate reagent.

The halogen compound (5-bromo-1-[(3-methyloxetan-3-yl)methyl]indazole, Compound 17b) used in the synthesis of Example Compound 17 was synthesized by the following process.

Step 17-1

[Chemical Formula 31]

The titled compound was synthesized from 3-methyl-3-[(4-methylphenyl)sulfonylmethyl]oxetane (Compound 17a) and 5-bromo-1H-indazole (Compound 6j) by performing an operation similar to Step 9-1 of Example 9 using an appropriate reagent.

LC/MS mass spectrometry: m/z 281 ([M+H]$^+$).

LC/MS retention time: 1.10 min. (Analysis Condition: SMD-FA05-2).

The halogen compound (2-(4-bromo-2-methoxyphenoxy)-2-methylpropan-1-ol, Compound 20b) used in the synthesis of Example Compound 20 was synthesized by the following process.

Step 20-1

2-(4-Bromo-2-methoxyphenoxy)-2-methylpropan-1-ol (Compound 20b)

[Chemical Formula 32]

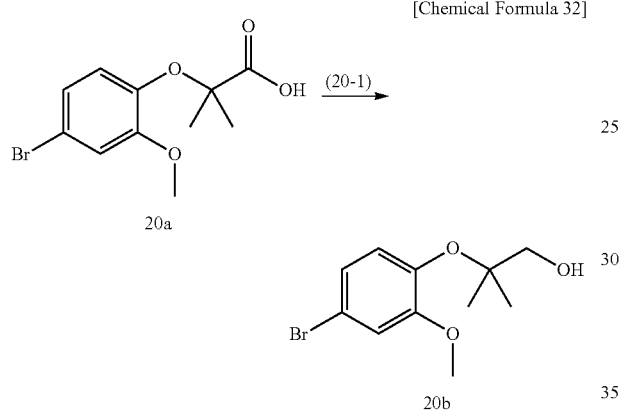

Under a nitrogen atmosphere, a THF solution (0.95M, 4.37 mL, 4.15 mmol) of borane was added dropwise at 0° C. to a THF solution (1.38 mL) of 2-(4-bromo-2-methoxyphenoxy)-2-methylpropane carboxylic acid (Compound 20a, 400 mg, 1.38 mmol) and the resulting mixture was stirred for 24 h. After 1M sodium hydroxide aqueous solution was added to the mixture and the mixture was stirred, 1N hydrochloric acid was added for neutralization. Then, ethyl acetate was added to perform extraction. The organic layer was washed with water and the solvent was removed by evaporation under reduced pressure to obtain the titled Compound 20b (339 mg, yield 89%).

LC/MS retention time: 1.04 min. (Analysis Condition: SMD-FA05-3).

$^1$H-NMR (400 MHz, CDCl$_3$) δ: 7.04-7.01 (2H, m), 6.90-6.86 (1H, m), 3.85 (3H, s), 3.44 (2H, m), 3.34 (1H, m), 1.28 (6H, s).

The halogen compound (5-bromo-1-[(3S)-oxolan-3-yl]indazole, Compound 22c) used in the synthesis of Example Compound 22 was synthesized by the following process.

[Chemical Formula 33]

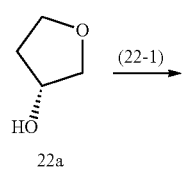

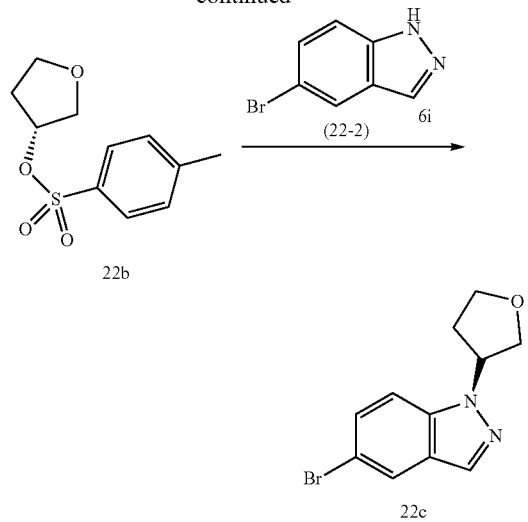

Step 22-1

(3R)-Oxolan-3-yl 4-methylbenzenesulfonate (Compound 22b)

The titled compound was synthesized by performing an operation similar to Step 8-3 of Example 8 using (3R)-oxolan-3-ol and an appropriate reagent.

LC/MS retention time: 0.95 min. (Analysis Condition: SMD-FA05-3).

Step 22-2

5-Bromo-1-[(3S)-oxolan-3-yl]indazole (Compound 22c)

The titled compound was synthesized from Compound 22b obtained in Step 22-1 and 5-bromo-1H-indazole by performing an operation similar to Step 8-4 of Example 8 using an appropriate reagent.

LC/MS mass spectrometry: m/z 267 ([M+H]$^+$).

LC/MS retention time: 1.06 min. (Analysis Condition: SMD-FA05-3).

The halogen compound (6-bromo-1,1-dimethyl-3,4-dihydroisochromene, Compound 24d) used in the synthesis of Example Compound 24 was synthesized by the following process.

[Chemical Formula 34]

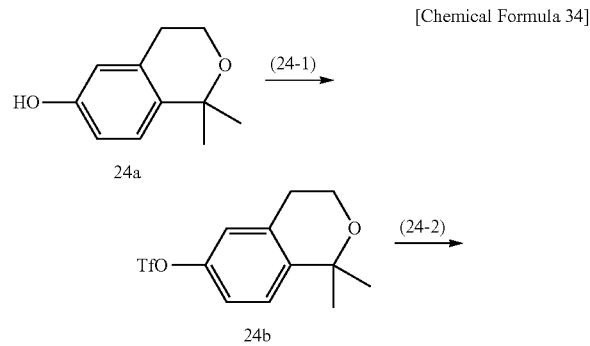

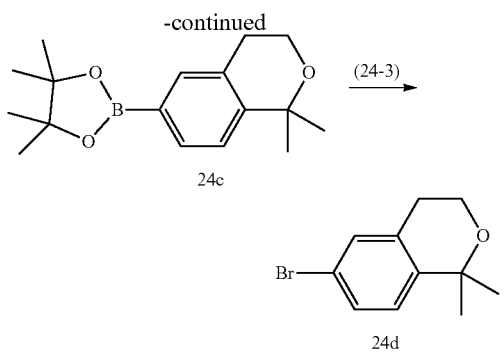

Step 24-1

(1,1-Dimethyl-3,4-dihydroisochromen-6-yl) trifluoromethanesulfonate (Compound 24b)

The titled compound was synthesized from 1,1-dimethyl-3,4-dihydroisochromen-6-ol (Compound 24a) and trifluoromethylsulfonyl trifluoromethanesulfonate (triflate anhydride) by performing an operation similar to Step 8-3 of Example 8 using an appropriate reagent.

LC/MS retention time: 0.96 min. (Analysis Condition: SQD-FA05-01).

Step 24-2

2-(1,1-Dimethyl-3,4-dihydroisochromen-6-yl)-4,4,5,5-tetramethyl-1,3,2-dioxaborolane (Compound 24c)

After the 1,4-dioxane (2.58 mL) solution of Compound 24b (120 mg, 0.387 mmol) obtained in Step 24-1,4,4,5,5-tetramethyl-2-(4,4,5,5-tetramethyl-1,3,2-dioxaborolan-2-yl)-1,3,2-dioxaborolane (147 mg, 0.580 mmol), triethyl amine (0.162 mL, 1.16 mmol), [1,1'-bis (diphenylphosphino)ferrocene]dichloropalladium(II) (14.2 mg, 0.019 mmol) was deaerated under reduced pressure, nitrogen was introduced in the vessel and the solution was stirred at 100° C. for 14 h. The solution was cooled to room temperature, then formic acid was added and the resulting product was purified by reversed-phase chromatography (acetonitrile/water, 0.1% formic acid) to obtain a mixture (134 mg) containing the titled Compound 24c as a light brown liquid.

LC/MS mass spectrometry: m/z 289 ([M+H]$^+$).
LC/MS retention time: 1.03 min. (Analysis Condition: SQD-FA05-1).

Step 24-3

6-Bromo-1,1-dimethyl-3,4-dihydroisochromene (Compound 24d)

To a methanol (1.9 mL) solution of Compound 24c (111 mg, 0.385 mmol) obtained in Step 24-2, an aqueous solution (1.9 mL) of copper(II) bromide (258 mg, 1.16 mmol) was added and the mixture was stirred at 60° C. for 6 h. After the mixture was cooled to room temperature, a saturated ammonium chloride solution was added, then extraction using dichloromethane was performed twice, and then the organic layer was dried with magnesium sulfate. After filtration, the filtrate was concentrated under reduced pressure and the residue was purified by silica gel column chromatography (ethyl acetate/hexane=1:4) to obtain the titled Compound 24d (47.7 mg, yield 51%) as a colorless liquid.

$^1$H-NMR (400 MHz, CDCl$_3$) δ: 7.29 (1H, dd, J=2.0, 8.4 Hz), 7.24-7.22 (1H, m), 6.97 (1H, d, J=8.4 Hz), 3.92 (2H, t, J=5.6 Hz), 2.80 (2H, t, J=5.6 Hz), 1.50 (6H, s).

LC/MS retention time: 0.96 min. (Analysis Condition: SQD-FA05-1).

The halogen compound (6-(4-bromo-2-methylphenyl)-N,N-dimethylpyrimidine-4-amine, Compound 25b) used in the synthesis of Example Compound 25 was synthesized by the following process.

[Chemical Formula 35]

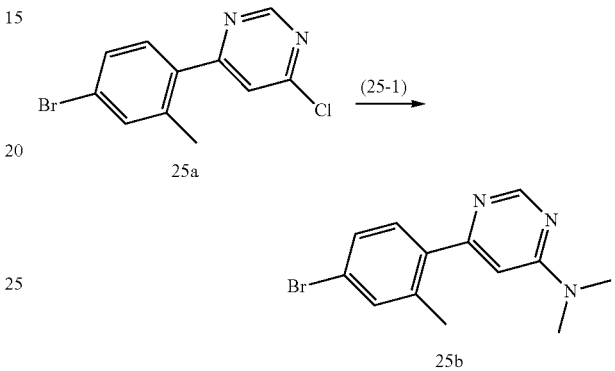

Step 25-1

6-(4-Bromo-2-methylphenyl)-N,N-dimethylpyrimidine-4-amine (Compound 25b)

To a methanol (0.2 mL) solution of 4-(4-bromo-2-methylphenyl)-6-chloropyrimidine (Compound 25a, 12.9 mg, 0.045 mmol) was added 2M dimethylamine THF solution (0.227 mL, 0.455 mmol), and the mixture was stirred at room temperature for 3 h. The reaction mixture was purified by the reversed-phase silica gel column chromatography (acetonitrile/water, 0.1% formic acid) to synthesize the titled Compound 25b (9.2 mg, yield 69%) as an off-white solid.

LC/MS mass spectrometry: m/z 292 ([M+H]$^+$).
LC/MS retention time: 0.67 min. (Analysis Condition: SMD-FA05-3).

The halogen compound (5-bromo-4-fluoro-1-(2,2,2-trifluoroethyl)indazole, Compound 28b) used in the synthesis of Example Compound 28 was synthesized by the following process.

[Chemical Formula 36]

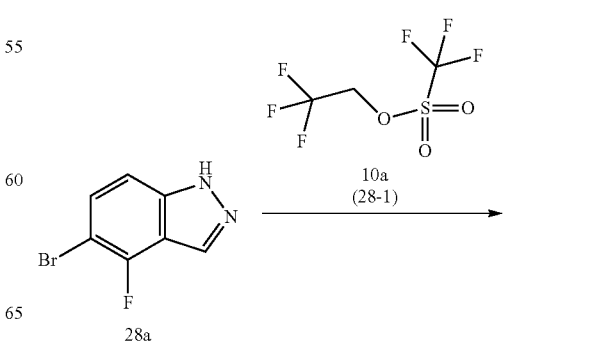

-continued

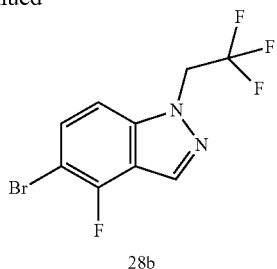
28b

Step 28-1

5-Bromo-4-fluoro-1-(2,2,2-trifluoroethyl)indazole (Compound 28b)

The titled compound was synthesized from 2,2,2-trifluoroethyl trifluoromethanesulfonate (Compound 10a) and 5-bromo-4-fluoro-1H-indazole (Compound 28a) by performing an operation similar to Step 8-4 of Example 8 using an appropriate reagent.

LC/MS mass spectrometry: m/z 297 ([M+H]$^+$).

LC/MS retention time: 1.20 min. (Analysis Condition: SMD-FA05-1).

The halogen compound (5-bromo-4-fluoro-1-[(3-methyloxetan-3-yl)methyl]indazole, Compound 29a) used in the synthesis of Example Compound 29 was synthesized by the following process.

[Chemical Formula 37]

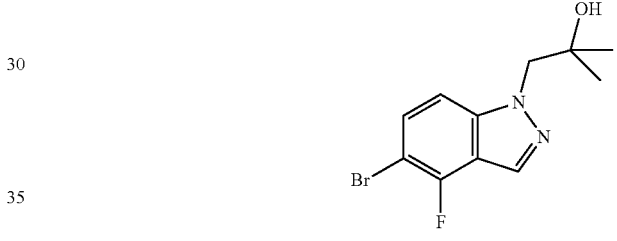

Step 29-1

5-Bromo-4-fluoro-1-[(3-methyloxetan-3-yl)methyl]indazole (Compound 29a)

The titled compound was synthesized from 3-methyl-3-[(4-methylphenyl)sulfonylmethyl]oxetane (Compound 17a)

and 5-bromo-4-fluoro-1H-indazole (Compound 28a) by performing an operation similar to Step 8-4 of Example 8 using an appropriate reagent.

LC/MS mass spectrometry: m/z 299 ([M+H]$^+$).

LC/MS retention time: 1.11 min. (Analysis Condition: SMD-FA05-1).

The halogen compound (1-(5-bromo-4-fluoroindazol-1-yl)-2-methylpropan-2-ol, Compound 30a) used in the synthesis of Example Compound 30 was synthesized by the following process.

[Chemical Formula 38]

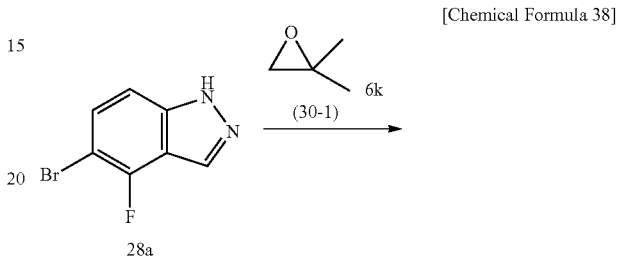

Step 30-1

1-(5-Bromo-4-fluoroindazol-1-yl)-2-methylpropan-2-ol (Compound 30a)

The titled compound was synthesized from 5-bromo-4-fluoro-1H-indazole (Compound 28a) and 2,2-dimethyloxirane (Compound 6k) by performing an operation similar to Step 6-7 of Example 6 using an appropriate reagent.

LC/MS mass spectrometry: m/z 287 ([M+H]$^+$).

LC/MS retention time: 1.01 min. (Analysis Condition: SMD-FA05-1).

The 2-oxoimidazole reagent (3-[(1S,2S)-1-[5-[(4S)-2,2-dimethyloxan-4-yl]-2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one, Compound 311) used in the synthesis of Example Compounds 31 to 40 was synthesized by the following process.

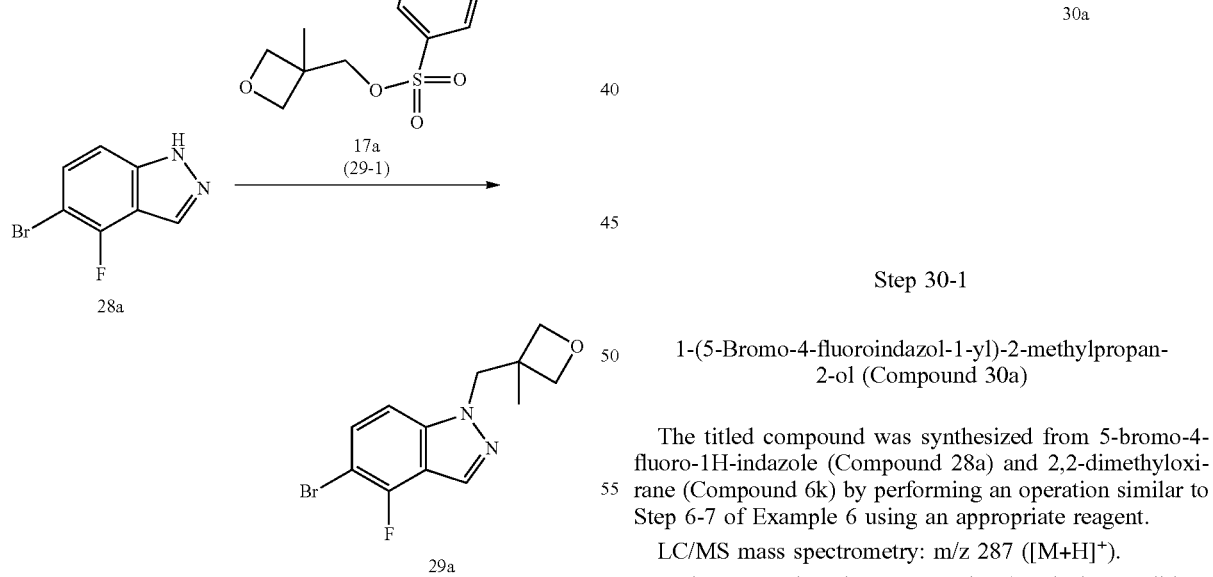

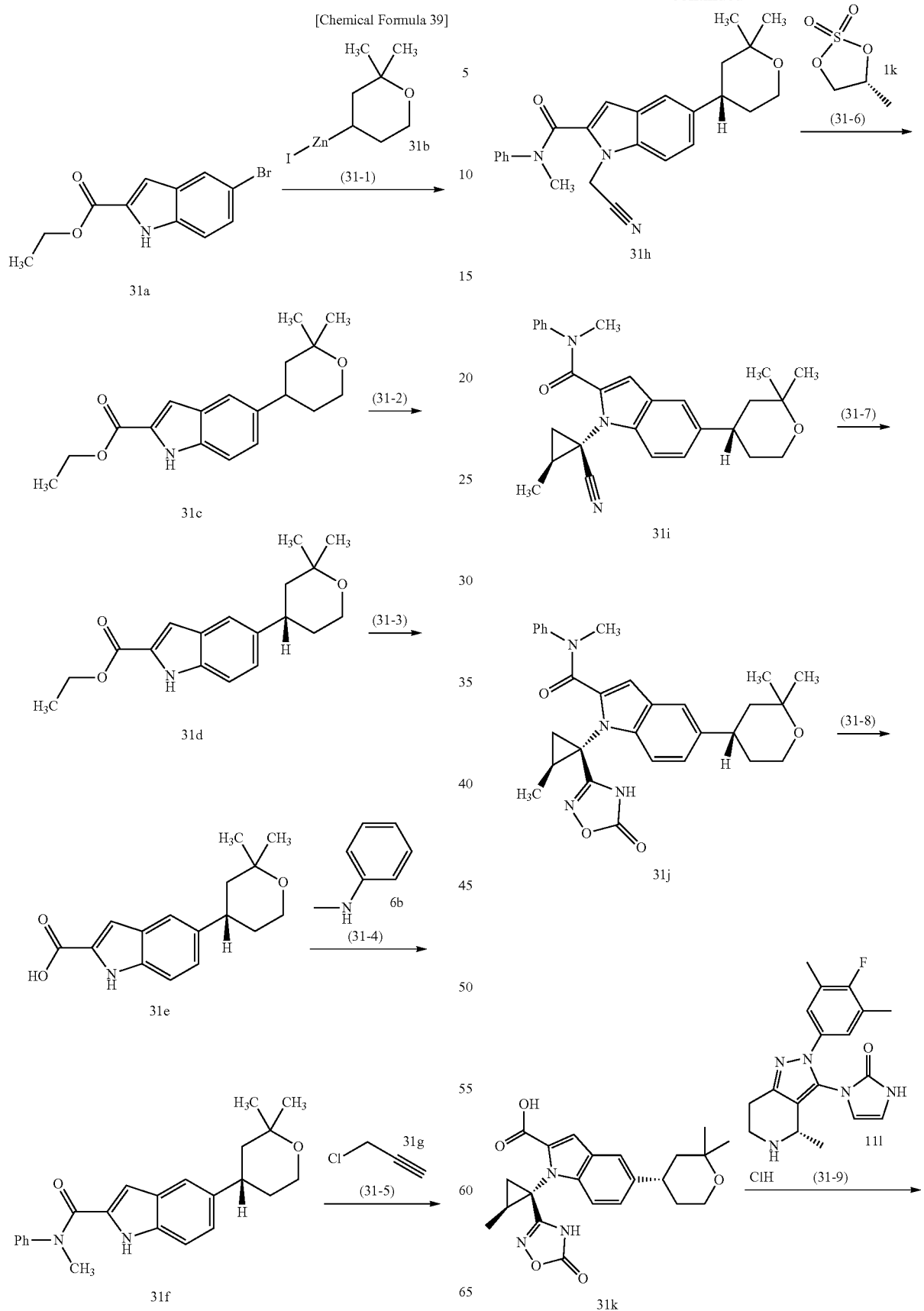
[Chemical Formula 39]

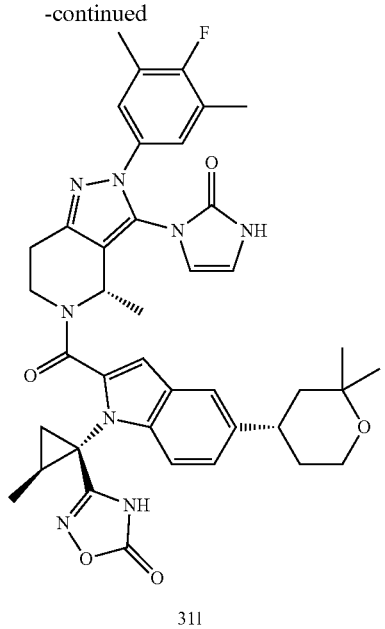

311

Step 31-1

Ethyl 5-(2,2-dimethyloxan-4-yl)-1H-indole-2-carboxylate (Compound 31c)

Zinc powder (1.95 g, 29.8 mmol) was suspended in DMF (6 mL), and the suspension was subjected to nitrogen substitution. Chlorotrimethylsilane (0.417 mL, 3.28 mmol), and 1,2-dibromoethane (0.284 mL, 3.28 mmol) were added and the resulting mixture was stirred at room temperature for 5 min. A DMF (9 mL) solution of 4-iodo-2,2-dimethyltetrahydropyran (5.37 g, 22.4 mmol) was added dropwise to the mixture, and the mixture was stirred at room temperature for 20 min. To this solution were added palladium(II) acetate (0.084 g, 0.373 mmol), and 4-(N,N-dimethylamino)phenyl] di-tert-butylphosphine (0.198 g, 0.746 mol), ethyl 5-bromoindole-2-carboxyl ate (2.0 g, 7.46 mmol), and nitrogen was introduced in the vessel. The mixture was stirred at an external temperature of 50° C. for 1 h., then the external temperature was cooled to 0° C., and 5N hydrochloric acid (6 mL) was added for neutralization. A 30% sodium chloride aqueous solution (50 mL) and ethyl acetate (100 mL) were added and the non-dissolved matters were removed with cerite. The filtrate was subjected to extraction using ethyl acetate and the organic layer was washed with 30% sodium chloride aqueous solution. Then, it was dried with magnesium sulfate and run through a filter, and the solvent was removed by evaporation under reduced pressure. The residue was purified by silica gel column chromatography (ethyl acetate/hexane) to synthesize the titled Compound 31c (1.86 g, yield 83%) as a pale pink solid.

LC/MS mass spectrometry: m/z 302 ([M+H]$^+$).

LC/MS retention time: 0.90 min. (Analysis Condition: SQD-FA05-4).

Step 31-2

Ethyl 5-[(4S)-2,2-dimethyloxan-4-yl]-1H-indole-2-carboxylate (Compound 31d)

The stereoisomers included in Compound 31c (900 mg) obtained by Step 31-1 were separated by supercritical-fluid chromatography to obtain the titled Compound 31d (423 mg, yield 47%).

Separation Condition
  Device: SFC15 (Waters)
  Column: CHIRALPAK-IE/SFC, 10×250 mm, 5 μm (Daicel)
  Column temperature: 40° C.
  Solvent: Super-critical carbon dioxide/methanol: ethyl acetate (1:1)=60/40
(Homogenous System)
  Flow rate: 15 mL/min., 140 bar
Analysis Condition
  Device: Nexera (Shimadzu)
  Column: CHIRALPAK-IE, 4.6×250 mm, 5 μm (Daicel)
  Column Temperature: 25° C.
  Solvent: hexane/ethanol=30/70 (homogenous system)
  Flow rate: 1 mL/min., room temperature
  Titled Compound retention time: 9.98 min., isomer retention time: 6.86 min.

Note that the titled compound was determined to be the S-isomer by X-ray crystallography of Compound 31j.

Step 31-3

5-[(4S)-2,2-Dimethyloxan-4-yl]-1H-indole-2-carboxylic acid (Compound 31e)

Compound 31d (993 mg, 3.29 mmol) obtained in Step 31-2 was dissolved in methanol (14.9 mL), and a 2M sodium hydroxide aqueous solution (3.62 mL, 7.25 mmol) was added dropwise into the mixture and the mixture was stirred at an external temperature of 65° C. for 1 h. The reaction solution was cooled at an external temperature of 15° C., and 5N hydrochloric acid (1.52 mL, 7.58 mmol) was added dropwise into the reaction solution. Water (7.45 mL) was added dropwise, and the precipitated solid was collected by filtration. The obtained solid was washed with water (5.0 mL) and dried under reduced pressure to obtain the titled Compound 31e (827 mg, yield 96%).

LC/MS mass spectrometry: m/z 274 ([M+H]$^+$).

LC/MS retention time: 0.65 min. (Analysis Condition: SQD-FA05-4).

Step 31-4

5-[(4S)-2,2-Dimethyloxan-4-yl]-N-methyl-N-phenyl-1H-indole-2-carboxamide (Compound 31f)

Compound 31e (805 mg, 2.95 mmol) obtained in Step 31-3 was dissolved in DMA (8.0 mL), and thionyl chloride (0.256 mL, 3.53 mmol) was added dropwise into the solution at an internal temperature of 10° C. or lower. After the solution was stirred for an hour, N-methylaniline (0.384 mL, 3.53 mmol) and triethyl amine (0.985 mL, 7.07 mmol) were added dropwise at 10° C. or lower, and the solution was stirred at room temperature for 1 h. Water (4.0 mL) was added dropwise into the solution, and the precipitated solid was collected by filtration. The obtained solid was washed with water (8.0 mL) and dried under reduced pressure to obtain the titled Compound 31f (995 mg, yield 93%).

LC/MS mass spectrometry: m/z 363 ([M+H]$^+$).
LC/MS retention time: 1.20 min. (Analysis Condition: SMD-FA05-1).

Step 31-5

1-(Cyanomethyl)-5-[(4S)-2,2-dimethyloxan-4-yl]-N-methyl-N-phenylindole-2-carboxamide (Compound 31h)

Compound 31f (101 mg, 0.276 mmol) obtained in Step 31-4 was dissolved in 1,3-dimethyl-2-imidazolidinone (DMI) (1.0 mL) at room temperature, and 8M potassium hydroxide aqueous solution (0.103 mL, 0.828 mmol) and water (0.10 mL) were added to the solution. To the obtained solution was added 2-chloroacetonitrile (0.026 mL, 0.414 mmol) at an external temperature of 10° C., and the solution was stirred for 2.5 h. 5N Hydrochloric acid (0.193 mL), water (0.10 mL), and cyclopentylmethyl ether (1.0 mL) were added to the reaction solution to perform extraction, and the aqueous layer was subjected to a second extraction using cyclopentylmethyl ether (1.0 mL). The combined organic layer was washed with 15% sodium chloride solution (1.0 mL), then, the titled Compound 31h was obtained as a light brown oil-like product by concentration under a reduced pressure at an external temperature of 40° C. and was put to use in the subsequent Step 31-6 without being purified.
LC/MS mass spectrometry: m/z 402 ([M+H]$^+$).
LC/MS retention time: 0.93 min. (Analysis Condition: SMD-FA05-1).

Step 31-6

1-[(1S,2S)-1-Cyano-2-methylcyclopropyl]-5-[(4S)-2,2-dimethyloxan-4-yl]-N-methyl-N-phenylindole-2-carboxamide (Compound 31i)

The titled compound was synthesized from Compound 31h obtained in Step 31-5 by performing an operation similar to Step 1-6 of Example 1 using an appropriate reagent.
LC/MS mass spectrometry: m/z 442 ([M+H]$^+$).
LC/MS retention time: 0.95 min. (Analysis Condition: SQD-FA05-1).

Step 31-7

5-[(4S)-2,2-Dimethyloxan-4-yl]-N-methyl-1-[(1S,2S)-2-methyl-1-(5-oxo-4H-1,2,4-oxadiazol-3-yl)cyclopropyl]-N-phenylindole-2-carboxamide (Compound 31j)

The titled compound was synthesized from Compound 31i obtained in Step 31-6 by performing an operation similar to Step 1-6 of Example 1 using an appropriate reagent.
LC/MS mass spectrometry: m/z 501 ([M+H]$^+$).
LC/MS retention time: 0.99 min. (Analysis Condition: SQD-FA05-1).

Step 31-8

5-[(4S)-2,2-Dimethyloxan-4-yl]-1-[(1S,2S)-2-methyl-1-(5-oxo-4H-1,2,4-oxadiazol-3-yl)cyclopropyl]indole-2-carboxylic acid (Compound 31k)

The titled compound was synthesized from Compound 31j obtained in Step 31-7 by performing an operation similar to Step 6-4 of Example 6 using an appropriate reagent.

LC/MS mass spectrometry: m/z 401 ([M–H]$^-$).
LC/MS retention time: 1.05 min. (Analysis Condition: SMD-FA05-1).

Step 31-9

3-[(1S,2S)-1-[5-[(4S)-2,2-Dimethyloxan-4-yl]-2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one (Compound 31l)

The titled compound was synthesized from Compound 1l1 obtained in Step 11-8 and Compound 31k obtained in Step 31-8 by performing an operation similar to Step 1-10 of Example 1 using an appropriate reagent.

The halogen compound 5-bromo-1-(2-methoxyethyl)-3-methylbenzoimidazol-2-one (Compound 33b) used in the synthesis of Example Compound 33 was synthesized by the following process.

Step 33-1

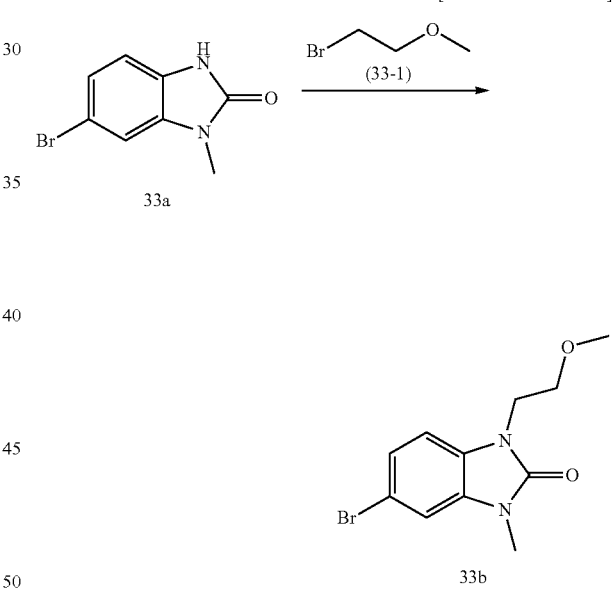

The titled compound was synthesized from 5-bromo-3-methyl-1H-benzoimidazol-2-one (Compound 33a) by performing an operation similar to Step 8-4 of Example 8 using an appropriate reagent.
LC/MS mass spectrometry: m/z 285 ([M+H]$^+$).
LC/MS retention time: 0.95 min. (Analysis Condition: SMD-FA05-1).

The halogen compound (5-bromo-4-fluoro-1-(2-methoxyethyl)indazole, Compound 36a) used in the synthesis of Example Compound 36 was synthesized by the following process.

Step 36-1

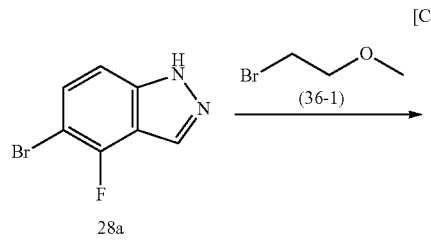

The titled compound was synthesized from 5-bromo-4-fluoro-1H-indazole (Compound 28a) by performing an operation similar to Step 8-4 of Example 8 using an appropriate reagent.

LC/MS mass spectrometry: m/z 273 ([M+H]+).
LC/MS retention time: 1.10 min. (Analysis Condition: SMD-FA05-1).

The halogen compound (5-bromo-4-fluoro-1-[(3S)-oxolan-3-yl]indazole, Compound 40a) used in the synthesis of Example Compound 40 was synthesized by the following process.

Step 40-1

[Chemical Formula 42]

The titled compound was synthesized from 5-bromo-4-fluoro-H-indazole (Compound 28a) and (3R)-oxolan-3-yl 4-methylbenzenesulfonate (Compound 22b) by performing an operation similar to Step 8-4 of Example 8 using an appropriate reagent.

LC/MS mass spectrometry: m/z 285 ([M+H]+).
LC/MS retention time: 1.10 min. (Analysis Condition: SMD-FA05-1).

The 2-oxoimidazole reagent (3-[(1S,2S)-1-[2-[(4S)-2-(4-fluoro-3,5-dimethylphenyl)-4-methyl-3-(2-oxo-1H-imidazol-3-yl)-6,7-dihydro-4H-pyrazolo[4,3-c]pyridine-5-carbonyl]-5-[(2S,4S)-2-methyloxan-4-yl]indol-1-yl]-2-methylcyclopropyl]-4H-1,2,4-oxadiazol-5-one, Compound 41f) used in the synthesis of Example Compound 41 was synthesized by the following process.

[Chemical Formula 43]

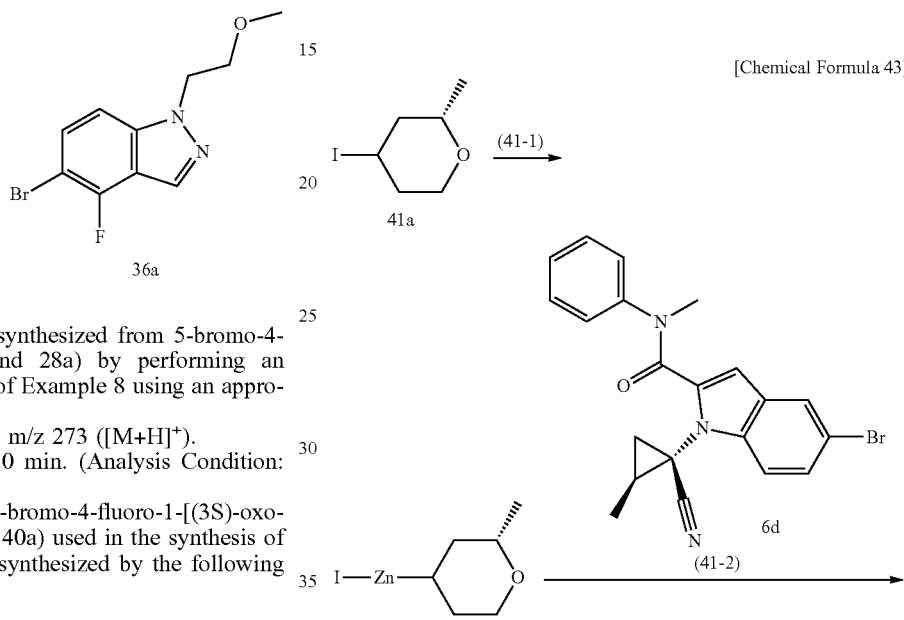

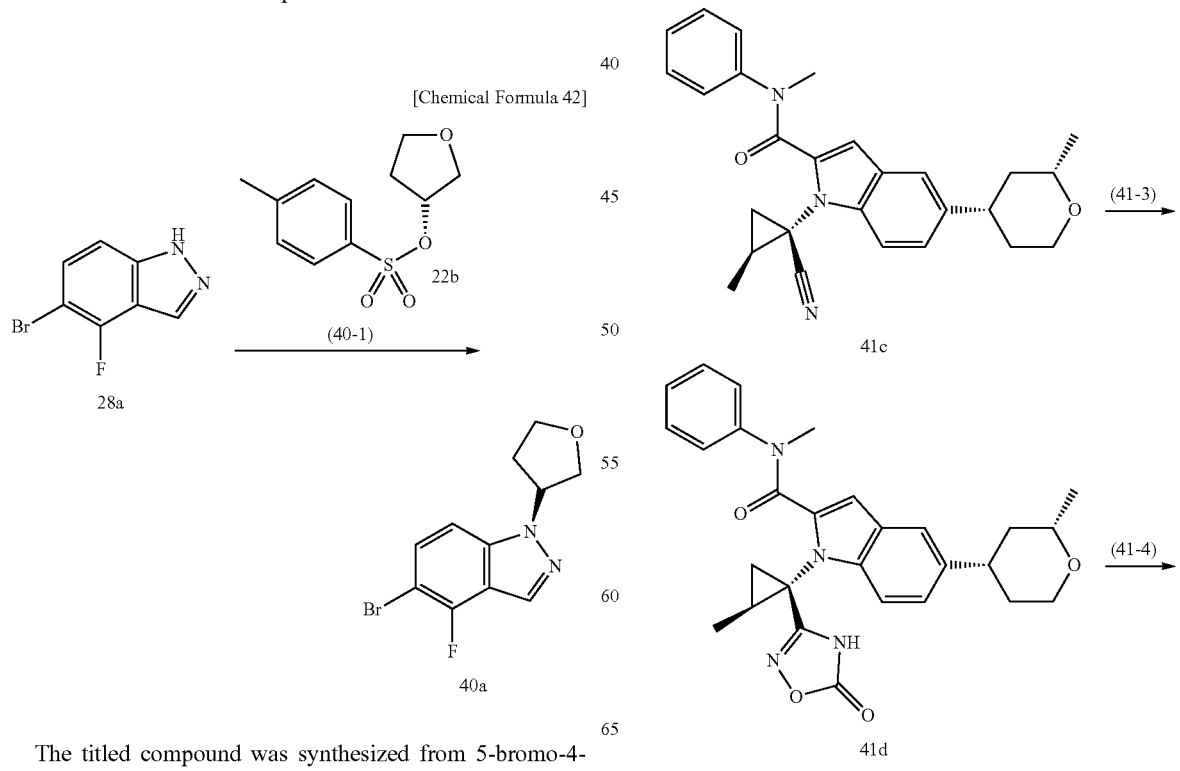

153

-continued

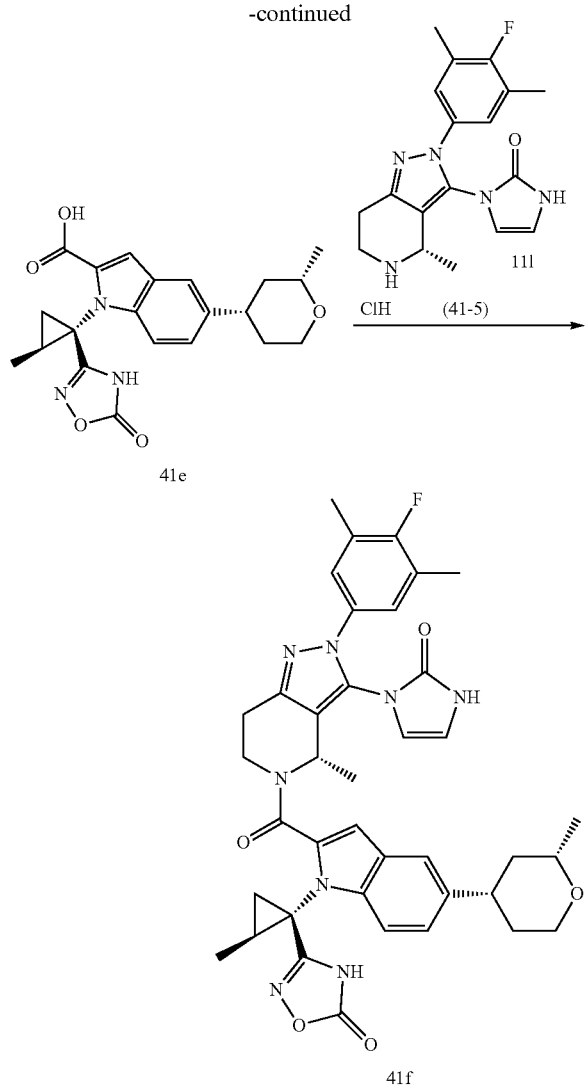

41e

41f

Steps 41-1 and 2

1-[(1S,2S)-1-Cyano-2-methylcyclopropyl]-N-methyl-5-[(2S,4S)-2-methyloxan-4-yl]-N-phenylindole-2-carboxamide (Compound 41c)

After a DMA (0.12 mL) suspension of zinc (29 mg, 0.44 mmol) was deaerated under at room temperature at room temperature, nitrogen was introduced in the vessel. Under a nitrogen atmosphere, a 7:5 mixed solution of chlorotrimethylsilane/1,2-dibromoethane (0.0083 mL, 0.039 mmol of chlorotrimethylsilane) was added, and the mixture was stirred for 15 min., then (2S)-4-iodo-2-methyltetrahydro-2H-pyran (80 mg, 0.35 mmol) was added dropwise at room temperature and the mixture was stirred for 30 min. to obtain a mixture containing iodo-[(2S)-2-methyloxan-4-yl]zinc (Compound 41b). Palladium(II) acetate (6.4 mg, 0.028 mmol), 2-dicyclohexylphosphino-2',6'-diisopropoxybiphenyl (26 mg, 0.057 mmol), 5-bromo-1-[(1S,2S)-1-cyano-2-methylcyclopropyl]-N-methyl-N-phenylindole-2-carboxamide (58 mg, 0.14 mmol), and DMA (0.123 mL) were added, and the mixture was deaerated under reduced pressure, then nitrogen was introduced in the vessel and the

154 mixture was stirred for an hour at 80° C. The mixture was cooled to room temperature, to which ethyl acetate and 1N hydrochloric acid were added, and the mixture was filtered. Then, the filtrate was subjected to extraction using ethyl acetate. The organic layer was washed once with brine and concentrated under reduced pressure, then, the residue was purified by silica gel column chromatography (ethyl acetate/hexane=1:1) to obtain the titled Compound 41c (31 mg, yield 51%).

LC/MS mass spectrometry: m/z 428 ([M+H]$^+$).

LC/MS retention time: 1.01 min. (Analysis Condition: SQD-AA05-1).

Step 41-3

N-Methyl-5-[(2S,4S)-2-methyloxan-4-yl]-1-[(1S,2S)-2-methyl-1-(5-oxo-4H-1,2,4-oxadiazol-3-yl)cyclopropyl]-N-phenylindole-2-carboxamide (Compound 41d)

The titled compound was synthesized from Compound 41c obtained in Step 41-2 by performing an operation similar to Step 1-8 of Example 1 using an appropriate reagent.

LC/MS mass spectrometry: m/z 487 ([M+H]$^+$).

LC/MS retention time: 1.30 min. (Analysis Condition: SMD-FA05-1).

Step 41-4

5-[(2S,4S)-2-Methyloxan-4-yl]-1-[(1S,2S)-2-methyl-1-(5-oxo-4H-1,2,4-oxadiazol-3-yl)cyclopropyl]indole-2-carboxylic acid (Compound 41e)

The titled compound was synthesized from Compound 41d obtained in Step 41-3 by performing an operation similar to Step 6-4 of Example 6 using an appropriate reagent.

LC/MS mass spectrometry: m/z 396 ([M–H]$^-$).

LC/MS retention time: 1.02 min. (Analysis Condition: SMD-FA05-1).

Step 41-5

3-[(1S,2S)-1-[2-[(4S)-2-(4-Fluoro-3,5-dimethylphenyl)-4-methyl-3-(2-oxo-1H-imidazol-3-yl)-6,7-dihydro-4H-pyrazolo[4,3-c]pyridine-5-carbonyl]-5-[(2S,4S)-2-methyloxan-4-yl]indol-1-yl]-2-methylcyclopropyl]-4H-1,2,4-oxadiazol-5-one (Compound 41f)

The titled compound was synthesized from Compound 41e obtained in Step 41-4 by performing an operation similar to Step 1-10 of Example 1 using an appropriate reagent.

The 2-oxoimidazole reagent (3-[(1S,2S)-1-[2-[(4S)-2-(4-chloro-3,5-dimethylphenyl)-4-methyl-3-(2-oxo-1H-imidazol-3-yl)-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one, Compound 42g) used in the synthesis of Example Compounds 42 and 43 were synthesized by the following process.

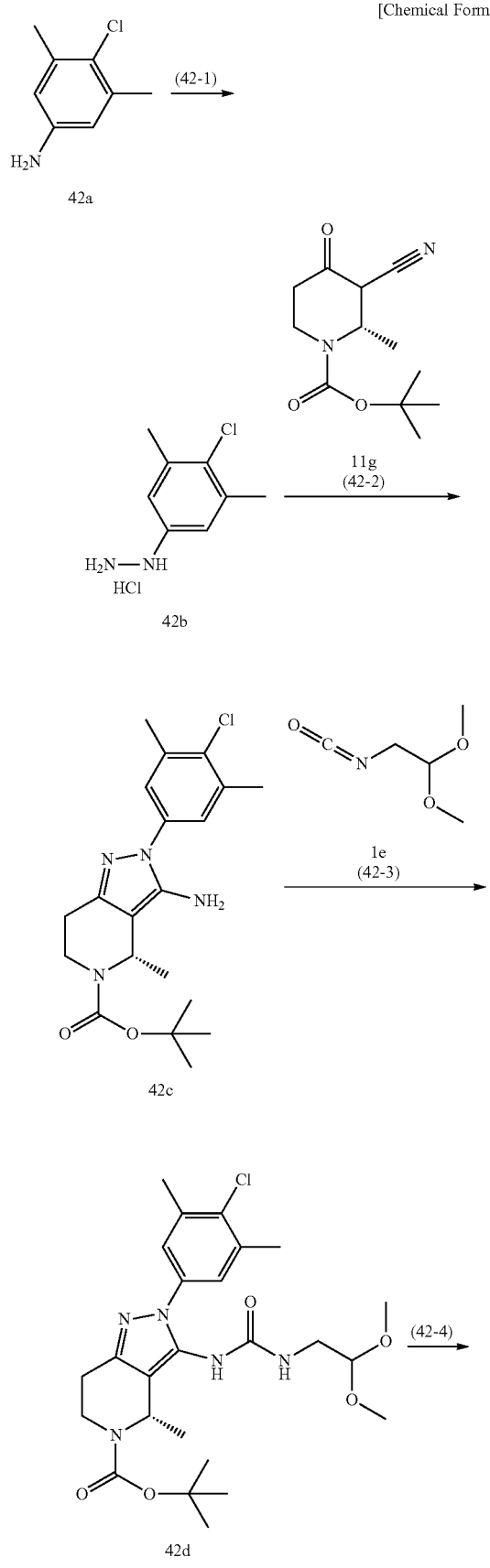
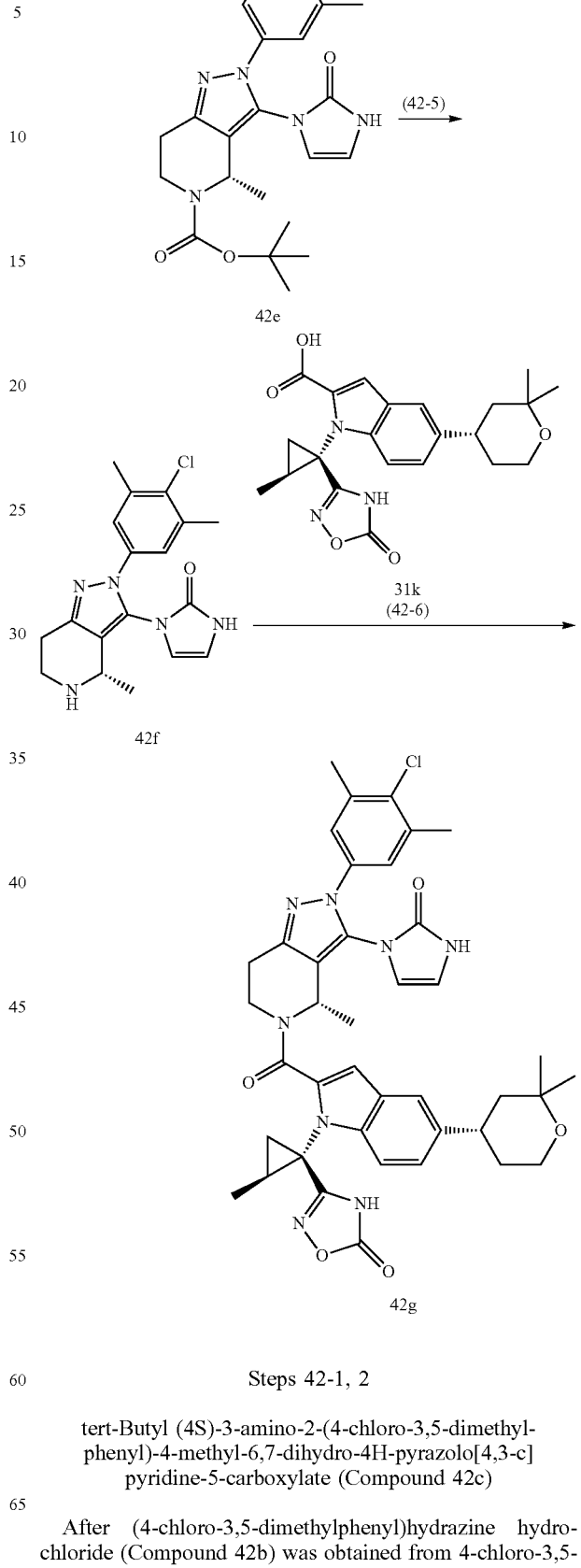
Steps 42-1, 2
tert-Butyl (4S)-3-amino-2-(4-chloro-3,5-dimethyl-phenyl)-4-methyl-6,7-dihydro-4H-pyrazolo[4,3-c]pyridine-5-carboxylate (Compound 42c)
After (4-chloro-3,5-dimethylphenyl)hydrazine hydrochloride (Compound 42b) was obtained from 4-chloro-3,5- dimethylaniline (Compound 42a) by performing an operation similar to Step 2-2 of Example 2 using an appropriate reagent, Compound 11g obtained in Step 11-4 and an appropriate reagent were used to synthesize Compound 42c by an operation similar to Step 1-2 of Example 1.

LC/MS mass spectrometry: m/z 391 ([M+H]$^+$).
LC/MS retention time: 1.22 min. (Analysis Condition: SMD-FA10-4).

Step 42-3 tert-Butyl (4S)-2-(4-chloro-3,5-dimethylphenyl)-3-(2,2-dimethoxyethylcarbamoylamino)-4-methyl-6,7-dihydro-4H-pyrazolo[4,3-c]pyridine-5-carboxylate (Compound 42d)

The titled compound was synthesized from Compound 42c obtained in Step 42-2 by performing an operation similar to Step 1-3 of Example 1 using an appropriate reagent.

LC/MS mass spectrometry: m/z 522 ([M+H]$^+$).
LC/MS retention time: 1.55 min. (Analysis Condition: SMD-TFA05-5).

Step 42-4 tert-Butyl (4S)-2-(4-chloro-3,5-dimethylphenyl)-4-methyl-3-(2-oxo-1H-imidazol-3-yl)-6,7-dihydro-4H-pyrazolo[4,3-c]pyridine-5-carboxylate (Compound 42e)

The titled compound was synthesized from Compound 42d obtained in Step 42-3 by performing an operation similar to Step 11-8 of Example 11 using an appropriate reagent.

LC/MS mass spectrometry: m/z 458 ([M+H]$^+$).
LC/MS retention time: 1.16 min. (Analysis Condition: SMD-FA05-1).

Step 42-5

3-[(4S)-2-(4-Chloro-3,5-dimethylphenyl)-4-methyl-4,5,6,7-tetrahydropyrazolo[4,3-c]pyridin-3-yl]-1H-imidazol-2-one hydrochloride (Compound 42f)

The titled compound was synthesized from Compound 42e obtained in Step 42-4 by performing an operation similar to Step 111-8 of Example 11 using an appropriate reagent.

LC/MS mass spectrometry: m/z 358 ([M+H]$^+$).
LC/MS retention time: 0.69 min. (Analysis Condition: SMD-FA05-1).

Step 42-6

3-[(1S,2S)-1-[2-[(4S)-2-(4-chloro-3,5-dimethylphenyl)-4-methyl-3-(2-oxo-1H-imidazol-3-yl)-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one (Compound 42g)

The titled compound was synthesized from Compound 42f obtained in Step 42-5 and Compound 31k obtained in Step 31-8 by performing an operation similar to Step 1-10 of Example 1 using an appropriate reagent.

The 2-oxoimidazole reagent (3-[(1S,2S)-1-[2-[(4S)-2-(4-chloro-3,5-dimethylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1, 2,4-oxadiazol-5-one, Compound 44a) used in the synthesis of Example Compounds 44 and 45 were synthesized by the following process.

[Chemical Formula 45]

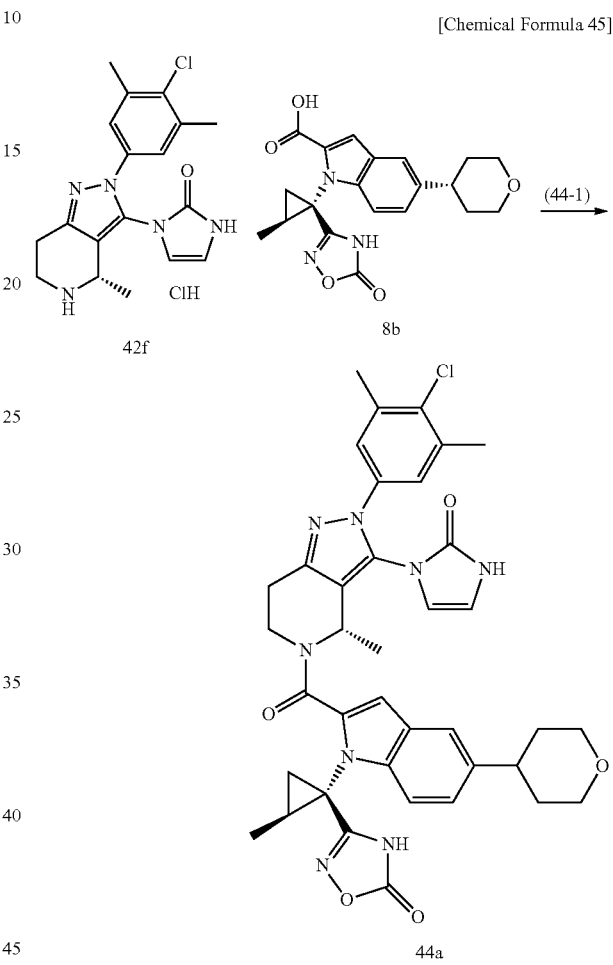

Step 44-1

3-[(1S,2S)-1-[2-[(4S)-2-(4-Chloro-3,5-dimethylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one (Compound 44a)

The titled compound was synthesized from Compound 42f obtained in Step 42-5 and Compound 8b obtained in Step 8-1 by performing an operation similar to Step 1-10 of Example 1 using an appropriate reagent.

The 2-oxoimidazole reagent (3-[(1S,2S)-1-[2-[(4S)-2-(4-fluoro-3-methylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one, Compound 46f) used in the synthesis of Example Compounds 46 and 47 was synthesized by the following process.

[Chemical Formula 46]
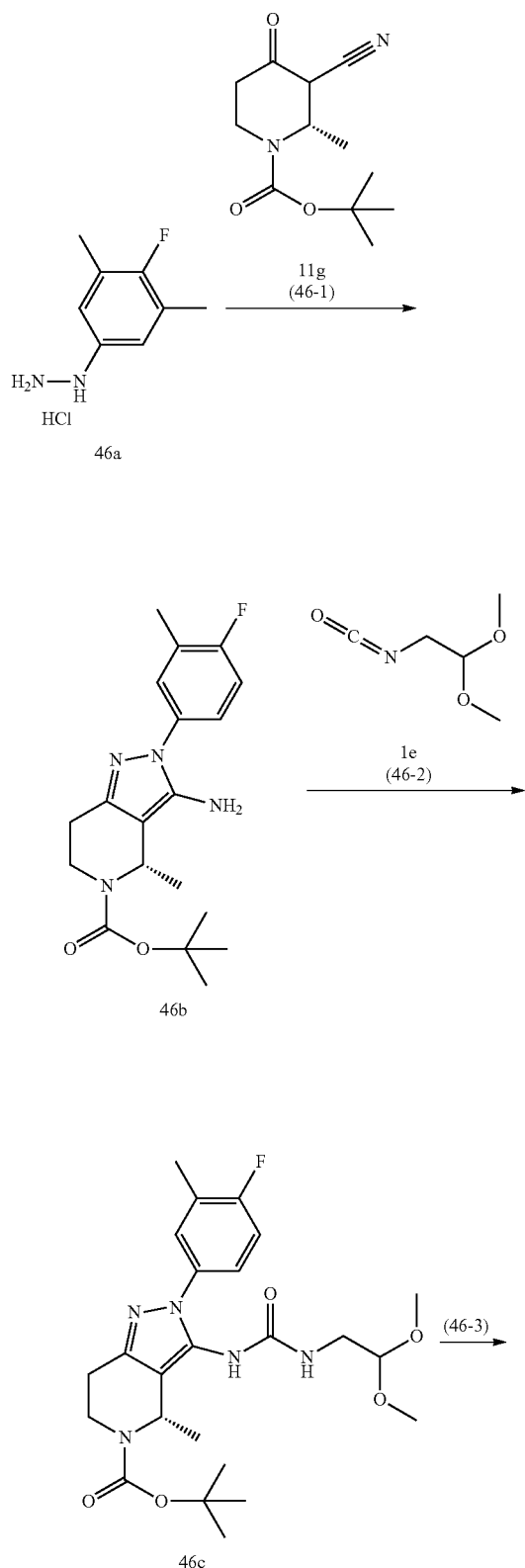
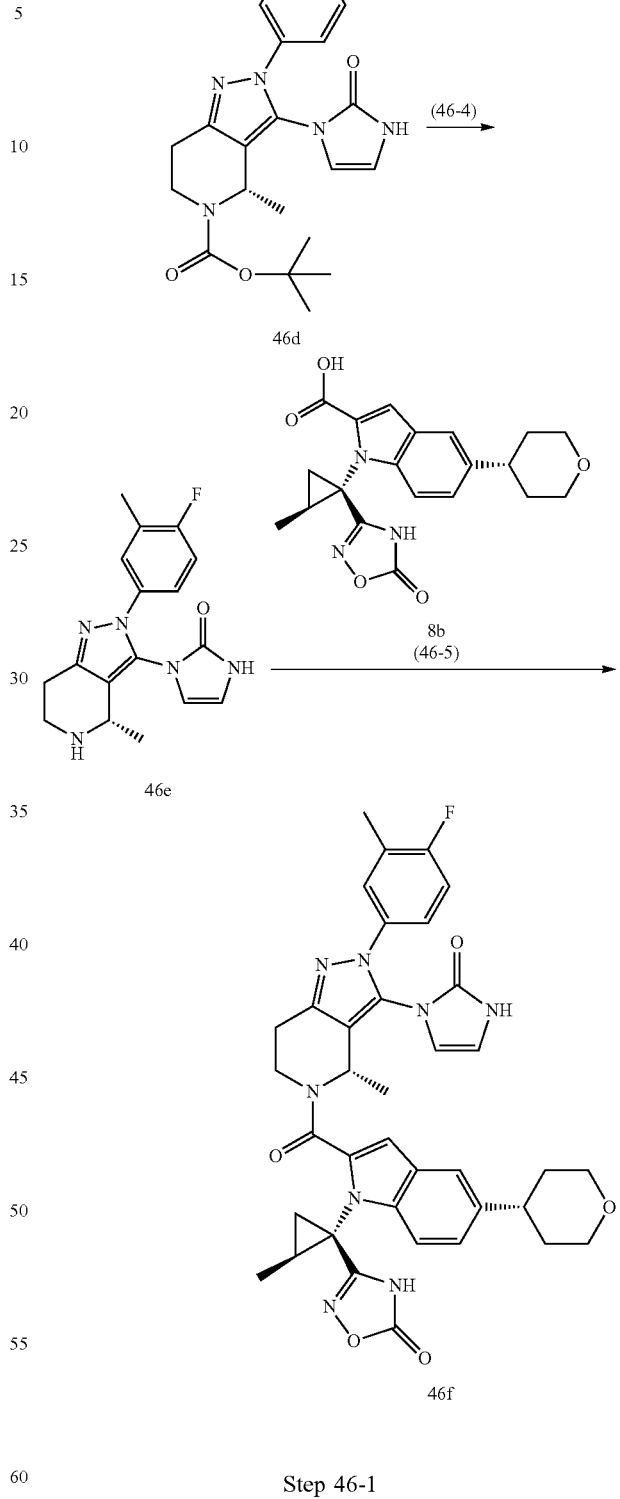
Step 46-1
tert-Butyl (4S)-3-amino-2-(4-fluoro-3-methylphenyl)-4-methyl-6,7-dihydro-4H-pyrazolo[4,3-c]pyridine-5-carboxylate (Compound 46b)
The titled compound was synthesized from (4-fluoro-3-methylphenyl)hydrazine hydrochloride (Compound 46a)

and Compound 11g obtained in Step 11-4 by performing an operation similar to Step 1-2 of Example 1 using an appropriate reagent.

LC/MS mass spectrometry: m/z 361 ([M+H]$^+$).
LC/MS retention time: 1.02 min. (Analysis Condition: SMD-FA05-1).

Step 46-2 tert-Butyl (4S)-3-(2,2-dimethoxyethylcarbamoylamino)-2-(4-fluoro-3-methylphenyl)-4-methyl-6,7-dihydro-4H-pyrazolo[4,3-c]pyridine-5-carboxylate (Compound 46c)

The titled compound was synthesized from Compound 46b obtained in Step 46-1 by performing an operation similar to Step 1-3 of Example 1 using an appropriate reagent.

LC/MS mass spectrometry: m/z 492 ([M+H]$^+$).
LC/MS retention time: 1.03 min. (Analysis Condition: SMD-FA05-1).

Step 46-3 tert-Butyl (4S)-2-(4-fluoro-3-methylphenyl)-4-methyl-3-(2-oxo-1H-imidazol-3-yl-6,7-dihydro-4H-pyrazolo[4,3-c]pyridine-5-carboxylate (Compound 46d)

The titled compound was synthesized from Compound 46c obtained in Step 46-2 by performing an operation similar to Step 11-7 of Example 11 using an appropriate reagent.

LC/MS mass spectrometry: m/z 428 ([M+H]$^+$).
LC/MS retention time: 2.11 min. (Analysis Condition: SMD-FA05-long).

Step 46-4

3-[(4S)-2-(4-Fluoro-3-methylphenyl)-4-methyl-4,5,6,7-tetrahydropyrazolo[4,3-c]pyridin-3-yl]-1H-imidazol-2-one hydrochloride (Compound 46e)

The titled compound was synthesized from Compound 46d obtained in Step 46-3 by performing an operation similar to Step 11-8 of Example 11 using an appropriate reagent.

LC/MS mass spectrometry: m/z 328 ([M+H]$^+$).
LC/MS retention time: 0.59 min. (Analysis Condition: SMD-FA05-3).

Step 46-5

3-[(1S,2S)-1-[2-[(4S)-2-(4-fluoro-3-methylphenyl)-4-methyl-3-(2-oxo-1H-imidazol-3-yl)-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one (Compound 46f)

The titled compound was synthesized from Compound 46e obtained in Step 46-4 and Compound 8b obtained in Step 8-1 by performing an operation similar to Step 1-10 of Example 1 using an appropriate reagent.

The 2-oxoimidazole reagent (3-[(1S,2S)-1-[5-[(4S)-2,2-dimethyloxan-4-yl]-2-[(4S)-2-(4-fluoro-3-methylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one, Compound 48a) used in the synthesis of Example Compounds 48 to 50 was synthesized by the following process.

[Chemical Formula 47]

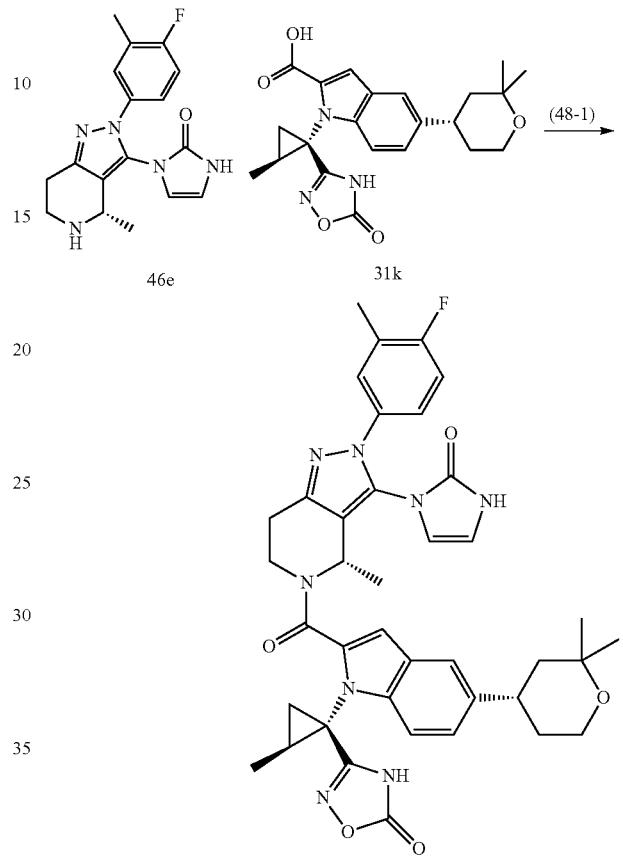

Step 48-1

3-[(1S,2S)-1-[5-[(4S)-2,2-dimethyloxan-4-yl]-2-[(4S)-2-(4-fluoro-3-methylphenyl)-4-methyl-3-(2-oxo-1H-imidazol-3-yl)-6,7-dihydro-4H-pyrazolo[4,3-c]pyridine-5-carbonyl]indol-1-yl]-2-methylcyclopropyl]-4H-1,2,4-oxadiazol-5-one (Compound 48a)

The titled compound was synthesized from Compound 46e obtained in Step 46-5 and Compound 31k obtained in Step 31-8 by performing an operation similar to Step 1-10 of Example 1 using an appropriate reagent.

Examples 51 to 53

An operation similar to Step 7-1 of Example 7 was performed using 3-[(1S,2S)-1-[5-bromo-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one (Compound 51d), substituted morpholine and an appropriate reagent to obtain Example Compounds 51 to 53 shown in Table 2-4 by the following reaction.

[Chemical Formula 48]
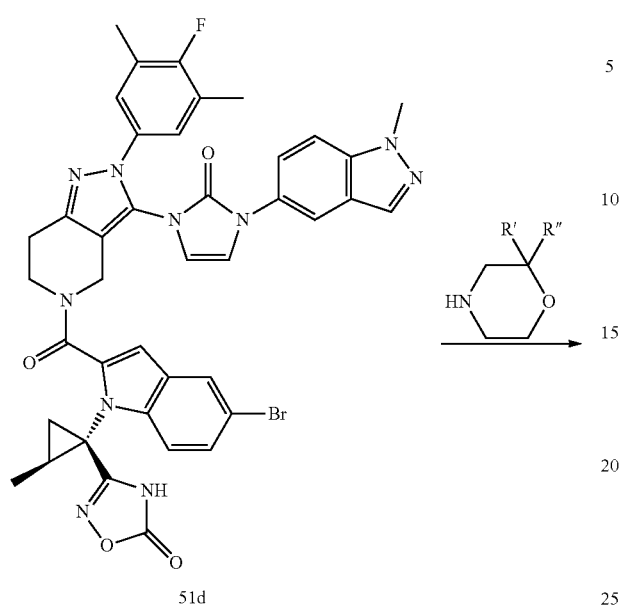
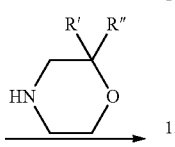
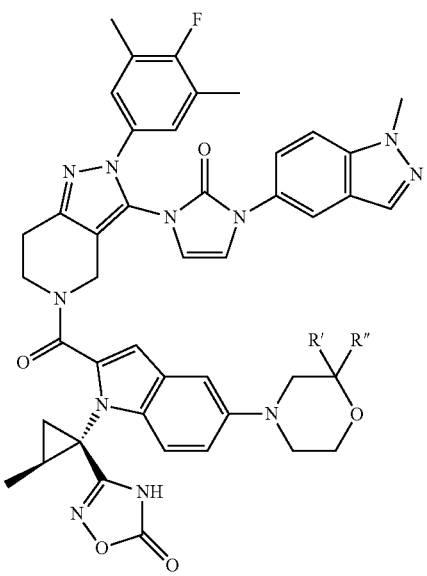
51-53
TABLE 2-4
The Obtained Example Compounds 51 to 53
| Example No. | Structure | Compound | Analysis Condition | LC/MS retention time (min.) | LC/MS mass spectrometry (m/z) |
|---|---|---|---|---|---|
| 51 | 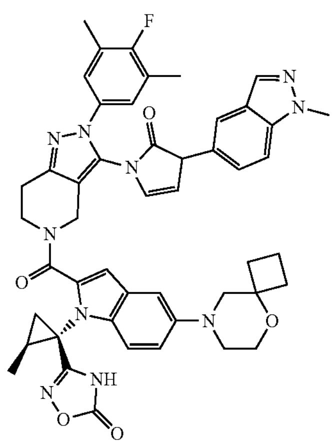 | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(5-oxa-8-azaspiro[3.5]nonan-8-yl)indol-1-yl]-2-methylcyclopropyl]-4H-1,2,4-oxadiazol-5-one | SMD-TFA05-3 | 1.31 | 864 ([M+H]⁺) |

TABLE 2-4-continued

The Obtained Example Compounds 51 to 53

| Example No. | Structure | Compound | Analysis Condition | LC/MS retention time (min.) | LC/MS mass spectrometry (m/z) |
|---|---|---|---|---|---|
| 52 | 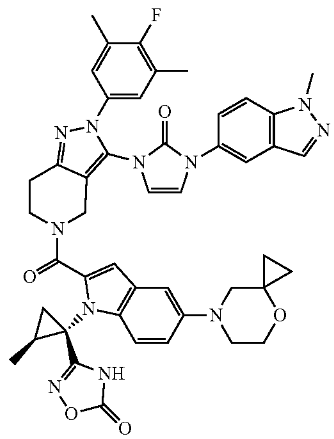 [SMILES: Cc1cc(-n2nc3c(c2-n2ccn(-c4ccc5c(cnn5C)c4)c2=O)CN(C(=O)c2cc4cc(N5CCOC6(CC6)C5)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(4-oxa-7-azaspiro[2.5]octan-7-yl)indol-1-yl]-2-methylcyclopropyl]-4H-1,2,4-oxadiazol-5-one | SMD-TFA05-3 | 1.16 | 850 ([M+H]+) |
| 53 | 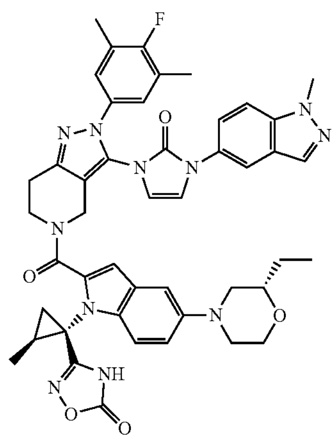 [SMILES: CC[C@H]1CN(c2ccc3c(c2)cc(C(=O)N2CCc4nn(-c5cc(C)c(F)c(C)c5)c(-n5ccn(-c6ccc7c(cnn7C)c6)c5=O)c4C2)n3[C@@]2(c3noc(=O)[nH]3)C[C@@H]2C)CCO1] | 3-[(1S,2S)-1-[5-[(2S)-2-ethylmorpholin-4-yl]-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl-4H-1,2,4-oxadiazol-5-one | SMD-TFA05-3 | 1.21 | 852 ([M+H]+) |

Compound 51d was synthesized as follows.

[Chemical Formula 49]

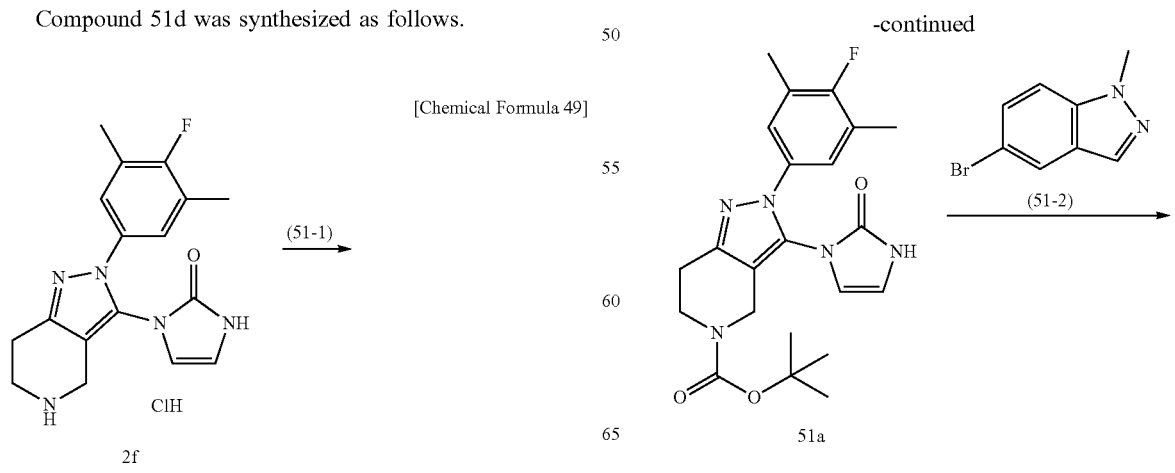

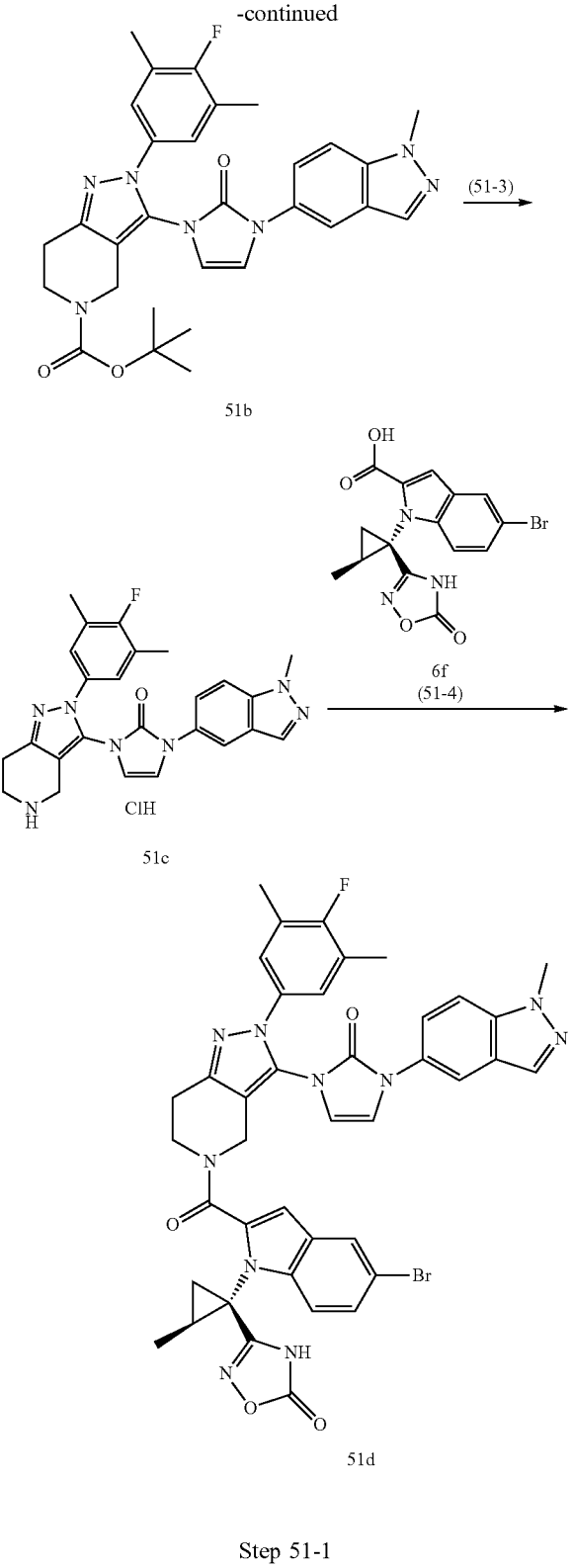

added triethyl amine (0.936 mL, 6.72 mmol), di-tert-butyl dicarbonate (0.425 mL, 1.85 mmol), and the suspension was stirred at room temperature for 2 h. Water (20.0 mL) and 5% potassium hydrogen sulfate aqueous solution (20.0 mL) were added to the reaction solution, then extraction was performed using dichloromethane, and the resulting product was dried using magnesium sulfate. After filtration, the filtrate was concentrated under reduced pressure and the residue was purified by silica gel column chromatography (ethyl acetate/hexane=0:1 to 1:0) to obtain the titled Compound 51a (0.360 g, yield 50%).

LC/MS mass spectrometry: m/z 428 ([M+H]⁺).
LC/MS retention time: 1.06 min. (Analysis Condition: SMD-FA05-3).

Step 51-2 tert-Butyl 2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carboxylate (Compound 51b)

The titled compound was synthesized from Compound 51a obtained in Step 51-1 and 5-bromo-1-methylindazole by performing an operation similar to Step 1-11 of Example 1 using an appropriate reagent.

LC/MS mass spectrometry: m/z 558 ([M+H]⁺).
LC/MS retention time: 1.25 min. (Analysis Condition: SMD-FA05-1).

Step 51-3

1-[2-(4-Fluoro-3,5-dimethylphenyl)-4,5,6,7-tetrahydropyrazolo[4,3-c]pyridin-3-yl]-3-(1-methylindazol-5-yl)imidazol-2-one hydrochloride (Compound 51c)

The titled compound was synthesized from Compound 51b obtained in Step 51-2 by performing an operation similar to Step 11-9 of Example 11 using an appropriate reagent.

LC/MS mass spectrometry: m/z 458 ([M+H]⁺).
LC/MS retention time: 0.78 min. (Analysis Condition: SMD-FA05-1).

Step 51-4

3-[(1S,2S)-1-[5-Bromo-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one (Compound 51d)

The titled compound was synthesized from Compound 51c obtained in Step 51-3 and Compound 6f obtained in Step 6-4 by performing an operation similar to Step 1-10 of Example 1 using an appropriate reagent.

LC/MS mass spectrometry: m/z 817 ([M+H]⁺).
LC/MS retention time: 1.41 min. (Analysis Condition: SMD-FA05-1).

Examples 54 to 73

An operation similar to Step 1-10 of Example 1 was performed using an amine derivative and a carboxylic acid derivative to obtain Example Compounds 54 to 72 shown in Table 2-5 and Example Compound 73 by the following reaction.

Step 51-1 tert-Butyl 2-(4-fluoro-3,5-dimethylphenyl)-3-(2-oxo-1H-imidazol-3-yl)-6,7-dihydro-4H-pyrazolo[4,3-c]pyridine-5-carboxylate (Compound 51a)

To a dichloromethane (16.8 mL) suspension of Compound 2f (0.611 g, 1.68 mmol) obtained in Step 2-5 was

[Chemical Formula 50]
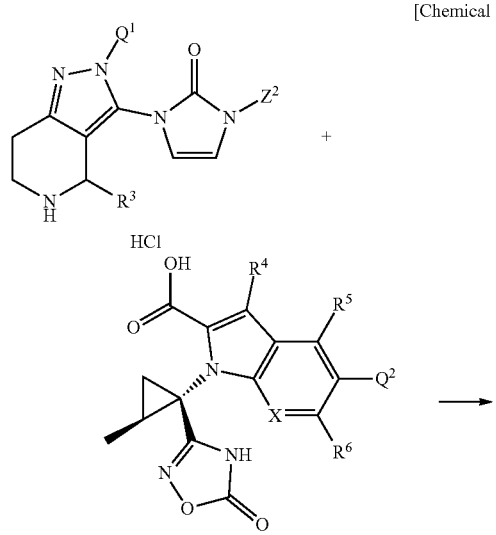
+
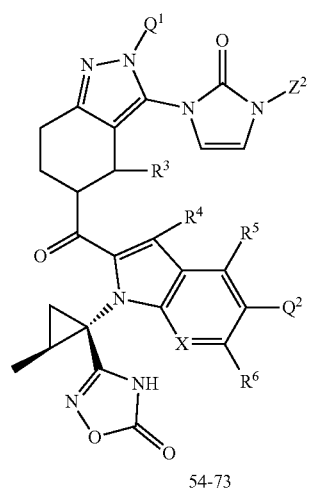
54-73
TABLE 2-5
The Obtained Example Compounds 54 to 72
| Example No. | Structure | Compound | Analysis Condition | LC/MS retention time (min.) | LC/MS mass spectrometry (m/z) |
|---|---|---|---|---|---|
| 54 | 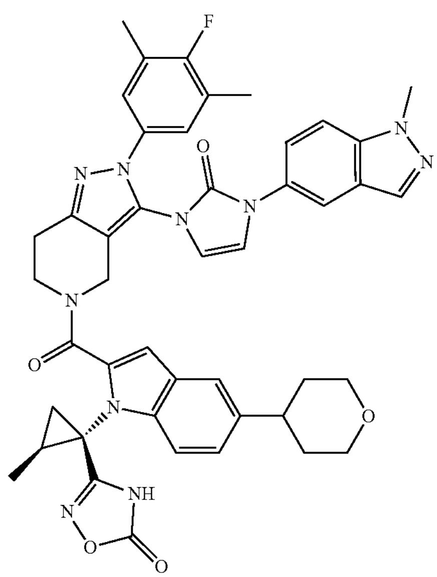 [SMILES: Cc1cc(-n2nc3c(c2-n2ccn(-c4ccc5c(cnn5C)c4)c2=O)CN(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-3 | 1.41 | 823 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 55 | 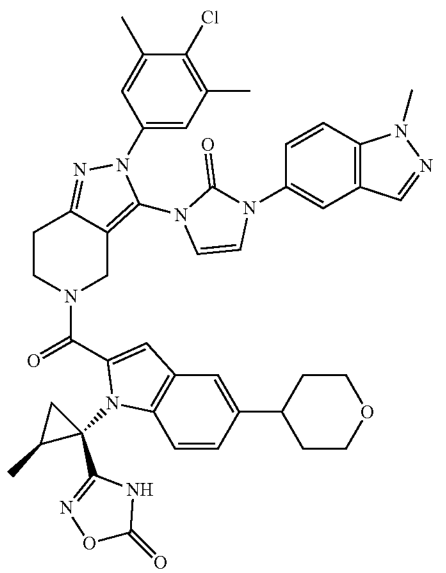 [SMILES: Cc1cc(-n2nc3c(c2-n2ccn(-c4ccc5c(cnn5C)c4)c2=O)CN(C(=O)c2cc4cc(C5CCOCC5)ccc4n2[C@@]2(c4noc(=O)[nH]4)C[C@@H]2C)CC3)cc(C)c1Cl] | 3-[(1S,2S)-1-[2-[2-(4-chloro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-2 | 1.43 | 839 |
| 56 | 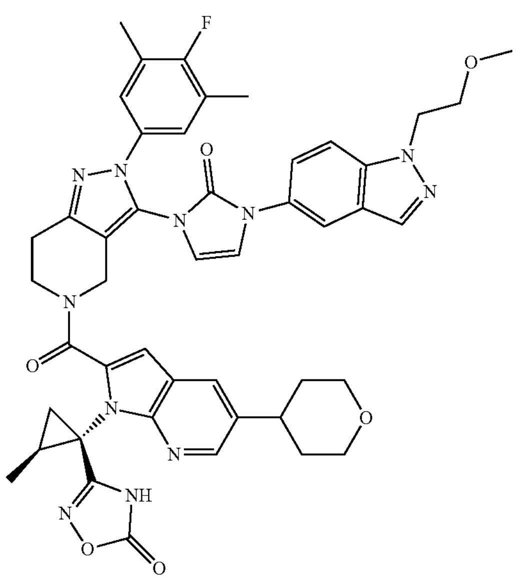 | 3-[(1S,2S)-1-[2-[2-(4-fluoro-3,5-dimethylphenyl)-3-[3-[1-(2-methoxyethyl)indazol-5-yl]-2-oxoimidazol-1-yl]-6,7-dihydro-4H-pyrazolo[4,3-c]pyridine-5-carbonyl]-5-(oxan-4-yl)pyrrolo[2,3-b]pyridin-1-yl]-2-methylcyclopropyl]-4H-1,2,4-oxadiazol-5-one | SMD-TFA05-2 | 1.23 | 868 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 57 | 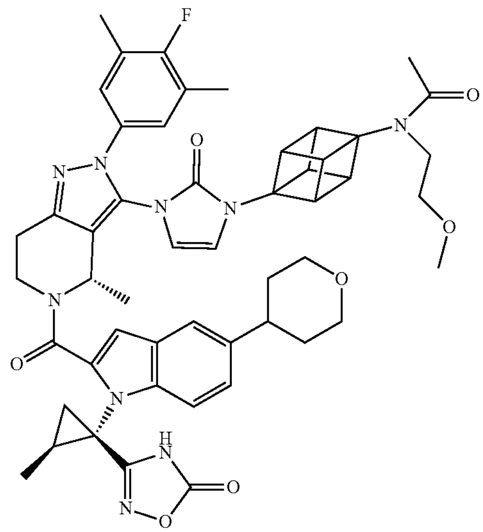 [SMILES: COCCN(C(C)=O)C12C3C4C1C1C2C3C41n1ccn(-c2c3c(nn2-c2cc(C)c(F)c(C)c2)CCN(C(=O)c2cc4cc(C5CCOCC5)ccc4n2[C@@]2(c4noc(=O)[nH]4)C[C@@H]2C)[C@H]3C)c1=O] | N-[4-[3-[(4S)-2-(4-fluoro-3,5-dimethylphenyl)-4-methyl-5-[1-[(1S,2S)-2-methyl-1-(5-oxo-4H-1,2,4-oxadiazol-3-yl)cyclopropyl]-5-(oxan-4-yl)indole-2-carbonyl]-6,7-dihydro-4H-pyrazolo[4,3-c]pyridin-3-yl]-2-oxoimidazol-1-yl]cuban-1-yl]-N-(2-methoxyethyl)acetamide | SMD-TFA05-1 | 1.34 | 924 |
| 58 | 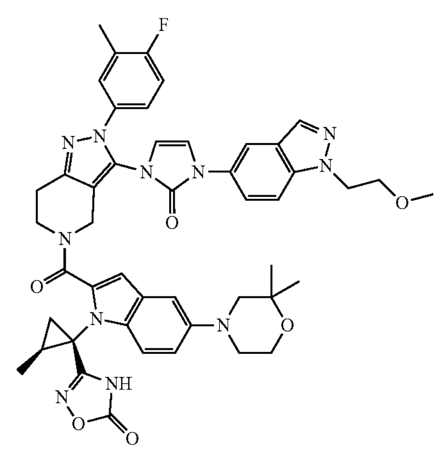 | 3-[(1S,2S)-1-[5-(2,2-dimethylmorpholin-4-yl)-2-[2-(4-fluoro-3-methylphenyl)-3-[3-[1-(2-methoxyethyl)indazol-5-yl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.29 | 883 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 59 | 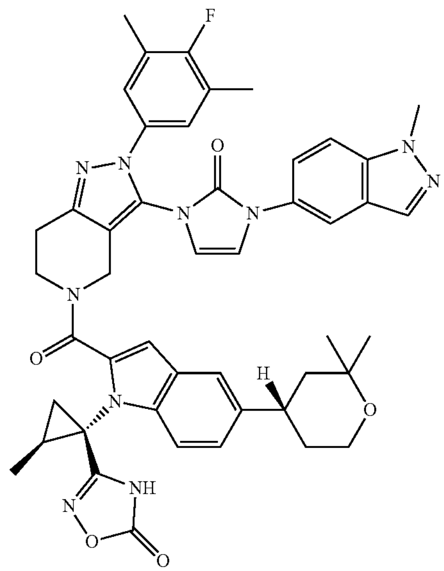 [SMILES: Cc1cc(-n2nc3c(c2-n2ccn(-c4ccc5c(cnn5C)c4)c2=O)CN(C(=O)c2cc4cc([C@H]5CCOC(C)(C)C5)ccc4n2[C@@]2(c4noc(=O)[nH]4)C[C@@H]2C)CC3)cc(C)c1F] | 3-[(1S,2S)-1-[5-[(4S)-2,2-dimethyloxan-4-yl]-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-2 | 1.44 | 851 |
| 60 | 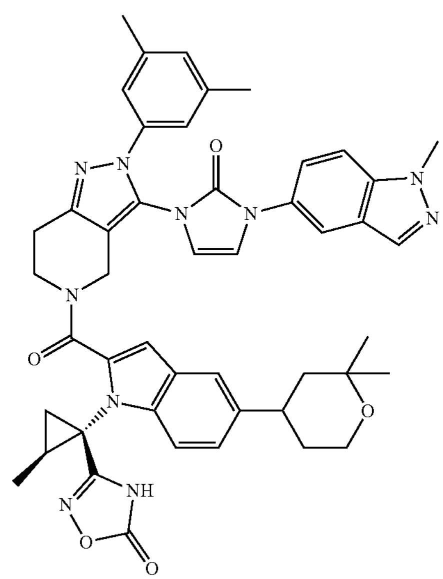 | 3-[1S,2S)-1-[5-[(4S)-2,2-dimethyloxan-4-yl]-2-[2-(3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.41 | 833 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 61 | 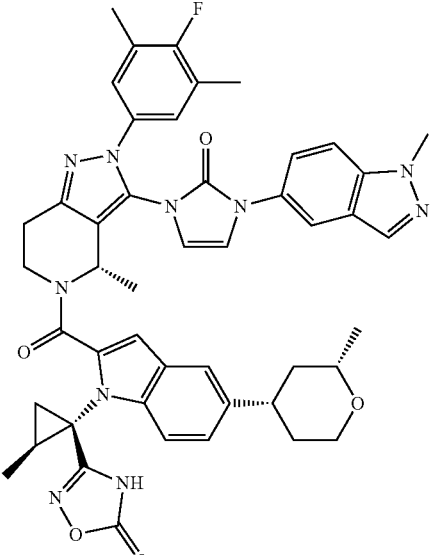 | 3-[(1S,2S)-1-[2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-[(2S,4S)-2-methyloxan-4-yl]indol-1-yl]-2-methylcyclopropyl]-4H-1,2,4-oxadiazol-5-one | SMD-TFA05-1 | 1.45 | 851 |
| 62 | 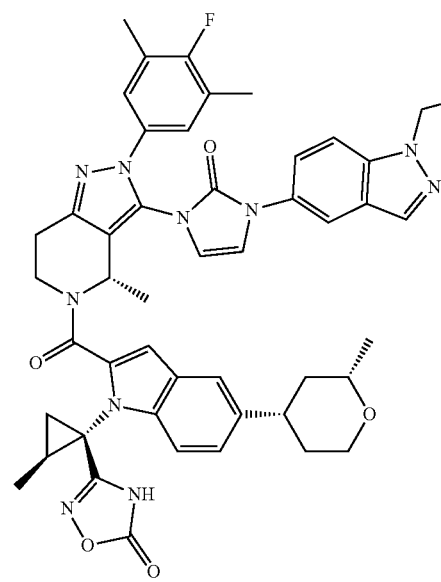 | 3-[(1S,2S)-1-[2-[(4S)-2-(4-fluoro-3,5-dimethylphenyl)-3-[3-[1-(2-methoxyethyl)indazol-5-yl]-2-oxoimidazol-1-yl]-4-methyl-6,7-dihydro-4H-pyrazolo[4,3-c]pyridine-5-carbonyl]-5-[(2S,4S)-2-methyloxan-4-yl]indol-1-yl]-2-methylcyclopropyl]-4H-1,2,4-oxadiazol-5-one | SMD TFA05-1 | 1.45 | 895 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 63 | 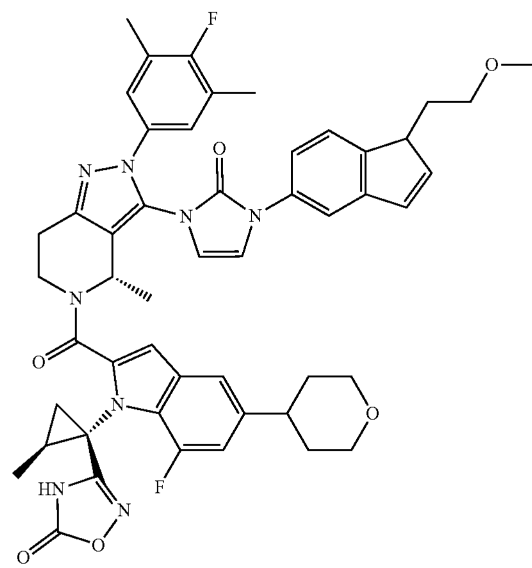 | 3-[(1S,2S)-1-[7-fluoro-2-[(4S)-2-(4-fluoro-3,5-dimethylphenyl)-3-[3-[1-(2-methoxyethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.38 | 899 |
| 64 | 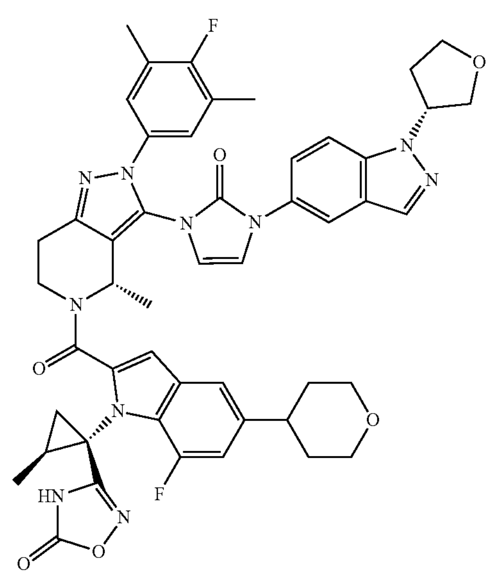 [SMILES: Cc1cc(-n2nc3c(c2-n2ccn(-c4ccc5c(cnn5[C@@H]5CCOC5)c4)c2=O)[C@H](C)N(C(=O)c2cc4cc(C5CCOCC5)cc(F)c4n2[C@@]2(c4noc(=O)[nH]4)C[C@@H]2C)CC3)cc(C)c1F] | 3-[(1S,2S)-1-[7-fluoro-2-[(4S)-2-(4-fluoro-3,5-dimethylphenyl)-4-methyl-3-[2-oxo-3-[1-[(3R)-oxolan-3-yl]indazol-5-yl]imidazol-1-yl]-6,7-dihydro-4H-pyrazolo[4,3-c]pyridine-5-carbonyl-5-(oxan-4-yl)indol-1-yl]-2-methylcyclopropyl]-4H-1,2,4-oxadiazol-5-one | SMD-TFA05-1 | 1.38 | 911 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 65 | 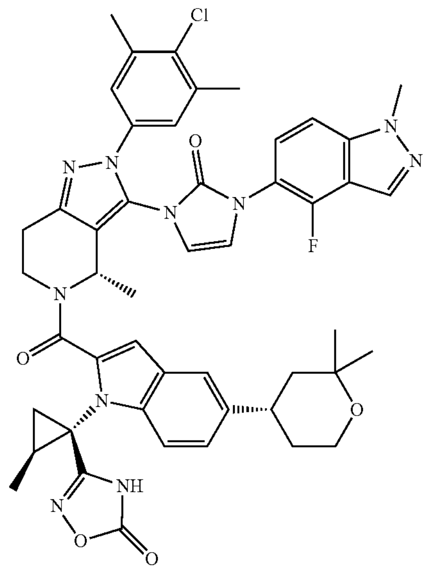 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1Cl] | 3-[(1S,2S)-1-[2-[(4S)-2-(4-chloro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-TFA05-1 | 1.53 | 899 |
| 66 | 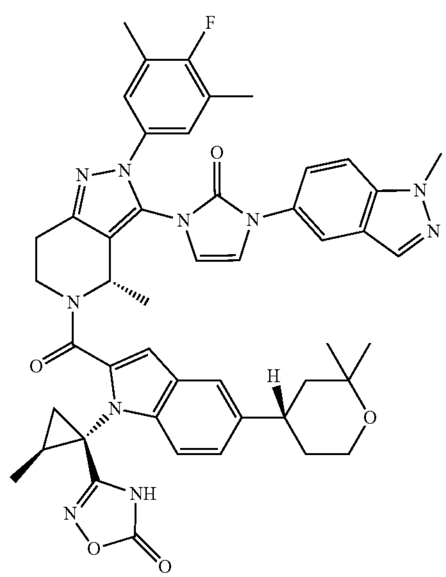 | 3-[(1S,2S)-1-[5-[(4S)-2,2-dimethyloxan-4-yl]-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-2 | 1.47 | 866 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 67 | 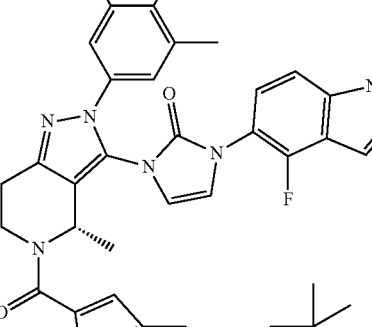 | 3-[(1S,2S)-1-[5-[(4S)-2,2-dimethyloxan-4-yl]-2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.46 | 883 |
| 68 | 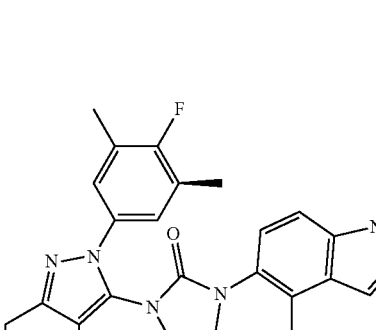 | 3-[(1S,2S)-1-[2-[(4S)-3-[3-(4-chloro-1-methylindazol-5-yl)-2-oxoimidazol-1-yl]-2-(4-fluoro-3,5-dimethylphenyl)-4-methyl-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-TFA05-1 | 1.47 | 899 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 69 | 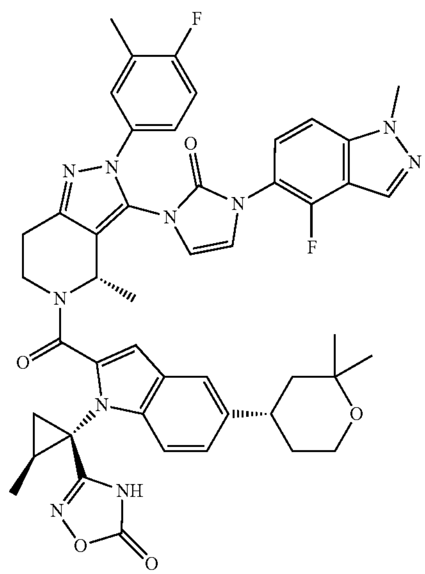 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)ccc1F] | 3-[(1S,2S)-1-[5-[(4S)-2,2-dimethyloxan-4-yl]-2-[(4S)-3-[3-(4-fluoro-1-methylindazol-5-yl)-2-oxoimidazol-1-yl]-2-(4-fluoro-3-methylphenyl)-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.40 | 869 |
| 70 | 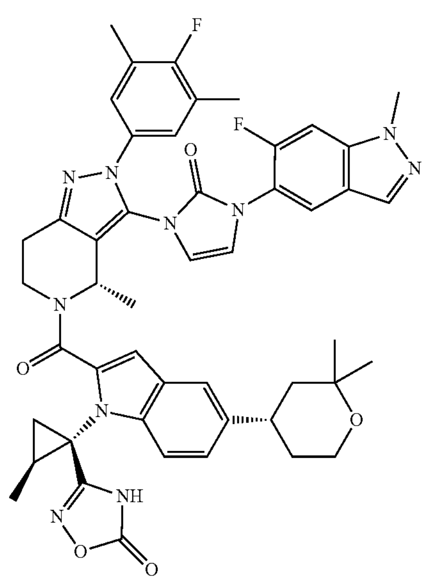 [SMILES: Cc1cc(-n2nc3c(c2-n2ccn(-c4cc5cnn(C)c5cc4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] | 3-[(1S,2S)-1-[(4S)-2,2-dimethyloxan-4-yl]-2-[(4S)-2-(4-fluoro-3,5-dimethylphenyl)-3-[3-(6-fluoro-1-methylindazol-5-yl)-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.43 | 883 |

TABLE 2-5-continued

The Obtained Example Compounds 54 to 72

| Example No. | Structure | Compound | Analysis Condition | LC/MS retention time (min.) | LC/MS mass spectrometry (m/z) |
|---|---|---|---|---|---|
| 71 | 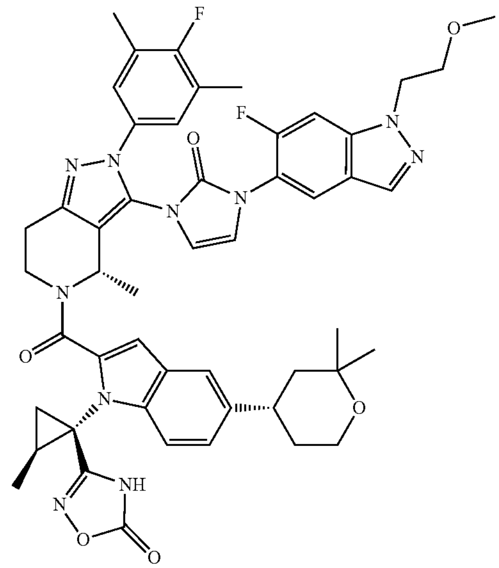 | 3-[(1S,2S)-1-[5-[(4S)-2,2-dimethyloxan-4-yl]-2-[(4S)-2-(4-fluoro-3,5-dimethylphenyl)-3-[3-[6-fluoro-1-(2-methoxyethyl)indazol-5-yl]-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.44 | 927 |
| 72 | 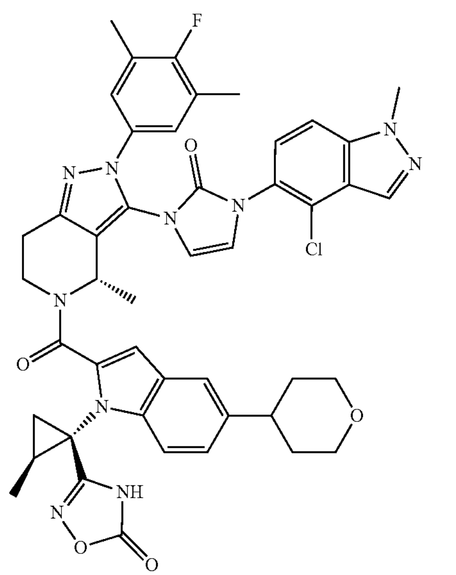 [SMILES: Cc1cc(-n2nc3c(c2-n2ccn(-c4ccc5c(cnn5C)c4Cl)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-3-[3-(4-chloro-1-methylindazol-5-yl)-2-oxoimidazol-1-yl]-2-(4-fluoro-3,5-dimethylphenyl)-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.40 | 871 |

Note that the compounds in Table 2-5 have rotational isomers, and by way of example, the H-NMR of Example Compounds 66 and 67 are shown below.

Example Compound 66

Main Rotational Isomer $^1$H-NMR (600 MHz, CDCl$_3$) δ: 11.32 (1H, s), 8.04 (1H, d, J=0.4 Hz), 7.86 (1H, d, J=1.4 Hz), 7.61 (1H, m), 7.59 (1H, m), 7.52 (1H, s), 7.50 (H, d, J=9.0 Hz), 7.27 (1H, m), 7.15 (2H, d, J$_{HF}$=6.0 Hz), 6.74 (1H, d, J=3.1 Hz), 6.70 (1H, s), 6.32 (1H, d, J=3.1 Hz), 5.79 (1H, q, J=6.6 Hz), 4.47 (1H, dd, J=13.6, 5.0 Hz), 4.12 (3H, s), 3.89-3.81 (2H, m), 3.60 (1H, ddd, J=13.6, 13.1, 3.6 Hz), 3.15 (1H, ddd, J=16.0, 13.1, 5.0 Hz), 3.09-2.98 (2H, m), 2.27 (6H, d, J$_{HF}$=1.4 Hz), 1.91 (1H, dd, J=6.0 Hz), 1.82-1.60 (4H, m), 1.60-1.50 (2H, m), 1.55 (3H, d, J=6.6 Hz), 1.34 (3H, s), 1.28 (3H, s), 1.19 (3H, d, J=5.9 Hz).

Secondary Rotational Isomer $^1$H-NMR (600 MHz, CDCl$_3$) δ: 11.26 (1H, s), 7.93 (1H, s), 7.65 (1H, s), 7.57 (1H, d, J=8.6 Hz), 7.49 (1H, m), 7.34 (2H, s), 7.25 (1H, m), 7.05 (2H, d, J$_{HF}$=6.0 Hz), 6.69 (1H, s), 6.59 (1H, d, J=3.1 Hz), 6.09 (1H, d, J=3.1 Hz), 5.26 (1H, q, J=6.6 Hz), 4.87 (1H, dd, J=12.8, 5.1 Hz), 4.07 (3H, s), 3.90-3.78 (2H, m), 3.40 (1H, ddd, J=12.8, 12.6, 4.5 Hz), 3.10-2.98 (3H, m), 2.23 (6H, s), 1.82-1.37 (10H, m), 1.33 (3H, s), 1.25 (3H, s), 1.06 (3H, d, J=6.2 Hz).

Example Compound 67

Main Rotational Isomer $^1$H-NMR (600 MHz, CDCl$_3$) δ: 11.32 (1H, s), 8.13 (1H, d, J$_{HF}$=0.7 Hz), 7.59 (1H, d, J=8.6 Hz), 7.52 (1H, s), 7.48 (1H, dd, J=8.9 Hz, JH$_F$=6.9 Hz), 7.28 (1H, d, J=8.9 Hz), 7.26 (1H, dd, J=8.6, 1.7 Hz), 7.16 (2H, d, J$_{HF}$=6.1 Hz), 6.70 (1H, s), 6.61 (1H, dd, J=3.0 Hz, J$_{HF}$=1.1 Hz), 6.31 (1H, d, J=3.0 Hz), 5.79 (1H, q, J=6.7 Hz), 4.47 (1H, dd, J=13.5, 5.2 Hz), 4.12 (3H, s), 3.88 (1H, m), 3.83 (1H, m), 3.60 (1H, ddd, J=13.5, 12.9, 3.6 Hz), 3.15 (1H, ddd, J=15.8, 12.9, 5.2 Hz), 3.04 (1H, m), 3.00 (1H, m), 2.29 (6H, d, J$_{HF}$=1.1 Hz), 1.91 (1H, dd, J=6.1, 5.8 Hz), 1.79-1.76 (2H, m), 1.74 (1H, m), 1.65 (1H, m), 1.57 (3H, d, J=6.7 Hz), 1.60-1.55 (1H, m), 1.52 (1H, dd, J=9.5, 5.8 Hz), 1.34 (3H, s), 1.28 (3H, s), 1.20 (3H, d, J=6.0 Hz).

Secondary Rotational Isomer $^1$H-NMR (600 MHz, CDCl$_3$) δ: 11.27 (1H, s), 8.04 (1H, s), 7.55 (1H, d, J=8.7 Hz), 7.52 (1H, s), 7.25-7.22 (2H, m), 7.12 (1H, d, J=8.8 Hz), 7.06 (2H, d, J$_{HF}$=6.0 Hz), 6.71 (1H, s), 6.47 (1H, m), 6.08 (1H, d, J=3.0 Hz), 5.26 (1H, q, J=6.6 Hz), 4.87 (1H, dd, J=13.1, 4.8 Hz), 4.07 (3H, s), 3.90-3.80 (2H, m), 3.39 (1H, ddd, J=13.1, 12.2, 4.6 Hz), 3.08-2.97 (3H, m), 2.25 (6H, s), 1.79-1.73 (3H, m), 1.67 (3H, d, J=6.6 Hz), 1.64 (1H, m), 1.45-1.37 (2H, m), 1.34 (3H, s), 1.28 (3H, s), 1.06 (3H, d, J=6.0 Hz).

Compound 55e used in the synthesis of Example Compound 55 was synthesized as follows.

[Chemical Formula 51]

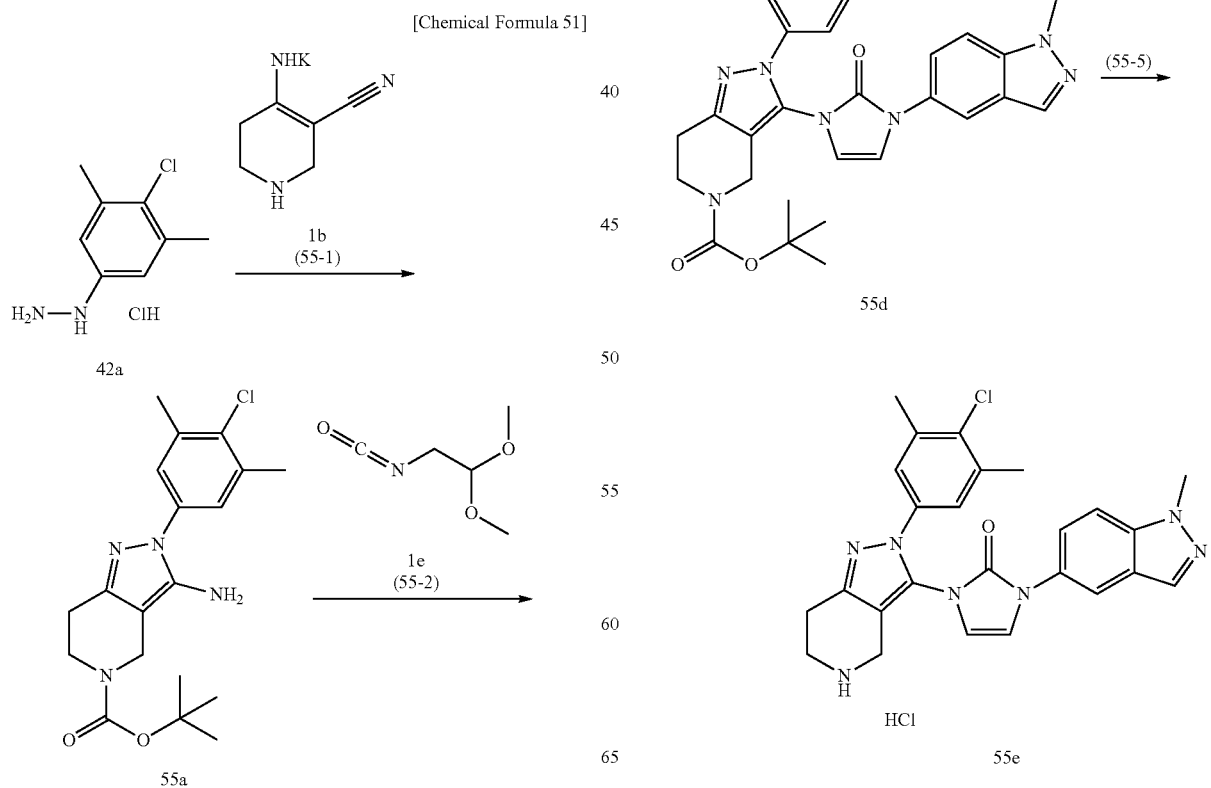

Step 55-1 tert-Butyl 3-amino-2-(4-chloro-3,5-dimethylphenyl)-6,7-dihydro-4H-pyrazolo[4,3-c]pyridine-5-carboxylate (Compound 55a)

The titled compound was synthesized from Compound 42a obtained in Step 42-1 and Compound 1b obtained in Step 1-1 by performing an operation similar to Step 1-2 of Example 1 using an appropriate reagent.

LC/MS mass spectrometry: m/z 377 ([M+H]$^+$).
LC/MS retention time: 0.87 min. (Analysis Condition: SQD-FA05-1).

Step 55-2 tert-Butyl 2-(4-chloro-3,5-dimethylphenyl)-3-(2,2-dimethoxyethylcarbamoylamino)-6,7-dihydro-4H-pyrazolo[4,3-c]pyridine-5-carboxyl ate (Compound 55b)

The titled compound was synthesized from Compound 55a obtained in Step 55-1 by performing an operation similar to Step 1-3 of Example 1 using an appropriate reagent.

LC/MS mass spectrometry: m/z 508 ([M+H]$^+$).
LC/MS retention time: 0.83 min. (Analysis Condition: SQD-FA05-1).

Step 55-3 tert-Butyl 2-(4-chloro-3,5-dimethylphenyl)-3-(2-oxo-1H-imidazol-3-yl)-6,7-dihydro-4H-pyrazolo[4,3-c]pyridine-5-carboxylate (Compound 55c)

The DMF (7.11 mL) suspension of Compound 55b (903 mg, 1.78 mmol) obtained in Step 55-2 and p-toluenesulfonic acid monohydrate (338 mg, 1.78 mmol) was stirred at 80° C. for 1 h. After the suspension was cooled to room temperature, potassium phosphate (377 mg, 1.78 mmol), water (3.5 mL), and di-tert-butyl dicarbonate (388 mg, 1.78 mmol) were added and the resulting mixture was stirred at room temperature for 1 h. Water was added to the reaction mixture, and extraction was performed using ethyl acetate, then the organic layer was washed with brine and the resulting product was dried with magnesium sulfate anhydride. After filtration, the filtrate was concentrated under reduced pressure and the residue was purified by silica gel column chromatography (ethyl acetate/hexane=1:4 to 1:0) to obtain the titled Compound 55c (799 mg, yield 100%) as a pale yellow foam.

LC/MS mass spectrometry: m/z 444 ([M+H]$^+$).
LC/MS retention time: 0.82 min. (Analysis Condition: SQD-FA05-1).

Step 55-4 tert-Butyl 2-(4-chloro-3,5-dimethylphenyl)-3-[3-(1-methylindazol-5-yl)-2-oxoimidazol-1-yl]-6,7-dihydro-4H-pyrazolo[4,3-c]pyridine-5-carboxylate (Compound 55d)

The titled compound was synthesized from Compound 55c obtained in Step 55-3 and 5-bromo-1-methylindazole (Compound 1q) by performing an operation similar to Step 1-11 of Example 1 using an appropriate reagent.

LC/MS mass spectrometry: m/z 574 ([M+H]$^+$).
LC/MS retention time: 1.34 min. (Analysis Condition: SMD-FA05-1).

Step 55-5

1-[2-(4-Chloro-3,5-dimethylphenyl)-4,5,6,7-tetrahydropyrazolo[4,3-c]pyridin-3-yl]-3-(1-methylindazol-5-yl)imidazol-2-one hydrochloride (Compound 55e)

The titled compound was synthesized from Compound 55d obtained in Step 55-4 by performing an operation similar to Step 11-8 of Example 11 using an appropriate reagent.

LC/MS mass spectrometry: m/z 474 ([M+H]$^+$).
LC/MS retention time: 0.81 min. (Analysis Condition: SMD-FA05-1).

Compound 56c used in the synthesis of Example Compound 56 was synthesized as follows.

[Chemical Formula 52]

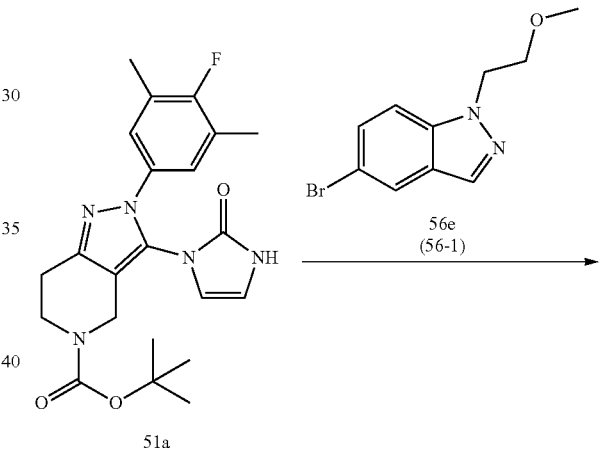

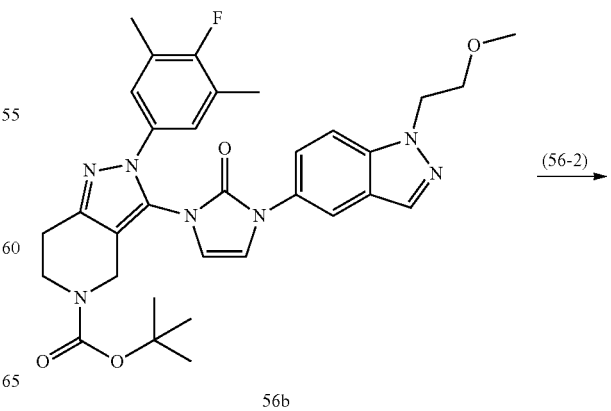

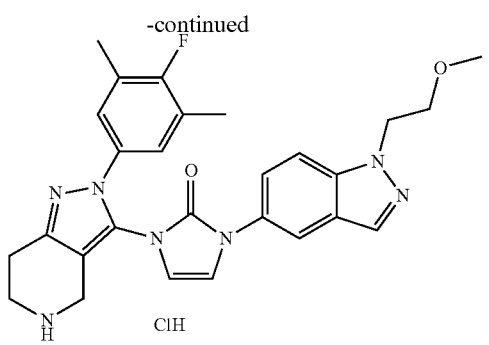

56c

Step 56-1 tert-Butyl 2-(4-fluoro-3,5-dimethylphenyl)-3-[3-[1-(2-methoxyethyl)indazol-5-yl]-2-oxoimidazol-1-yl]-6,7-dihydro-4H-pyrazolo[4,3-c]pyridine-5-carboxylate (Compound 56b)

The titled compound was synthesized from Compound 51a obtained in Step 51-1 and 5-bromo-1-(2-methoxyethyl)indazole (Compound 56a) by performing an operation similar to Step 1-11 of Example 1 using an appropriate reagent.

LC/MS mass spectrometry: m/z 602 ([M+H]$^+$).

LC/MS retention time: 1.30 min. (Analysis Condition: SMD-FA05-2).

Step 56-2

1-[2-(4-Fluoro-3,5-dimethylphenyl)-4,5,6,7-tetrahydropyrazolo[4,3-c]pyridin-3-yl]-3-[1-(2-methoxyethyl)indazol-5-yl]imidazol-2-one hydrochloride (Compound 56c)

The titled compound was synthesized from Compound 56b obtained in Step 56-1 by performing an operation similar to Step 11-8 of Example 11 using an appropriate reagent.

LC/MS mass spectrometry: m/z 502 ([M+H]$^+$).

LC/MS retention time: 0.54 min. (Analysis Condition: SQD-FA05-1).

The amine derivative (Compound 57j) used in the synthesis of Example Compound 57 was synthesized as follows.

[Chemical Formula 53]

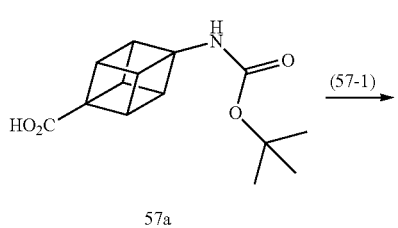

57a

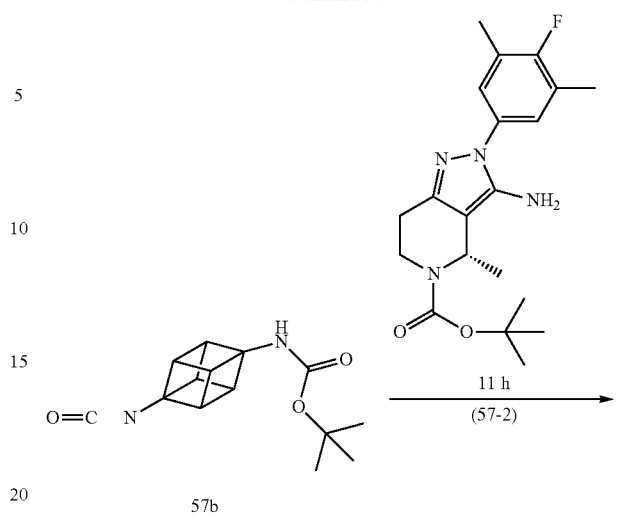

57b

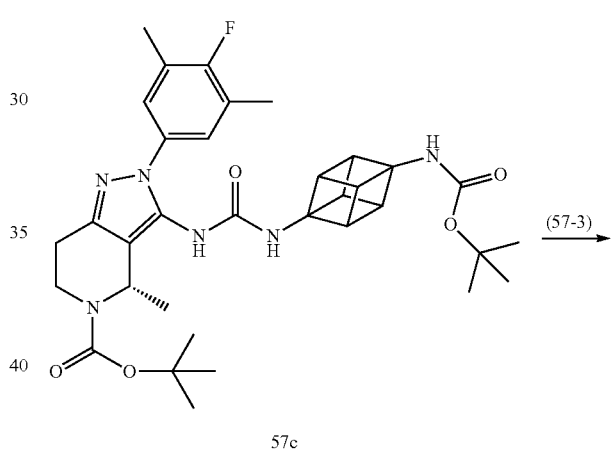

57c

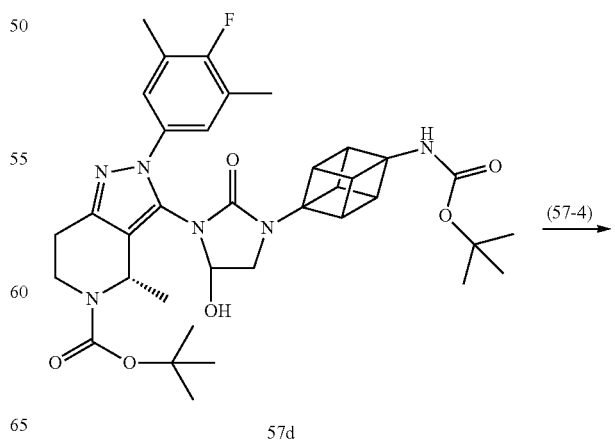

57d

195
-continued

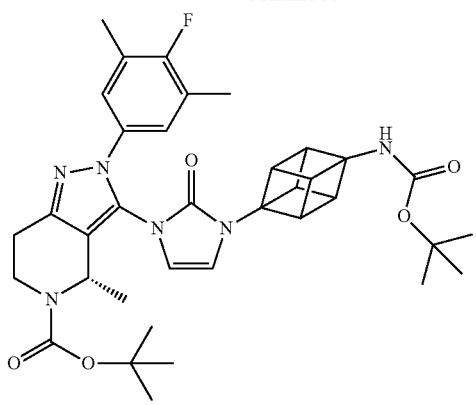

57e

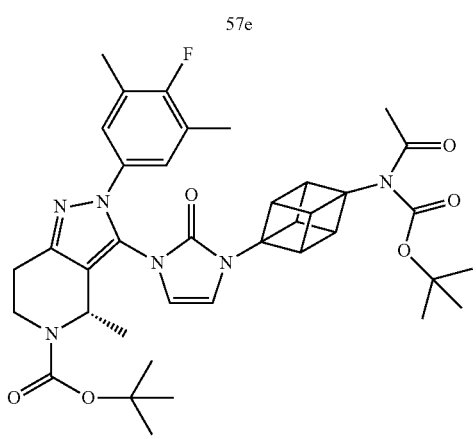

57f

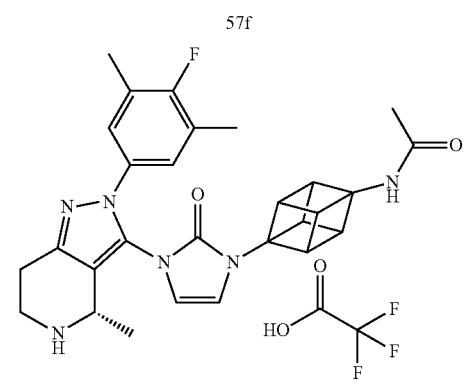

57g

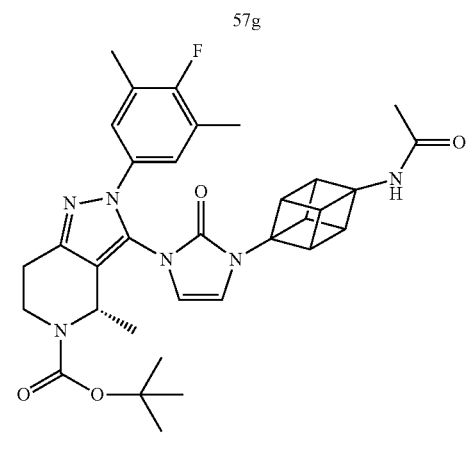

57h

196
-continued

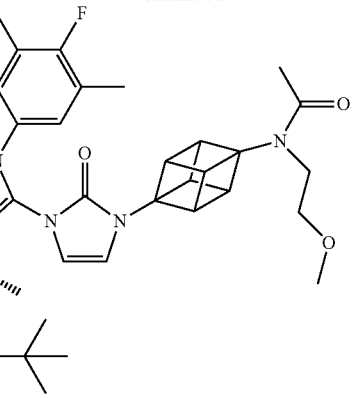

57i

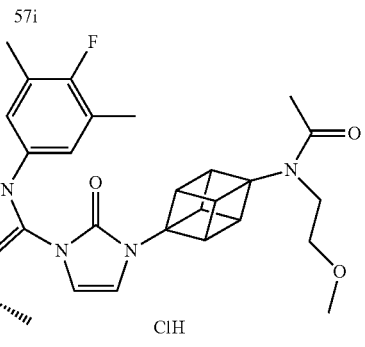

57j

Step 57-1 tert-Butyl N-(4-isocyanatocuban-1-yl) carbamate
(Compound 57b)

To a toluene (2.1 mL) solution of 4-[(2-methylpropan-2-yl)oxycarbonylamino]cubane-1-carboxylic acid (Compound 57a, 111 mg, 0.423 mmol) was added at room temperature triethyl amine (0.0676 mL, 0.487 mmol) and diphenylphosphoryl azide (0.10 mL, 0.465 mmol), and the resulting mixture was stirred at room temperature for 100 min., then at 85° C. for 3.5 h. The solvent in the reaction mixture was removed by evaporation under reduced pressure, and the titled Compound 57b was obtained as a crude product.

$^1$H-NMR (400 MHz, CDCl$_3$) δ: 12.3 (1H, brs), 3.95 (6H, brs), 1.45 (9H, s).

Step 57-2 tert-Butyl (4S)-2-(4-fluoro-3,5-dimethylphenyl)-4-methyl-3-[[4-[(2-methylpropan-2-yl)oxycarbonylamino]cuban-1-yl]carbamoylamino]-6,7-dihydro-4H-pyrazolo[4,3-c]pyridine-5-carboxylate
(Compound 57c)

The titled compound was synthesized from Compound 57b obtained in Step 57-1 and Compound 11h obtained by Step 11-5 by performing an operation similar to Step 1-3 of Example 1 using an appropriate reagent.

LC/MS mass spectrometry: m/z 636 ([M+H]$^+$).

LC/MS retention time: 0.93 min. (Analysis Condition: SQD-FA05-1).

Step 57-3 tert-Butyl (4S)-2-(4-fluoro-3,5-dimethylphenyl)-3-[5-hydroxy3-[4-[(2-methylpropan-2-yl)oxycarbonylamino]cuban-1-yl]-2-oxoimidazolidin-1-yl]-4-methyl-6,7-dihydro-4H-pyrazolo[4,3-c]pyridine-5-carboxylate (Compound 57d)

To a DMA (0.25 mL) suspension of Compound 57c (31.6 mg, 0.050 mmol) obtained in Step 57-2 and cesium carbonate (82.8 mg, 0.254 mmol) were added at room temperature 1,2-dichloro-1-ethoxyethane (0.0155 mL, 0.127 mmol), and the mixture was stirred at room temperature for 170 min. Cesium carbonate (104 mg, 0.32 mmol) followed by 1,2-dichloro-1-ethoxyethane (0.0184 mL, 0.162 mmol) were added to the reaction mixture at room temperature, and the resulting mixture was stirred at room temperature for 16 h. The reaction mixture was diluted with ethyl acetate and water, then 1N hydrochloric acid (0.54 mL) was added to adjust the pH to 7, and then extraction was performed using ethyl acetate. The organic layer was dried using magnesium sulfate, then the solvent was removed by evaporation under reduced pressure, and then toluene was added and the solvent was removed by evaporation under reduced pressure to obtain the titled Compound 57d as a crude product.

LC/MS mass spectrometry: m/z 678 ([M+H]$^+$).
LC/MS retention time: 0.98 min. (Analysis Condition: SQD-FA05-1).

Step 57-4 tert-Butyl (4S)-2-(4-fluoro-3,5-dimethylphenyl)-4-methyl-3-[3-[4-[(2-methylpropan-2-yl)oxycarbonylamino]cuban-1-yl]-2-oxoimidazol-1-yl]-6,7-dihydro-4H-pyrazolo[4,3-c]pyridine-5-carboxylate (Compound 57e)

To a THF (1.1 mL) solution of Compound 57d (115 mg, 0.17 mmol) obtained in Step 57-3 was added at room temperature methylsulfonic acid (0.011 mL, 0.17 mmol), then the mixture was stirred at 60° C. for 90 min. Potassium phosphate (36.5 mg, 0.172 mmol), water (0.45 mL) and (2-methylpropan-2-yl)oxycarbonyl tert-butyl carbonate (0.012 mL, 0.052 mmol) were added to the reaction mixture, and the resulting mixture was stirred for 1 h. Then, after the reaction mixture was diluted with dichloromethane, it was washed with water. The organic layer was dried using magnesium sulfate, and the solvent was removed by evaporation under reduced pressure. The residue was purified by silica gel column chromatography (ethyl acetate/hexane=1:2 to 1:1) to obtain the titled Compound 57e (48.5 mg, yield 43%).

LC/MS mass spectrometry: m/z 660 ([M+H]$^+$).
LC/MS retention time: 1.04 min. (Analysis Condition: SQD-FA05-1).

Step 57-5 tert-Butyl (4S)-3-[3-[4-[acetyl-[(2-methylpropan-2-yl)oxycarbonyl]amino]cuban-1-yl]-2-oxoimidazol-1-yl]-2-(4-fluoro-3,5-dimethylphenyl)-4-methyl-6,7-dihydro-4H-pyrazolo[4,3-c]pyridine-5-carboxylate (Compound 57f)

To a THF (0.22 mL) solution of Compound 57e (16.1 mg, 0.024 mmol) obtained in Step 57-4 was added at −26° C., a 1.7M potassium pentoxide toluene solution (0.024 mL, 0.041 mmol), and the mixture was stirred at −30° C. for 3 min. Acetic anhydride (8 μL, 0.085 mmol) was added to the reaction mixture at −30° C., and the mixture was stirred at a temperature of −30° C. to −25° C. for 5 min. and at a temperature of −25° C. to room temperature for 3 min. After water (0.5 mL) was added to the reaction mixture, the mixture was diluted using ethyl acetate, and more water was added and extraction was performed using ethyl acetate. The organic layer was dried using magnesium sulfate, and the solvent was removed by distillation under reduced pressure, then the resulting product was purified by silica gel column chromatography (ethyl acetate/hexane=1:3 to 2:3) to obtain the titled Compound 57f (9.2 mg, yield 54%).

LC/MS mass spectrometry: m/z 701 ([M+H]$^+$).
LC/MS retention time: 1.12 min. (Analysis Condition: SQD-FA05-1).

Step 57-6

N-[4-[3-[(4S)-2-(4-Fluoro-3,5-dimethylphenyl)-4-methyl-4,5,6,7-tetrahydropyrazolo[4,3-c]pyridin-3-yl]-2-oxoimidazol-1-yl]cuban-1-yl]acetamide 2,2,2-trifluoroacetate (Compound 57g)

To a dichloromethane (0.097 mL) solution of Compound 57f (8.5 mg, 0.012 mmol) obtained in Step 57-5 was added TFA (0.019 mL) at room temperature, and the resulting mixture was stirred at room temperature for 3 h. After the solvent in the reaction mixture was removed by evaporation under reduced pressure, toluene was added and the solvent was removed by evaporation, and hexane-dichloromethane was added and the solvent was removed by evaporation to obtain the titled Compound 57g (9.4 mg) as a crude product.

LC/MS mass spectrometry: m/z 501 ([M+H]$^+$).
LC/MS retention time: 0.49 min. (Analysis Condition: SQD-FA05-1).

Step 57-7 tert-Butyl (4S)-3-[3-(4-acetamidecuban-1-yl)-2-oxoimidazol-1-yl]-2-(4-fluoro-3,5-dimethylphenyl)-4-methyl-6,7-dihydro-4H-pyrazolo[4,3-c]pyridine-5-carboxylate (Compound 57h)

The titled compound was synthesized from Compound 57g obtained in Step 57-6 by performing an operation similar to Step 51-1 of Example 51 using an appropriate reagent.

LC/MS mass spectrometry: m/z 602 ([M+H]$^+$).
LC/MS retention time: 0.85 min. (Analysis Condition: SQD-FA05-1).

Step 57-8 tert-Butyl (4S)-3-[3-[4-[acetyl(2-methoxyethyl)amino]cuban-1-yl]-2-oxoimidazol-1-yl]-2-(4-fluoro-3,5-dimethylphenyl)-4-methyl-6,7-dihydro-4H-pyrazolo[4,3-c]pyridine-5-carboxylate (Compound 57i)

The titled compound was synthesized from Compound 57h obtained in Step 57-7 by performing an operation similar to Step 57-5 of Example 57 using an appropriate reagent.

LC/MS mass spectrometry: m/z 660 ([M+H]$^+$).
LC/MS retention time: 0.93 min. (Analysis Condition: SQD-FA05-1).

199

Step 57-9

N-[4-[3-[(4S)-2-(4-Fluoro-3,5-dimethylphenyl)-4-methyl-4,5,6,7-tetrahydropyrazolo[4,3-c]pyridin-3-yl]-2-oxoimidazol-1-yl]cuban-1-yl]-N-(2-methoxy-ethyl)acetamide; hydrochloride (Compound 57i)

The titled compound was synthesized from Compound 57i obtained in Step 57-8 by performing an operation similar to Step 11-8 of Example 11 using an appropriate reagent.

LC/MS mass spectrometry: m/z 560 ([M+H]$^+$).

LC/MS retention time: 0.53 min. (Analysis Condition: SQD-FA05-1).

Compound 58e used in the synthesis of Example Compound 58 was synthesized as follows.

200

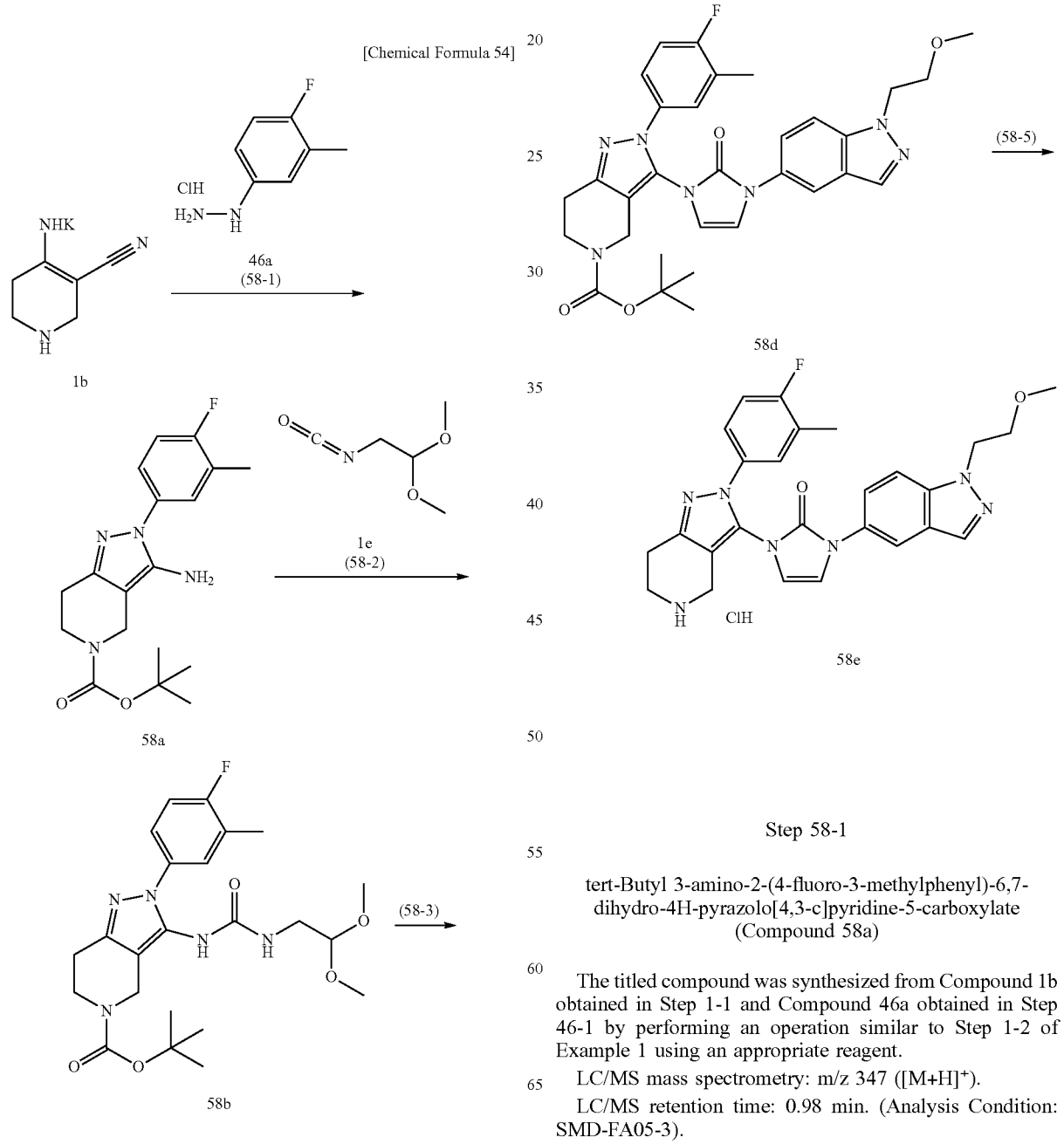

Step 58-1 tert-Butyl 3-amino-2-(4-fluoro-3-methylphenyl)-6,7-dihydro-4H-pyrazolo[4,3-c]pyridine-5-carboxylate (Compound 58a)

The titled compound was synthesized from Compound 1b obtained in Step 1-1 and Compound 46a obtained in Step 46-1 by performing an operation similar to Step 1-2 of Example 1 using an appropriate reagent.

LC/MS mass spectrometry: m/z 347 ([M+H]$^+$).

LC/MS retention time: 0.98 min. (Analysis Condition: SMD-FA05-3).

Step 58-2 tert-Butyl 3-(2,2-dimethoxyethylcarbamoylamino)-2-(4-fluoro-3-methylphenyl)-6,7-dihydro-4H-pyrazolo[4,3-c]pyridine-5-carboxylate (Compound 58b)

The titled compound was synthesized from Compound 58a obtained in Step 58-1 by performing an operation similar to Step 1-3 of Example 1 using an appropriate reagent.

LC/MS mass spectrometry: m/z 478 ([M+H]$^+$).

LC/MS retention time: 1.03 min. (Analysis Condition: SMD-FA05-3).

Step 58-3 tert-Butyl 2-(4-fluoro-3-methylphenyl)-3-(2-oxo-1H-imidazol-3-yl)-6,7-dihydro-4H-pyrazolo[4,3-c]pyridine-5-carboxylate (Compound 58c)

The titled compound was synthesized from Compound 58b obtained in Step 58-2 by performing an operation similar to Step 11-7 of Example 11 using an appropriate reagent.

LC/MS mass spectrometry: m/z 414 ([M+H]$^+$).

LC/MS retention time: 0.72 min. (Analysis Condition: SQD-FA05-1).

Step 58-4 tert-Butyl 2-(4-fluoro-3-methylphenyl)-3-[3-[1-(2-methoxyethyl)indazol-5-yl]-2-oxoimidazol-1-yl]-6,7-dihydro-4H-pyrazolo[4,3-c]pyridine-5-carboxylate (Compound 58d)

The titled compound was synthesized from Compound 58c obtained in Step 58-3 and 5-bromo-1-(2-methoxyethyl)indazole (Compound 56a) by performing an operation similar to Step 1-11 of Example 1 using an appropriate reagent.

LC/MS mass spectrometry: m/z 588 ([M+H]$^+$).

LC/MS retention time: 0.88 min. (Analysis Condition: SQD-FA05-1).

Step 58-5

1-[2-(4-Fluoro-3-methylphenyl)-4,5,6,7-tetrahydropyrazolo[4,3-c]pyridin-3-yl]-3-[1-(2-methoxyethyl)indazol-5-yl]imidazol-2-one hydrochloride (Compound 58e)

The titled compound was synthesized from Compound 58d obtained in Step 58-4 by performing an operation similar to Step 11-9 of Example 11 using an appropriate reagent.

LC/MS mass spectrometry: m/z 488 ([M+H]$^+$).

LC/MS retention time: 0.50 min. (Analysis Condition: SQD-FA05-1).

Compound 60c used in the synthesis of Example Compound 60 was synthesized by the following process.

[Chemical Formula 55]

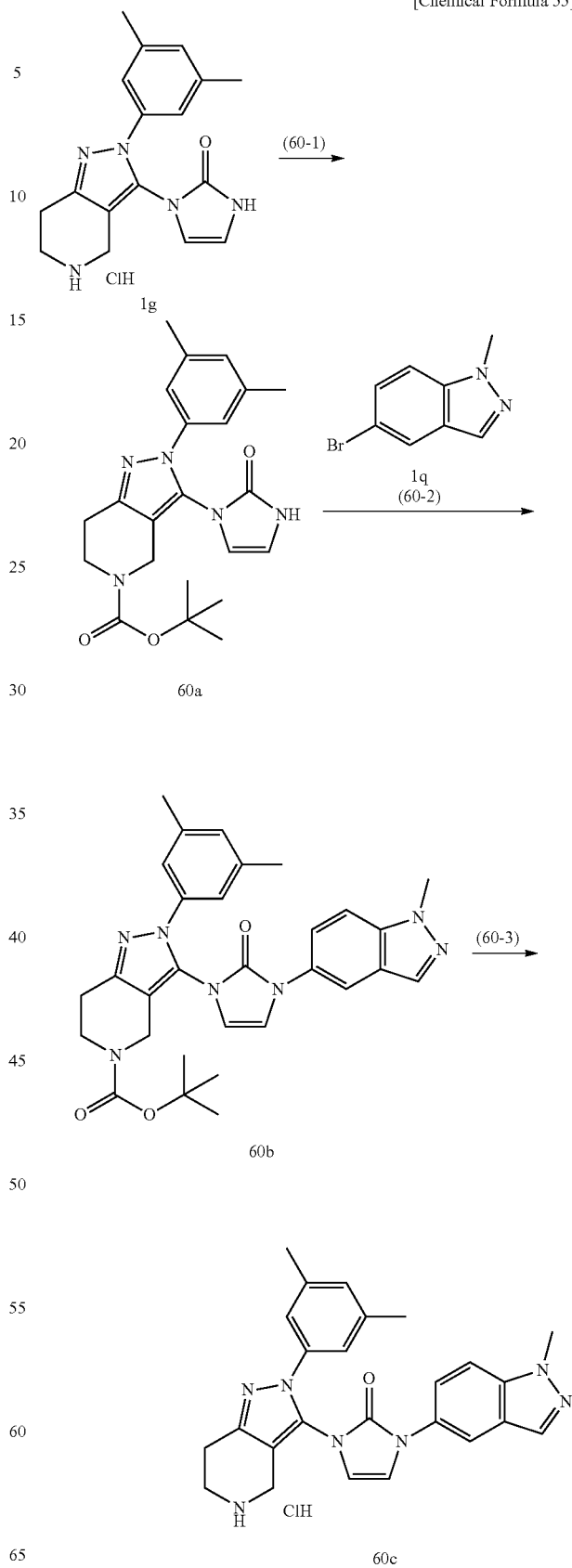

Step 60-1 tert-Butyl 2-(3,5-dimethylphenyl)-3-(2-oxo-1H-imidazol-3-yl)-6,7-dihydro-4H-pyrazolo[4,3-c]pyridine-5-carboxylate (Compound 60a)

The titled compound was synthesized from Compound 1g obtained in Step 1-4 by performing an operation similar to Step 51-1 of Example 51 using an appropriate reagent.

LC/MS mass spectrometry: m/z 410 ([M+H]$^+$).

LC/MS retention time: 0.77 min. (Analysis Condition: SQD-FA05-1).

Step 60-2 tert-Butyl 2-(3,5-dimethylphenyl)-3-[3-(1-methylindazol-5-yl)-2-oxoimidazol-1-yl]-6,7-dihydro-4H-pyrazolo[4,3-c]pyridine-5-carboxylate (Compound 60b)

The titled compound was synthesized from Compound 60a obtained in Step 60-1 and 5-bromo-1-methylindazole (Compound 1q) by performing an operation similar to Step 1-11 of Example 1 using an appropriate reagent.

LC/MS mass spectrometry: m/z 540 ([M+H]$^+$).

LC/MS retention time: 1.24 min. (Analysis Condition: SMD-FA05-3).

Step 60-3

1-[2-(3,5-Dimethylphenyl)-4,5,6,7-tetrahydropyrazolo[4,3-c]pyridin-3-yl]-3-(1-methylindazol-5-yl)imidazol-2-one hydrochloride (Compound 60c)

The titled compound was synthesized from Compound 60b obtained in Step 60-2 by performing an operation similar to Step 11-8 of Example 11 using an appropriate reagent.

LC/MS mass spectrometry: m/z 440 ([M+H]$^+$).

LC/MS retention time: 0.74 min. (Analysis Condition: SMD-FA05-2).

Compound 61b used in the synthesis of Example Compound 61 was synthesized by the following process.

[Chemical Formula 56]

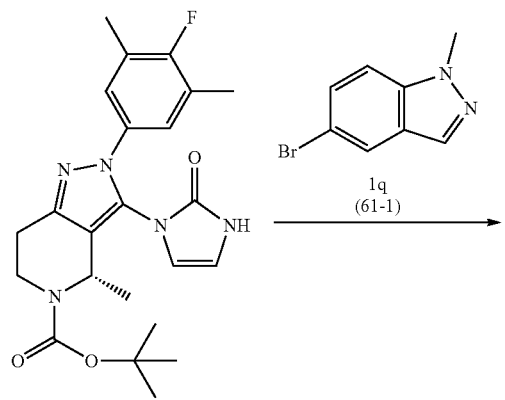

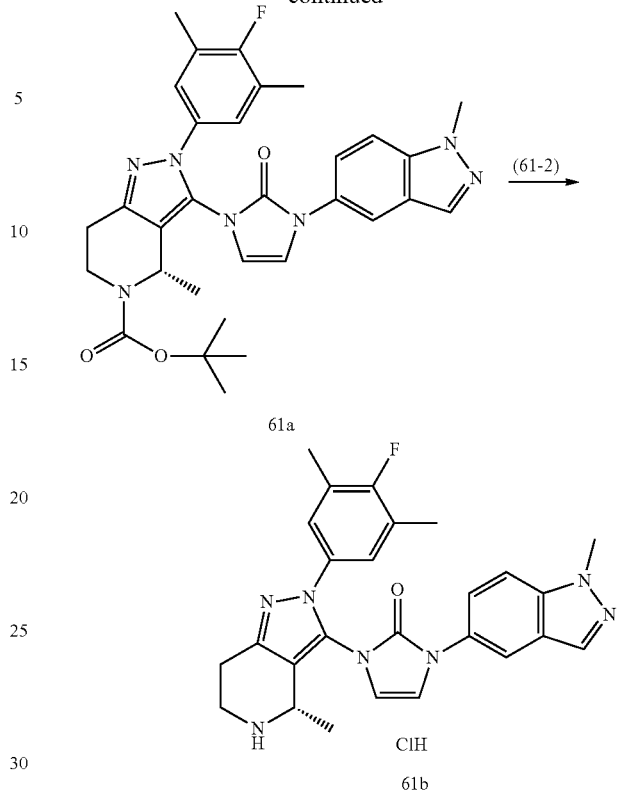

Step 61-1 tert-Butyl (4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carboxylate (Compound 61a)

The titled compound was synthesized from Compound 11k obtained in Step 11-7 and 5-bromo-1-methylindazole (Compound 1q) by performing an operation similar to Step 1-11 of Example 1 using an appropriate reagent.

LC/MS mass spectrometry: m/z 572 ([M+H]$^+$).

LC/MS retention time: 1.30 min. (Analysis Condition: SMD-FA05-1).

Step 61-2

1-[(4S)-2-(4-Fluoro-3,5-dimethylphenyl)-4-methyl-4,5,6,7-tetrahydropyrazolo[4,3-c]pyridin-3-yl]-3-(1-methylindazol-5-yl)imidazol-2-one hydrochloride (Compound 61b)

The titled compound was synthesized from Compound 61a obtained in Step 61-1 by performing an operation similar to Step 11-8 of Example 11 using an appropriate reagent.

LC/MS mass spectrometry: m/z 472 ([M+H]$^+$).

LC/MS retention time: 0.79 min. (Analysis Condition: SMD-FA05-1).

Compound 62b used in the synthesis of Example Compound 62 was synthesized by the following process.

[Chemical Formula 57]

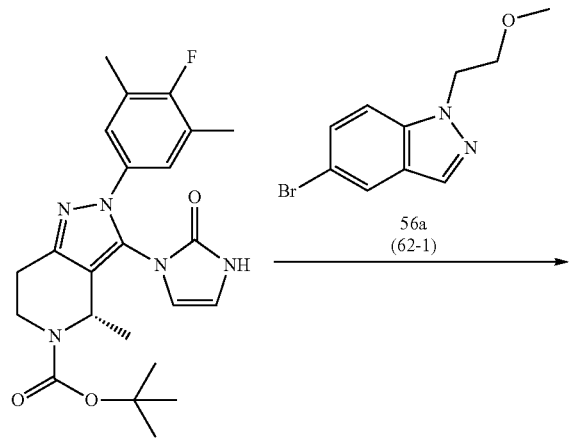

Step 62-1 tert-Butyl (4S)-2-(4-fluoro-3,5-dimethylphenyl)-3-[3-[1-(2-methoxyethyl)indazol-5-yl]-2-oxoimidazol-1-yl]-4-methyl-6,7-dihydro-4H-pyrazolo[4,3-c]pyridine-5-carboxylate (Compound 62a)

The titled compound was synthesized from Compound 11k obtained in Step 11-7 and 5-bromo-1-(2-methoxyethyl)indazole (Compound 56a) by performing an operation similar to Step 1-11 of Example 1 using an appropriate reagent.
LC/MS mass spectrometry: m/z 616 ([M+H]$^+$).
LC/MS retention time: 1.29 min. (Analysis Condition: SMD-FA05-1).

Step 62-2

1-[(4S)-2-(4-Fluoro-3,5-dimethylphenyl)-4-methyl-4,5,6,7-tetrahydropyrazolo[4,3-c]pyridin-3-yl]-3-[1-(2-methoxyethyl)indazol-5-yl]imidazol-2-one hydrochloride (Compound 62b The titled compound was synthesized from Compound 62a obtained in Step 62-1 by performing an operation similar to Step 11-8 of Example 11 using an appropriate reagent.
LC/MS mass spectrometry: m/z 516 ([M+H]$^+$).
LC/MS retention time: 0.76 min. (Analysis Condition: SMD-FA05-1).

Compound 63g used in the synthesis of Example Compound 63 was synthesized by the following process.

[Chemical Formula 58]

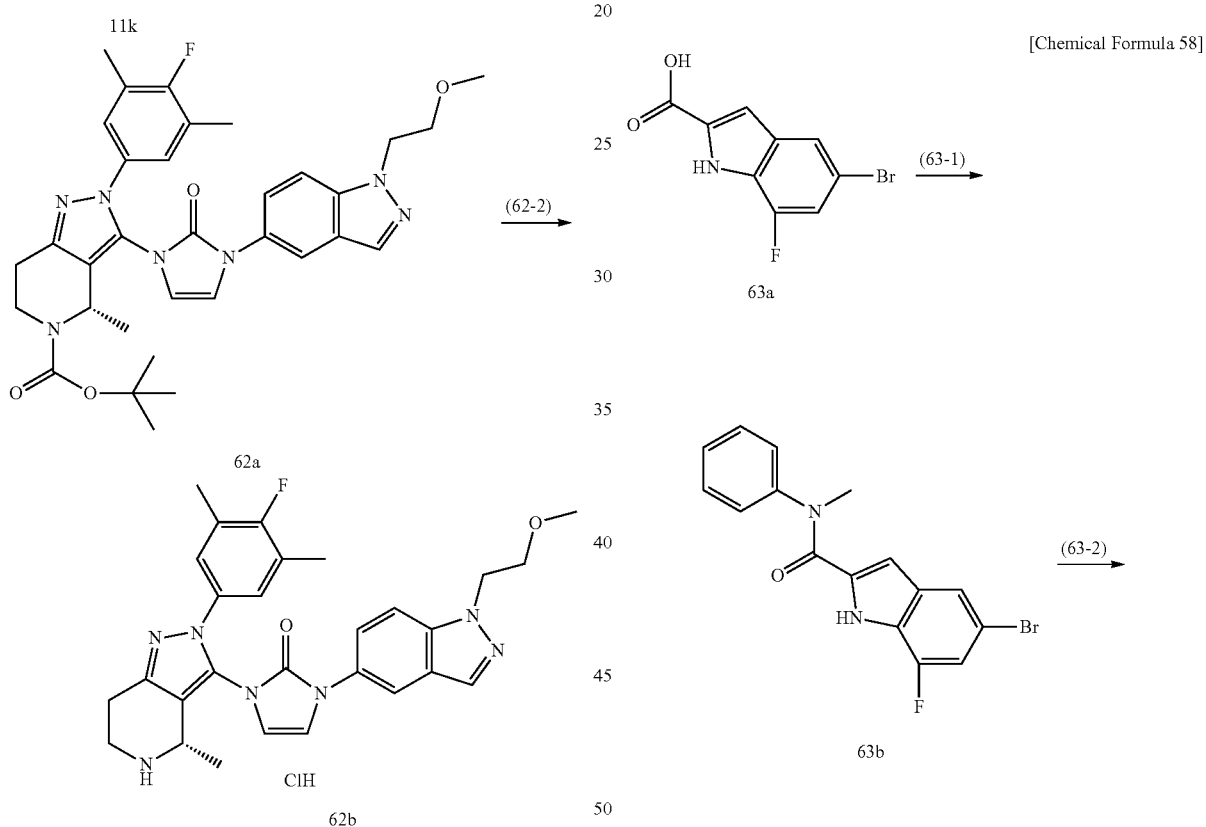

-continued

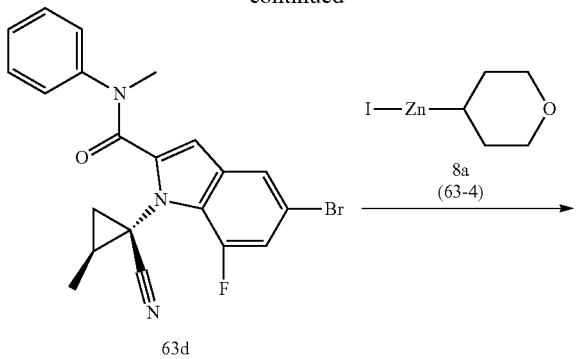

63d

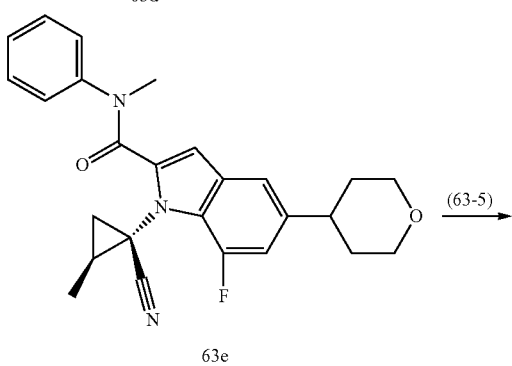

63e

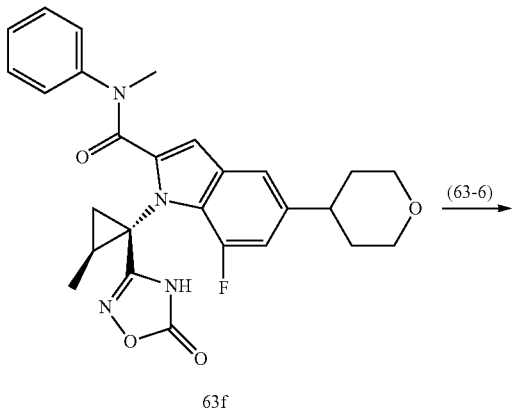

63f

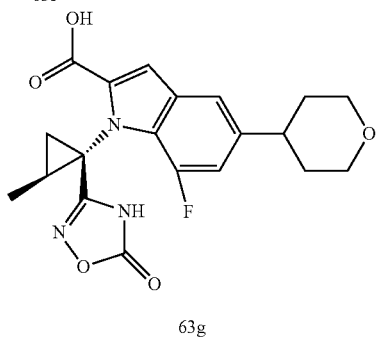

63g

Step 63-1

5-Bromo-7-fluoro-N-methyl-N-phenyl-1H-indole-2-carboxamide (Compound 63b)

The titled compound was synthesized from 5-bromo-7-fluoro-1H-indole-2-carboxylic acid (Compound 63a) by performing an operation similar to Step 1-10 of Example 1 using an appropriate reagent.

Step 63-2

5-Bromo-1l-(cyanomethyl)-7-fluoro-N-methyl-N-phenylindole-2-carboxamide (Compound 63c)

The titled compound was synthesized from Compound 63b obtained in Step 63-1 by performing an operation similar to Step 9-1 of Example 9 using an appropriate reagent.
LC/MS mass spectrometry: m/z 386 ([M+H]$^+$).
LC/MS retention time: 3.17 min. (Analysis Condition: SMD-FA10-long).

Step 63-3

5-Bromo-1-[(1S,2S)-1-cyano-2-methylcyclopropyl]-7-fluoro-N-methyl-N-phenylindole-2-carboxamide (Compound 63d)

The titled compound was synthesized from Compound 63c obtained in Step 63-2 by performing an operation similar to Step 1-6 of Example 1 using an appropriate reagent.
LC/MS mass spectrometry: m/z 426 ([M+H]$^+$).
LC/MS retention time: 1.36 min. (Analysis Condition: SMD-FA05-1).
$^1$H-NMR (300 MHz, CDCl$_3$) δ: 7.75 (1H, s), 7.43-7.30 (6H, m), 6.08 (1H, brs), 3.44 (3H, s), 2.11-1.69 (3H, m), 1.40-1.35 (3H, m).

Step 63-4

1-[(1S,2S)-1-Cyano-2-methylcyclopropyl]-7-fluoro-N-methyl-5-(oxan-4-yl)-N-phenylindole-2-carboxamide (Compound 63e)

The titled compound was synthesized from Compound 63d obtained in Step 63-3 and (tetrahydro-2H-pyran-4-yl)zinc (II) iodide (Compound 8a) by performing an operation similar to Step 8-1 of Example 8 using an appropriate reagent.
LC/MS mass spectrometry: m/z 432 ([M+H]$^+$).
LC/MS retention time: 1.22 min. (Analysis Condition: SMD-FA05-1).

Step 63-5

7-Fluoro-N-methyl-1-[(1S,2S)-2-methyl-1-(5-oxo-4H-1,2,4-oxadiazol-3-yl)cyclopropyl]-5-(oxan-4-yl)-N-phenylindole-2-carboxamide (Compound 63f)

The titled compound was synthesized from Compound 63e obtained in Step 63-4 by performing an operation similar to Step 1-8 of Example 1 using an appropriate reagent.
LC/MS mass spectrometry: m/z 491 ([M+H]$^+$).
LC/MS retention time: 1.21 min. (Analysis Condition: SQD-FA05-01).

Step 63-6

7-Fluoro-1-[(1S,2S)-2-methyl-1-(5-oxo-4H-1,2,4-oxadiazol-3-yl)cyclopropyl]-5-(oxan-4-yl)indole-2-carboxylic acid (Compound 63g)

The titled compound was synthesized from Compound 63f obtained in Step 63-5 by performing an operation similar to Step 6-4 of Example 6 using an appropriate reagent.

LC/MS mass spectrometry: m/z 402 ([M+H]+).

LC/MS retention time: 0.97 min. (Analysis Condition: SMD-FA05-1).

Compound 64b used in the synthesis of Example Compound 64 was synthesized by the following process.

[Chemical Formula 59]

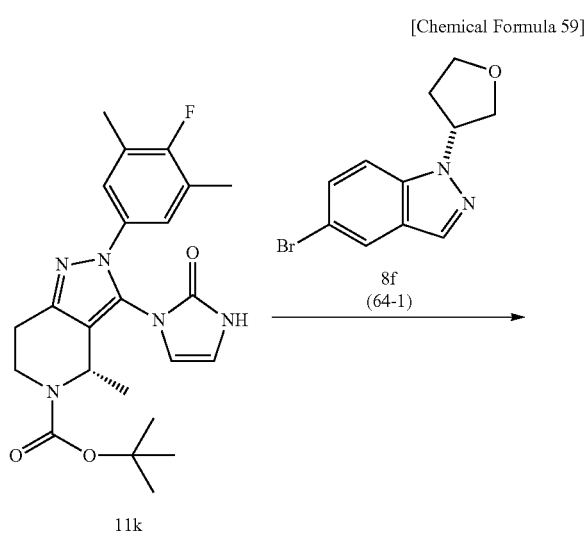

Step 64-1 tert-Butyl (4S)-2-(4-fluoro-3,5-dimethylphenyl)-4-methyl-3-[2-oxo-3-[1-[(3R)-oxolan-3-yl]indazol-5-yl]imidazol-1-yl]-6,7-dihydro-4H-pyrazolo[4,3-c]pyridine-5-carboxylate (Compound 64a)

The titled compound was synthesized from Compound 11k obtained in Step 11-7 and Compound 8f obtained in Step 8-4 by performing an operation similar to Step 1-11 of Example 1 using an appropriate reagent.

LC/MS mass spectrometry: m/z 628 ([M+H]+).

LC/MS retention time: 1.32 min. (Analysis Condition: SMD-FA05-1).

Step 64-2

1-[(4S)-2-(4-Fluoro-3,5-dimethylphenyl)-4-methyl-4,5,6,7-tetrahydropyrazolo[4,3-c]pyridin-3-yl]-3-[1-[(3R)-oxolan-3-yl]indazol-5-yl]imidazol-2-one hydrochloride (Compound 64b)

The titled compound was synthesized from Compound 64a obtained in Step 64-1 by performing an operation similar to Step 11-8 of Example 11 using an appropriate reagent.

LC/MS mass spectrometry: m/z 528 ([M+H]+).

LC/MS retention time: 0.78 min. (Analysis Condition: SMD-FA05-1).

Compound 65c used in the synthesis of Example Compound 65 was synthesized by the following process.

[Chemical Formula 60]

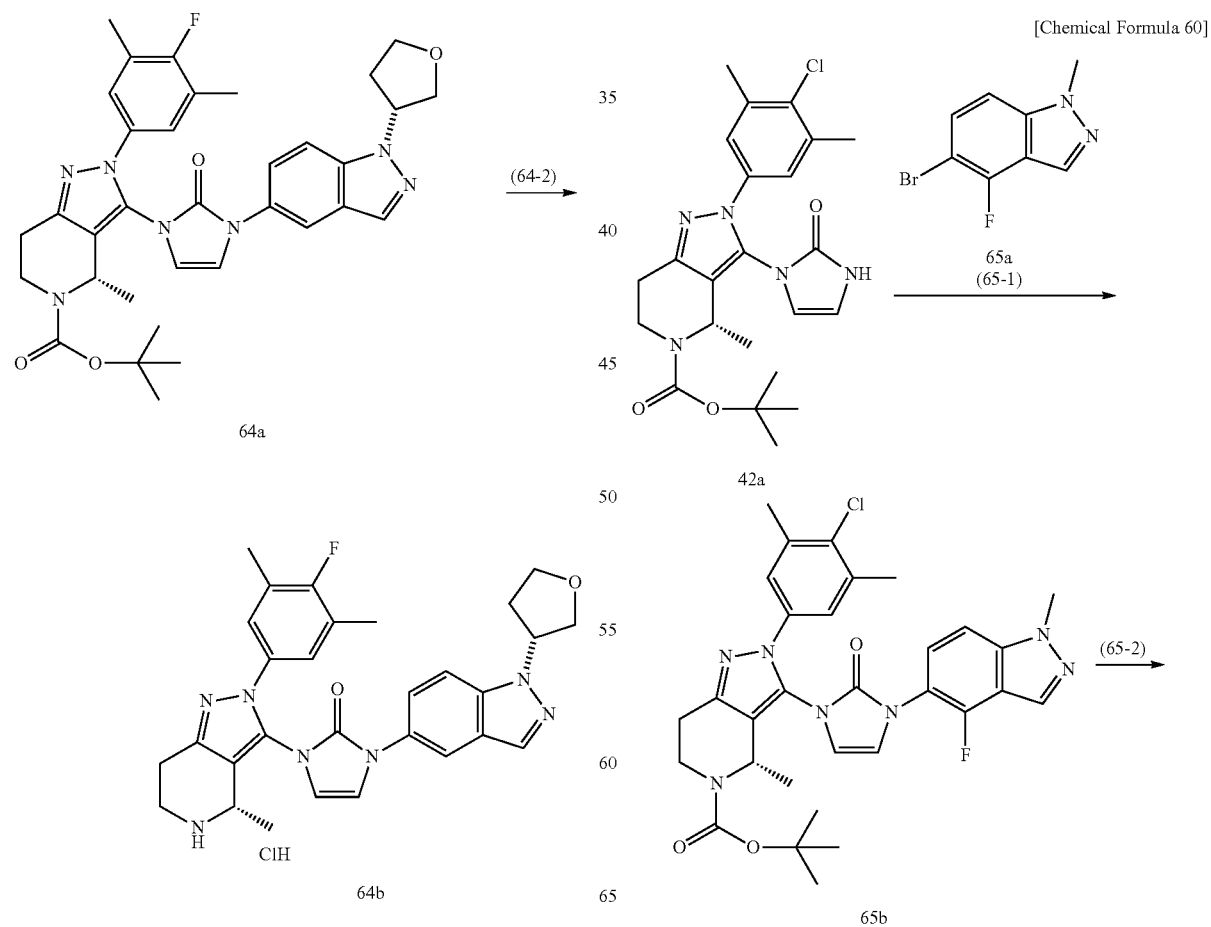

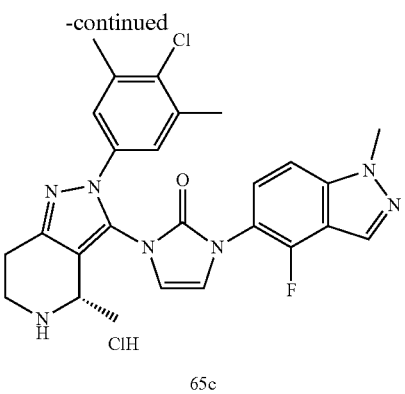

65c

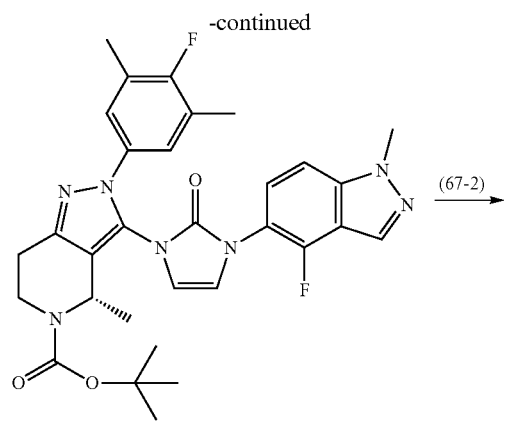

(67-2)

Step 65-1 tert-Butyl (4S)-2-(4-chloro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carboxylate (Compound 65b)

The titled compound was synthesized from Compound 42e obtained in Step 42-4 and 5-bromo-4-fluoro-1-methylindazole (Compound 65a) by performing an operation similar to Step 1-11 of Example 1 using an appropriate reagent.
LC/MS mass spectrometry: m/z 606 ([M+H]$^+$).
LC/MS retention time: 1.38 min. (Analysis Condition: SMD-FA05-1).

Step 65-2

1-[(4S)-2-(4-Chloro-3,5-dimethylphenyl)-4-methyl-4,5,6,7-tetrahydropyrazolo[4,3-c]pyridin-3-yl]-3-(4-fluoro-1-methylindazol-5-yl)imidazol-2-one hydrochloride (Compound 65c The titled compound was synthesized from Compound 65b obtained in Step 65-1 by performing an operation similar to Step 11-8 of Example 11 using an appropriate reagent.
LC/MS mass spectrometry: m/z 506 ([M+H]$^+$).
LC/MS retention time: 0.86 min. (Analysis Condition: SMD-FA05-1).
Compound 67b used in the synthesis of Example Compound 67 was synthesized by the following process.

[Chemical Formula 61]

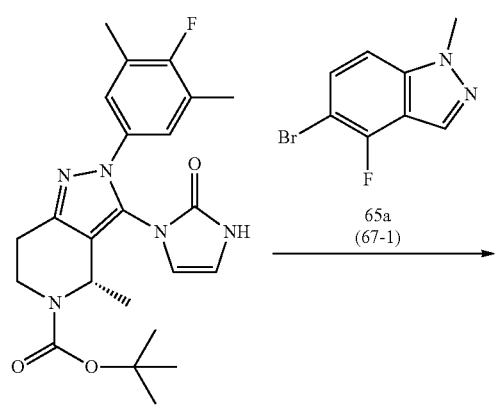

11k    65a (67-1)

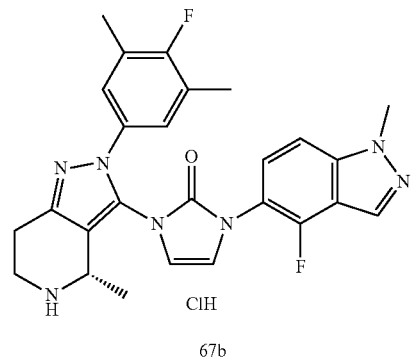

67a

67b

Step 67-1 tert-Butyl (4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carboxylate (Compound 67a)

The titled compound was synthesized from Compound 11k obtained in Step 11-7 and 5-bromo-4-fluoro-1-methylindazole (Compound 65a) by performing an operation similar to Step 1-11 of Example 1 using an appropriate reagent.
LC/MS mass spectrometry: m/z 590 ([M+H]$^+$).
LC/MS retention time: 1.31 min. (Analysis Condition: SMD-FA05-1).

Step 67-2

1-[(4S)-2-(4-Fluoro-3,5-dimethylphenyl)-4-methyl-4,5,6,7-tetrahydropyrazolo[4,3-c]pyridin-3-yl]-3-(4-fluoro-1-methylindazol-5-yl)imidazol-2-one hydrochloride (Compound 67b)

The titled compound was synthesized from Compound 67a obtained in Step 67-1 by performing an operation similar to Step 11-8 of Example 11 using an appropriate reagent.
LC/MS mass spectrometry: m/z 490 ([M+H]$^+$).
LC/MS retention time: 0.80 min. (Analysis Condition: SQD-FA05-1).
Compound 68c used in the synthesis of Example Compound 68 was synthesized by the following process.

[Chemical Formula 62]

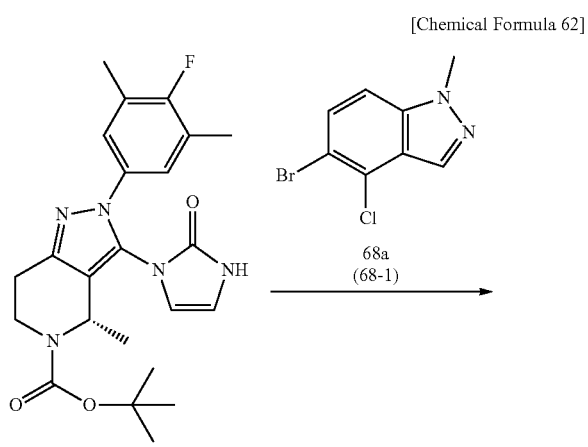

Step 68-2

1-(4-Chloro-1-methylindazol-5-yl)-3-[(4S)-2-(4-fluoro-3,5-dimethylphenyl)-4-methyl-4,5,6,7-tetrahydropyrazolo[4,3-c]pyridin-3-yl]imidazol-2-one hydrochloride (Compound 68c)

The titled compound was synthesized from Compound 68b obtained in Step 68-1 by performing an operation similar to Step 11-8 of Example 11 using an appropriate reagent.
LC/MS mass spectrometry: m/z 506 ([M+H]$^+$).
LC/MS retention time: 0.83 min. (Analysis Condition: SMD-FA05-1).

Compound 69b used in the synthesis of Example Compound 69 was synthesized by the following process.

[Chemical Formula 63]

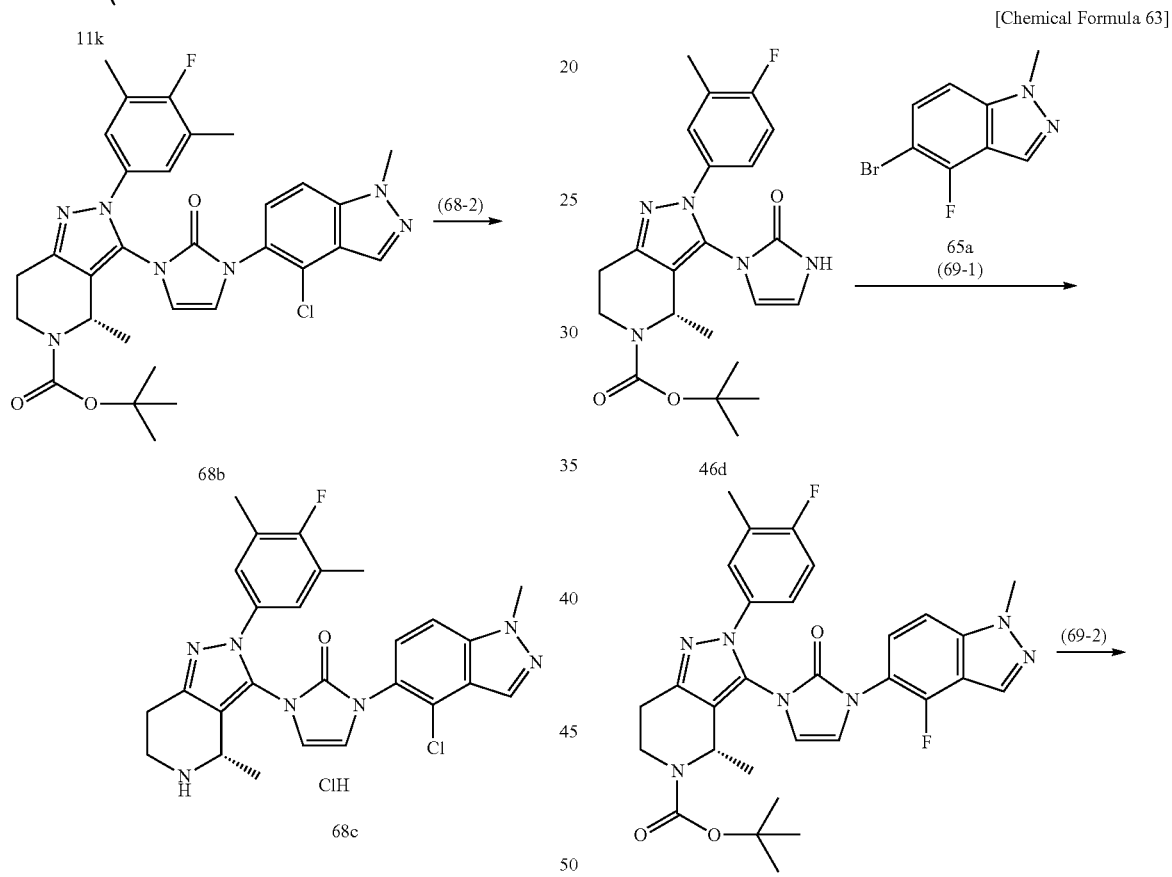

Step 68-1 tert-Butyl (4S)-3-[3-(4-chloro-1-methylindazol-5-yl)-2-oxoimidazol-1-yl]-2-(4-fluoro-3,5-dimethylphenyl)-4-methyl-6,7-dihydro-4H-pyrazolo[4,3-c]pyridine-5-carboxylate (Compound 68b)

The titled compound was synthesized from Compound 11k obtained in Step 11-7 and 5-bromo-4-chloro-1-methylindazole (Compound 68a) by performing an operation similar to Step 1-11 of Example 1 using an appropriate reagent.
LC/MS mass spectrometry: m/z 606 ([M+H]$^+$).
LC/MS retention time: 1.34 min. (Analysis Condition: SMD-FA05-1).

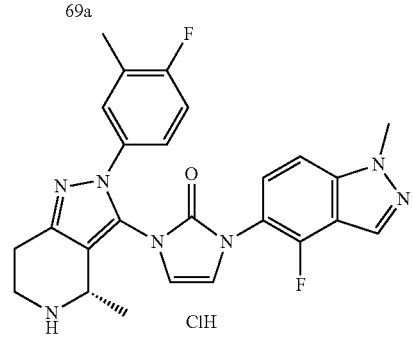

Step 69-1 tert-Butyl (4S)-3-[3-(4-fluoro-1-methylindazol-5-yl)-2-oxoimidazol-1-yl]-2-(4-fluoro-3-methylphenyl)-4-methyl-6,7-dihydro-4H-pyrazolo[4,3-c]pyridine-5-carboxylate (Compound 69a)

The titled compound was synthesized from Compound 46d obtained in Step 46-3 and 5-bromo-4-fluoro-1-methylindazole (Compound 65a) by performing an operation similar to Step 1-11 of Example 1 using an appropriate reagent.
LC/MS mass spectrometry: m/z 576 ([M+H]$^+$).
LC/MS retention time: 1.25 min. (Analysis Condition: SMD-FA05-1).

Step 69-2

1-(4-Fluoro-1-methylindazol-5-yl)-3-[(4S)-2-(4-fluoro-3-methylphenyl)-4-methyl-4,5,6,7-tetrahydropyrazolo[4,3-c]pyridin-3-yl]imidazol-2-one hydrochloride (Compound 69b)

The titled compound was synthesized from Compound 69a obtained in Step 69-1 by performing an operation similar to Step 11-8 of Example 11 using an appropriate reagent.
LC/MS mass spectrometry: m/z 476 ([M+H]$^+$).
LC/MS retention time: 0.77 min. (Analysis Condition: SMD-FA05-1).

Compound 70c used in the synthesis of Example Compound 70 was synthesized by the following process.

[Chemical Formula 64]

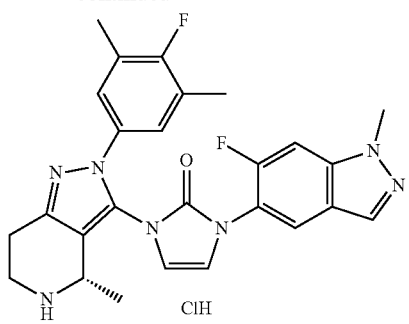

Step 70-1 tert-Butyl (4S)-2-(4-fluoro-3,5-dimethylphenyl)-3-[3-(6-fluoro-1-methylindazol-5-yl)-2-oxoimidazol-1-yl]-4-methyl-6,7-dihydro-4H-pyrazolo[4,3-c]pyridine-5-carboxylate (Compound 70b)

The titled compound was synthesized from Compound 11k obtained in Step 11-7 and 5-bromo-6-fluoro-1-methylindazole (Compound 70a) by performing an operation similar to Step 1-11 of Example 1 using an appropriate reagent.
LC/MS mass spectrometry: m/z 590 ([M+H]$^+$).
LC/MS retention time: 1.28 min. (Analysis Condition: SMD-FA05-1).

Step 70-2

1-[(4S)-2-(4-Fluoro-3,5-dimethylphenyl)-4-methyl-4,5,6,7-tetrahydropyrazolo[4,3-c]pyridin-3-yl]-3-(6-fluoro-1-methylindazol-5-yl)imidazol-2-one hydrochloride (Compound 70c)

The titled compound was synthesized from Compound 70b obtained in Step 70-1 by performing an operation similar to Step 11-8 of Example 11 using an appropriate reagent.
LC/MS mass spectrometry: m/z 490 ([M+H]$^+$).
LC/MS retention time: 0.81 min. (Analysis Condition: SMD-FA05-1).

Compound 71b used in the synthesis of Example Compound 71 was synthesized by the following process.

[Chemical Formula 65]

-continued

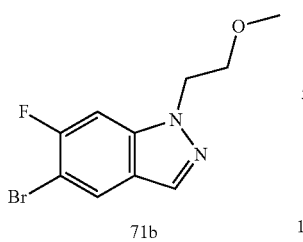

71b

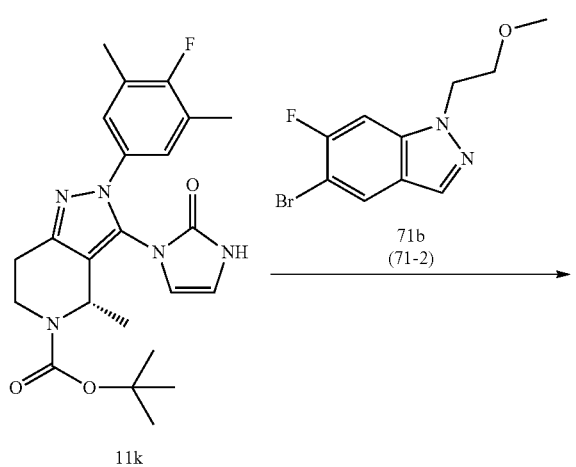

11k

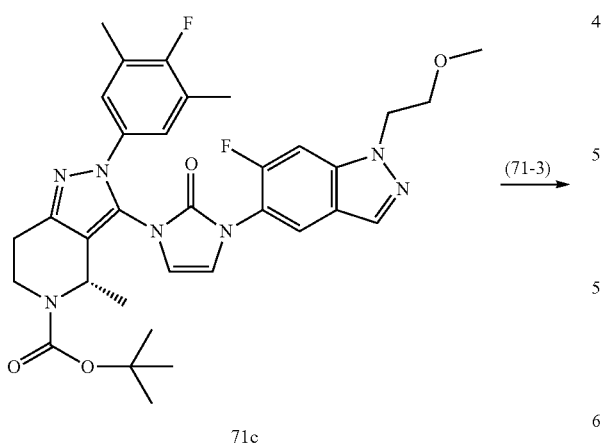

71c

-continued

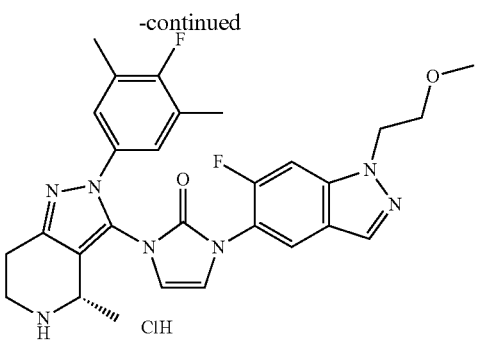

71d

Step 71-1

5-Bromo-6-fluoro-1-(2-methoxyethyl)indazole (Compound 71b)

The titled compound was synthesized from 5-bromo-6-fluoro-1H-indazole (Compound 71a) by performing an operation similar to Step 8-4 of Example 8 using an appropriate reagent.

LC/MS mass spectrometry: m/z 273 ([M+H]$^+$).

LC/MS retention time: 1.06 min. (Analysis Condition: SMD-FA05-1).

Step 71-2 tert-Butyl (4S)-2-(4-fluoro-3,5-dimethylphenyl)-3-[3-[6-fluoro-1-(2-methoxyethyl)indazol-5-yl]-2-oxoimidazol-1l-yl]-4-methyl-6,7-dihydro-4H-pyrazolo[4,3-c]pyridine-5-carboxylate (Compound 71c)

The titled compound was synthesized from Compound 11k obtained in Step 11-7 and Compound 71b obtained in Step 71-1 by performing an operation similar to Step 1-11 of Example 1 using an appropriate reagent.

LC/MS mass spectrometry: m/z 634 ([M+H]$^+$).

LC/MS retention time: 1.30 min. (Analysis Condition: SMD-FA05-1).

Step 71-3

1-[(4S)-2-(4-Fluoro-3,5-dimethylphenyl]-4-methyl-4,5,6,7-tetrahydropyrazolo[4,3-c]pyridin-3-yl]-3-[6-fluoro-1-(2-methoxyethyl)indazol-5-yl]imidazol-2-one hydrochloride (Compound 71d)

The titled compound was synthesized from Compound 71c obtained in Step 71-2 by performing an operation similar to Step 11-8 of Example 11 using an appropriate reagent.

LC/MS mass spectrometry: m/z 534 ([M+H]$^+$).

LC/MS retention time: 0.83 min. (Analysis Condition: SMD-FA05-1).

<Example 73> Synthesis of 3-[(1S,2S)-1-[5-(2-ethyl-3-methylpyridin-4-yl)-2-[(4S)-2-(4-fluoro-3,5-dimethylphenyl)-4-methyl-3-[3-(1-methylindazol-5-yl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one (Compound 73)

Step 73-1

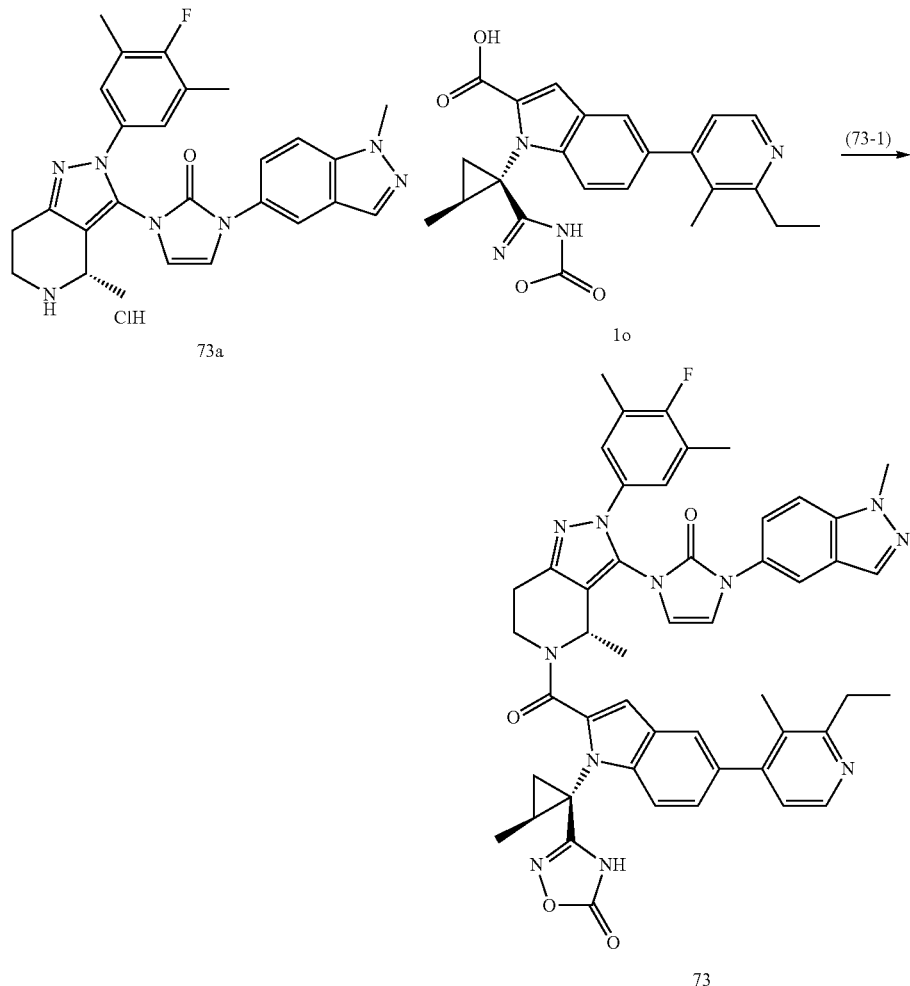

[Chemical Formula 66]

To a DMF (1.5 mL) solution of a racemic form (Compound 73a, 29.6 mg, 0.058 mmol) synthesized by a method similar to the compound obtained in Step 61-2 and Compound 1o (26.8 mg, 0.064 mmol) obtained in Step 1-9 were added HATU (26.6 mg, 0.070 mmol) and N,N-diisopropylethylamine (18.1 mg, 0.14 mmol), and the mixture was stirred at room temperature for an hour. The reaction solution was diluted by ethyl acetate, and washed with distilled water. The organic layer was concentrated under reduced pressure to obtain a residue which is a mixture of stereoisomers. The stereoisomers were separated by reversed-phase HPLC to obtain Entity A (14.5 mg, yield 29%) and Entity B (15.5 mg, yield 31%), which is a white, solid, titled Compound 73.

Separation Condition

Column: YMC Actus ODS-A, 20×100 mm, 5 μm

Solvent: 0.1% formic acid aqueous solution/0.1% formic acid acetonitrile solution=40/60 (homogenous system)

Flow rate: 20 mL/min., room temperature

Entity A

LC/MS mass spectrometry: m/z 872 ([M+H]$^+$).

LC/MS retention time: 0.99 min. (Analysis Condition: SMD-FA05-3).

Entity B (Compound 73)

LC/MS mass spectrometry: m/z 872 ([M+H]$^+$).

LC/MS retention time: 1.01 min. (Analysis Condition: SMD-FA05-3).

<Example 74> Synthesis of 3-[(1S,2S)-1-[6-Fluoro-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one (Compound 74)
[Chemical Formula 67]
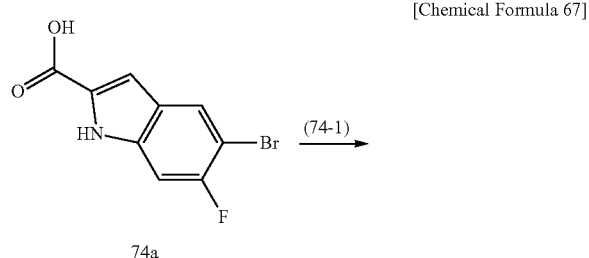
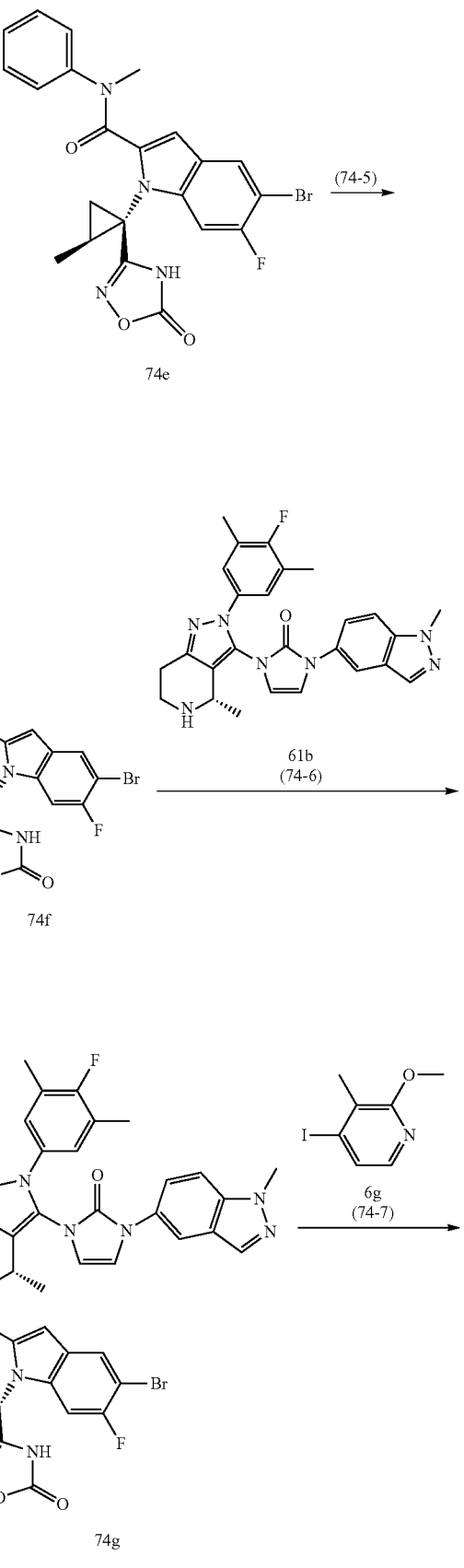

-continued

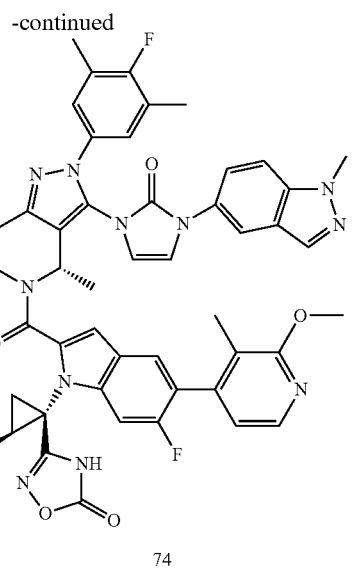

74

Step 74-1

5-Bromo-6-fluoro-N-methyl-N-phenyl-1H-indole-2-carboxamide (Compound 74b)

The titled compound was synthesized from 5-bromo-6-fluoro-1H-indole-2-carboxylic acid (Compound 74a) by performing an operation similar to Step 1-10 of Example 1 using an appropriate reagent.

LC/MS mass spectrometry: m/z 347 ([M+H]$^+$).

LC/MS retention time: 1.06 min. (Analysis Condition: SMD-TFA05-4).

Step 74-2

5-Bromo-1-(cyanomethyl)-6-fluoro-N-methyl-N-phenylindole-2-carboxamide (Compound 74c)

The titled compound was synthesized from Compound 74b obtained in Step 74-1 by performing an operation similar to Step 9-1 of Example 9 using an appropriate reagent.

LC/MS mass spectrometry: m/z 386 ([M+H]$^+$).

LC/MS retention time: 1.06 min. (Analysis Condition: SMD-TFA50-4).

Step 74-3

5-Bromo-1-[(1S,2S)-1-cyano-2-methylcyclopropyl]-6-fluoro-N-methyl-N-phenylindole-2-carboxamide (Compound 74d)

The titled compound was synthesized from Compound 74c obtained in Step 74-2 and (4R)-4-methyl-1,3,2-dioxathiolane 2,2-dioxide (Compound 1k) by performing an operation similar to Step 1-6 of Example 1 using an appropriate reagent.

LC/MS mass spectrometry: m/z 426 ([M+H]$^+$).

LC/MS retention time: 1.04 min. (Analysis Condition: SMD-FA10-5).

Step 74-4

5-Bromo-6-fluoro-N-methyl-1-[(1S,2S)-2-methyl-1-(5-oxo-4H-1,2,4-oxadiazol-3-yl)cyclopropyl]-N-phenylindole-2-carboxamide (Compound 74e)

The titled compound was synthesized from Compound 74d obtained in Step 74-3 by performing an operation similar to Step 1-8 of Example 1 using an appropriate reagent.

LC/MS mass spectrometry: m/z 485 ([M+H]$^+$).

LC/MS retention time: 1.33 min. (Analysis Condition: SMD-FA05-1).

Step 74-5

5-Bromo-6-fluoro-1-[(1S,2S)-2-methyl-1-(5-oxo-4H-1,2,4-oxadiazol-3-yl)cyclopropyl]indole-2-carboxylic acid (Compound 74f)

The titled compound was synthesized from Compound 74e obtained in Step 74-4 by performing an operation similar to Step 6-4 of Example 6 using an appropriate reagent.

LC/MS mass spectrometry: m/z 396 ([M+H]$^+$).

LC/MS retention time: 0.80 min. (Analysis Condition: SQD-FA05-1).

Step 74-6

3-[(1S,2S)-1-[5-Bromo-6-fluoro-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one (Compound 74g)

The titled compound was synthesized from Compound 74f obtained in Step 74-5 and Compound 61b obtained in Step 61-2 by performing an operation similar to Step 1-10 of Example 1 using an appropriate reagent.

LC/MS mass spectrometry: m/z 849 ([M+H]$^+$).

LC/MS retention time: 1.42 min. (Analysis Condition: SMD-FA05-1).

Step 74-7

3-[(1S,2S)-1-[6-Fluoro-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-(2-methoxy-3-methylpyridin-4-yl)indol-1-yl]-2-methylcyclopropyl]-4H-1,2,4-oxadiazol-5-one (Compound 74)

The titled compound was synthesized by performing an operation similar to Step 6-5 of Example 6 using Compound 74g obtained in Step 74-6 and 4-iodo-2-methoxy3-methylpyridine (Compound 6g), and an appropriate reagent.

LC/MS mass spectrometry: m/z 892 ([M+H]$^+$).

LC/MS retention time: 1.48 min. (Analysis Condition: SMD-TFA05-1).

Examples 75-77

An operation similar to Step 8-1 of Example 8 was performed using an indole bromide compound and an iodo (oxan-4-yl) zinc derivative, and an appropriate reagent to obtain Example Compounds 75 to 77 shown in Table 2-6 by the following reaction.

[Chemical Formula 68]

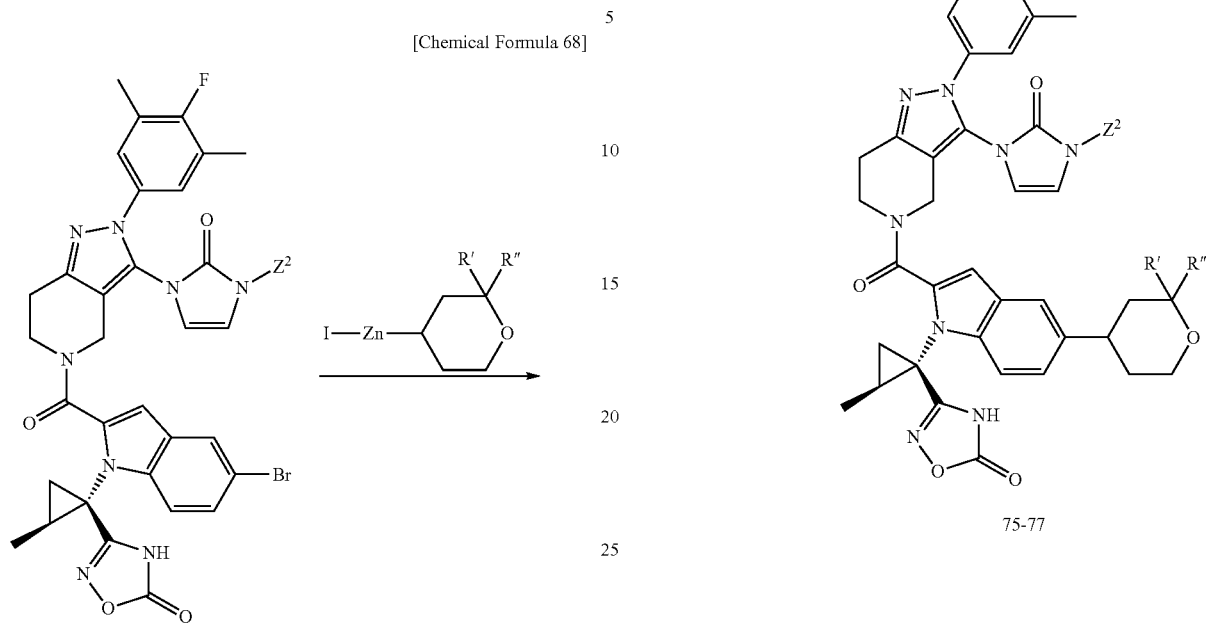

TABLE 2-6

The Obtained Example Compounds 75 to 77

| Example No. | Structure | Compound | Analysis Condition | LC/MS retention time (min.) | LC/MS mass spectrometry (m/z) |
|---|---|---|---|---|---|
| 75 | 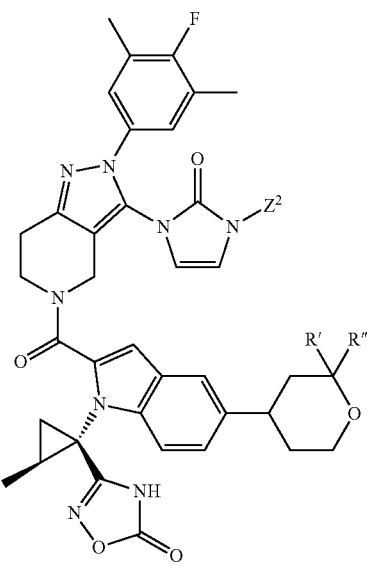 | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(6-oxaspiro[4.5]decan-9-yl)indol-1-yl]-2-methylcyclopropyl]-4H-1,2,4-oxadiazol-5-one | SMD-TFA05-2 | 1.57 | 878 ([M+H]+) |

TABLE 2-6-continued

The Obtained Example Compounds 75 to 77

| Example No. | Structure | Compound | Analysis Condition | LC/MS retention time (min.) | LC/MS mass spectrometry (m/z) |
|---|---|---|---|---|---|
| 76 | 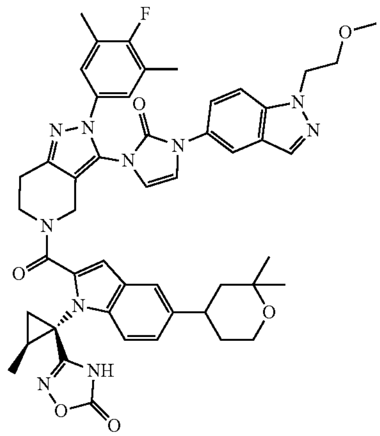 | 3-[(1S,2S)-1-[5-(2,2-dimethyloxan-4-yl)-2-[2-(4-fluoro-3,5-dimethylphenyl)-3-[3-[1-(2-methoxyethyl)indazol-5-yl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-2 | 1.44 | 895 ([M+H]$^+$) |
| 77 | 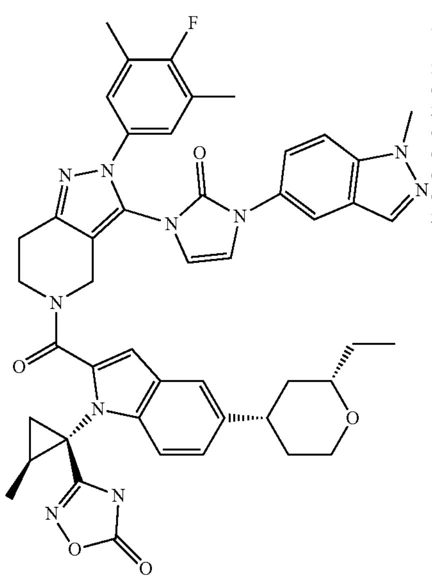 [SMILES: CC[C@H]1C[C@@H](c2ccc3c(c2)cc(C(=O)N2CCc4nn(-c5cc(C)c(F)c(C)c5)c(-n5ccn(-c6ccc7c(cnn7C)c6)c5=O)c4C2)n3[C@@]2(c3noc(=O)[nH]3)C[C@@H]2C)CCO1] | 3-[(1S,2S)-1-[5-[(2S,4S)-(2-ethyloxan-4-yl)-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-2 | 1.51 | 851 ([M+H]$^+$) |

Compound 75b used in the synthesis of Example Compound 75 was synthesized by the following process.

Step 75-1

Iodo(6-oxaspiro[4.5]decan-9-yl) zinc (Compound 75b)

[Chemical Formula 69]

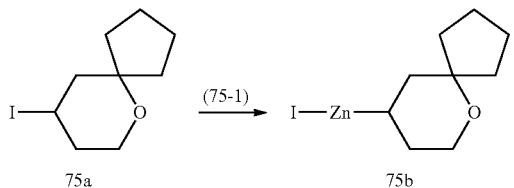

The titled compound was synthesized from 9-iodo-6-oxaspiro[4.5]decane (Compound 75a) by performing an operation similar to Step 41-1 of Example 41 using an appropriate reagent.

The compound was directly put to use in the next step.

Compound 76a used in the synthesis of Example Compound 76 was synthesized by the following process.

Step 76-1

3-[(1S,2S)-1-[5-Bromo-2-[2-(4-fluoro-3,5-dimethyl-phenyl)-3-[1-(2-methoxyethyl)indazol-5-yl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one (Compound 76a)

The titled compound was synthesized from Compound 56b obtained in Step 56-1 and Compound 6f obtained in Step 6-4 by performing an operation similar to Step 1-10 of Example 1 using an appropriate reagent.

LC/MS mass spectrometry: m/z 861 ([M+H]$^+$).

LC/MS retention time: 1.45 min. (Analysis Condition: SMD-FA05-2).

Example 77

[Chemical Formula 71]

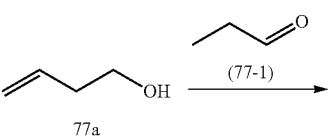

[Chemical Formula 70]

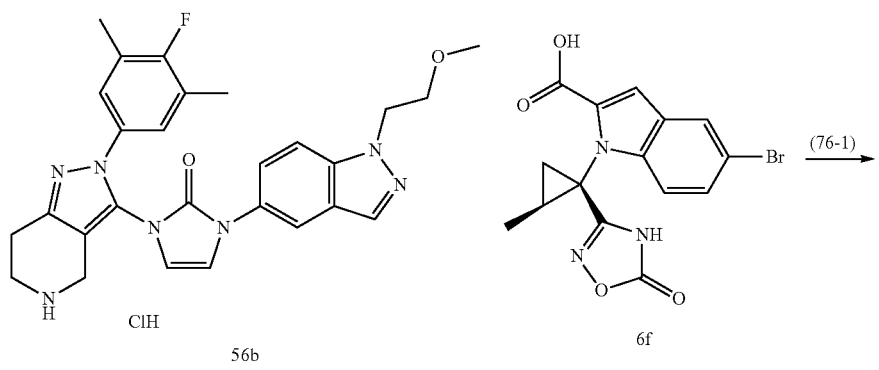

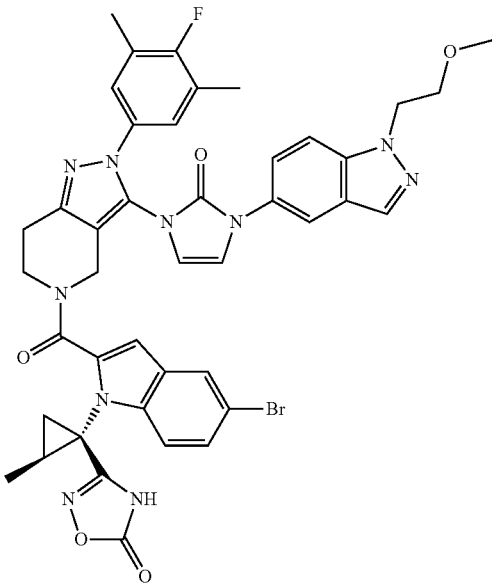

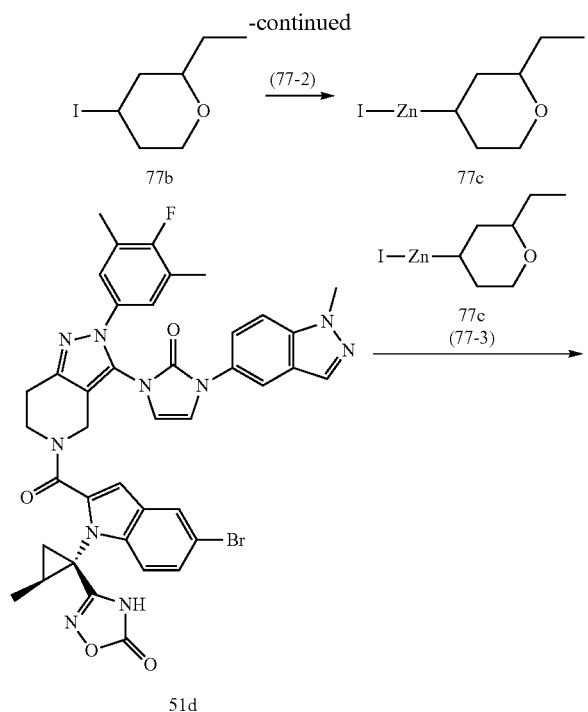

matography (ethyl acetate/hexane=0:1 to 1:9) to obtain the titled Compound 77b as a pale yellow oil-like diastereomer mixture (1.12 g, yield 67%, syn:anti=1.00:0.45).

¹H-NMR (400 MHz, CDCl₃):

syn δ: 4.31-4.23 (1H, m), 3.90-3.82 (1H, m), 3.44-3.37 (1H, m), 3.21-3.15 (1H, m), 2.37-1.38 (6H, m), 0.92 (3H, t, J=7.4 Hz).

anti δ: 4.87-4.84 (1H, m), 3.90-3.82 (2H, m), 3.70-3.64 (1H, m), 2.37-1.38 (6H, m), 0.94 (3H, t, J=7.6 Hz).

Step 77-2

(2-Ethyloxan-4-yl)-iodozinc (Compound 77c)

To a DMA (0.25 mL) solution of zinc (102 mg, 1.56 mmol) was slowly added dropwise a mixture of chloro (trimethyl)silane (0.017 mL, 0.137 mmol) and 1,2-dibromoethane (0.012 mL, 0.137 mmol) under a nitrogen atmosphere while maintaining a temperature of 65° C. or lower, and the mixture was stirred at room temperature for 15 min. Then, the DMA (0.625 mL) solution of Compound 77b (300 mg, 1.25 mmol) obtained in Step 77-1 was added dropwise slowly into the mixture while maintaining a temperature of 65° C. or lower, and the mixture was stirred under a nitrogen atmosphere at room temperature for 30 min. to obtain a DMA solution (0.86M) of a diastereomer mixture of the titled Compound 77c.

Step 77-3

3-[(1S,2S)-1-[5-(2-Ethyloxan-4-yl)-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one (Compound 77)

To a DMA (0.163 mL) solution of Compound 51d (40.0 mg, 0.049 mmol) obtained in Step 51-4 were added palladium(II) acetate (2.20 mg, 0.00978 mmol), and 2-(2-dicyclohexylphosphanylphenyl)-1-N,1-N,3-N,3-N-tetramethylbenzene-1,3-diamine (8.54 mg, 0.020 mmol), and the mixture was deaerated under reduced pressure, then nitrogen was introduced in the vessel and the mixture was stirred at room temperature for 5 min. Then, a DMA (0.86 M, 0.398 mL, 0.342 mmol) solution of Compound 77c obtained in Step 77-2 was added and the mixture was stirred at room temperature for 1.5 h. Formic acid was added to the reaction mixture, and the reaction mixture was purified by reversed-phase silica gel chromatography (acetonitrile/water, 0.1% formic acid) to obtain the syn-type diastereomer mixture. The syn-type diastereomer mixture was separated into stereoisomers by the reversed-phase HPLC to obtain a white, amorphous Entity A (17.4 mg, yield 41%) and a white, amorphous Entity B (14.9 mg, yield 37%), which is the titled Compound 77.

Separation Condition

Column: CHIRALCEL OD-RH 5 μm, 4.6 mm×150 mm (Daicel)

Solvent: 0.1% formic acid aqueous solution/0.1% formic acid acetonitrile solution=20/80 (homogenous system)

Flow rate: 1.0 mL/min., room temperature

Entity A

LC/MS mass spectrometry: m/z 851 ([M+H]⁺).

HPLC retention time: 4.99 min. (Separation condition).

LC/MS retention time: 1.46 min. (Analysis Condition: SMD-FA05-1).

Step 77-1

2-Ethyl-4-iodooxane (Compound 77b)

To an acetic acid (2.48 mL) solution of but-3-en-1-ol (0.588 mL, 6.93 mmol) was sequentially added propionaldehyde (0.650 mL, 9.01 mmol) and lithium iodide (2.78 g, 20.8 mmol), and the mixture was stirred at 60° C. for 1 h. Water was added to the reaction mixture, and extraction was performed using dichloromethane. The organic layer was washed with 10% sodium thiosulfate aqueous solution and saturated sodium acid carbonate aqueous solution, then dried with magnesium sulfate. After filtration, the filtrate was concentrated under reduced pressure (lower limit being 150 hpa), and the residue was purified by silica gel chro- Entity B (Compound 77)
LC/MS mass spectrometry: m/z 851 ([M+H]⁺).
HPLC retention time: 6.64 min. (Separation condition).
LC/MS retention time: 1.46 min. (Analysis Condition: SMD-FA05-1).
<Example 78> Synthesis of 3-[(1S,2S)-2-Ethyl-1-[2-[2-(4-fluoro-3,5-dimethylphenyl)-3-[3-(1-methyl-indazol-5-yl)-2-oxoimidazol-1-yl]-6,7-dihydro-4H-pyrazolo[4,3-c]pyridine-5-carbonyl]-5-(oxan-4-yl)indol-1-yl]cyclopropyl]-4H-1.2.4-oxadiazol-5-one (Compound 78)
[Chemical Formula 72]
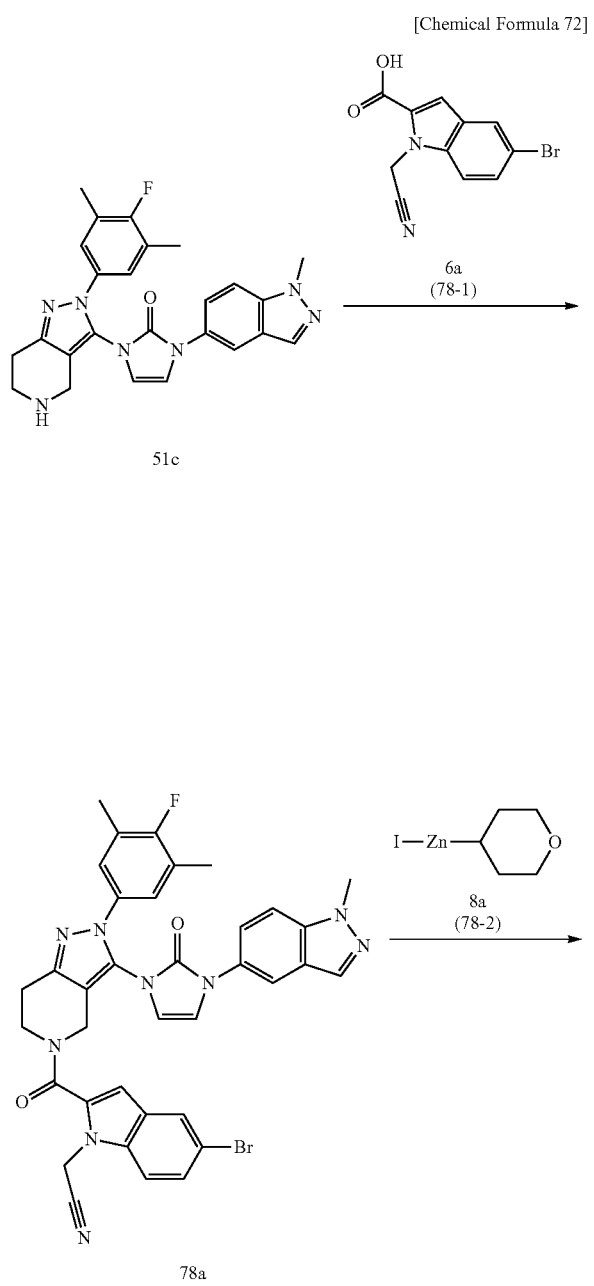
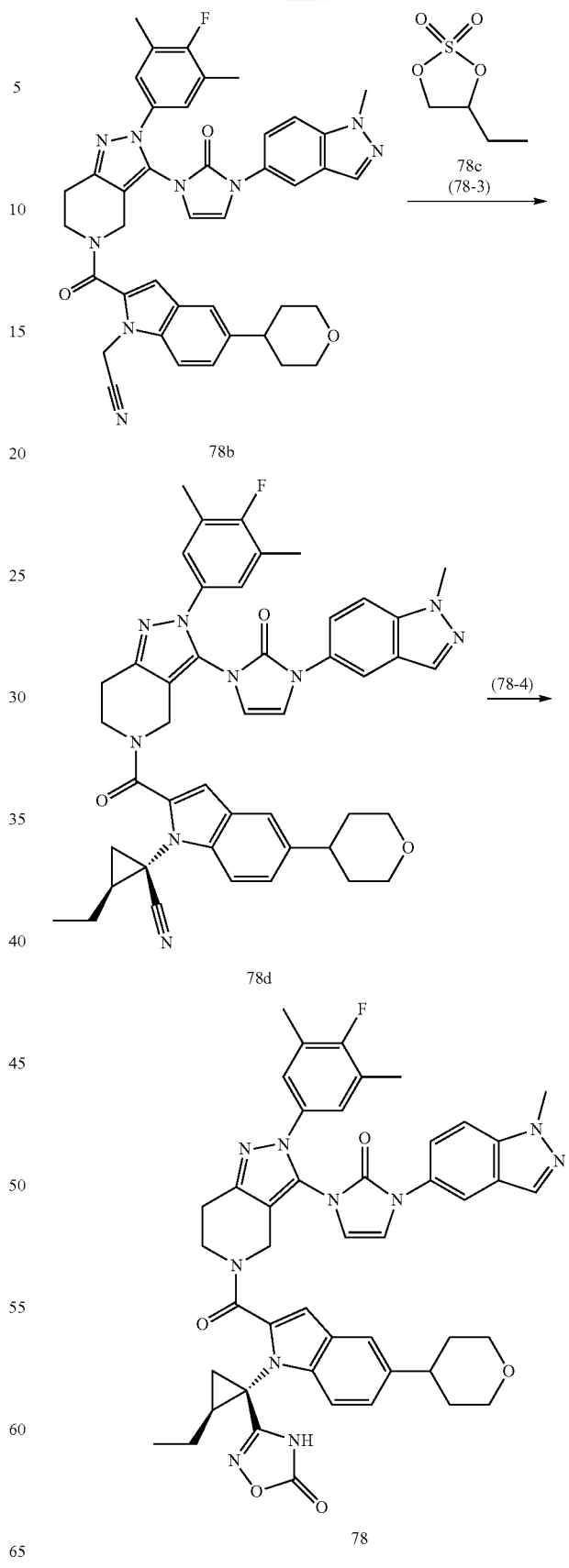

Step 78-1

2-[5-Bromo-2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]indol-1-yl]acetonitrile (Compound 78a)

The titled compound was synthesized from Compound 51c obtained in Step 51-3 and 5-bromo-1-(cyanomethyl)indole-2-carboxylic acid (Compound 6a) by performing an operation similar to Step 1-10 of Example 1 using an appropriate reagent.
LC/MS mass spectrometry: m/z 718 ([M+H]$^+$).
LC/MS retention time: 1.30 min. (Analysis Condition: SMD-FA05-1).

Step 78-2

2-[2-[2-(4-Fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]acetonitrile (Compound 78b)

The titled compound was synthesized from Compound 78a obtained in Step 78-1 and (tetrahydro-2H-pyran-4-yl)zinc (II) iodide (Compound 8a) by performing an operation similar to Step 8-1 of Example 8 using an appropriate reagent.
LC/MS mass spectrometry: m/z 724 ([M+H]$^+$).
LC/MS retention time: 1.21 min. (Analysis Condition: SMD-FA05-1).

Step 78-3

(1S,2S)-2-Ethyl-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]cyclopropane-1-carbonitrile (Compound 78d)

The titled compound was synthesized from Compound 78b obtained in Step 78-2 by performing an operation similar to Step 1-6 of Example 1 using an appropriate reagent.
LC/MS mass spectrometry: m/z 778 ([M+H]$^+$).
LC/MS retention time: 1.27 min. (Analysis Condition: SMD-FA05-RP).

Step 78-4

3-[(1S,2S)-2-Ethyl-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]cyclopropyl]-4H-1,2,4-oxadiazol-5-one (Compound 78)

The titled compound was synthesized from Compound 78d obtained in Step 78-2 by performing an operation similar to Step 1-8 of Example 1 using an appropriate reagent.
LC/MS mass spectrometry: m/z 837 ([M+H]$^+$).
LC/MS retention time: 1.39 min. (Analysis Condition: SMD-TFA05-2).

<Example 79> Synthesis of 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-(hydroxymethyl)cyclopropyl]-4H-1,2,4-oxadiazol-5-one (Compound 79)

[Chemical Formula 73]

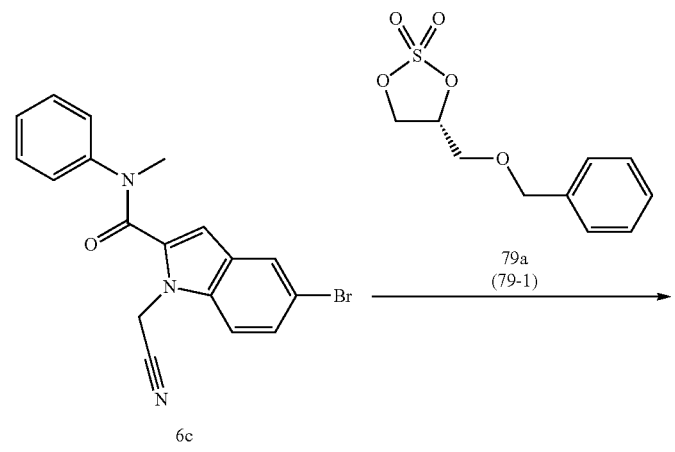

-continued
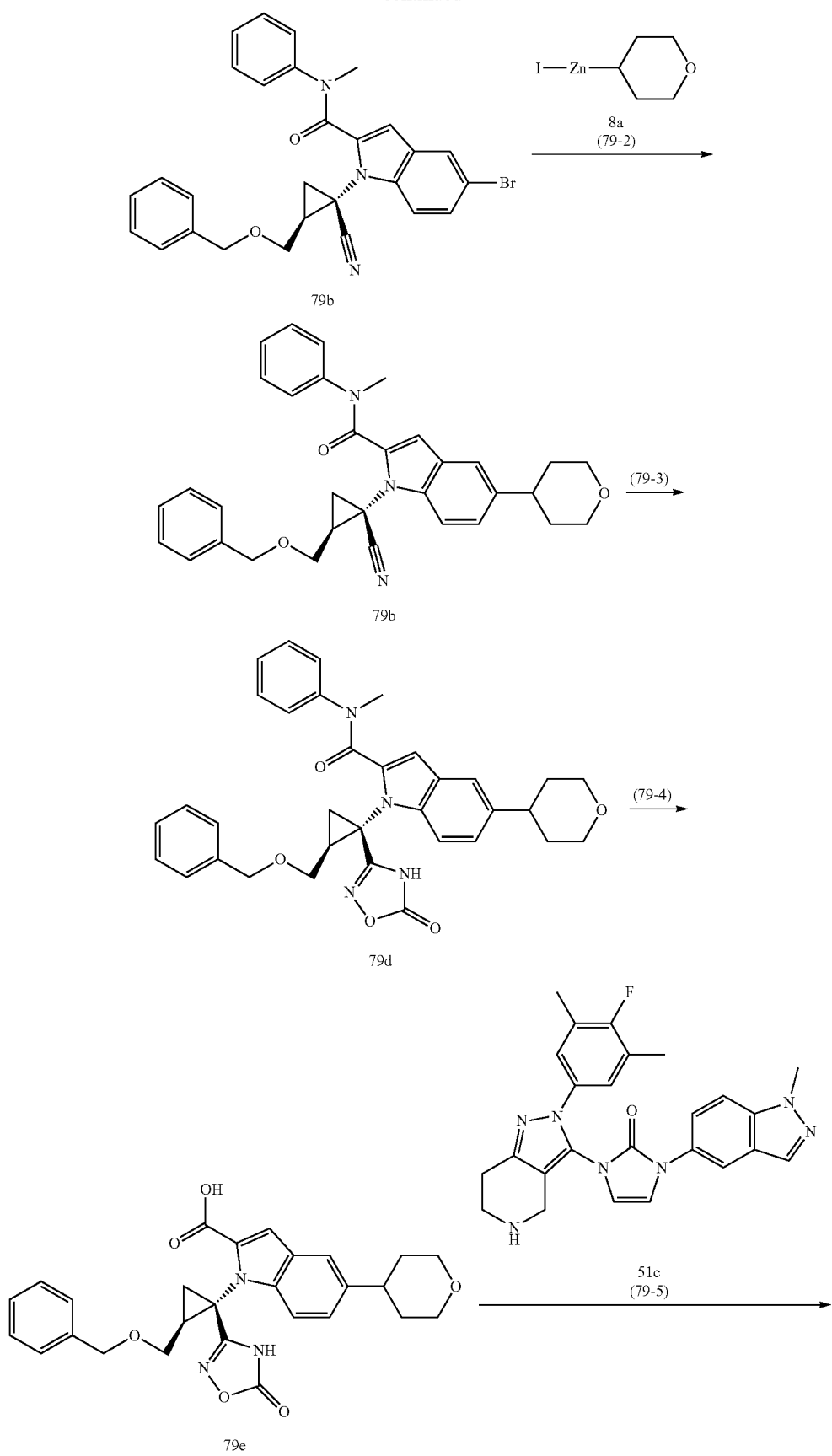

239

240

-continued

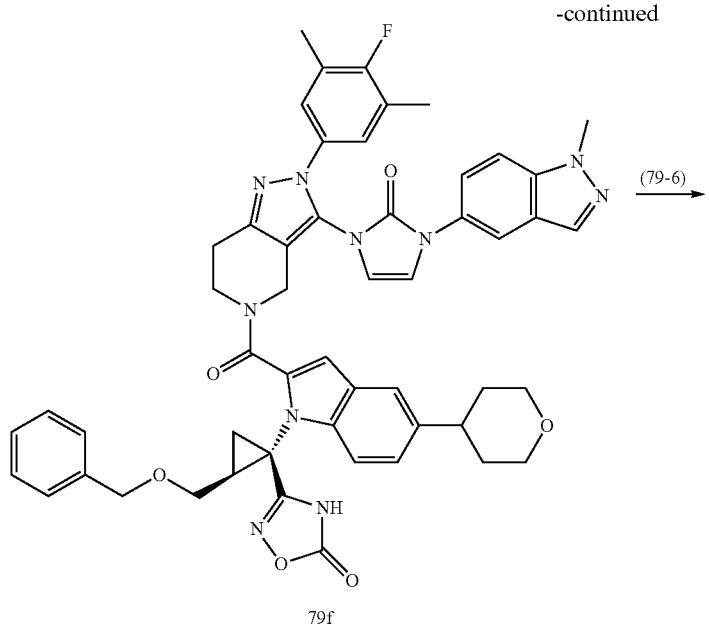

79f (79-6)

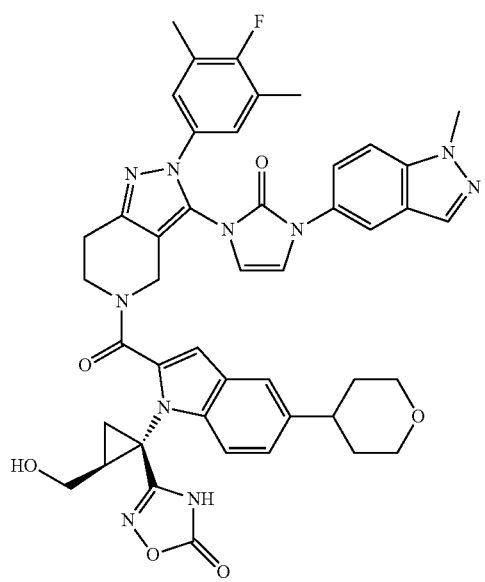

79

Step 79-1

5-Bromo-1l-[(1S,2S)-1-cyano-2-(phenylmethoxymethyl)cyclopropyl]-N-methyl-N-phenylindole-2-carboxamide (Compound 79b)

The titled compound was synthesized from Compound 6c obtained in Step 6-1 and (4R)-4-(phenylmethoxymethyl)-1,3,2-dioxathiolane 2,2-dioxide (Compound 79a) by performing an operation similar to Step 1-6 of Example 1 using an appropriate reagent.

LC/MS mass spectrometry: m/z 514 ([M+H]$^+$).
LC/MS retention time: 1.48 min. (Analysis Condition: SMD-FA05-1).

Step 79-2

1-[(1S,2S)-1-Cyano-2-(phenylmethoxymethyl)cyclopropyl]-N-methyl-5-(oxan-4-yl)-N-phenylindole-2-carboxamide (Compound 79c)

The titled compound was synthesized from Compound 79b obtained in Step 79-1 and (tetrahydro-2H-pyran-4-yl) zinc (II) iodide (Compound 8a) by performing an operation similar to Step 8-1 of Example 8 using an appropriate reagent.

LC/MS mass spectrometry: m/z 520 ([M+H]$^+$).
LC/MS retention time: 1.37 min. (Analysis Condition: SMD-FA05-1).

Step 79-3

N-Methyl-5-(oxan-4-yl)-1-[(1S,2S)-1-(5-oxo-4H-1,2,4-oxadiazol-3-yl)-2-(phenylmethoxymethyl)cyclopropyl]-N-phenylindole-2-carboxamide (Compound 79d)

The titled compound was synthesized from Compound 79c obtained in Step 79-2 by performing an operation similar to Step 1-8 of Example 1 using an appropriate reagent.

LC/MS mass spectrometry: m/z 579 ([M+H]$^+$).
LC/MS retention time: 1.37 min. (Analysis Condition: SMD-FA05-1).

Step 79-4

5-(Oxan-4-yl)-1-[(1S,2S)-1-(5-oxo-4H-1,2,4-oxadiazol-3-yl)-2-(phenylmethoxymethyl)cyclopropyl] indole-2-carboxylic acid (Compound 79e)

The titled compound was synthesized from Compound 79d obtained in Step 79-3 by performing an operation similar to Step 6-4 of Example 6 using an appropriate reagent.

LC/MS mass spectrometry: m/z 490 ([M+H]$^+$).
LC/MS retention time: 1.12 min. (Analysis Condition: SMD-FA05-1).

Step 79-5

3-[(1S,2S)-1-[2-[2-(4-Fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-(phenylmethoxymethyl) cyclopropyl]-4H-1,2,4-oxadiazol-5-one (Compound 79f)

The titled compound was synthesized from Compound 79e obtained in Step 79-4 and Compound 51c obtained in Step 51-3 by performing an operation similar to Step 1-10 of Example 1 using an appropriate reagent.

LC/MS mass spectrometry: m/z 929 ([M+H]$^+$).
LC/MS retention time: 1.41 min. (Analysis Condition: SMD-FA05-1).

Step 79-6

3-[(1S,2S)-1-[2-[2-(4-Fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-(hydroxymethyl)cyclopropyl]-4H-1,2,4-oxadiazol-5-one (Compound 79)

The dichloromethane (0.762 mL) solution of Compound 79f (35.4 mg, 0.0381 mmol) obtained in Step 79-5 was cooled to 0° C., and a hexane solution (0.191 mL, 0.191 mmol) of 1M boron trichloride was slowly added. The reaction solution was warmed to room temperature and stirred for 105 min., and then a saturated sodium acid carbonate solution was added to the reaction solution and the water layer was subjected to extraction using dichloromethane. The organic layer was washed with brine and dried with sodium sulfate. After filtration, the filtrate was concentrated under reduced pressure and the residue was purified by reversed-phase column chromatography (acetonitrile/water, 0.1% formic acid) to obtain the titled compound (18.5 mg, yield 50%).

LC/MS mass spectrometry: m/z 839 ([M+H]$^+$).

LC/MS retention time: 1.20 min. (Analysis Condition: SMD-TFA05-1).

<Example 80> Synthesis of 3-[(1S,2S)-1-[2-[(4S,6R)-2-(4-fluoro-3,5-dimethylphenyl)-4,6-dimethyl-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one (Compound 80)

[Chemical Formula 74]

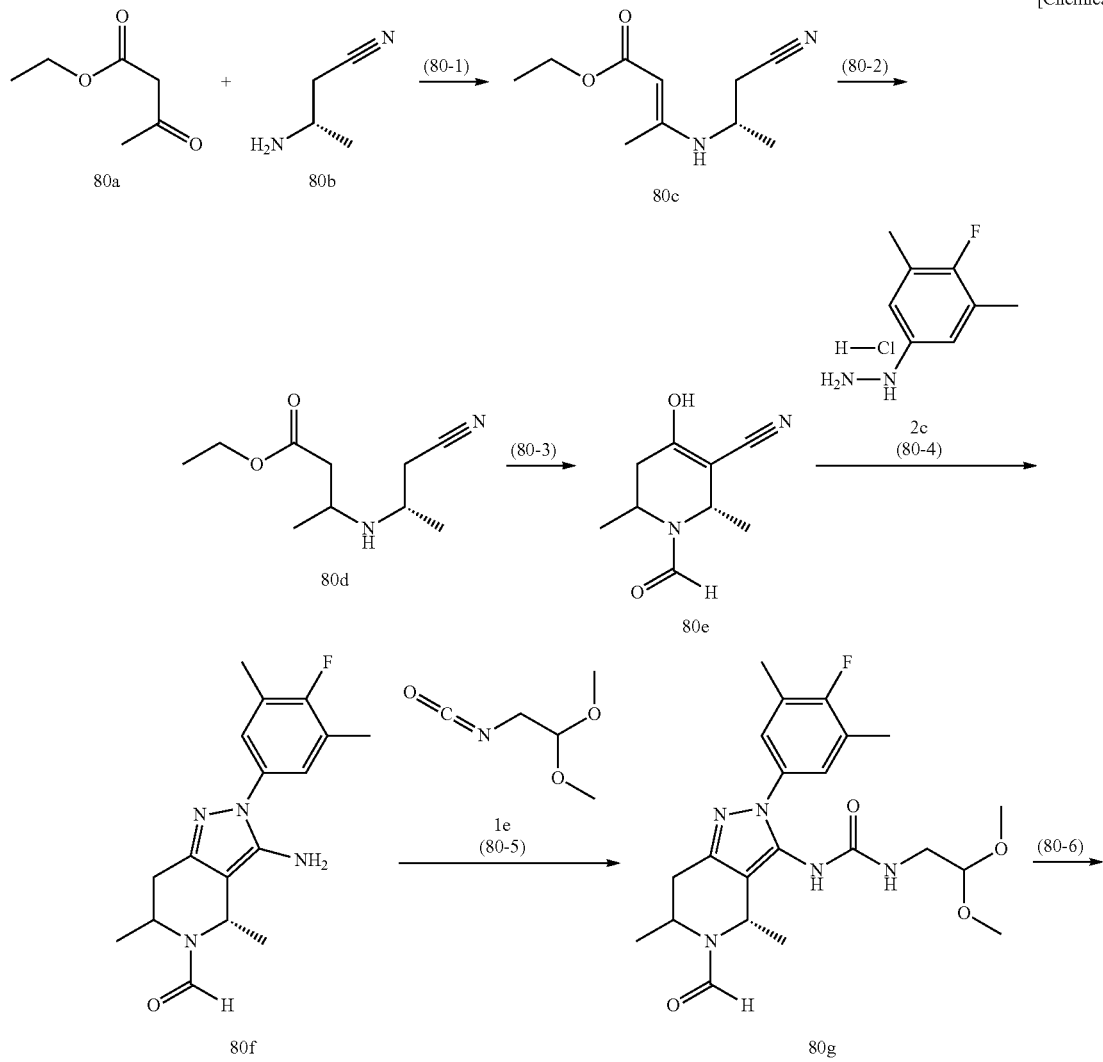

-continued
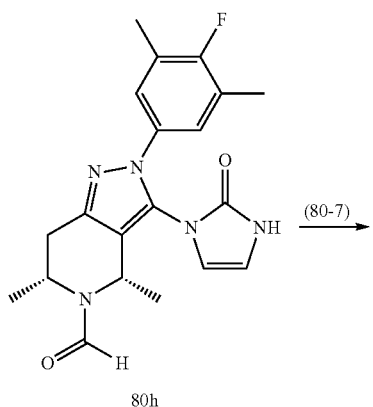
80h
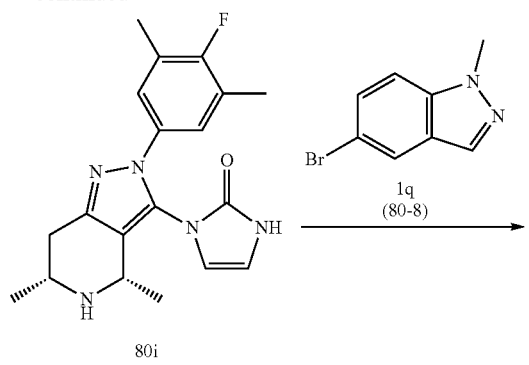
80i
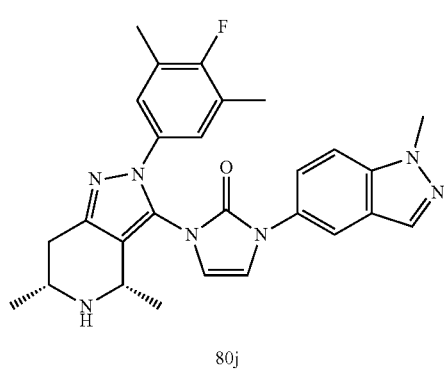
80j
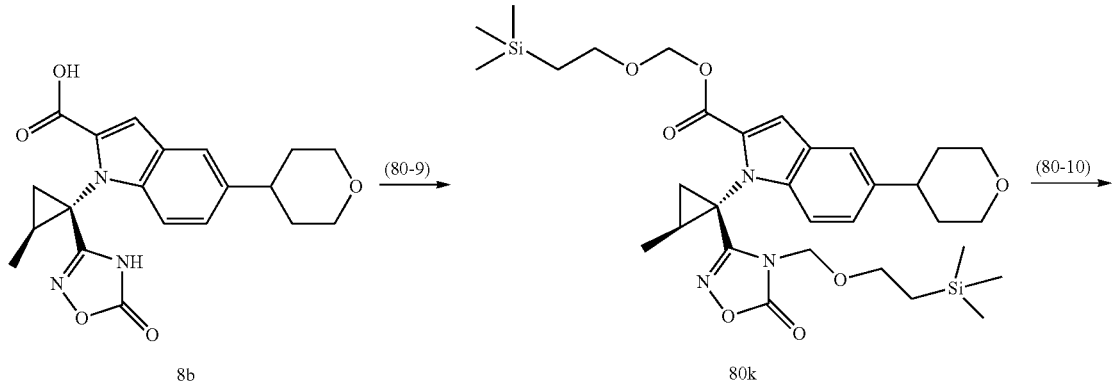
8b → 80k
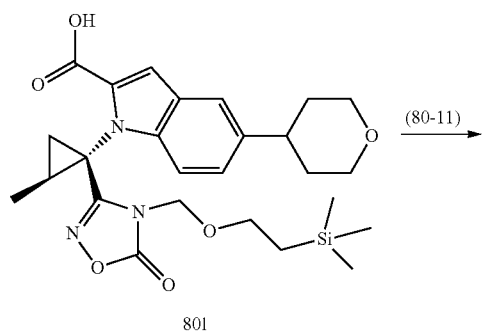
80l

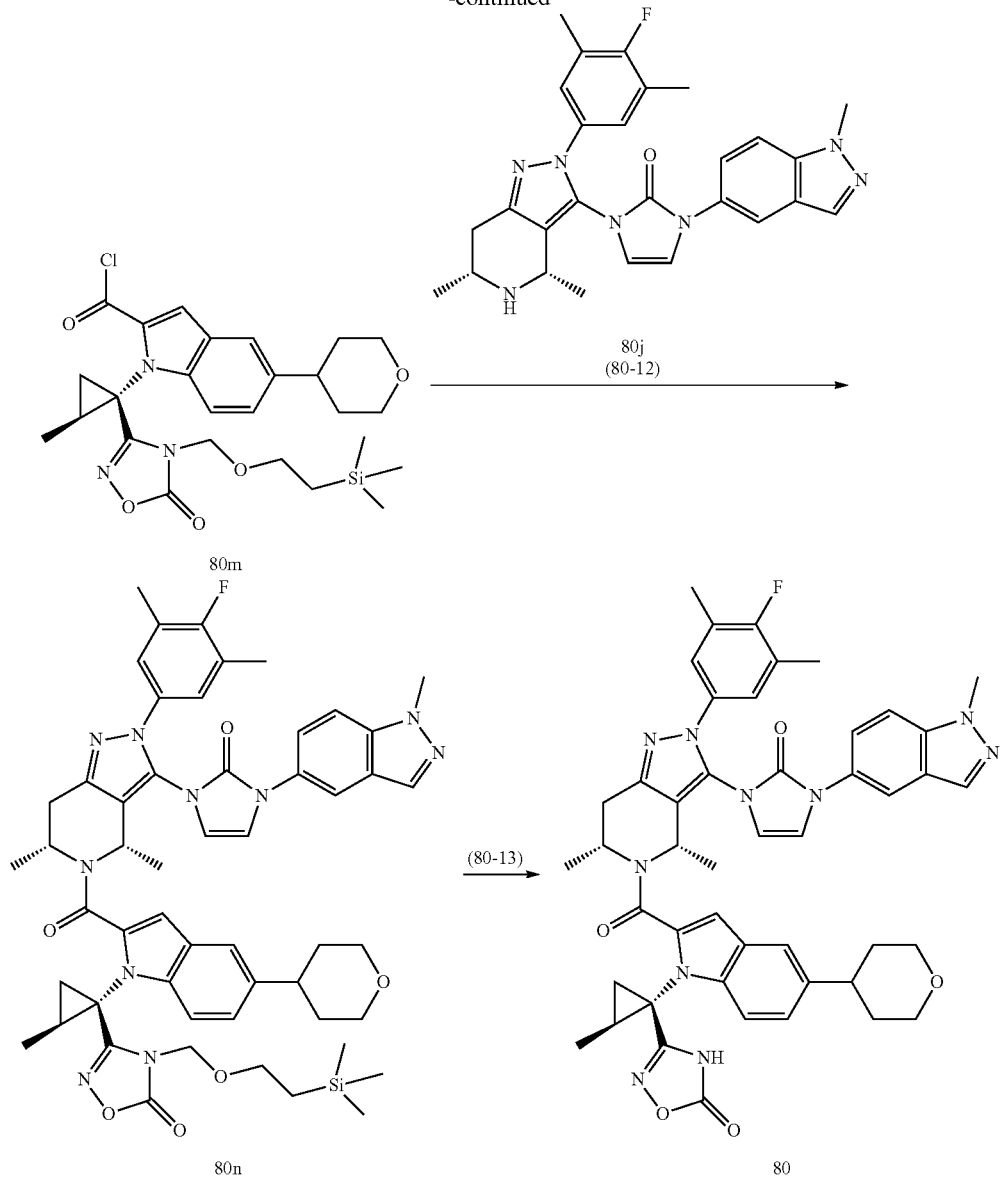

Step 80-1

Ethyl (E)-3-[[(2S)-1-Cyanopropan-2-yl]amino]but-2-enoate (Compound 80c)

To an acetonitrile (50 mL) solution of (3S)-3-aminobutanenitrile (Compound 80b, 7.0 g, 83.2 mmol) and iodine (2.12 g, 8.35 mmol) was added ethyl 3-oxobutanoate (Compound 80a, 13 g, 99.9 mmol), and the mixture was stirred at room temperature for 4 h. The reaction solution was concentrated under reduced pressure and the solvent was removed by evaporation, and then the residue was purified by silica gel column chromatography (petroleum ether/ethyl acetate=1:0 to 3:2) to obtain the titled Compound 80c (9.5 g, yield 58%) as a yellow oil-like material.

LC/MS mass spectrometry: m/z 197 ([M+H]$^+$).

LC/MS retention time: 0.86 min. (Analysis Condition: SMD-FA10-1).

Step 80-2

Ethyl 3-[[(2S)-1-Cyanopropan-2-yl]amino]butanoate (Compound 80d)

To a dichloromethane (200 mL) solution of Compound 80c (10 g, 51.0 mmol) obtained in Step 80-1 and sodium triacetoxyborohydride (43.3 g, 204 mmol) was added acetic acid (3 mL), and the mixture was stirred at room temperature for 16 h. Water and acetic acid were added to the reaction solution, and the pH was adjusted to 5, and then the water layer was subjected to extraction using ethyl acetate. The organic layer was washed with brine and dried using sodium sulfate. After filtration, the filtrate was concentrated under reduced pressure, and the residue was purified by silica gel column chromatography (petroleum ether/ethyl acetate=1:0 to 1:4) to obtain the titled Compound 80d (5.5 g, yield 54%) as a yellow oil-like material.

LC/MS retention time: 0.83 min. (Analysis Condition: SMD-FA10-4).

Step 80-3

(6S)-1-Formyl-4-hydroxy-2,6-dimethyl-3,6-dihydro-2H-pyridine-5-carbonitrile (Compound 80e)

A toluene (5 mL) solution of Compound 80d (1.0 g, 5.04 mmol) obtained in Step 80-2 was added dropwise slowly at 80° C. to a toluene (10 mL) solution of potassium tert-butoxide (680 mg, 6.06 mmol). After the solution was stirred at 80° C. for 1 h., the solution was cooled to room temperature to obtain a toluene solution of (6S)-4-hydroxy-2,6-dimethyl-1,2,3,6-tetrahydropyridine-5-carbonitrile.

A toluene (5 mL) solution of acetic anhydride (12.1 g, 118 mmol) was added dropwise slowly into formic acid (7.26 g) at 0° C. and stirred at 0° C. for 30 min., and then the toluene solution of (6S)-4-hydroxy-2,6-dimethyl-1,2,3,6-tetrahydropyridine-5-carbonitrile that had been prepared was added dropwise slowly. After the reaction solution was stirred at 110° C. for 16 h., it was cooled to room temperature and concentrated under reduced pressure to remove the solvent by evaporation, and a mixture (1.3 g) containing the titled Compound 80e was obtained as an oil-like material.

Step 80-4

(4S)-3-Amino-2-(4-fluoro-3,5-dimethylphenyl)-4,6-dimethyl-6,7-dihydro-4H-pyrazolo[4,3-c]pyridine-5-carbaldehyde (Compound 80f)

The ethanol (30 mL) solution of Compound 80e (1.30 g, 7.21 mmol) obtained in Step 80-3 and (4-fluoro-3,5-dimethylphenyl)hydrazine hydrochloride (Compound 2c, 690 mg, 3.62 mmol) was heated to 75° C. and was stirred for 16 h. The reaction solution was cooled to room temperature and concentrated under reduced pressure. The residue was purified by silica gel column chromatography (dichloromethane/methanol=1:0 to 9:1), and the titled Compound 80f (2 steps from Step 80-3, 800 mg, yield 35%) was obtained as a yellow solid.

LC/MS mass spectrometry: m/z 317 ([M+H]$^+$).
LC/MS retention time: 0.79 min. (Analysis Condition: SMD-FA10-3).

Step 80-5

1-(2,2-Dimethoxyethyl)-3-[(4S)-2-(4-fluoro-3,5-dimethylphenyl)-5-formyl-4,6-dimethyl-6,7-dihydro-4H-pyrazolo[4,3-c]pyridin-3-yl]urea (Compound 80g)

2,2-Dimethoxyethane-1-amine (1.14 g, 10.8 mmol) was added at 0° C. to a DMA (50 mL) solution of N,N'-carbodiimidazole (1.63 g, 10.1 mmol), and the mixture was stirred for 30 min. To the solution was added sequentially potassium tert-butoxide (5.62 g, 50.1 mmol) and Compound 80f (2.64 g, 8.34 mmol) obtained in Step 80-4. After the mixture was stirred at room temperature for 6 h., water was added, and the water layer was subjected to extraction using ethyl acetate. After the organic layer was washed with brine, it was dried with sodium sulfate. After filtration, the filtrate was concentrated under reduced pressure to obtain the titled Compound 80g (2.80 g, yield 75%) as a brown oil-like material.

LC/MS mass spectrometry: m/z 448 ([M+H]$^+$).
LC/MS retention time: 0.84 min. (Analysis Condition: SMD-FA10-2).

Step 80-6

(4S,6R)-2-(4-Fluoro-3,5-dimethylphenyl)-4,6-dimethyl-3-(2-oxo-1H-imidazol-3-yl)-6,7-dihydro-4H-pyrazolo[4,3-c]pyridine-5-carbaldehyde (Compound 80h)

A DMF (30 mL) solution of Compound 80g (2.50 g, 5.59 mmol) obtained in Step 80-5 and 4-methylbenzenesulfonic acid (1.06 g, 6.16 mmol) was heated to 80° C. and stirred for 2 h. After the solution was cooled to room temperature, water was added and the water layer was subjected to extraction using ethyl acetate. The organic layer was washed with brine, and dried with sodium sulfate. After filtration, the filtrate was concentrated under reduced pressure. The obtained residue was purified by silica gel column chromatography (petroleum ether/ethyl acetate=1:0 to 3:1), to obtain the diastereomer mixture (480 mg) containing the titled compound (Compound 80h) as a white solid.

LC/MS mass spectrometry: m/z 384 ([M+H]$^+$).
LC/MS retention time: 1.64 min. (Analysis Condition: SMD-TFA05-6).

The diasteromer mixture (480 mg, 5.59 mmol) containing the titled compound (Compound 80h: (4S,6R)-2-(4-fluoro-3,5-dimethylphenyl)-4,6-dimethyl-3-(2-oxo-1H-imidazol-3-yl)-6,7-dihydro-4H-pyrazolo[4,3-c]pyridine-5-carbaldehyde) was separated to stereoisomers by SFC to obtain Entity A (155 mg, yield 7.0%) which is the titled Compound 80h and Entity B (270 mg, yield 12%).

SFC Separation Condition
Column: CHIRALPAK AD-H, 50×500 mm, 3 m (Daicel)
Solvent: supercritical carbon dioxide/ethanol=70:30 (homogenous system)
Flow rate: 150 mL/min., 35° C.
Detected wavelength: 254 nm
Entity A (Compound 80h)
SFC retention time: 4.07 min.
LC/MS mass spectrometry: m/z 384 ([M+H]$^+$).
LC/MS retention time: 2.15 min. (Analysis Condition: SMD-FA1060-1).
$^1$H-NMR (300 MHz, DMSO-D$_6$) δ: 10.35 (1H, s), 8.24 (1H, s), 7.11 (2H, d, J=6.3 Hz), 6.60-6.58 (2H, m), 5.21-5.14 (1H, m), 4.46-4.21 (1H, m), 2.96-2.89 (1H, m), 2.74-2.68 (1H, m), 2.20 (6H, s), 1.27-1.13 (6H, m).

Note that the Compound 80h was determined to be the R-isomer from the result obtained by 2D-NOESY that the steric configuration thereof is a cis configuration.

Entity B
SFC retention time: 5.60 min.
LC/MS mass spectrometry: m/z 384 ([M+H]$^+$).
LC/MS retention time: 2.16 min. (Analysis Condition: SMD-FA1060-1).
$^1$H-NMR (300 MHz, DMSO-D$_6$) δ: 10.35 (1H, s), 8.31 (1H, s), 7.08 (2H, d, J=6.3 Hz), 6.61-6.54 (2H, m), 5.39 (1H, q, J=6.9 Hz), 3.89-3.84 (1H, m), 2.90 (1H, dd, J=3.3, 15.6 Hz), 2.59-2.51 (1H, m), 2.20 (6H, d, J=2.1 Hz), 1.55 (3H, d, J=6.6 Hz), 1.18 (3H, d, J=6.6 Hz).

Step 80-7

3-[(4S,6R)-2-(4-Fluoro-3,5-dimethylphenyl)-4,6-dimethyl-4,5,6,7-tetrahydropyrazolo[4,3-c]pyridin-3-yl]-1H-imidazol-2-one (Compound 80i)

5M Sodium hydroxide solution (0.261 mL) was added to an ethanol (1.0 mL) solution of Compound 80h (100 mg, 0.261 mmol) obtained in Step 80-6, and the mixture was stirred at 80° C. for 10 h. After the mixture was cooled to room temperature and stirred for 60 h., saturated ammonium chloride aqueous solution was added and the mixture was subjected to extraction using ethyl acetate to synthesize the titled Compound 80i (79%, 73 mg) as a white solid.

LC/MS mass spectrometry: m/z 356 ([M+H]$^+$).
LC/MS retention time: 0.44 min. (Analysis Condition: SQD-FA05-2).

Step 80-8

1-[(4S,6R)-2-(4-Fluoro-3,5-dimethylphenyl)-4,6-dimethyl-4,5,6,7-tetrahydropyrazolo[4,3-c]pyridin-3-yl]-3-(1-methylindazol-5-yl)imidazol-2-one (Compound 80j)

Copper iodide (I) (4.02 mg, 0.021 mmol) was added at a room temperature to a N-methylpiperazine (0.188 mL) suspension of Compound 80i (15 mg, 0.042 mmol) obtained in Step 80-7,5-bromo-1-methylindazole (Compound 1q, 10.7 mg, 0.051 mmol), (1S,2S)-1-N,2-N-dimethylcyclohexane-1,2-diamine (6.00 mg, 0.042 mmol), and potassium carbonate (17.5 mg, 0.127 mmol), and the mixture was stirred under a nitrogen atmosphere at 130° C. for 90 min. The reaction mixture was purified by reversed-phase silica gel chromatography (acetonitrile/water, 0.1% formic acid) and concentrated under a reduced pressure. A saturated sodium acid carbonate aqueous solution was added to the residue, and extraction was performed using ethyl acetate, and then the organic layer was concentrated under reduced pressure to obtain the titled Compound 80j (17.4 mg, yield 85%).

LC/MS mass spectrometry: m/z 486 ([M+H]$^+$).
LC/MS retention time: 0.51 min. (Analysis Condition: SQD-FA05-2).

Step 80-9

2-Trimethylsilylethoxymethyl 5-(oxan-4-yl)-1-[(1S,2S)-2-[5-oxo-4-(2-trimethylsilylethoxymethyl)-1,2,4-oxadiazol-3-yl]-2-methylcyclopropyl]indole-2-carboxylate (Compound 80k)

To a DMF (2.6 mL) solution of Compound 8b (100 mg, 0.261 mmol) obtained in Step 8-1 was added 55 wt % sodium hydride (34.1 mg, 0.782 mmol) and 2-(trimethylsilyl)ethoxymethylchloride (0.116 mL, 0.652 mmol), and the mixture was stirred under room temperature for 1 h. A saturated ammonium chloride solution was added, and extraction was performed using ethyl acetate. Then, the residue obtained after concentration was purified by normal phase column chromatography (ethyl acetate/hexane) to obtain the titled Compound 80k (147 mg, yield 88%) as a yellow gum-like material.

LC/MS retention time: 1.21 min. (Analysis Condition: SQD-FA05-2).

Step 80-10

5-(Oxan-4-yl)-1-[(1S,2S)-1-[5-oxo-4-(2-trimethylsilylethoxymethyl)-1,2,4-oxadiazol-3-yl]-2-methylcyclopropyl]indole-2-carboxylic acid (80l)

To a dichloromethane (2.3 mL) solution of Compound 80k (147 mg, 0.228 mmol) obtained in Step 80-9 was added a magnesium bromide/diethyl ether complex (295 mg, 1.14 mmol), and the mixture was stirred at 0° C. for 6.5 h. The mixture was warmed to room temperature and stirred for 30 min., and then a saturated ammonium chloride aqueous solution was added. Then, extraction was performed using ethyl acetate, and the resulting product was concentrated, and then the residue was diluted with DMSO and water and purified by reversed-phase chromatography (acetonitrile/water, 0.1% formic acid) to synthesize the titled Compound 80l (60 mg, yield 51%).

LC/MS mass spectrometry: m/z 512 ([M−H]$^−$).
LC/MS retention time: 1.03 min. (Analysis Condition: SQD-FA05-2).

Step 80-11

5-(Oxan-4-yl)-1-[(1S,2S)-2-[5-oxo-4-(2-trimethylsilylethoxymethyl)-1,2,4-oxadiazol-3-yl]-2-methylcyclopropyl]indole-2-carbonylchloride (Compound 80m)

To an acetonitrile (0.36 mL) solution of Compound 80l (18 mg, 0.036 mmol) obtained in Step 80-10 was added 1-chloro-N,N,2-trimethylprop-1-en-1-amine (0.0057 mg, 0.043 mmol), and the mixture was stirred at room temperature for 2 h., and then it was concentrated to obtain a crude product of the titled Compound 80m. This compound was directly put to use in the next step.

Step 80-12

3-[(1S,2S)-2-[2-[(4S,6R)-2-(4-Fluoro-3,5-dimethylphenyl)-4,6-dimethyl-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4-(2-trimethylsilylethoxymethyl)-1,2,4-oxadiazol-5-one (Compound 80n)

Compound 80m obtained in Step 80-11 was dissolved in THF (0.717 mL), and Compound 80j (19.1 mg, 0.036 mmol) obtained in Step 80-8 and N,N-diisopropylethylamine (0.0188 mL, 0.108 mmol) were added to the solution, then the mixture was stirred at room temperature for 22 h., and then methanol and formic acid were added. The mixture was concentrated, and the residue was diluted with DMSO and water and purified by reversed-phase column chromatography (acetonitrile/water, 0.1% formic acid) to synthesize the titled Compound 80n (32 mg, yield 91%).

LC/MS mass spectrometry: m/z 982 ([M+H]$^+$).
LC/MS retention time: 1.12 min. (Analysis Condition: SQD-FA50-1).

Step 80-13

3-[(1S,2S)-1-[2-[(4S,6R)-2-(4-Fluoro-3,5-dimethylphenyl)-4,6-dimethyl-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one (Compound 80)

To a THF (0.326 mL) solution of Compound 80n (32 mg, 0.033 mmol) obtained in Step 80-12 was added acetic acid (0.0019 mL, 0.033 mmol) and a THF solution (0.065 mL, 0.065 mmol) of 1M tetrabutylammonium fluoride, and the mixture was stirred at 80° C. for 66 h. Acetic acid (0.0019 mL, 0.033 mmol) and a THF solution (0.065 mL, 0.065 mmol) of 1M tetrabutylammonium fluoride were added, and the mixture was stirred for 23.5 h. Further, a THF solution (0.065 mL, 0.065 mmol) of 1M tetrabutylammonium fluoride was added, then the mixture was stirred for 7 h., and then formic acid was added. After concentration, the mixture was diluted with DMSO and water and purified by reversed-phase column chromatography (acetonitrile/water, 0.1% formic acid) to synthesize the titled Compound 80 (18 mg, yield 65%).

LC/MS mass spectrometry: m/z 851 ([M+H]$^+$).

LC/MS retention time: 1.42 min. (Analysis Condition: SMD-TFA05-1).

Example Compounds 101 to 159 shown in Table 2-7 below was obtained similarly to Examples 1 to 80.

TABLE 2-7

The Obtained Example Compounds 101 to 159

| Example No. | Structure | Compound | Analysis Condition | LC/MS retention time (min.) | LC/MS mass spectrometry (m/z) |
|---|---|---|---|---|---|
| 101 | 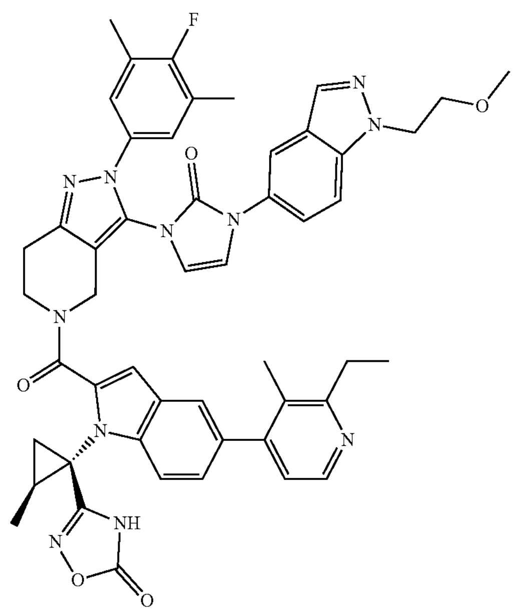 | 3-[(1S,2S)-1-[5-(2-ethyl-3-methylpyridin-4-yl)-2-[2-(4-fluoro-3,5-dimethylphenyl)-3-[1-(2-methoxyethyl)indazol-5-yl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.16 | 902 ([M+H]$^+$) |
| 102 | 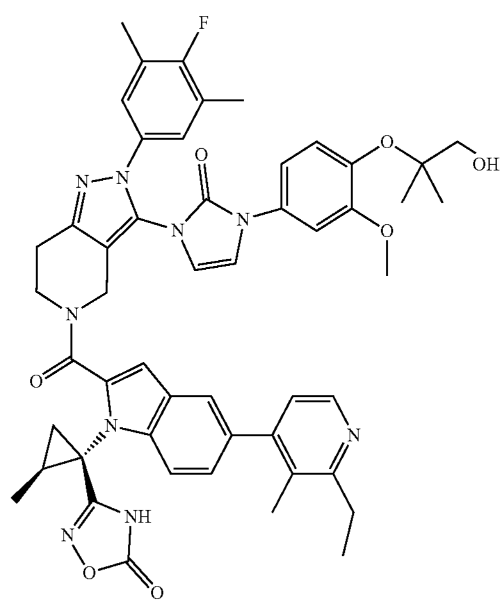 [SMILES: CCc1nccc(-c2ccc3c(c2)cc(C(=O)N2CCc4nn(-c5cc(C)c(F)c(C)c5)c(-n5ccn(-c6ccc(OC(C)(C)CO)c(OC)c6)c5=O)c4C2)n3[C@@]2(c3noc(=O)[nH]3)C[C@@H]2C)c1C] | 3-[(1S,2S)-1-[5-(2-ethyl-3-methylpyridin-4-yl)-2-[2-(4-fluoro-3,5-dimethylphenyl)-3-[4-(1-hydroxy-2-methylpropan-2-yl)oxy-3-methoxyphenyl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.17 | 922 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 103 | 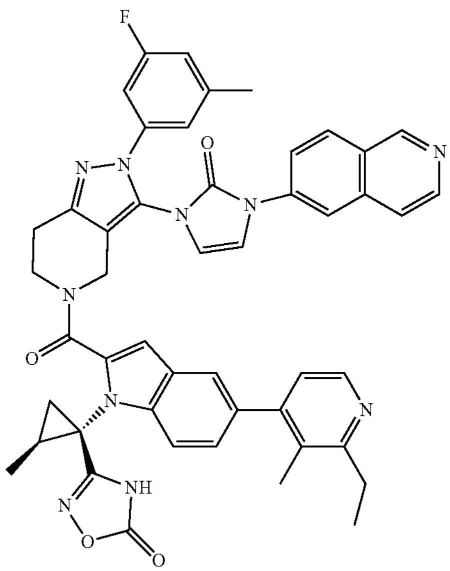 [SMILES: CCc1nccc(-c2ccc3c(c2)cc(C(=O)N2CCc4nn(-c5cc(C)cc(F)c5)c(-n5ccn(-c6ccc7cnccc7c6)c5=O)c4C2)n3[C@@]2(c3noc(=O)[nH]3)C[C@@H]2C)c1C] | 3-[(1S,2S)-1-[5-(2-ethyl-3-methylpyridin-4-yl)-2-[2-(3-fluoro-5-methylphenyl)-3-(3-isoquinolin-6-yl-2-oxoimidazol-1-yl)-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 0.96 | 841 ([M+H]$^+$) |
| 104 | 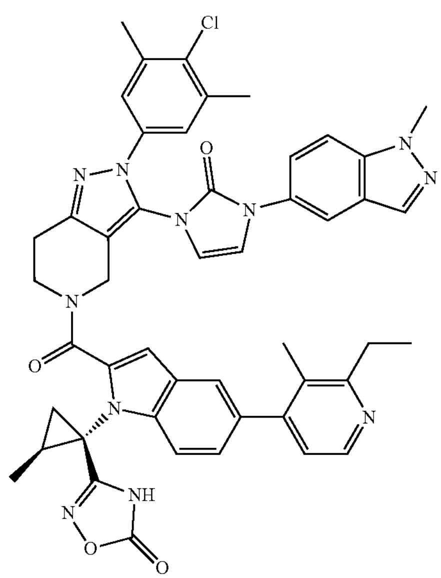 [SMILES: CCc1nccc(-c2ccc3c(c2)cc(C(=O)N2CCc4nn(-c5cc(C)c(Cl)c(C)c5)c(-n5ccn(-c6ccc7c(cnn7C)c6)c5=O)c4C2)n3[C@@]2(c3noc(=O)[nH]3)C[C@@H]2C)c1C] | 3-[(1S,2S)-1-[2-[2-(4-chloro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.20 | 875 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 105 | 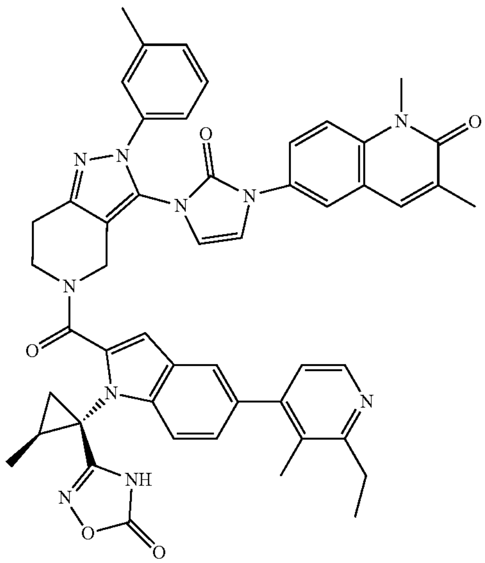 [SMILES: CCc1nccc(-c2ccc3c(c2)cc(C(=O)N2CCc4nn(-c5cccc(C)c5)c(-n5ccn(-c6ccc7c(c6)cc(C)c(=O)n7C)c5=O)c4C2)n3[C@@]2(c3noc(=O)[nH]3)C[C@@H]2C)c1C] | 3-[(1S,2S)-1-[2-[3-[3-(1,3-dimethyl-2-oxoquinolin-6-yl)-2-oxoimidazol-1-yl]-2-(3-methylphenyl)-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.16 | 867 ([M+H]$^+$) |
| 106 | 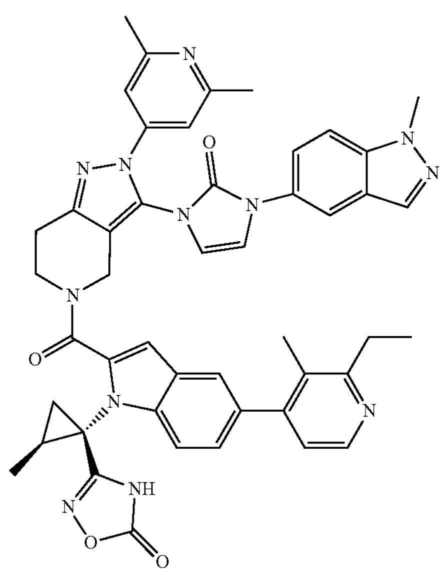 [SMILES: CCc1nccc(-c2ccc3c(c2)cc(C(=O)N2CCc4nn(-c5cc(C)nc(C)c5)c(-n5ccn(-c6ccc7c(cnn7C)c6)c5=O)c4C2)n3[C@@]2(c3noc(=O)[nH]3)C[C@@H]2C)c1C] | 3-[(1S,2S)-1-[2-[2-(2,6-dimethylpyridin-4-yl)-3-[3-(1-methylindazol-5-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 0.86 | 841 ([M+H]$^+$) |

TABLE 2-7-continued

The Obtained Example Compounds 101 to 159

| Example No. | Structure | Compound | LC/MS Analysis Condition | LC/MS retention time (min.) | LC/MS mass spectrometry (m/z) |
|---|---|---|---|---|---|
| 107 | 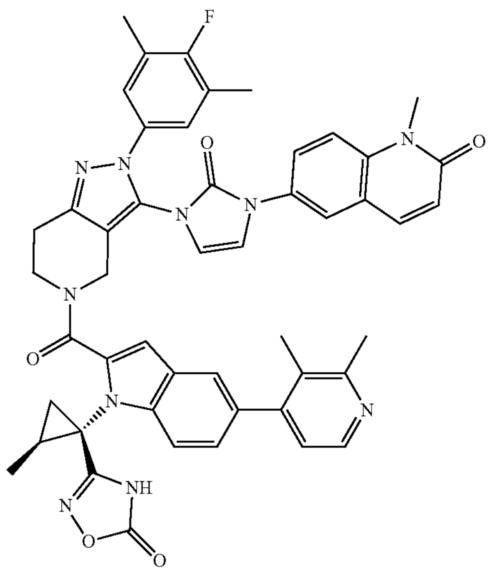 [SMILES: Cc1cc(-n2nc3c(c2-n2ccn(-c4ccc5c(ccc(=O)n5C)c4)c2=O)CN(C(=O)c2cc4cc(-c5ccnc(C)c5C)ccc4n2[C@@]2(c4noc(=O)[nH]4)C[C@@H]2C)CC3)cc(C)c1F] | 3-[(1S,2S)-1-[5-(2,3-dimethylpyridin-4-yl)-2-[2-(4-fluoro-3,5-dimethylphenyl)-3-[3-(1-methyl-2-oxoquinolin-6-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.09 | 871 ([M+H]$^+$) |
| 108 | 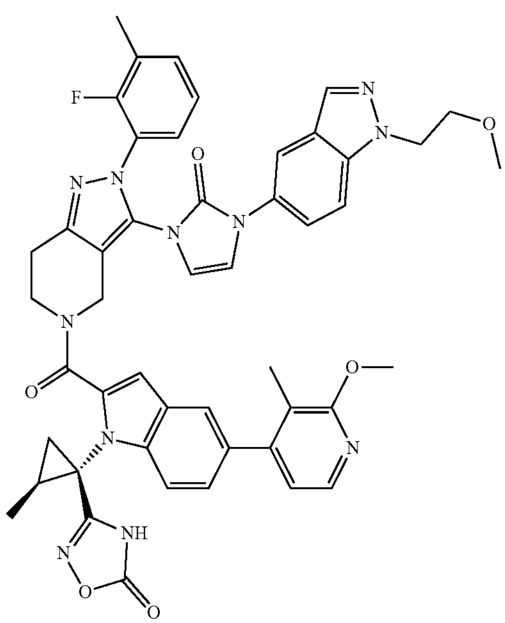 | 3-[(1S,2S)-1-[2-[2-(2-fluoro-3-methylphenyl)-3-[3-[1-(2-methoxyethyl)indazol-5-yl]-2-oxoimidazol-1-yl]-6,7-dihydro-4H-pyrazolo[4,3-c]pyridine-5-carbonyl]-5-(2-methoxy-3-methylpyridin-4-y)indol-1-yl]-2-methylcyclopropyl]-4H-1,2,4-oxadiazol-5-one | SMD-TFA05-3 | 1.38 | 890 ([M+H]$^+$) |

TABLE 2-7-continued

The Obtained Example Compounds 101 to 159

| Example No. | Structure | Compound | LC/MS Analysis Condition | LC/MS retention time (min.) | LC/MS mass spectrometry (m/z) |
|---|---|---|---|---|---|
| 109 | 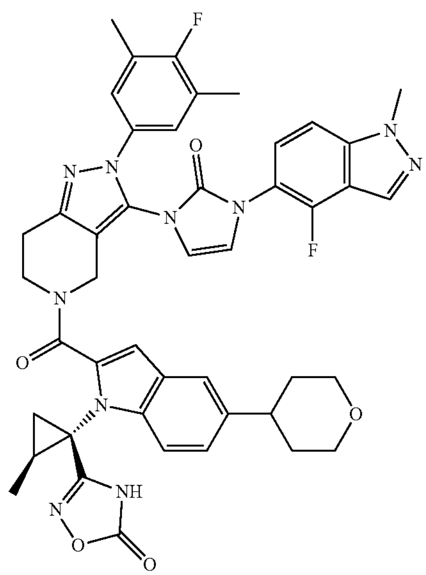 [SMILES: Cc1cc(-n2nc3c(c2-n2ccn(-c4ccc5c(cnn5C)c4F)c2=O)CN(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-[3-(4-fluoro-1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.34 | 841 ([M+H]$^+$) |
| 110 | 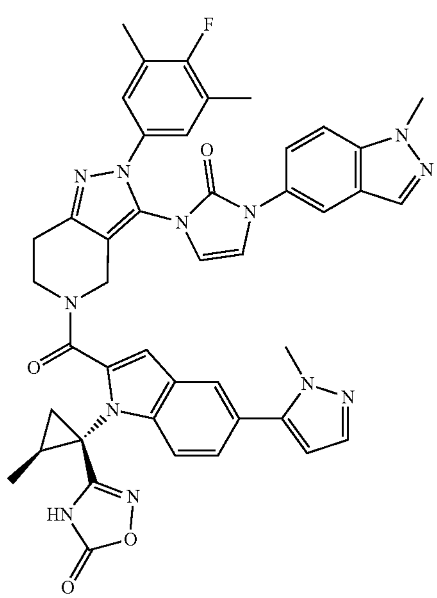 [SMILES: Cc1cc(-n2nc3c(c2-n2ccn(-c4ccc5c(cnn5C)c4)c2=O)CN(C(=O)c2cc4cc(-c5ccnn5C)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-methylpyrazol-3-yl)indol-1-yl]-2-methylcyclopropyl]-4H-1,2,4-oxadiazol-5-one | SMD-TFA05-3 | 1.30 | 820 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 111 | 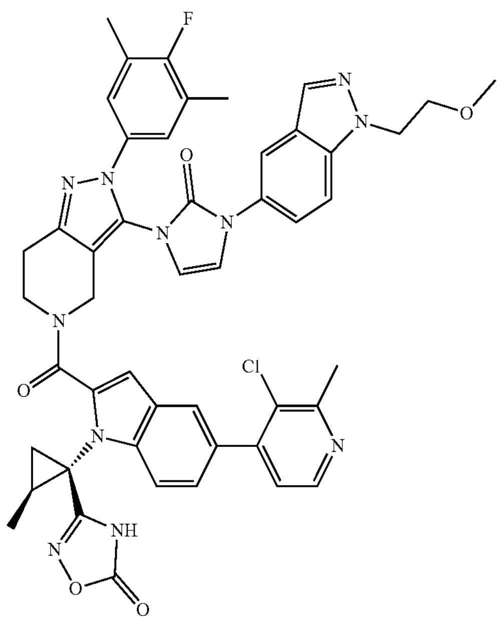 | 3-[(1S,2S)-1-[5-(3-chloro-2-methylpyridin-4-yl)-242-(4-fluoro-3,5-dimethylphenyl)-3-[3-[1-(2-methoxyethyl)indazol-5-yl]-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.24 | 908 ([M+H]$^+$) |
| 112 | 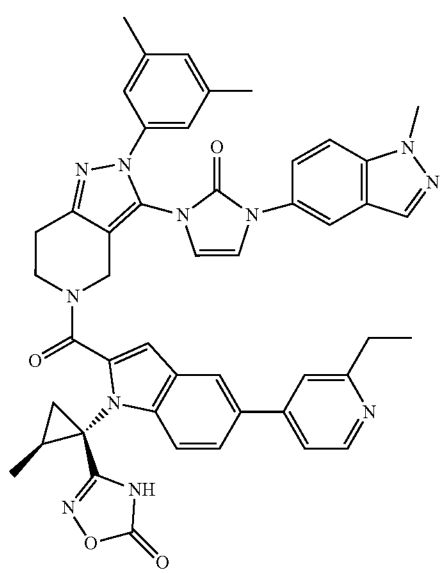 [SMILES: CCc1cc(-c2ccc3c(c2)cc(C(=O)N2CCc4nn(-c5cc(C)cc(C)c5)c(-n5ccn(-c6ccc7c(cnn7C)c6)c5=O)c4C2)n3[C@@]2(c3noc(=O)[nH]3)C[C@@H]2C)ccn1] | 3-[(1S,2S)-1-[2-[2-(3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-ethylpyridin-4-yl)indol-1-yl]-2-methylcyclopropyl]-4H-1,2,4-oxadiazol-5-one | SMD-FA05-3 | 0.95 | 826 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 113 | 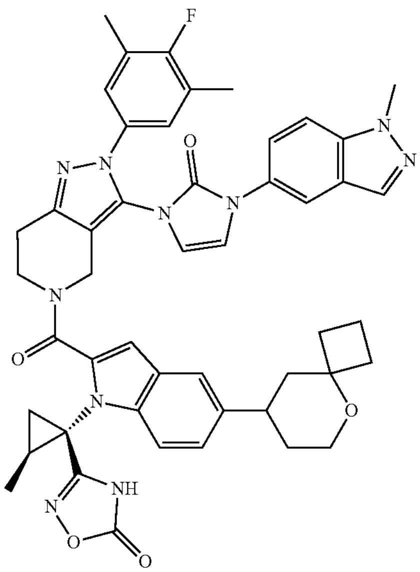 [SMILES: Cc1cc(-n2nc3c(c2-n2ccn(-c4ccc5c(cnn5C)c4)c2=O)CN(C(=O)c2cc4cc(C5CCOC6(CCC6)C5)ccc4n2[C@@]2(c4noc(=O)[nH]4)C[C@@H]2C)CC3)cc(C)c1F] | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(5-oxaspiro[3.5]nonan-8-yl)indol-1-yl]-2-methylcyclopropyl]-4H-1,2,4-oxadiazol-5-one | SMD-TFA05-2 | 1.47 | 863 ([M+H]+) |
| 114 | 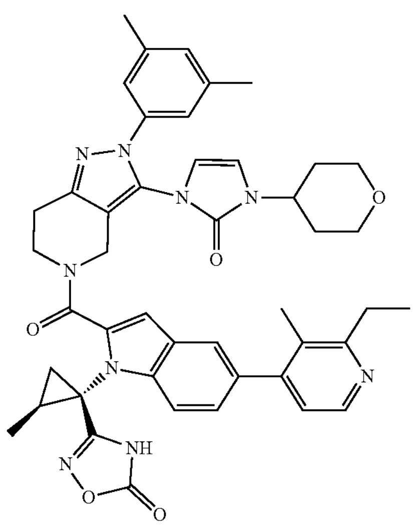 [SMILES: CCc1nccc(-c2ccc3c(c2)cc(C(=O)N2CCc4nn(-c5cc(C)cc(C)c5)c(-n5ccn(C6CCOCC6)c5=O)c4C2)n3[C@@]2(c3noc(=O)[nH]3)C[C@@H]2C)c1C] | 3-[(1S,2S)-1-[2-[2-(3,5-dimethylphenyl)-3-[3-(oxan-4-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.07 | 795 ([M+H]+) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 115 | 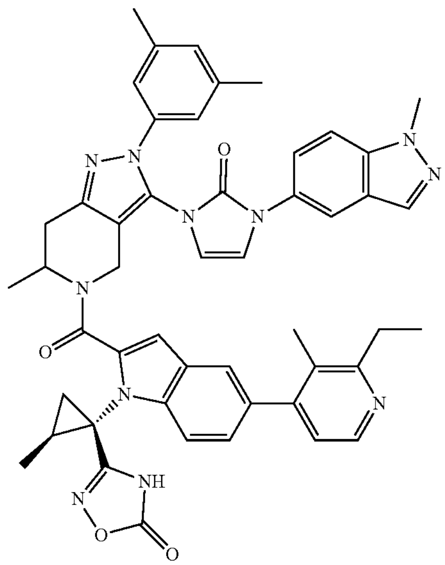 [SMILES: CCc1nccc(-c2ccc3c(c2)cc(C(=O)N2Cc4c(nn(-c5cc(C)cc(C)c5)c4-n4ccn(-c5ccc6c(cnn6C)c5)c4=O)CC2C)n3[C@@]2(c3noc(=O)[nH]3)C[C@@H]2C)c1C] | 3-[(1S,2S)-1-[2-[2-(3,5-dimethylphenyl)-6-methyl-3-[3-(1-methylidndazio-5-yl)-2-oxoimidazol-1-yl]6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.17 | 854 ([M+H]⁺) |
| 116 | 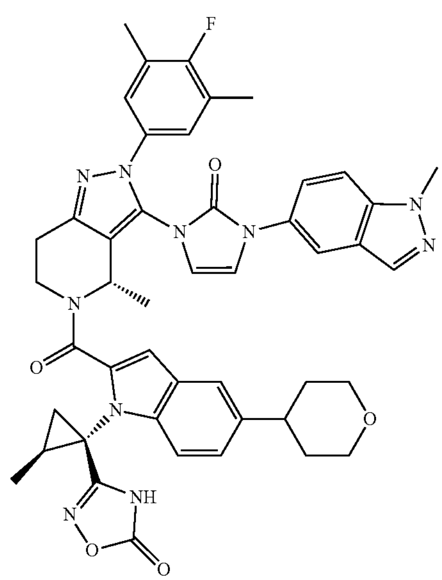 | 3-[(1S,2S)-1-[2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-2 | 1.39 | 837 ([M+H]⁺) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 117 | 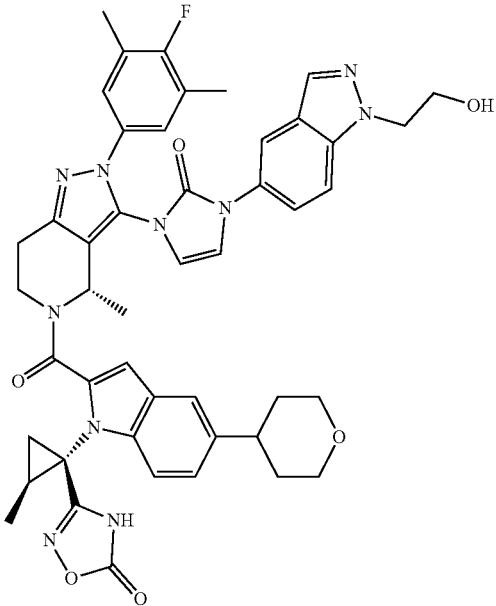 [SMILES: Cc1cc(-n2nc3c(c2-n2ccn(-c4ccc5c(cnn5CCO)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-3-[3-[1-(2-hydroxyethyl)indazol-5-yl]-2-oxoimidazol-1-yl]-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.27 | 867 ([M+H]$^+$) |
| 118 | 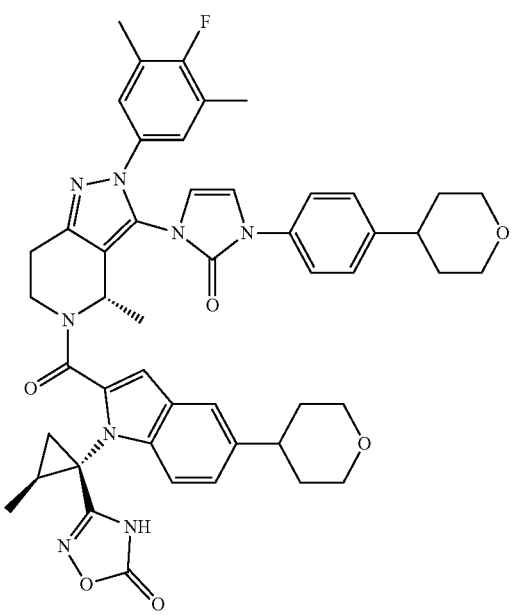 [SMILES: Cc1cc(-n2nc3c(c2-n2ccn(-c4ccc(C5CCOCC5)cc4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-4-methyl-3-[3-[4-(oxan-4-yl)phenyl]-2-oxoimidazol-1-yl]-6,7-dihydro-4H-pyrazolo[4,3-c]pyridine-5-carbonyl]-5-(oxan-4-y)indol-1-yl]-2-methylcyclopropyl]-4H-1,2,4-oxadiazol-5-one | SMD-TFA05-1 | 1.49 | 867 ([M+H]$^+$) |

TABLE 2-7-continued

The Obtained Example Compounds 101 to 159

| Example No. | Structure | Compound | LC/MS Analysis Condition | LC/MS retention time (min.) | LC/MS mass spectrometry (m/z) |
|---|---|---|---|---|---|
| 119 | 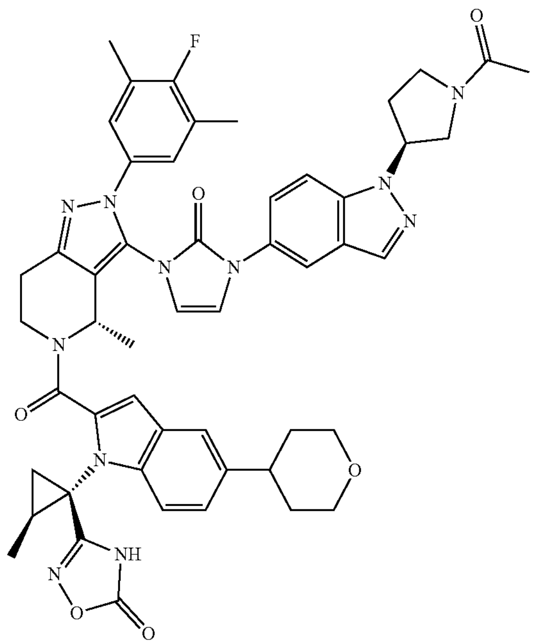 [SMILES: CC(=O)N1CC[C@H](n2ncc3cc(-n4ccn(-c5c6c(nn5-c5cc(C)c(F)c(C)c5)CCN(C(=O)c5cc7cc(C8CCOCC8)ccc7n5[C@@]5(c7noc(=O)[nH]7)C[C@@H]5C)[C@H]6C)c4=O)ccc32)C1] | 3-[(1S,2S)-1-[2-[(4S)-3-3-[1-[(3S)-1-acetylpyrrolidin-3-yl]indazol-5-yl]-2-oxoimidazol-1-yl]-2-(4-fluoro-3,5-dimethylphenyl)-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.29 | 934 ([M+H]⁺) |
| 120 | 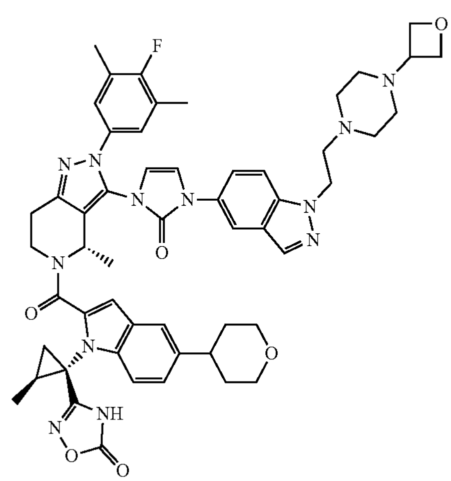 [SMILES: Cc1cc(-n2nc3c(c2-n2ccn(-c4ccc5c(cnn5CCN5CCN(C6COC6)CC5)c4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-4-methyl-3-[3-[1-[2-[4-(oxetan-3-yl)piperazin-1-yl]ethyl]indazol-5-yl]-2-oxoimidazol-1-yl]-6,7-dihydro-4H-pyrazolo[4,3-c]pyridine-5-carbonyl]-5-(oxan-4-y)indol-1-yl]-2-methylcyclopropyl]-4H-1,2,4-oxadiazol-5-one | SMD-TFA05-1 | 1.08 | 992 ([M+H]⁺) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 121 | 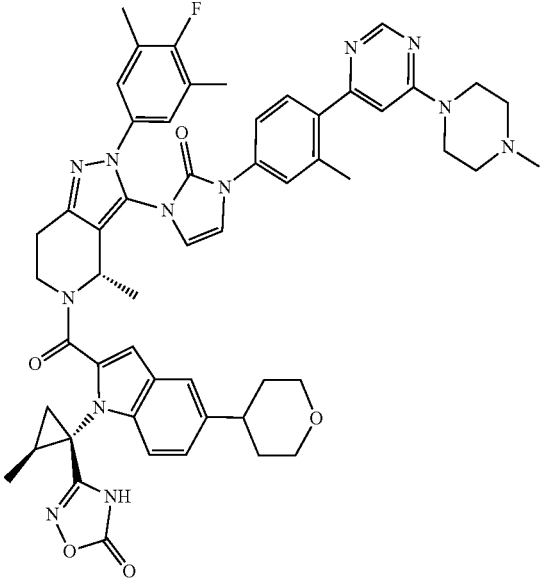 | 3-[(1S,2S)-1-[2-[(4S)-2-(4-fluoro-3,5-dimethylphenyl)-4-methyl-3-[3-[3-methyl-4-[6-(4-methylpiperazin-1-yl)pyrimidin-4-yl]phenyl]-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 0.96 | 973 ([M+H]+) |
| 122 | 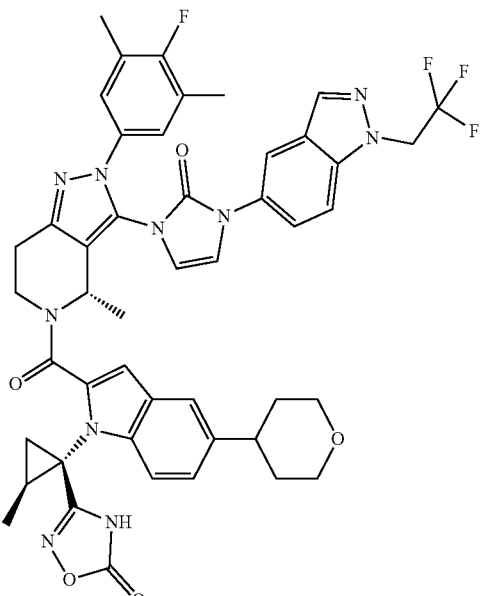 | 3-[(1S,2S)-1-[[2-[(4S)-2-(4-fluoro-3,5-dimethylphenyl)-4-methyl-3-[2-oxo-3-[1-(2,2,2-trifluoroethyl)indazol-5-yl]imidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.45 | 905 ([M+H]+) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 123 | 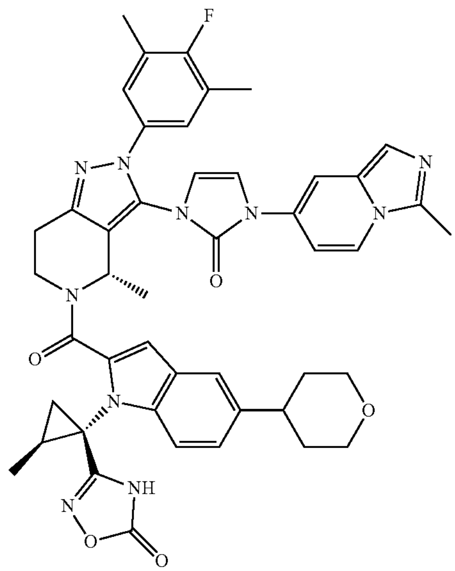 | 3-[(1S,2S)-1-[2-[(4S)-2-(4-fluoro-3,5-dimethylphenyl)-4-methyl-3-[3-(3-methylimidazo[1,5-a]pyridin-7-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.07 | 837 ([M+H]$^+$) |
| 124 | 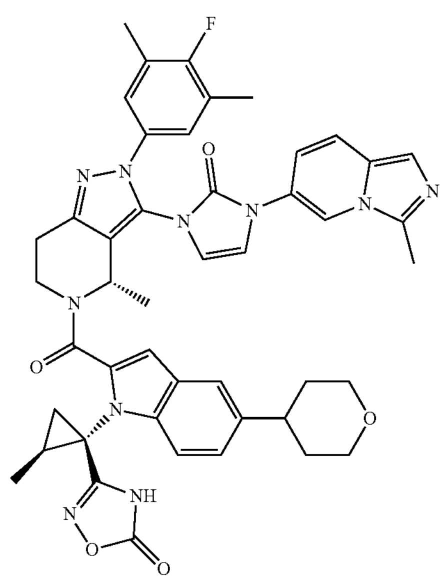 [SMILES: Cc1cc(-n2nc3c(c2-n2ccn(-c4ccc5cnc(C)n5c4)c2=O)[C@H](C)N(C(=O)c2cc4cc(C5CCOCC5)ccc4n2[C@@]2(c4noc(=O)[nH]4)C[C@@H]2C)CC3)cc(C)c1F] | 3-[(1S,2S)-1-[2-[(4S)-2-(4-fluoro-3,5-dimethylphenyl)-4-methyl-3-[3-(3-methylimidazo[1,5-a]pyridin-6-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.07 | 837 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 125 | 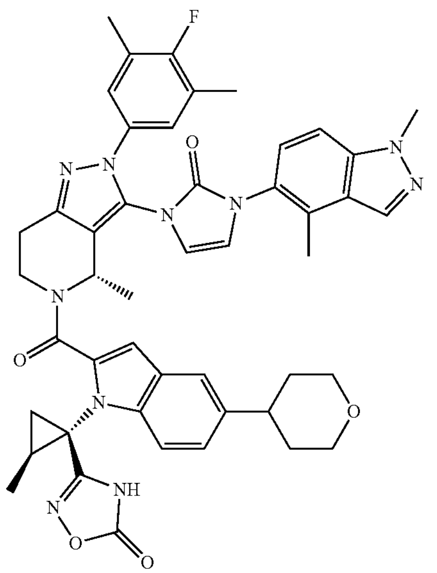 | 3-[(1S,2S)-1-[[2-[(4S)-3-[3-(1,4-dimethylindazol-5-yl)-2-oxoimidazol-1-yl]-1-2-(4-fluoro-3,5-dimethylphenyl)-4-methyl-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.37 | 851 ([M+H]+) |
| 126 | 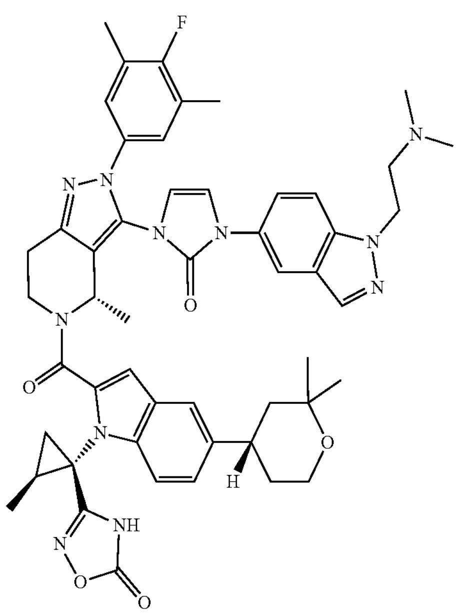 | 3-[(1S,2S)-1-[2-[(4S)-3-[3-[1-[2-(dimethylamino)ethyl]indazol-5-yl]-2-oxoimidazol-1-yl]-2-(4-fluoro-3,5-dimethylphenyl)-4-methyl-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-TFA05-1 | 1.15 | 922 ([M+H]+) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 127 | 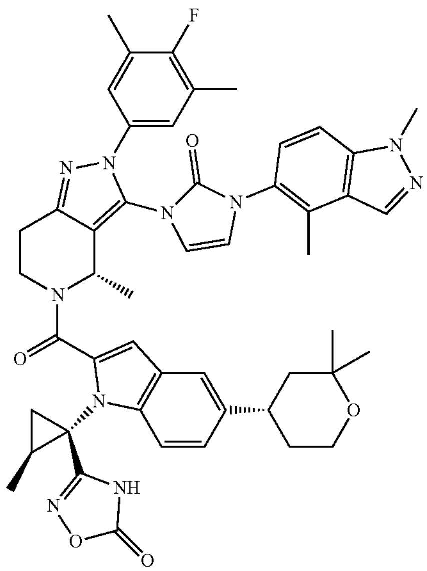 | 3-[(1S,2S)-1-[2-[(4S)-3-[3-(1,4-dimethylindazol-5-yl)-2-oxoimidazol-1-yl]-2-(4-fluoro-3,5-dimethylphenyl)-4-methyl-6,7-dihydro-4H-pyrazolo[4,3-c]pyridine-5-carbonyl]-5-[(4S)-2,2-dimethyloxan-4-yl]indol-1-yl]-2-methylcyclopropyl]-4H-1,2,4-oxadiazol-5-one | SMD-TFA05-1 | 1.44 | 879 ([M+H]$^+$) |
| 128 | 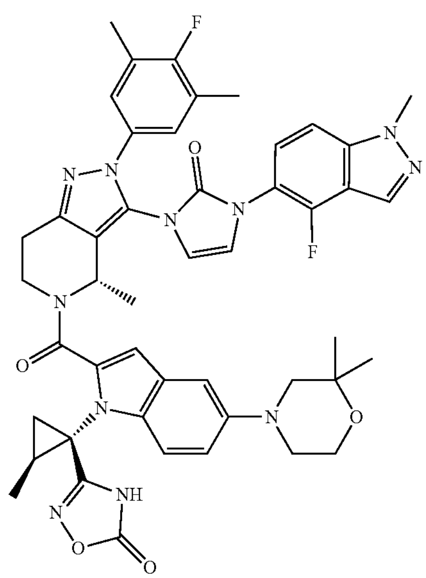 [SMILES: Cc1cc(-n2nc3c(c2-n2ccn(-c4ccc5c(cnn5C)c4F)c2=O)[C@H](C)N(C(=O)c2cc4cc(N5CCOC(C)(C)C5)ccc4n2[C@@]2(c4noc(=O)[nH]4)C[C@@H]2C)CC3)cc(C)c1F] | 3-[(1S,2S)-1-[5-(2,2-dimethylmorpholin-4-yl)-2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-1 | 1.30 | 884 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 129 | 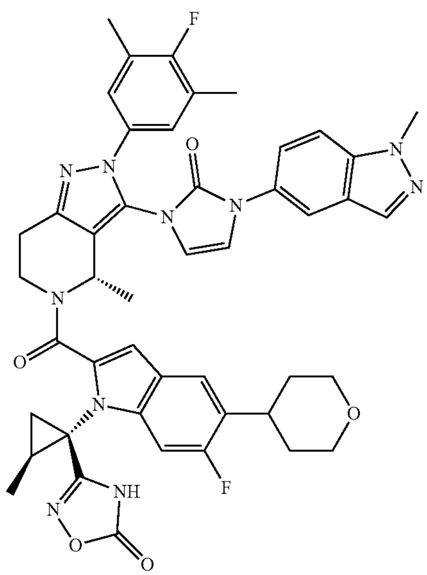 | 3-[(1S,2S)-1-[6-fluoro-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.38 | 855 ([M+H]$^+$) |
| 130 | 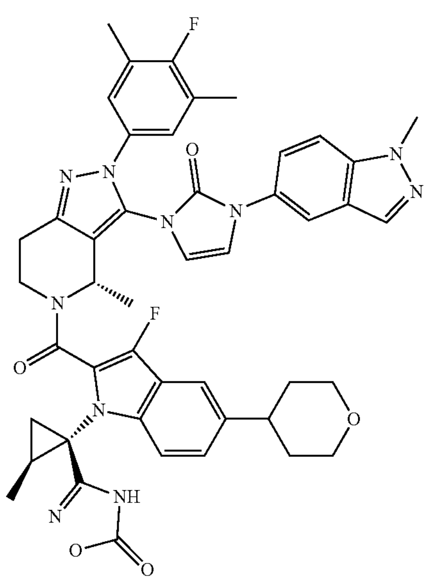 | 3-[(1S,2S)-1-[3-fluoro-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.40 | 855 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 131 | 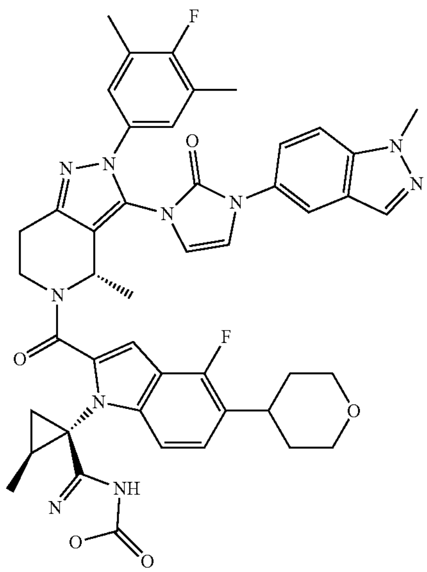 | 3-[(1S,2S)-1-fluoro-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-oxadiazol-5-one | SMD-TFA05-1 | 1.38 | 855 ([M+H]+) |
| 132 | 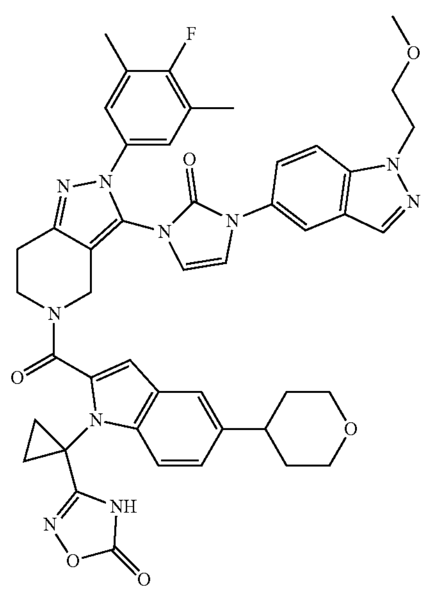 [SMILES: COCCn1ncc2cc(-n3ccn(-c4c5c(nn4-c4cc(C)c(F)c(C)c4)CCN(C(=O)c4cc6cc(C7CCOCC7)ccc6n4C4(c6noc(=O)[nH]6)CC4)C5)c3=O)ccc21] | 3-[1-[2-[2-(4-fluoro-3,5-dimethylphenyl)-3-[3-[1-(2-methoxyethyl)indazol-5-yl]-2-oxoimidazol-1-yl]-6,7-dihydro-4H-pyrazolo[4,3-c]pyridine-5-carbonyl]-5-(oxan-4-yl)indol-1-yl]cyclopropyl]-4H-1,2,4-oxadiazol-5-one | SMD-TFA05-2 | 1.28 | 853 ([M+H]+) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 133 | 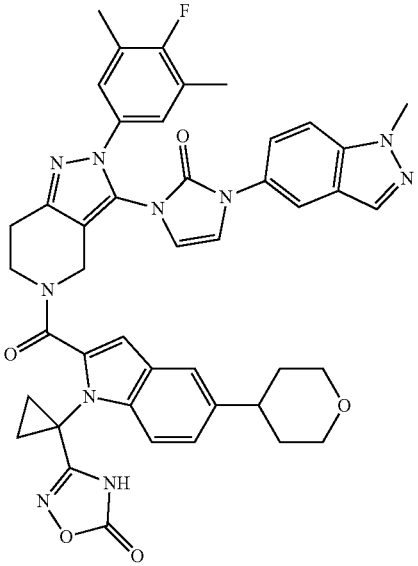 [SMILES: Cc1cc(-n2nc3c(c2-n2ccn(-c4ccc5c(cnn5C)c4)c2=O)CN(C(=O)c2cc4cc(C5CCOCC5)ccc4n2C2(c4noc(=O)[nH]4)CC2)CC3)cc(C)c1F] | 3-[1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]cyclopropyl]-4H-1,2,4-oxadiazol-5-one | SMD-TFA05-2 | 1.26 | 809 ([M+H]+) |
| 134 | 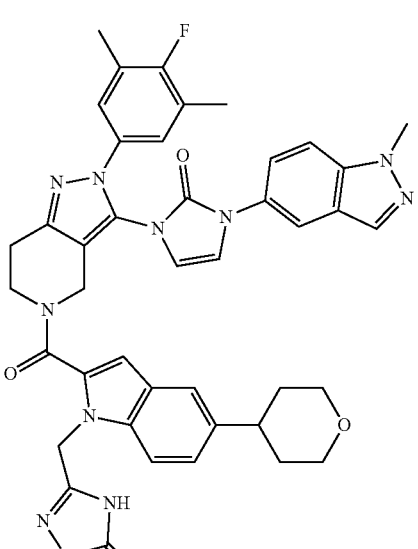 | 3-[[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]methyl]-4H-1,2,4-oxadiazol-5-one | SMD-TFA05-2 | 1.18 | 783 ([M+H]+) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 135 | 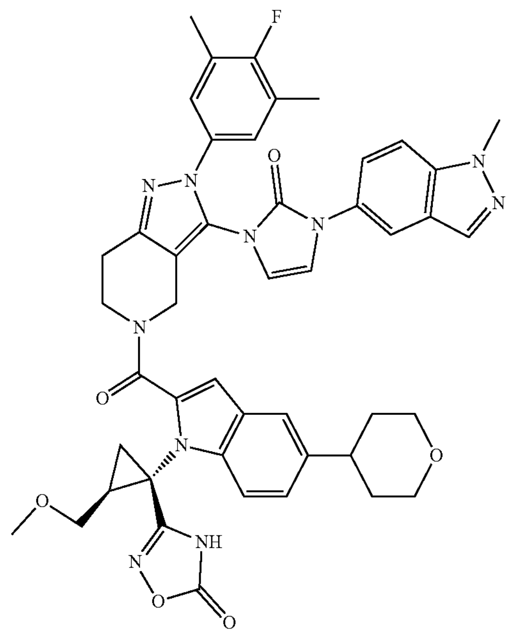 | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-(methoxymethyl)cyclopropyl]-4H-1,2,4-oxadiazol-5-one | SMD-TFA05-2 | 1.30 | 853 ([M+H]$^+$) |
| 136 | 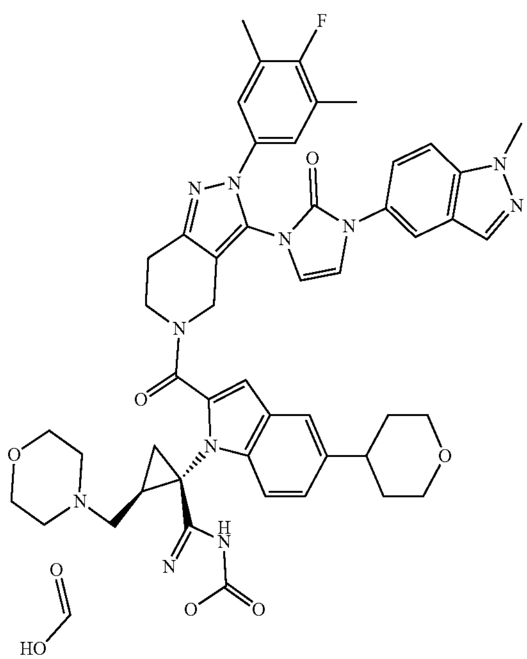 | 3-[(1S,2R)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-(morpholin-4-ylmethyl)cyclopropyl]-4H-1,2,4-oxadiazol-5-one; formic acid | SMD-TFA05-1 | 1.04 | 908 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 137 | 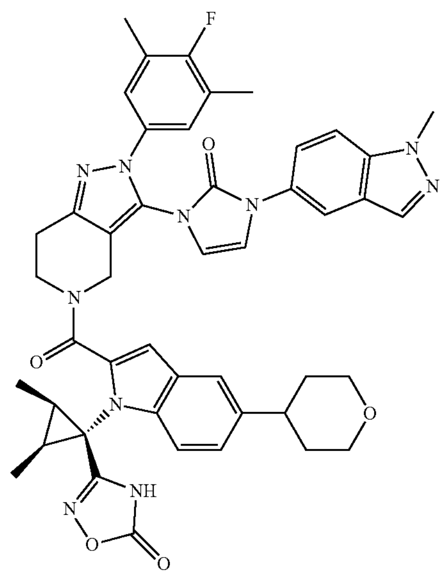 | 3-[(2S,3R)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2,3-dimethylcyclopropyl]-4H-1,2,4-oxadiazol-5-one | SMD-TFA05-2 | 1.39 | 837 ([M+H]+) |
| 138 | 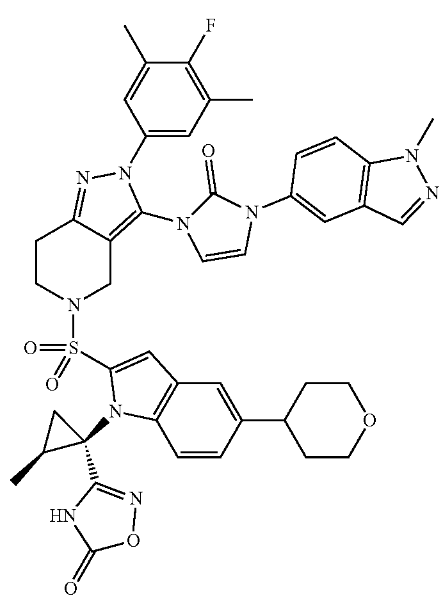 | 3-[(1R,2S)-1-[2-[[2-(4-fluoro-3,5-dimethylphenyl)-3-[3-(1-methylindazol-5-yl)-2-oxoimidazol-1-yl]-6,7-dihydro-4H-pyrazolo[4,3-c]pyridin-5-yl]sulfonyl]-5-(oxan-4-yl)indol-1-yl]-2-methylcyclopropyl]-4H-1,2,4-oxadiazol-5-one | SMD-TFA05-1 | 1.28 | 859 ([M+H]+) |

TABLE 2-7-continued

The Obtained Example Compounds 101 to 159

| Example No. | Structure | Compound | LC/MS Analysis Condition | LC/MS retention time (min.) | LC/MS mass spectrometry (m/z) |
|---|---|---|---|---|---|
| 139 | 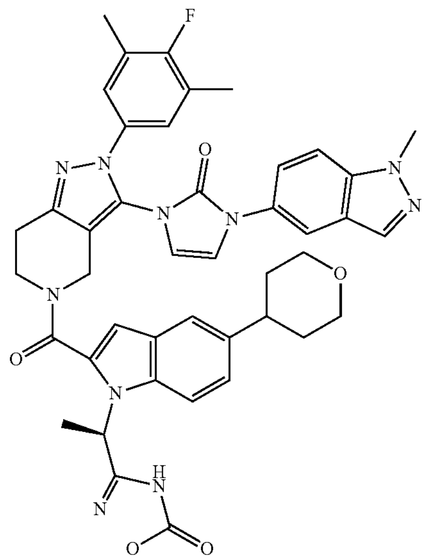 [SMILES: Cc1cc(-n2nc3c(c2-n2ccn(-c4ccc5c(cnn5C)c4)c2=O)CN(C(=O)c2cc4cc(C5CCOCC5)ccc4n2[C@H](C)C(=N)NC(=O)O)CC3)cc(C)c1F] | 3-[(1R)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]ethyl]-4H-1,2,4-oxadiazol-5-one | SMD-TFA05-2 | 1.28 | 797 ([M+H]⁺) |
| 140 | 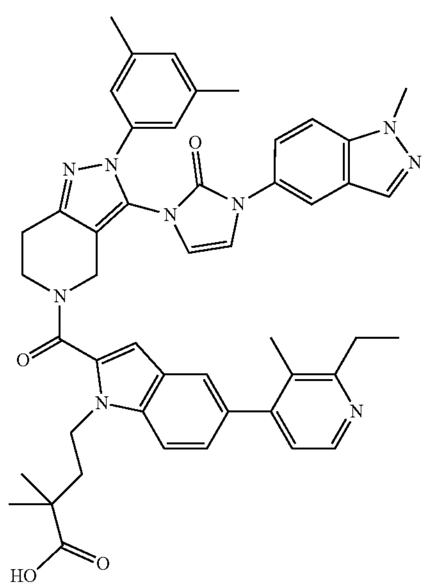 [SMILES: CCc1nccc(-c2ccc3c(c2)cc(C(=O)N2CCc4nn(-c5cc(C)cc(C)c5)c(-n5ccn(-c6ccc7c(cnn7C)c6)c5=O)c4C2)n3CCC(C)(C)C(=O)O)c1C] | 4-[2-[2-(3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]-2,2-dimethylbutanoic acid | SMD-FA05-3 | 0.90 | 816 ([M+H]⁺) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 141 | 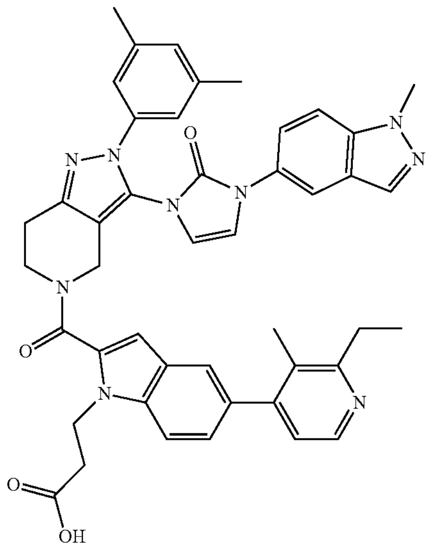 [SMILES: CCc1nccc(-c2ccc3c(c2)cc(C(=O)N2CCc4nn(-c5cc(C)cc(C)c5)c(-n5ccn(-c6ccc7c(cnn7C)c6)c5=O)c4C2)n3CCC(=O)O)c1C] | 3-[2-[2-(3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]propanoic acid | SMD-TFA05-3 | 1.02 | 774 ([M+H]$^+$) |
| 142 | 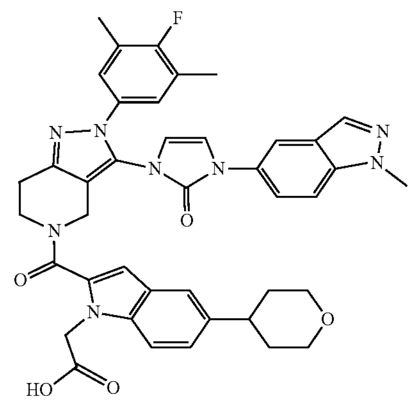 [SMILES: Cc1cc(-n2nc3c(c2-n2ccn(-c4ccc5c(cnn5C)c4)c2=O)CN(C(=O)c2cc4cc(C5CCOCC5)ccc4n2CC(=O)O)CC3)cc(C)c1F] | 2-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-y)indol-1-yl]acetic acid | SMD-TFA05-2 | 1.21 | 743 ([M+H]$^+$) |
| 143 | 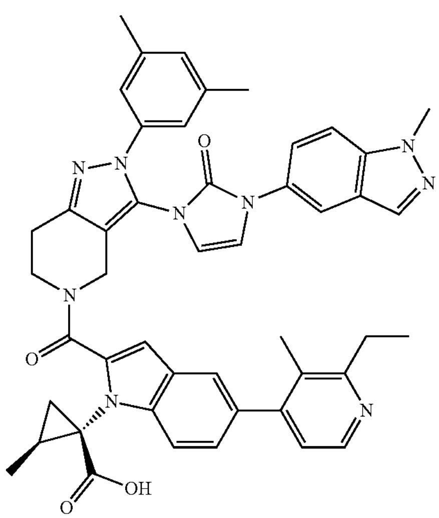 | (1S,2S)-1-[2-[2-(3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(2-ethyl-3-methylpyridin-4-yl)indol-1-yl]-2-methylcyclopropane-1-carboxylic acid | SMD-TFA05-3 | 1.08 | 800 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 144 | 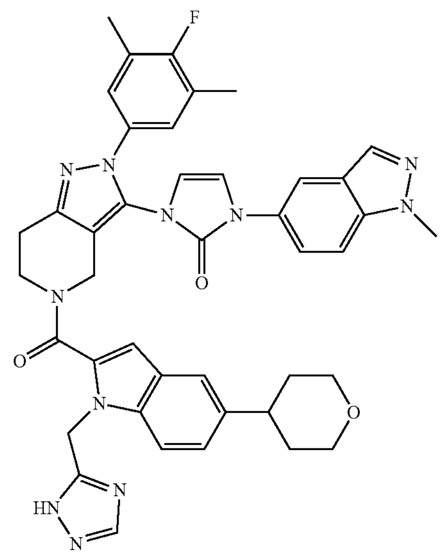 [SMILES: Cc1cc(-n2nc3c(c2-n2ccn(-c4ccc5c(cnn5C)c4)c2=O)CN(C(=O)c2cc4cc(C5CCOCC5)ccc4n2Cc2ncn[nH]2)CC3)cc(C)c1F] | 1-[2-(4-fluoro-3,5-dimethylphenyl)-5-[5-(oxan-4-yl)-1-(1H-1,2,4-triazol-5-ylmethyl)indole-2-carbonyl]-6,7-dihydro-4H-pyrazolo[4,3-c]pyridin-3-yl]-3-(1-methylindazol-5-yl)imidazol-2-one | SMD-TFA05-1 | 1.10 | 766 ([M+H]$^+$) |
| 145 | 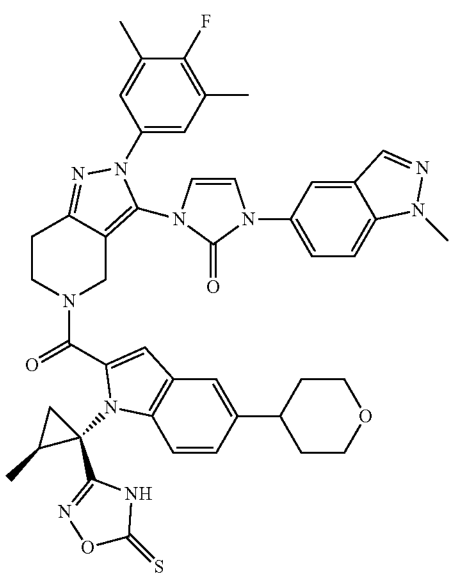 | 1-[2-(4-fluoro-3,5-dimethylphenyl)-5-[1-[(1S,2S)-2-methyl-1-(5-sulfanylidene-4H-1,2,4-oxadiazol-3-yl)cyclopropyl]-5-(oxan-4-yl)indole-2-carbonyl]-6,7-dihydro-4H-pyrazolo[4,3-c]pyridin-3-yl]-3-(1-methylindazol-5-yl)imidazol-2-one | SMD-TFA05-2 | 1.45 | 839 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 146 | 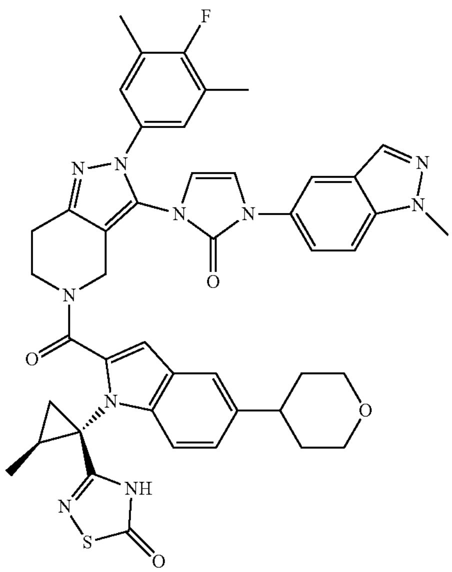 | 3-[(1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-yl)indol-1-yl]-2-methylcyclopropyl]-4H-1,2,4-thiadiazol-5-one | SMD-TFA05-2 | 1.46 | 839 ([M+H]+) |
| 147 | 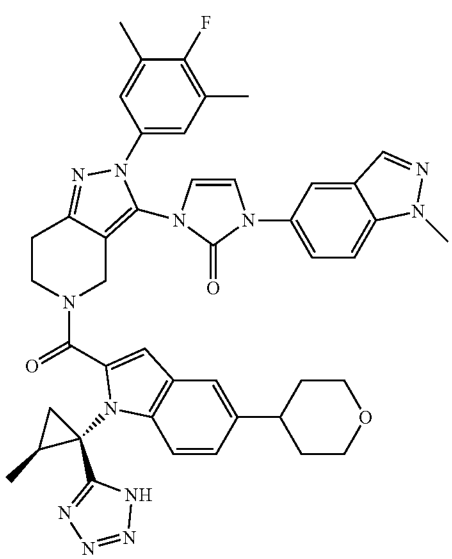 | 1-[2-(4-fluoro-3,5-dimethylphenyl)-5-[1-[(1S,2S)-2-methyl-1-(1H-tetrazol-5-yl)cyclopropyl]-5-(oxan-4-yl)indole-2-carbonyl]-6,7-dihydro-4H-pyrazolo[4,3-c]pyridin-3-yl]-3-(1-methylindazol-5-yl)imidazol-2-one | SMD-TFA05-2 | 1.26 | 807 ([M+H]+) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 148 | 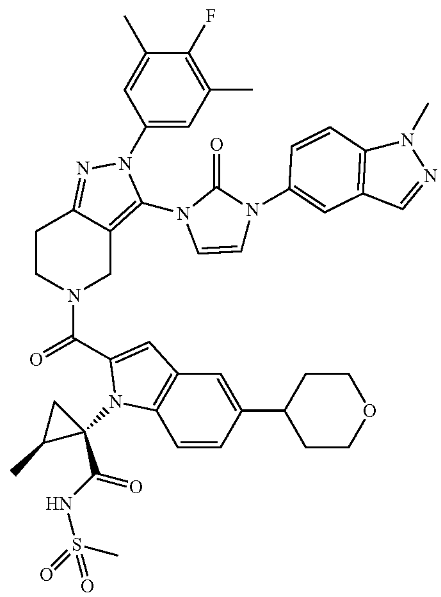 [SMILES: Cc1cc(-n2nc3c(c2-n2ccn(-c4ccc5c(cnn5C)c4)c2=O)CN(C(=O)c2cc4cc(C5CCOCC5)ccc4n2[C@@]2(C(=O)NS(C)(=O)=O)C[C@@H]2C)CC3)cc(C)c1F] | (1S,2S)-1-[2-[2-(4-fluoro-3,5-dimethylphenyl)-3-[3-(1-methylindazol-5-yl)-2-oxoimidazol-1-yl]-6,7-dihydro-4H-pyrazolo[4,3-c]pyridine-5-carbonyl]-5-(oxan-4-y)indol-1-yl]-2-methyl-N-methylsulfonylcyclopropane-1-carboxamide | SMD-TFA05-1 | 1.31 | 860 ([M+H]⁺) |
| 149 | 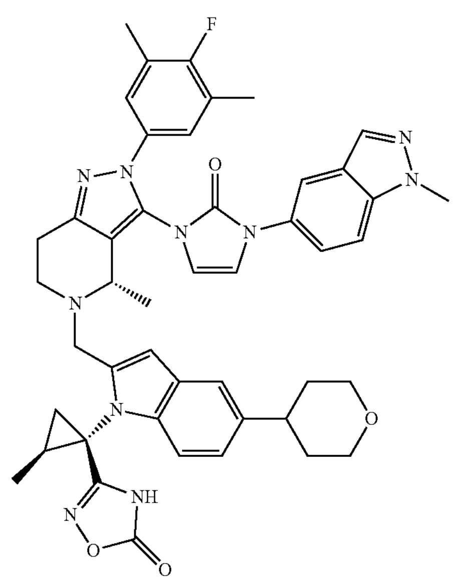 | 3-[(1S,2S)-1-[2-[[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridin-5-yl]methyl]-5-(oxan-4-yl)indol-1-yl]-2-methylcyclopropyl]-4H-1,2,4-oxadiazol-5-one | SMD-TFA05-2 | 1.17 | 823 ([M+H]⁺) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 150 | 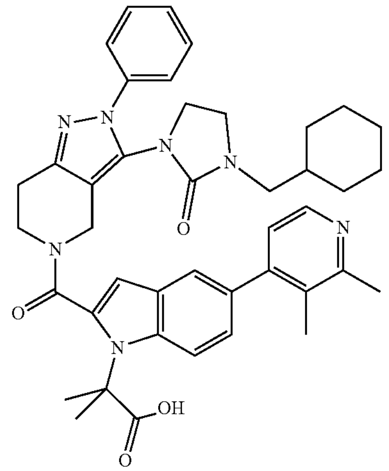 [SMILES: Cc1nccc(-c2ccc3c(c2)cc(C(=O)N2CCc4nn(-c5ccccc5)c(N5CCN(CC6CCCCC6)C5=O)c4C2)n3C(C)(C)C(=O)O)c1C] | 2-[2-[3-[3-(cyclohexylmethyl)-2-oxoimidazolidin-1yl]-2-phenyl-6,7-dihydro-4H-pyrazolo[4,3-c]pyridine-5-carbonyl]-5-(2,3-dimethylpyridin-4-yl)indol-yl]-2-methylpropanoic acid | SMD-TFA05-3 | 1.13 | 714 ([M+H]⁺) |
| 151 | 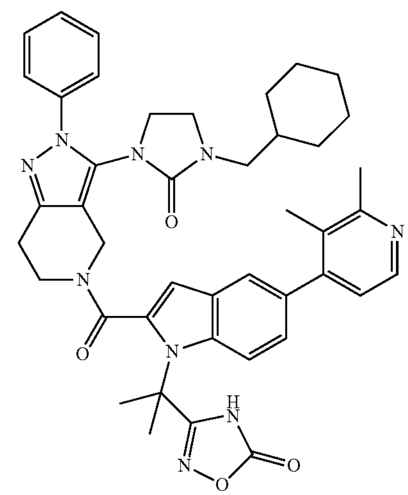 [SMILES: Cc1nccc(-c2ccc3c(c2)cc(C(=O)N2CCc4nn(-c5ccccc5)c(N5CCN(CC6CCCCC6)C5=O)c4C2)n3C(C)(C)c2noc(=O)[nH]2)c1C] | 3-[2-[2-[3-[3-(cyclohexylmethyl)-2-oxoimidazolidin-1-yl]-2-phenyl-6,7-dihydro-4H-pyrazolo[4,3-c]pyridine-5-carbonyl]-5-(2,3-dimethylpyridin-4-yl)indol-1-yl]propan-2-yl]-4H-1,2,4-oxadiazol-5-one | SMD-TFA05-3 | 1.10 | 755 ([M+H]⁺) |
| 152 | 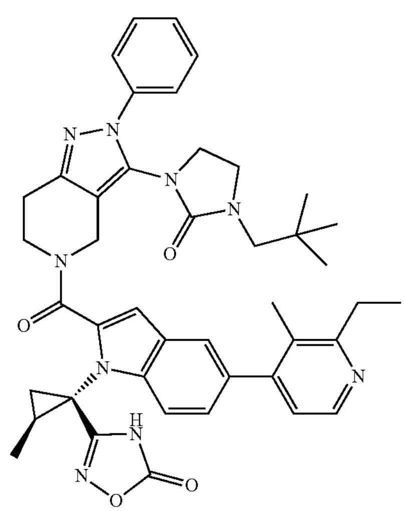 [SMILES: CCc1nccc(-c2ccc3c(c2)cc(C(=O)N2CCc4nn(-c5ccccc5)c(N5CCN(CC(C)(C)C)C5=O)c4C2)n3[C@@]2(c3noc(=O)[nH]3)C[C@@H]2C)c1C] | 3-[(1S,2S)-1-[2-[3-[3-(2,2-dimethylpropyl)-2-oxoimidazolidin-1-yl]-2-phenyl-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.11 | 754 ([M+H]⁺) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 153 | 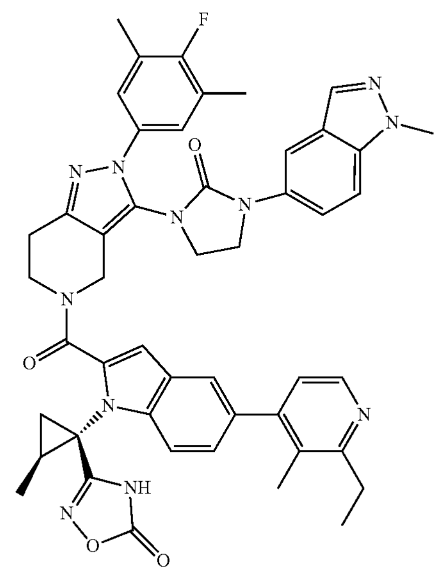 | 3-[(1S,2S)-1-[5-(2-ethyl-3-methylpyridin-4-yl)-2-[2-(4-fluoro-3,5-dimethylphenyl)-3-[3-(1-methylindazol-5-yl)-2-oxoimidazolidin-1-yl]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.15 | 860 ([M+H]$^+$) |
| 154 | 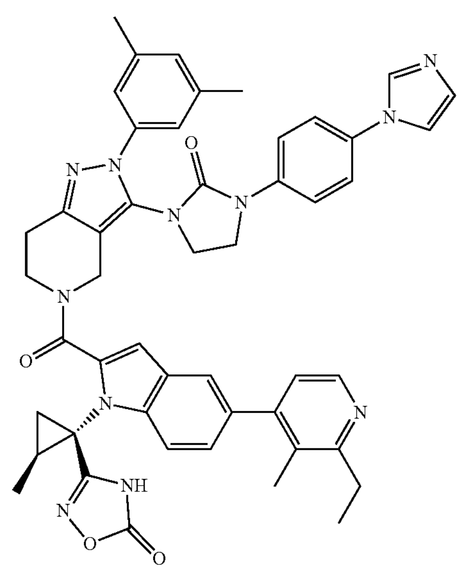 [SMILES: CCc1nccc(-c2ccc3c(c2)cc(C(=O)N2CCc4nn(-c5cc(C)cc(C)c5)c(N5CCN(c6ccc(-n7ccnc7)cc6)C5=O)c4C2)n3[C@@]2(c3noc(=O)[nH]3)C[C@@H]2C)c1C] | 3-[(1S,2S)-1-[2-[2-(3,5-dimethylphenyl)-3-[3-(4-imidazol-1-ylphenyl)-2-oxoimidazolidin-1-yl]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-1 | 0.86 | 854 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 155 | 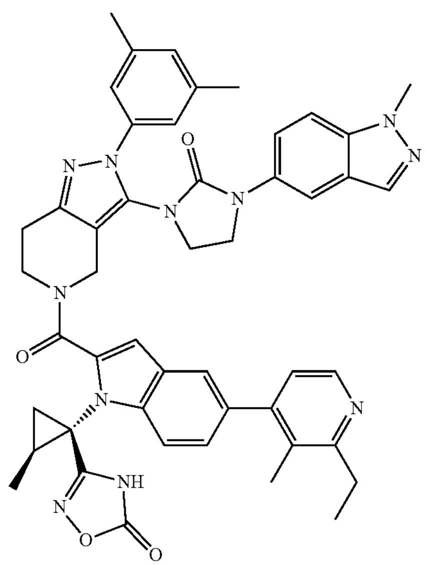 [SMILES: CCc1nccc(-c2ccc3c(c2)cc(C(=O)N2CCc4nn(-c5cc(C)cc(C)c5)c(N5CCN(c6ccc7c(cnn7C)c6)C5=O)c4C2)n3[C@@]2(c3noc(=O)[nH]3)C[C@@H]2C)c1C] | 3-[(1S,2S)-1-[2-[2-(3,5-dimethylphenyl)-3-[3-(1-methylindazol-5-yl)-2-oxoimidazolidin-1-yl]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.14 | 842 ([M+H]⁺) |
| 156 | 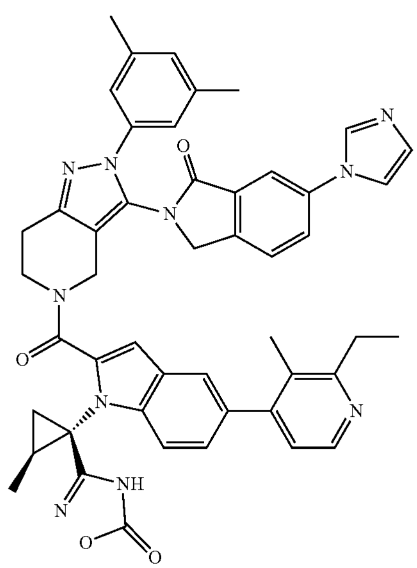 [SMILES: CCc1nccc(-c2ccc3c(c2)cc(C(=O)N2CCc4nn(-c5cc(C)cc(C)c5)c(N5Cc6ccc(-n7ccnc7)cc6C5=O)c4C2)n3[C@@]2(C(=N)NC(=O)O)C[C@@H]2C)c1C] | 3-[(1S,2S)-1-[2-[2-(3,5-dimethylphenyl)-3-(5-imidazol-1-yl-3-oxo-1H-isoindol-2-yl)-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-FA05-3 | 0.79 | 825 ([M+H]⁺) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 157 | 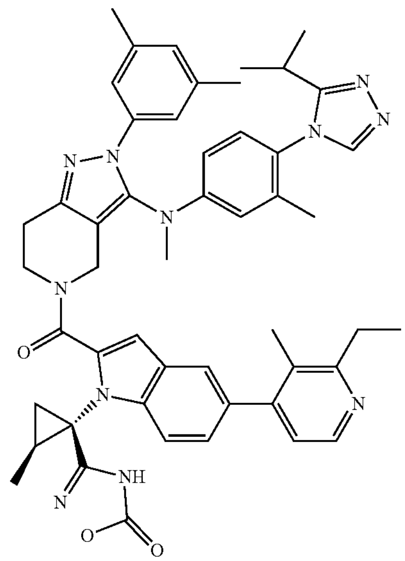 [SMILES: CCc1nccc(-c2ccc3c(c2)cc(C(=O)N2CCc4nn(-c5cc(C)cc(C)c5)c(N(C)c5ccc(-n6cnnc6C(C)C)c(C)c5)c4C2)n3[C@@]2(C(=N)NC(=O)O)C[C@@H]2C)c1C] | 3-[(1S,2S)-1-[2-[2-(3,5-dimethylphenyl)-3-[N,3-dimethyl-4-(3-propan-2-yl-1,2,4-triazol-4-yl)anilino]-6,7-dihydro-4H-pyrazolo[4,3-c]pyridine-5-carbonyl]-5-(2-ethyl-3-methylpyridin-4-yl)indol-1-yl]-2-methylcyclopropyl]-4H-1,2,4-oxadiazol-5-one | SMD-TFA05-3 | 1.10 | 856 ([M+H]$^+$) |
| 158 | 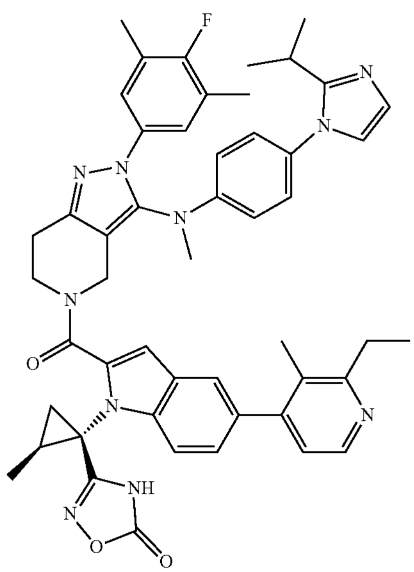 [SMILES: CCc1nccc(-c2ccc3c(c2)cc(C(=O)N2CCc4nn(-c5cc(C)c(F)c(C)c5)c(N(C)c5ccc(-n6ccnc6C(C)C)cc5)c4C2)n3[C@@]2(c3noc(=O)[nH]3)C[C@@H]2C)c1C] | 3-[(1S,2S)-1-[5-(2-ethyl-3-methylpyridin-4-yl)-2-[2-(4-fluoro-3,5-dimethylphenyl)-3-[N-methyl-4-(2-propan-2-ylimidazol-1-yl)anilino]-6,7-dihydro-4H-pyrazolo[4,3-c]pyridine-5-carbonyl]indol-1-yl]-2-methylcyclopropyl]-4H-1,2,4-oxadiazol-5-one | SMD-TFA05-3 | 1.05 | 859 ([M+H]$^+$) |

TABLE 2-7-continued

The Obtained Example Compounds 101 to 159

| Example No. | Structure | Compound | Analysis Condition | LC/MS retention time (min.) | LC/MS mass spectrometry (m/z) |
|---|---|---|---|---|---|
| 159 | 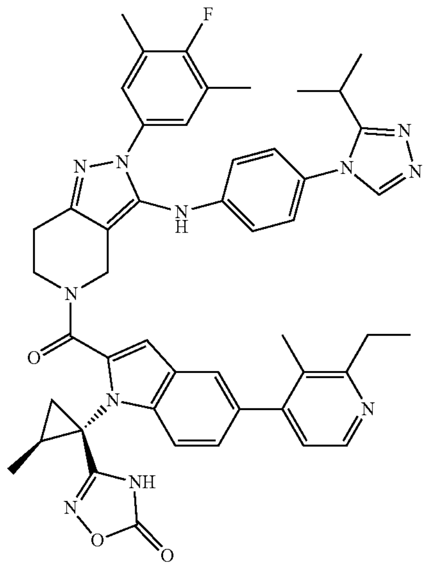 [SMILES: CCc1nccc(-c2ccc3c(c2)cc(C(=O)N2CCc4nn(-c5cc(C)c(F)c(C)c5)c(Nc5ccc(-n6cnnc6C(C)C)cc5)c4C2)n3[C@@]2(c3noc(=O)[nH]3)C[C@@H]2C)c1C] | 3-[(1S,2S)-1-[5-(2-ethyl-3-methylpyridin-4-yl)-2-[2-(4-fluoro-3,5-dimethylphenyl)-3-[4-(3-propan-2-yl-1,2,4-triazol-4-yl)anilino]-6,7-dihydro-4H-pyrazolo[4,3-c]pyridine-5-carbonyl]indol-1-yl]-2-methylcyclopropyl]-4H-1,2,4-oxadiazol-5-one | SMD-FA05-3 | 0.91 | 846 ([M+H]⁺) |

<Example 160> Preparation of Monosodium Salt Hydrate Crystal of Compound 1

Acetonitrile (3.02 mL) was added to 3-[(1S,2S)-1-[5-[(4S)-2,2-dimethyloxan-4-yl]-2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one (Compound 1, 1005.5 mg) obtained in Example 1 to dissolve the compound at room temperature. 5M Sodium hydroxide aqueous solution (0.495 mL) and seed crystals of sodium salt hydrate of Compound 1 were added to the solution, and the mixture was stirred at room temperature for 2 h. Tert-Butylmethyl ether (3.02 mL) was also added, and the mixture was stirred at room temperature for 1 h., and then tert-butylmethyl ether (9.05 mL) was added and the mixture was stirred at room temperature for 2 h. to obtain sodium salt hydrate crystals of the titled compound (1007.0 mg) as powder crystals (Sample 160a). Note that seed crystals were obtained by the following method.

DMSO (0.244 mL) and 2M sodium hydroxide aqueous solution (0.032 mL) were added to Compound 1 (26.9 mg). This solution (0.030 mL) was freeze-dried at −20° C. for 2 days. Acetonitrile (0.015 mL) was added to the obtained, freeze-dried product, and the mixture was stirred by shaking at room temperature for 2 days, and then tert-butylmethyl ether (0.015 mL) was added, and the mixture was stirred by shaking at room temperature for 12 days to obtain sodium salt hydrate crystals of Compound 1 as powder crystals (Sample 160b).

<Example 161> Preparation of Crystal of Example Compound 66

3-[(1S,2S)-1-[5-[(4S)-2,2-Dimethyloxan-4-yl]-2-[(4S)-2-(4-fluoro-3,5-dimethylphenyl)-4-methyl-3-[3-(1-methylindazol-5-yl)-2-oxoimidazol-1-yl]-6,7-dihydro-4H-pyrazolo[4,3-c]pyridine-5-carbonyl]indol-1-yl]-2-methylcyclopropyl]-4H-1,2,4-oxadiazol-5-one (Example Compound 66, 400.3 mg) was suspended in ethanol (8.00 mL), to which seed crystals of Example Compound 66 were added, and the mixture was stirred at 70° C. for 5 min. After the suspension was stirred at 50° C. for 1 h., it was stirred at room temperature for 17 h. to obtain crystals (381.1 mg) of Example Compound 66 as powder crystals (Sample 161a). Note that seed crystals were obtained by the following method.

Example Compound 66 (31.8 mg) was suspended in ethanol (0.636 mL), and stirred at 80° C. After the suspension was stirred at 40° C. for 1 h., it was stirred at room temperature for 22 h. to obtain crystals (24.2 mg) of Example Compound 66 as powder crystals (Sample 161b).

<Example 162> Preparation of Hemicalcium Salt Hydrate Crystal of Example Compound 67

Ethanol (5.60 mL) and 2M sodium hydroxide aqueous solution (0.75 mL) were added to 3-[(1S,2S)-1-[5-[(4S)-2,2-dimethyloxan-4-yl]-2-[(4S)-2-(4-fluoro-3,5-dimethylphenyl)-3-[3-(4-fluoro-1-methylindazol-5-yl)-2-oxoimidazol-1-yl]-4-methyl-6,7-dihydro-4H-pyrazolo[4,3-c]pyridine-5-carbonyl]indol-1-yl]-2-methylcyclopropyl]-4H-1,2,4-oxadiazol-5-one (Example Compound 67, 1120 mg) and the compound was dissolved at room temperature. 1.26 M calcium acetate aqueous solution (0.68 mL), seed crystals of the calcium salt hydrate of Example Compound 67 and water (0.68 mL) were added to the solution, and the mixture was stirred at room temperature for 3 h. Further, water (1.2 mL) was added and the mixture was stirred at room temperature for 1 h., and then water (2.3 mL) was added and the mixture was stirred at room temperature for 1 h. to obtain calcium salt hydrate crystals (973.0 mg) of Example Compound 67 as powder crystals (Sample 162a). Note that seed crystals were obtained by the following method.

Example Compound 67 (69.0 mg) was dissolved in DMSO (0.229 mL), and 1.06M calcium methoxyethoxide (0.147 mL) was added. This solution (0.015 mL) was freeze-dried at −20° C. for 2 days. Water-acetonitrile mixture (3:1, 0.015 mL) was added to the obtained, freeze-dried product, and the mixture was stirred by shaking at room temperature for 7 days to obtain calcium salt hydrate crystals of Example Compound 67 as powder crystals (Sample 162b).

<Example 163> Powder X-ray diffractometry

The sodium salt hydrate crystals (Samples 160a and 160b) of Compound 1 obtained in Example 160, the crystals (Samples 161a and 161b) of Example Compound 66 obtained in Example 161, the calcium salt hydrate crystals (Samples 162a and 162b) of Example Compound 67 obtained in Example 162 were each subjected to powder X-ray diffractometry by the following measurement method. The results are shown in FIG. 1 to FIG. 6.

Measurement Device: D8 Discover with GADDS CS diffractometer (Bruker AXS)

Anode: Cu
Voltage: 40 kV
Current: 40 mA
Scan Range: 5-25.3°
Step Width: 0.02°

<Example 164> Thermogravimetry/Differential Thermal Analysis

Figure 7:
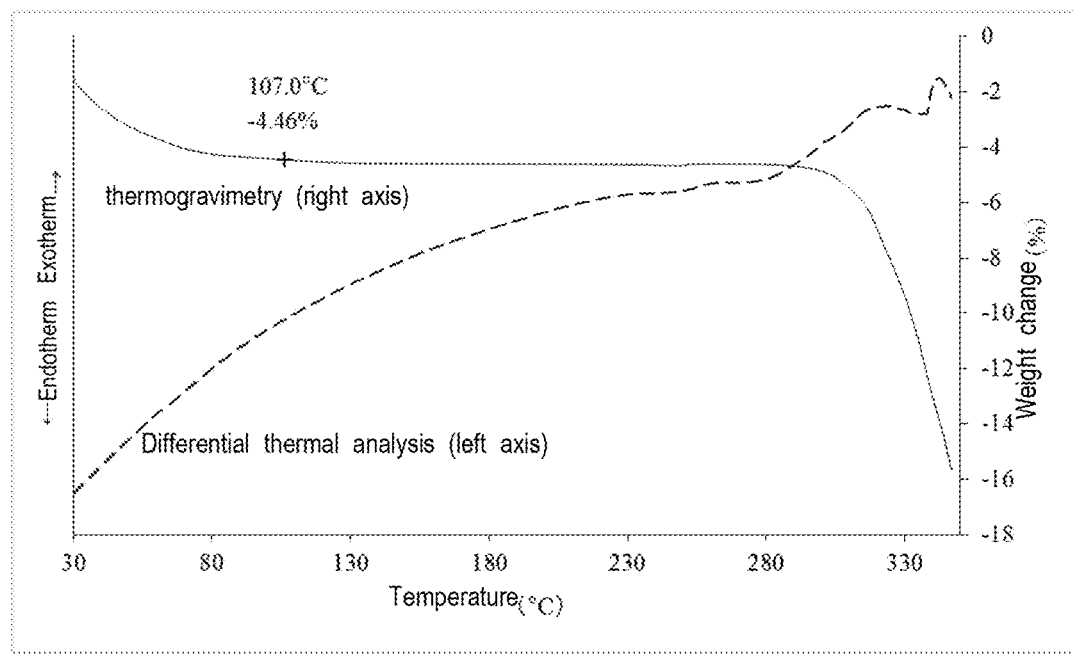
FIG. 7 shows the result of thermogravimetry/differential thermal analysis of the crystal of a sodium salt hydrate of Compound 1 obtained in Example 164. The horizontal axis shows temperature (° C.), and the right vertical axis shows the weight change (%) of the sample in thermogravimetry. The left vertical axis shows the heat flow observed in the differential thermal analysis.
Figure 8:
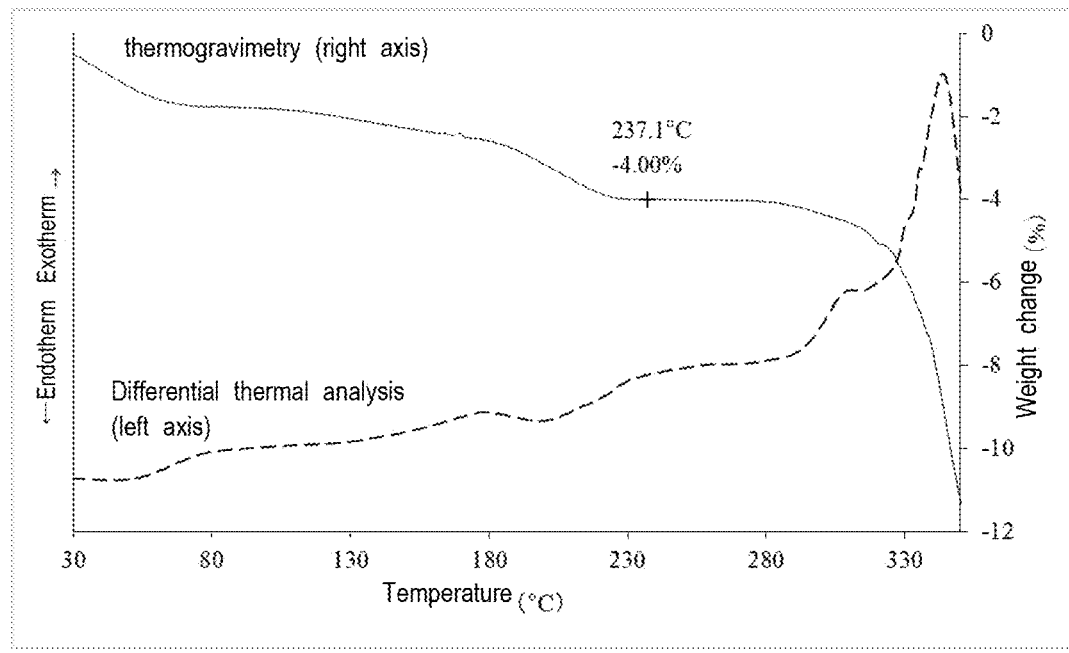
FIG. 8 shows the result of thermogravimetry/differential thermal analysis of the crystal of a calcium salt hydrate of Example Compound 67 obtained in Example 164. The horizontal axis shows temperature (° C.), and the right vertical axis shows the weight change (%) of the sample in thermogravimetry. The left vertical axis shows the heat flow observed in the differential thermal analysis.

The sodium salt hydrate crystal of Compound 1 (Sample 160a) and the calcium salt hydrate crystal of Example Compound 67 (Sample 162a) were each subjected to thermogravimetry/differential thermal analysis by the following measurement method. The results are shown in FIG. 7 and FIG. 8. Note that Sample 160a was dehydrated by approximately 110° C. and showed no clear melting point. Also, Sample 162a was dehydrated by approximately 240° C. and showed no clear melting point.

Measurement Device: EXSTAR TG/DTA6200R (Seiko Instruments Inc. (Current Company Name: Hitachi High-Tech Science Corporation))

Measurement Range: 30-350° C.
Heat rate: 10° C./min.
Atmosphere: Nitrogen

<Example 165> Karl Fischer Water Measurement

The rate of water content in the sodium salt hydrate crystal of Compound 1 (Sample 160a) and the calcium salt hydrate crystal (Sample 162a) of Example Compound 67 were measured using the coulometric Karl Fischer moisture meter (Metrohm, 756 KF Coulometer). The result was 7.4% for Sample 160a and 6.2% for Sample 162a.

From the results of Example 164 and Example 165, it was confirmed that the waters contained in the sodium salt hydrate crystal of Compound 1 and the calcium salt hydrate crystal of Example Compound 67 were mainly crystalline water.

<Test Example 1> Measurement of In Vitro cAMP Signal Activation of a Compound in Human GLP1R <Peptide>

The human GLP-1 (7-37) was obtained from PEPTIDE INSTITUTE, INC., and it was dissolved in phosphate buffered saline to 200 µM, then stored in a freezer of −80° C.

<Cell Culture>

A human GLP1R stably-expressing cell line (hGLP1R-HEK293) was used in the experiment. The cells were cultured in a Dulbecco's modified Eagle's medium (DMEM) containing 10% fetal bovine serum (Sigma-Aldrich), 100 units/mL penicillin G and 100 µg/mL streptomycin sulfate (Gibco), and 500 µg/mL Geneticin (Gibco), under a moist atmosphere containing 5% $CO_2$, at 37° C.

<cAMP Assay> hGLP1R-HEK293 was seeded in 96 well plates at $2.0 \times 10^4$ cells per well and cultured over night. The medium for culturing the cells was changed to 50 µL of Medium A (DMEM, 20 mM HEPES, 0.05% BSA, 0.5 mM 3-isobutyl-1-methylxanthine) the next day, and the cells were incubated at 37° C. for 30 min. Then, 50 µL of Medium B (DMEM, 20 mM HEPES, 0.05% BSA, 0.5 mM 3-isobutyl-1-methylxanthine) containing GLP-1 or the compound was added, and the cells were incubated at 37° C. for an additional 30 min. Then, 100 µL of Assay lysis buffer (Applied Bioscience) was added, and the cells were incubated at 37° C. for 30 min. The cAMP concentration was quantified using cAMP HiRange kit (Cisbio Bioassays).

<Calculation of $EC_{50}$>

By setting the cAMP concentration when the human GLP-1 (7-37) was put into action at a concentration of 1 nM to 100%, the cAMP concentration of each well was converted to a reaction rate (%). By using a 4 parameter logistic regression analysis by XLfit (ver 5.4.0.8), dose-response curves of the each Example Compound were created, and the half maximal (50%) effective concentrations ($EC_{50}$) were calculated. The results are shown in Table 3.

TABLE 3

| $EC_{50}$ of each Example Compound | |
|---|---|
| Example No. | $EC_{50}$ (nM) |
| 1 | 8.8 |
| 2 | 5.6 |
| 3 | 6.1 |
| 4 | 12 |
| 5 | 6.1 |
| 6 | 2.9 |
| 7 | 3.2 |
| 8 | 2.5 |
| 9 | 1.8 |
| 10 | 2.8 |
| 11 | 1.1 |
| 12 | 2.7 |
| 13 | 3.7 |
| 14 | 2.3 |
| 15 | 2.2 |
| 16 | 0.51 |
| 17 | 1.0 |
| 18 | 1.3 |
| 19 | 1.3 |
| 20 | 1.9 |
| 21 | 1.6 |
| 22 | 2.3 |
| 23 | 1.8 |
| 24 | 2.5 |
| 25 | 4.0 |

TABLE 3-continued

EC$_{50}$ of each Example Compound

| Example No. | EC$_{50}$ (nM) |
|---|---|
| 26 | 0.77 |
| 27 | 2.3 |
| 28 | 1.9 |
| 29 | 1.4 |
| 30 | 1.4 |
| 31 | 0.74 |
| 32 | 0.94 |
| 33 | 1.6 |
| 34 | 3.0 |
| 35 | 3.2 |
| 36 | 2.1 |
| 37 | 2.5 |
| 38 | 1.7 |
| 39 | 1.0 |
| 40 | 2.2 |
| 41 | 2.4 |
| 42 | 1.9 |
| 43 | 1.5 |
| 44 | 1.5 |
| 45 | 1.6 |
| 46 | 3.3 |
| 47 | 2.0 |
| 48 | 3.0 |
| 49 | 3.8 |
| 50 | 2.9 |
| 51 | 8.7 |
| 52 | 6.7 |
| 53 | 2.9 |
| 54 | 3.9 |
| 55 | 3.7 |
| 56 | 3.4 |
| 57 | 8.1 |
| 58 | 7.6 |
| 59 | 1.5 |
| 60 | 4.9 |
| 61 | 1.6 |
| 62 | 1.1 |
| 63 | 1.1 |
| 64 | 2.0 |
| 65 | 3.5 |
| 66 | 0.81 |
| 67 | 1.2 |
| 68 | 1.8 |
| 69 | 2.8 |
| 70 | 1.5 |
| 71 | 1.3 |
| 72 | 2.3 |
| 73 | 2.5 |
| 74 | 6.2 |
| 75 | 6.2 |
| 76 | 2.4 |
| 77 | 1.4 |
| 78 | 3.6 |
| 79 | 2.4 |
| 80 | 2.4 |

<Test Example 2>: Insulin Secretion Promoting and Blood Glucose Lowering Effects A solution of Example Compound 67 (solvent composition: PEG400 (10 vol %): propylene glycol (10 vol %): 100 mM Glycine-NaOH buffer, pH 9.0 (80 vol %)) was intravenously administered to a male cynomolgus monkey under anesthesia, for 40 min. continuously, and a steady-state drug concentration in plasma of 0.94, 1.6 or 4.8 nmol/L was achieved. Likewise, a solution of exenatide (solvent: Tween 0.05%/PBS(-)), which is a control drug, was administered in the same manner, and a steady-state drug concentration in plasma of 9.2 or 23.9 pmol/L was achieved. To the vehicle control group, the solvent of Example Compound 67 was administered. Next, a 50% glucose solution (glucose administration weight to the monkey: 0.5 g/kg) was intravenously administered and a blood sample was collected every 5 min or 10 min to measure the plasma insulin and glucose concentrations. The area under the curve was calculated from the time course of each parameter after the drug administration to evaluate the insulin secretion promoting effect and the blood glucose lowering effect.

Figure 9:
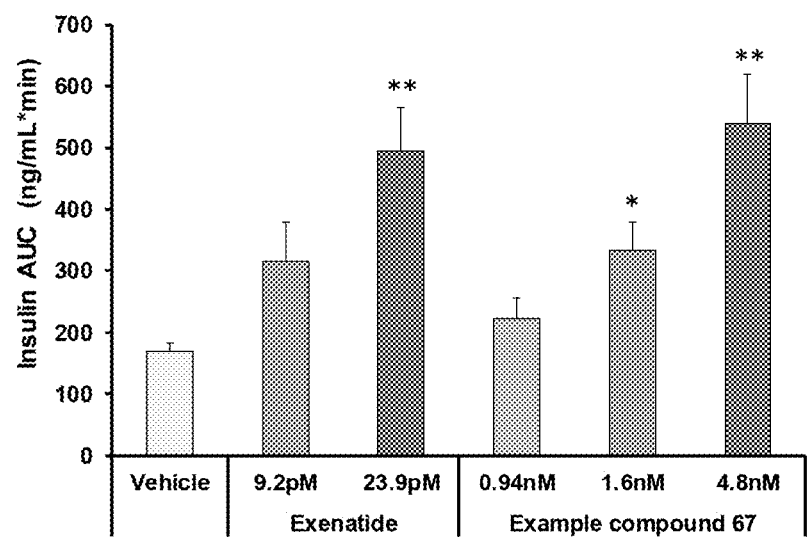
FIG. 9 shows the impact of Example Compound 67 and exenatide against insulin secretion after intravenous administration of glucose in male cynomolgus monkeys. The area under the curve of insulin is shown by a mean value±standard error (n=6). Each pharmaceutical agent was administered in a crossover design. * indicates that the value of the group shows a statistically significant difference versus that of vehicle group at P<0.025 and ** indicates that the value of the group shows a statistically significant difference versus that of vehicle group at P<0.005 (Williams test). The concentration of each drug is a mean value of the measured plasma concentration of the drug.
Figure 10:
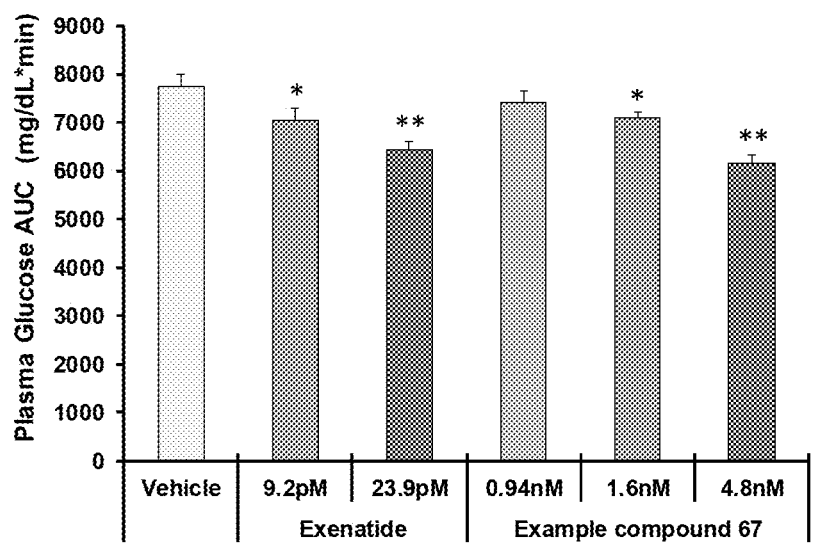
FIG. 10 shows the impact of Example Compound 67 and exenatide against plasma glucose levels after intravenous administration of glucose in male cynomolgus monkeys. The area under the curve of plasma glucose is shown by a mean value±standard error (n=6). Each pharmaceutical agent was administered in a crossover design. * indicates that the value of the group shows a statistically significant difference versus that of vehicle group at P<0.025, and ** indicates that the value of the group shows a statistically significant difference versus that of vehicle group at P<0.005 (Williams test). The concentration of each drug is a mean value of the measured plasma concentration of drug.

In the Example Compound 67 administered group, an increase in the area under the curve of insulin (FIG. 9) and a decrease in the area under the curve of plasma glucose (FIG. 10) in a dose-dependent manner, were observed at a steady-state concentration in plasma of 0.94 to 4.8 nmol/L. A similar increase in the area under the curve of insulin (FIG. 9) and decrease in the the area under the curve of plasma glucose (FIG. 10) were observed in exenatide (control drug) administered group at a steady-state plasma concentration of 9.2 to 23.9 pmol/L by the continuous intravenous administrations Note that the 9.2 pmol/L (38.5 pg/mL) of exenatide was close to the lower limit of the therapeutic concentration range (50-350 pg/mL) of exenatide in human diabetes patients (Drug interview form, Byetta hypodermic injection 5 μg Pen 300, Byetta hypodermic injection 10 g Pen 300, September 2016 (revised ver. 9)). This result indicates that Example Compound 67 exhibits an insulin secretion promoting effect and a blood glucoselowering effect that are equivalent to exenatide, at a plasma concentration of 1.6 nmol/L or higher.

<Test Example 3>: Anorexigenic Effects

Example Compound 67 was orally administered to male cynomolgus monkeys, for 5 consecutive days, and its effects on the food intake for 90 min. from 3 h, after administration were evaluated everyday. Likewise, exenatide, which is a control drug, was subcutaneously administered for 5 consecutive days, and its effect on the food intake for 90 min. from 30 min. after administration were evaluated. To the vehicle control group, both a solvent for oral administration of Example Compound 67 (DMSO (10 vol %): Cremophor EL (10 vol %): PEG 400 (15 vol %): 100 mM Glycine-NaOH buffer, pH 10 (65 vol %), 1 mL/kg) and a solvent for subcutaneous administration of exenatide (0.05 w/v % Tween/PBS(-), 0.1 mL/kg) were administered. At the same time, the solvent for subcutaneous administration was additionally administered to the Example Compound 67 administered group (concentration of administered drug, 0.05 or 0.1 mg/mL), and the solvent for oral administration was additionally administered to the exenatide administered group (concentration of administered drug, 3 or 6 g/mL).

Figure 11:
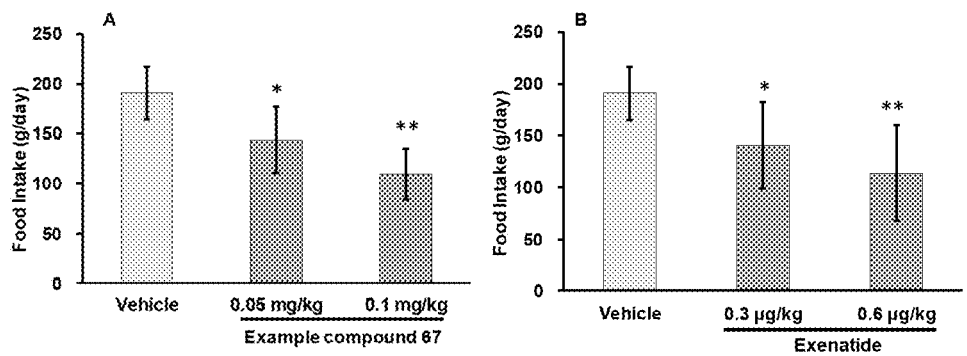
FIG. 11 shows the impact of Example Compound 67 and exenatide against the food intake of male cynomolgus monkeys. The food intake is shown by a mean value±standard deviation (n=6). Each pharmaceutical agent was administered in a crossover design. * indicates that the value of the group shows a statistically significant difference versus that of vehicle group at P<0.025, and ** indicates that the value of the group shows a statistically significant difference versus that of vehicle group at P<0.005 (Williams test).

Example Compound 67 suppressed the food intake in a dosage dependent manner (FIG. 11A). The degree of suppression was almost equivalent to the control drug exenatide (FIG. 11B). The plasma concentration of drug (mean value±standard error) immediately after measuring the food intake in each group were 8.0±1.0 nM (0.05 mg/kg group) and 16.3±2.3 nM (0.1 mg/kg group) for the Example Compound 67 administered group and 91±8.5 pM (0.3 μg/kg group) and 199±13.1 pM (0.6 μg/kg group) for the exenatide administered group.

<Test Example 4> Pharmacokinetics of the Compounds

Figure 12:
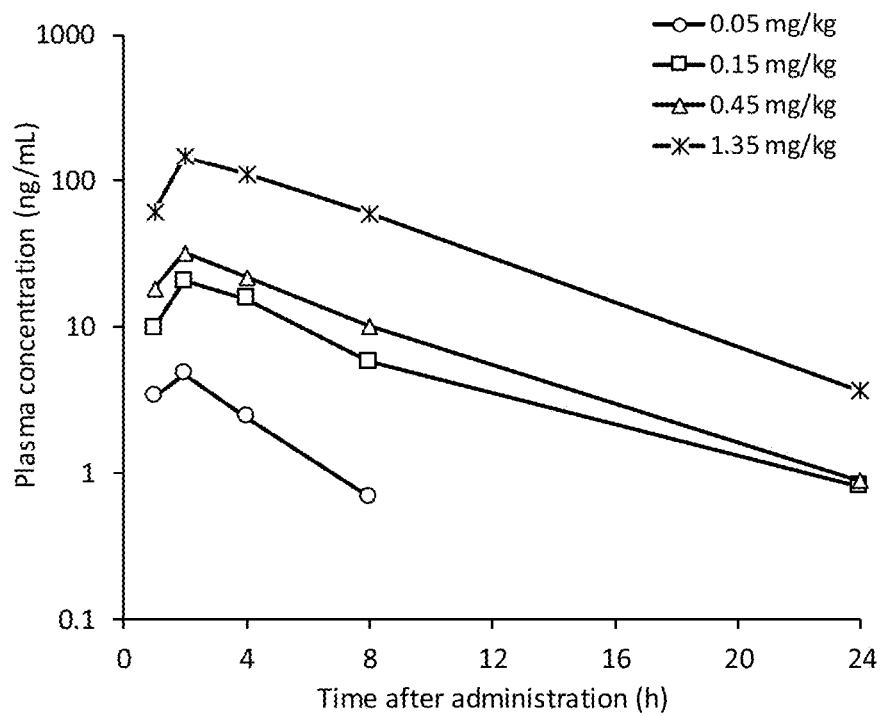
FIG. 12 shows the time profile of the plasma concentrations for the drug after oral administration of this substance to male cynomolgus monkeys. Plasma concentrations are represented by mean values of n=2 for each dosage.

After oral administration (gavage administration using a gastric catheter) of a calcium salt hydrate crystal (Sample 162a) suspension (Dosage: 0.05, 0.15, 0.45 and 1.35 mg/kg)

prepared from Example Compound 67 obtained in Example 162 to a male cynomolgus monkey (n=2 for each dosage), blood was sequentially collected from the vein to obtain plasma. The plasma concentrations of the drug were determined by liquid chromatography tandem-mass spectrometry. The lower limit of quantification was 0.3 ng/mL. The time profile of the plasma concentrations for the drug are shown in FIG. 12 and the time to reach the maximum plasma concentration of the drug ($T_{max}$), the maximum plasma concentration of the drug ($C_{max}$) and the area under the plasma concentration—time curve of the drug up to 24 h, after administration ($AUC_{0-24h}$) are shown in Table 4.

In all dosages, the plasma concentrations of the drug reached $C_{max}$ at 2 h after oral administration, and then decreased in a similar time profile pattern. The increase in the plasma exposure of drug at dosages of 0.05, 0.15, 0.45 and 1.35 mg/kg (Dosage ratio: 1:3:9:27) was nearly proportional to the increase in the dosage ($C_{max}$ ratio: 1.0:4.3:6.7:31, $AUC_{0-24h}$ ratio: 1.0:5.7:8.8:44). It was shown that the present substance was dose-proportionally absorbed in the intestinal tract and eliminated.

TABLE 4

The Tmax, Cmax, and AUC0-24 h after oral administration of the present substance to male cynomolgus monkeys

| Dose (mg/kg) | (Ratio) | $T_{max}$ (h) | $C_{max}$ (ng/mL) | (Ratio) | $AUC_{0-24h}$ (ng · h/mL) | (Ratio) |
|---|---|---|---|---|---|---|
| 0.05 | 1.0 | 2.0 | 4.78 | 1.0 | 23.7 | 1.0 |
| 0.15 | 3.0 | 2.0 | 20.7 | 4.3 | 135 | 5.7 |
| 0.45 | 9.0 | 2.0 | 32.0 | 6.7 | 208 | 8.8 |
| 1.35 | 27 | 2.0 | 148 | 31 | 1040 | 44 |

The invention claimed is:
1. A compound represented by Formula (I):

[Chemical Formula 1]

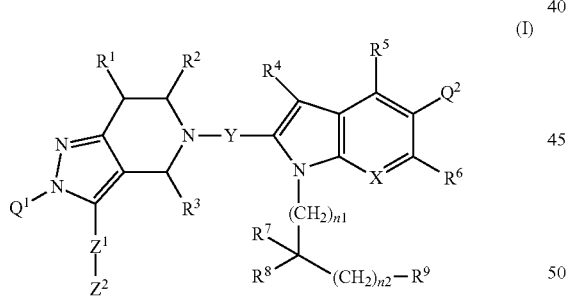

(I)

wherein, X is —N═ or —CR$^a$═; R$^a$ is selected from a hydrogen atom, a halogen atom, and C$_{1-6}$ alkyl;

Y is selected from —C(═O)—, —CHR—, and —S(═O)$_2$—; R is a hydrogen atom or C$_{1-6}$ alkyl;

Q$^1$ is C$_{6-10}$ aryl or 5 to 10 membered heteroaryl, wherein C$_{6-10}$ aryl and 5 to 10 membered heteroaryl are optionally substituted with one to five substituents independently selected from a halogen atom, C$_{1-6}$ alkyl (wherein C$_{1-6}$ alkyl is optionally substituted with one or more halogen atoms), and C$_{1-6}$ alkoxy;

Q$^2$ is 3 to 12 membered heterocyclyl or 5 to 10 membered heteroaryl, wherein 3 to 12 membered heterocyclyl and 5 to 10 membered heteroaryl are optionally substituted with one to three substituents independently selected from a halogen atom, C$_{1-6}$ alkyl (wherein C$_{1-6}$ alkyl is optionally substituted with one or more halogen atoms), C$_{1-6}$ alkoxy, and —NR$^{Qa}$R$^{Qb}$, and two C$_{1-6}$ alkyl groups together with a carbon atom to which they are attached may form C$_{3-8}$ carbocyclic ring; and R$^{Qa}$ and R$^{Qb}$ are independently selected from a hydrogen atom, C$_{1-6}$ alkyl, and (C$_{1-6}$ alkyl)carbonyl;

R$^1$, R$^2$ and R$^3$ are each independently selected from a hydrogen atom and C$_{1-6}$ alkyl (wherein C$_{1-6}$ alkyl is optionally substituted with one or more substituents independently selected from a halogen atom, C$_{1-6}$ alkoxy, and hydroxy);

R$^4$, R$^5$ and R$^6$ are independently selected from a hydrogen atom, a halogen atom, and C$_{1-6}$ alkyl;

R$^7$ and R$^8$ are independently a hydrogen atom or C$_{1-6}$ alkyl, wherein C$_{1-6}$ alkyl is optionally substituted with one or more substituents independently selected from a halogen atom and C$_{3-15}$ cycloalkyl, or R$^7$ and R$^8$ together with a carbon atom to which they are attached may form C$_{3-15}$ cycloalkane ring, wherein C$_{3-15}$ cycloalkane ring formed by R$^7$ and R$^8$ together is optionally substituted with one to three C$_{1-6}$ alkyl, wherein C$_{1-6}$ alkyl is optionally substituted with one or more substituents independently selected from a halogen atom, hydroxy, —NR$^{7a}$R$^{7b}$, C$_{1-6}$ alkoxy, and 3 to 12 membered heterocyclyl, and R$^{7a}$ and R$^{7b}$ are independently selected from a hydrogen atom, C$_{1-6}$ alkyl, and (C$_{1-6}$ alkyl)carbonyl;

n1 is an integer of 0 to 3; n2 is an integer of 0 to 5;

R$^9$ is selected from the group consisting of

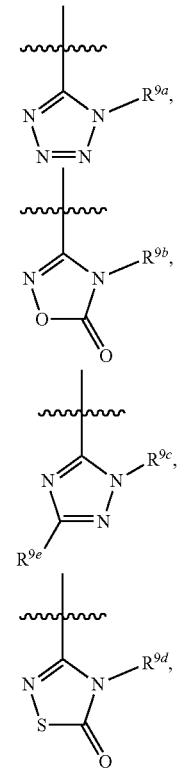

—CO$_2$R$^{9f}$, and —C(═O)—NR$^{9g}$R$^{9h}$;

R$^{9a}$, R$^{9b}$, R$^{9c}$, R$^{9d}$, and R$^{9g}$ are each independently selected from a hydrogen atom, C$_{1-6}$ alkyl (wherein C$_{1-6}$ alkyl is optionally substituted with one or more substituents independently selected from a halogen atom and C$_{1-6}$ alkoxy), and (C$_{1-6}$ alkyl)carbonyl; R$^{9e}$ is a hydrogen atom, or C$_{1-6}$ alkyl that is optionally substituted with one or more halogen atoms; R$^{9f}$ is a hydrogen atom or C$_{1-6}$ alkyl; R$^{9h}$ is a hydrogen atom, C$_{1-6}$ alkyl, (C$_{1-6}$ alkyl)carbonyl, cyano, or —S(=O)$_{n3}$—R$^{9'}$; n3 is an integer of 0 to 2; and R$^{9i}$ is C$_{1-6}$ alkyl;

Z$^1$ is selected from the group consisting of

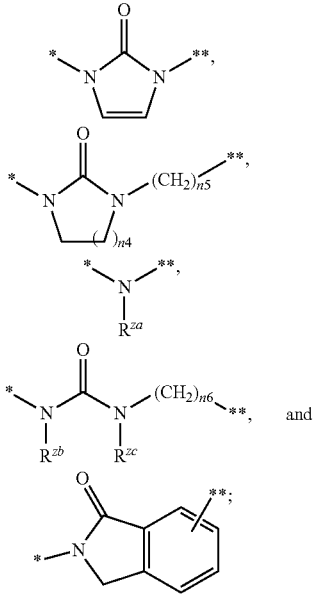

wherein R$^{za}$ is selected from a hydrogen atom, C$_{1-6}$ alkyl, and (C$_{1-6}$ alkyl)carbonyl; R$^{zb}$ and R$^{zc}$ are independently a hydrogen atom or C$_{1-6}$ alkyl; n4 is an integer of 1 to 3; n5 and n6 are independently an integer of 0 to 10 (* represents a binding position with a pyrazolopyridine structure, and ** represents a binding position with Z$^2$);

Z$^2$ is selected from the group consisting of C$_{1-6}$ alkyl, C$_{3-15}$ cycloalkyl, 3 to 12 membered heterocyclyl, C$_{6-10}$ aryl and 5 to 10 membered heteroaryl, wherein C$_{3-15}$ cycloalkyl, 3 to 12 membered heterocyclyl, C$_{6-10}$ aryl, and 5 to 10 membered heteroaryl are optionally substituted with one to five substituents independently selected from Group A:

Group A: a) oxo,
b) a halogen atom,
c) cyano,
d) —NR$^{zd}$R$^{ze}$; wherein R$^{zd}$ and R$^{ze}$ are independently selected from a hydrogen atom, C$_{1-6}$ alkyl and (C$_{1-6}$ alkyl)carbonyl, wherein C$_{1-6}$ alkyl is optionally substituted with one or more substituents independently selected from hydroxy, a halogen atom and C$_{1-6}$ alkoxy,
e) —C(=O)—NR$^{zf}$R$^{zg}$; wherein R$^{zf}$ and R$^{zg}$ are independently selected from a hydrogen atom, C$_{1-6}$ alkyl and (C$_{1-6}$ alkyl)carbonyl, wherein C$_{1-6}$ alkyl is optionally substituted with one or more substituents independently selected from hydroxy, a halogen atom and C$_{1-6}$ alkoxy,
f) —S(=O)$_{n7}$—R$^{zh}$; wherein n7 is an integer of 0 to 2; and R$^{zh}$ is a hydrogen atom or C$_{1-6}$ alkyl,
g) C$_{1-6}$ alkyl; wherein C$_{1-6}$ alkyl is optionally substituted with one or more substituent independently selected from a halogen atom, hydroxy, —NR$^{zi}$R$^{zj}$, C$_{1-6}$ alkoxy, and 3 to 12 membered heterocyclyl, wherein R$^{zi}$ and R$^{zj}$ are independently a hydrogen atom or C$_{1-6}$ alkyl, and wherein 3 to 12 membered heterocyclyl is optionally substituted with one or more substituents independently selected from hydroxy, C$_{1-6}$ alkyl and 3 to 12 membered heterocyclyl,
h) C$_{1-6}$ alkoxy; wherein C$_{1-6}$ alkoxy is optionally substituted with one or more substituent independently selected from hydroxy, a halogen atom, and C$_{1-6}$ alkoxy,
i) 3 to 12 membered heterocyclyl; wherein 3 to 12 membered heterocyclyl is optionally substituted with one or more substituents independently selected from C$_{1-6}$ alkyl and (C$_{1-6}$ alkyl)carbonyl,
j) C$_{6-10}$ aryl; wherein C$_{6-10}$ aryl is optionally substituted with one or more (C$_{1-6}$ alkyl)carbonyl, and
k) 5 to 10 membered heteroaryl; wherein 5 to 10 membered heteroaryl is optionally substituted with one or more substituents independently selected from C$_{1-6}$ alkyl, C$_{1-6}$ alkoxy, —NR$^{zk}$R$^{zl}$, and 3 to 12 membered heterocyclyl, wherein R$^{zk}$ and R$^{zl}$ are independently selected from a hydrogen atom, C$_{1-6}$ alkyl and (C$_{1-6}$ alkyl)carbonyl, and wherein 3 to 12 membered heterocyclyl is optionally substituted with one or more substituents independently selected from C$_{1-6}$ alkyl and (C$_{1-6}$ alkyl)carbonyl;

or a salt thereof.

2. The compound according to claim 1, or a salt thereof, wherein Q$^1$ is phenyl or pyridyl, and phenyl or pyridyl is substituted with one to four substituents independently selected from a halogen atom and C$_{1-6}$ alkyl.

3. The compound according to claim 2, or a salt thereof, wherein R$^7$ and R$^8$ are both a hydrogen atom; R$^7$ and R$^8$ are both C$_{1-6}$ alkyl; R$^7$ is a hydrogen atom and R$^8$ is C$_{1-6}$ alkyl; or R$^7$ and R$^8$ together with a carbon atom to which they are attached form C$_{3-8}$ cycloalkane ring, wherein C$_{3-8}$ cycloalkyl formed is optionally substituted with one to two C$_{1-6}$ alkyl, and C$_{1-6}$ alkyl is optionally substituted with one or more substituents independently selected from hydroxy, C$_{1-6}$ alkoxy, and 3 to 12 membered heterocyclyl.

4. The compound according to claim 3 or a salt thereof, wherein Z$^2$ is selected from C$_{1-6}$ alkyl, C$_{3-15}$ cycloalkyl, 3 to 12 membered heterocyclyl, C$_{6-10}$ aryl, and 5 to 10 membered heteroaryl, wherein C$_{3-15}$ cycloalkyl, 3 to 12 membered heterocyclyl, C$_{6-10}$ aryl, and 5 to 10 membered heteroaryl are optionally substituted with one to four substituents independently selected from Group B:

Group B: a) oxo,
b) a halogen atom,
c) —NR$^{zd1}$R$^{ze1}$; wherein R$^{zd1}$ and R$^{ze1}$ are independently selected from a hydrogen atom, C$_{1-6}$ alkyl and (C$_{1-6}$ alkyl)carbonyl, and C$_{1-6}$ alkyl is optionally substituted with one or more C$_{1-6}$ alkoxy,
d) —S(=O)$_{n7}$—R$^{zh1}$; wherein n7 is an integer of 0 to 2, R$^{zh1}$ is C$_{1-6}$ alkyl,
e) C$_{1-6}$ alkyl; wherein C$_{1-6}$ alkyl is optionally substituted with one or more substituents independently selected from a halogen atom, hydroxy, —NR$^{zi}$R$^{zj}$, C$_{1-6}$ alkoxy, and 3 to 12 membered heterocyclyl, wherein R$^{zi}$ and R$^{zj}$ are independently a hydrogen atom or C$_{1-6}$ alkyl, and wherein 3 to 12 membered heterocyclyl is optionally substituted with one or more substituents independently selected from hydroxy, C$_{1-6}$ alkyl and 3 to 12 membered heterocyclyl,
f) C$_{1-6}$ alkoxy; wherein C$_{1-6}$ alkoxy is optionally substituted with one or more hydroxy,
g) 3 to 12 membered heterocyclyl; wherein 3 to 12 membered heterocyclyl is optionally substituted with one or more (C$_{1-6}$ alkyl)carbonyl, h) 5 to 10 membered heteroaryl; wherein 5 to 10 membered heteroaryl is optionally substituted with one or more substituents independently selected from $C_{1-6}$ alkyl, and —$NR^{zk1}R^{zl1}$; and $R^{zk1}$ and $R^{zl1}$ are independently selected from a hydrogen atom and $C_{1-6}$ alkyl.

5. The compound according to claim 4, or a salt thereof, wherein Y is —C(=O)—.

6. The compound according to claim 5, or a salt thereof, wherein $R^1$ is a hydrogen atom.

7. The compound according to claim 6, or a salt thereof, wherein n1 and n2 are both 0.

8. The compound according to claim 7, or a salt thereof, wherein $R^9$ is the Formula

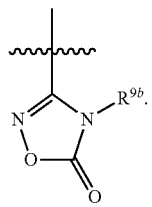

9. The compound according to claim 8, or a salt thereof, wherein X is —N=, —CH=, or —CF=.

10. The compound according to claim 9, or a salt thereof, wherein $Z^1$ is the Formula:

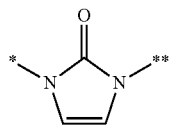

(IIIa)

wherein * represents a binding position with a pyrazolopyridine structure, and ** represents a binding position with $Z^2$.

11. A pharmaceutical composition comprising the compound according to claim 10, or a salt thereof, as an active ingredient.

12. A method for treating non-insulin-dependent diabetes mellitus (Type 2 diabetes) or obesity comprising administering an effective amount of the compound according to claim 1, or a salt thereof, as an active ingredient to a patient in need of such treatment.

13. The compound according to claim 1, or a salt thereof, represented by the formula:

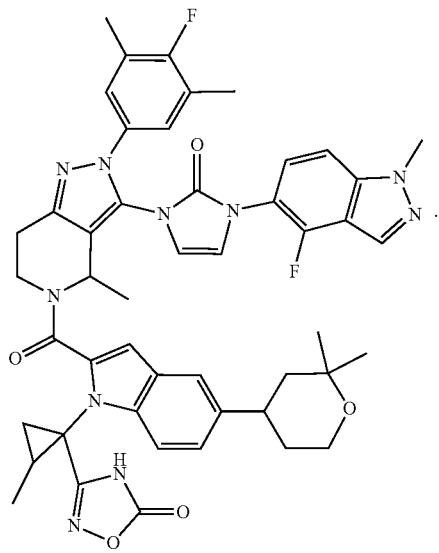

14. The compound according to claim 13, or a salt thereof, of the formula:

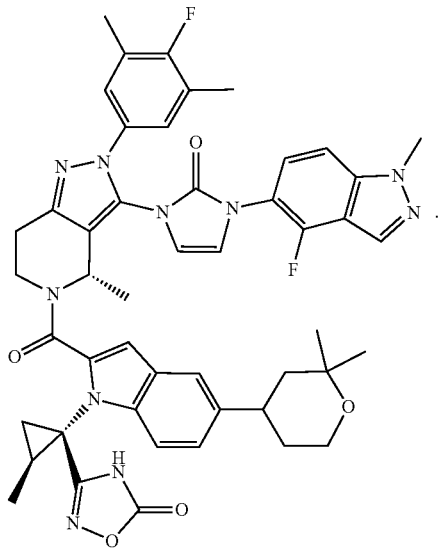

15. The hemicalcium salt hydrate of the compound according to claim 14.

16. A pharmaceutical composition comprising the compound according to claim 14 or, a salt thereof, or of claim 15 as an active ingredient.

17. A method for treating non-insulin-dependent diabetes mellitus (Type 2 diabetes) or obesity in a patient in need thereof, comprising administering an effective amount of a compound according to claim 14 or a salt thereof, or of claim 15.

* * * * *

UNITED STATES PATENT AND TRADEMARK OFFICE
CERTIFICATE OF CORRECTION

PATENT NO.        : 10,858,356 B2
APPLICATION NO.   : 15/759872
DATED             : December 8, 2020
INVENTOR(S)       : Hitoshi Yoshino It is certified that error appears in the above-identified patent and that said Letters Patent is hereby corrected as shown below:

In the Claims

Column 315, Line 5: In Claim 1, delete "-$R^{9'}$;" and insert -- -$R^{9i}$; --, therefor.

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*